(12) United States Patent
Dantanarayana et al.

(10) Patent No.: US 11,420,008 B2
(45) Date of Patent: Aug. 23, 2022

(54) VENT AND VENT ADAPTOR FOR PATIENT INTERFACE

(71) Applicant: RESMED PTY LTD, Bella Vista (AU)

(72) Inventors: Muditha Pradeep Dantanarayana, Sydney (AU); Charles Harry Finch, Sydney (AU); Justin John Formica, Sydney (AU); Richard Llewelyn Jones, Sydney (AU); Joseph Samuel Ormrod, Sydney (AU); Jamie Graeme Wehbeh, Sydney (AU); Chia Ik Tan, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 622 days.

(21) Appl. No.: 16/334,442

(22) PCT Filed: Sep. 21, 2017

(86) PCT No.: PCT/AU2017/051028
§ 371 (c)(1),
(2) Date: Mar. 19, 2019

(87) PCT Pub. No.: WO2018/053589
PCT Pub. Date: Mar. 29, 2018

(65) Prior Publication Data
US 2019/0209804 A1    Jul. 11, 2019

Related U.S. Application Data

(60) Provisional application No. 62/443,305, filed on Jan. 6, 2017, provisional application No. 62/397,544, filed on Sep. 21, 2016.

(30) Foreign Application Priority Data

Sep. 23, 2016  (WO) ............... PCT/AU2016/050893

(51) Int. Cl.
*A61M 16/00*    (2006.01)
*A61M 16/20*    (2006.01)
(Continued)

(52) U.S. Cl.
CPC ...... *A61M 16/208* (2013.01); *A61M 16/0816* (2013.01); *A61M 39/24* (2013.01);
(Continued)

(58) Field of Classification Search
CPC ............ A61M 16/208; A61M 16/0666; A61M 16/0816; A61M 16/06; A61M 16/206;
(Continued)

(56) References Cited

U.S. PATENT DOCUMENTS 2,944,547 A    7/1960  Ziherl et al.
3,109,425 A *  11/1963 Gongoll ............... A62B 18/10
                                                    128/201.19
(Continued)

FOREIGN PATENT DOCUMENTS

CN    101098727 A    1/2008
CN    101516300 A    8/2009
(Continued)

OTHER PUBLICATIONS

Office Action dated Aug. 30, 2021 issued in Japanese Application No. 2019-515587 with English translation (11 pages).
(Continued)

*Primary Examiner* — Victoria Murphy
*Assistant Examiner* — Tyler A Raubenstraw
(74) *Attorney, Agent, or Firm* — Nixon & Vanderhye P.C.

(57) ABSTRACT

A vent system for use during respiratory therapy with a flow of pressurized gas may provide a continuous vent flow of gas. The vent system may include a vent housing having an outer wall; an inner wall, the inner wall defining an inlet for the flow of gas; and a base positioned between the outer wall
(Continued)

and the inner wall, the base having at least one first orifice and at least one second orifice. The vent system may include a membrane, the membrane being shaped and dimensioned such that the membrane does not cover the at least one first orifice to allow the vent flow through the at least one first orifice, and the membrane being shaped and dimensioned such that in a first position the membrane is positioned over the at least one second orifice to allow the vent flow through the at least one second orifice.

30 Claims, 98 Drawing Sheets

(51) Int. Cl.
    *A61M 16/08*     (2006.01)
    *A61M 39/24*     (2006.01)
    *F16K 15/14*     (2006.01)
    *A61M 16/06*     (2006.01)

(52) U.S. Cl.
    CPC ........... *F16K 15/145* (2013.01); *A61M 16/06* (2013.01); *A61M 16/0666* (2013.01); *A61M 16/0683* (2013.01); *A61M 16/0875* (2013.01); *A61M 2202/0225* (2013.01)

(58) Field of Classification Search
    CPC ........... A61M 2202/0225; A61M 39/24; F16K 15/145; F16K 15/141; F16K 15/14; A62B 18/00; A62B 18/02; A62B 18/10; B63C 11/12
    See application file for complete search history.

(56) References Cited

U.S. PATENT DOCUMENTS

| | | | |
|---|---|---|---|
| 3,688,794 A * | 9/1972 | Bird | F16K 15/00 137/529 |
| 3,942,547 A * | 3/1976 | Pfitzner | A61B 5/097 137/102 |
| 3,995,625 A * | 12/1976 | Needham | A61M 16/20 128/204.26 |
| 4,007,758 A * | 2/1977 | Gray | A62B 18/10 137/472 |
| 4,354,520 A * | 10/1982 | Easley, Jr. | A62B 18/10 128/205.24 |
| 4,406,302 A * | 9/1983 | Olesen | A61M 16/209 137/514.5 |
| 4,458,679 A | 7/1984 | Ward | |
| RE32,553 E * | 12/1987 | Bennett | A61M 16/206 137/271 |
| 4,782,832 A | 11/1988 | Trimble et al. | |
| 4,944,310 A | 7/1990 | Sullivan | |
| 4,997,217 A | 3/1991 | Kunze | |
| 5,002,050 A | 3/1991 | McGinnis | |
| 5,127,400 A * | 7/1992 | DeVries | A61M 16/205 128/205.24 |
| 5,271,601 A | 12/1993 | Bonzer et al. | |
| 5,647,355 A * | 7/1997 | Starr | A61M 16/208 128/205.24 |
| 5,685,296 A | 11/1997 | Zdrojkowski et al. | |
| 5,687,715 A | 11/1997 | Landis | |
| 5,738,087 A * | 4/1998 | King | A61M 15/0086 128/200.23 |
| 5,762,382 A | 6/1998 | Pernetti et al. | |
| 5,896,857 A | 4/1999 | Hely et al. | |
| 5,937,851 A | 8/1999 | Serowski et al. | |
| 5,979,444 A | 11/1999 | Sherrod | |
| 6,189,532 B1 | 2/2001 | Hely et al. | |
| 6,427,692 B1 | 8/2002 | Höglund | |
| 6,532,959 B1 | 3/2003 | Berthon-Jones | |
| 6,561,190 B1 * | 5/2003 | Kwok | A61M 16/06 128/207.12 |
| 6,561,191 B1 * | 5/2003 | Kwok | A61M 16/06 128/205.11 |
| 6,581,594 B1 | 6/2003 | Drew et al. | |
| 6,584,977 B1 * | 7/2003 | Serowski | A61M 16/06 128/206.24 |
| 6,662,803 B2 | 12/2003 | Gradon et al. | |
| 7,089,939 B2 | 8/2006 | Waker et al. | |
| 7,096,864 B1 | 8/2006 | Mayer et al. | |
| 7,134,434 B2 | 11/2006 | Truitt et al. | |
| 7,302,950 B2 | 12/2007 | Berthon-Jones et al. | |
| 7,559,326 B2 | 7/2009 | Smith et al. | |
| 7,866,944 B2 | 1/2011 | Kenyon et al. | |
| 7,987,847 B2 | 8/2011 | Wickham | |
| 7,987,851 B2 | 8/2011 | Blom | |
| 8,365,731 B2 | 2/2013 | Ho et al. | |
| 8,439,035 B2 | 5/2013 | Dantanarayana et al. | |
| 8,496,004 B2 | 7/2013 | Lang et al. | |
| 8,544,465 B2 | 10/2013 | Smith et al. | |
| 8,573,201 B2 * | 11/2013 | Rummery | A62B 9/04 128/202.27 |
| 8,573,208 B2 | 11/2013 | Ho | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 9,808,594 B2 | 11/2017 | Dantanarayana et al. | |
| 9,861,774 B2 | 1/2018 | Fu et al. | |
| 10,004,924 B1 * | 6/2018 | Anderson | B63C 11/06 |
| 10,086,166 B1 * | 10/2018 | Nashed | A61M 16/104 |
| 10,220,179 B2 | 3/2019 | Dantanarayana et al. | |
| 10,898,662 B2 * | 1/2021 | Huddart | A61M 16/0825 |
| 2003/0037788 A1 * | 2/2003 | Gallem | A61M 16/08 128/206.21 |
| 2003/0079751 A1 * | 5/2003 | Kwok | A61M 16/0875 128/206.15 |
| 2004/0255948 A1 * | 12/2004 | Smith | A61M 16/0683 128/206.15 |
| 2009/0044808 A1 | 2/2009 | Guney et al. | |
| 2009/0050156 A1 | 2/2009 | Ng et al. | |
| 2009/0120434 A1 | 5/2009 | Smith et al. | |
| 2009/0133694 A1 | 5/2009 | Solci et al. | |
| 2009/0260628 A1 * | 10/2009 | Flynn, Sr. | A61M 16/0078 128/203.28 |
| 2010/0000534 A1 | 1/2010 | Kooij et al. | |
| 2010/0083969 A1 | 4/2010 | Crumblin et al. | |
| 2010/0282262 A1 | 11/2010 | Boussignac | |
| 2011/0067709 A1 | 3/2011 | Doshi et al. | |
| 2012/0325205 A1 | 12/2012 | Allum et al. | |
| 2012/0325218 A1 | 12/2012 | Brambilla et al. | |
| 2013/0184602 A1 | 7/2013 | Brambilla | |
| 2015/0114504 A1 | 4/2015 | Cecka et al. | |
| 2016/0310688 A1 * | 10/2016 | Rothermel | A61M 16/0816 |
| 2016/0361575 A1 * | 12/2016 | Gerson | A62B 18/10 |
| 2018/0200467 A1 * | 7/2018 | Finch | A61M 16/1045 |
| 2018/0207389 A1 * | 7/2018 | Fyfe | A61M 16/0858 |
| 2018/0344953 A1 | 12/2018 | Cegla | |
| 2019/0001095 A1 * | 1/2019 | Rose | A61M 16/0605 |
| 2019/0105458 A1 * | 4/2019 | Hammes | F24F 1/0071 |
| 2019/0209804 A1 | 7/2019 | Dantanarayana | |

FOREIGN PATENT DOCUMENTS

| | | |
|---|---|---|
| CN | 202951092 U | 5/2013 |
| CN | 108136150 A | 6/2018 |
| EP | 1027905 A2 | 8/2000 |
| EP | 3 352 830 | 4/2021 |
| GB | 2500061 A1 | 9/2013 |
| JP | 2001-506883 A | 5/2001 |
| JP | 2004-522487 | 7/2004 |
| JP | 2008-540056 | 11/2008 |
| JP | 2013-501541 A | 1/2013 |
| WO | 98/004310 A1 | 2/1998 |
| WO | 98/26830 A1 | 6/1998 |
| WO | 98/034665 A1 | 8/1998 |
| WO | 2000/078381 A1 | 12/2000 |
| WO | 2002/051486 A1 | 7/2002 |
| WO | 2004/073778 A1 | 9/2004 |
| WO | 2005/063326 A1 | 7/2005 |
| WO | 2005/063328 A1 | 7/2005 |

(56) References Cited

FOREIGN PATENT DOCUMENTS

| WO | 2006/074513 | A1 |   | 7/2006  |            |
|----|-------------|----|---|---------|------------|
| WO | 2006/130903 | A1 |   | 12/2006 |            |
| WO | 2009/052560 | A1 |   | 4/2009  |            |
| WO | WO-2009052560 | A1 | * | 4/2009 | ............ A61M 16/06 |
| WO | 2010/135785 | A1 |   | 12/2010 |            |
| WO | 2011/080604 | A1 |   | 7/2011  |            |
| WO | 2012/171072 | A1 |   | 12/2012 |            |
| WO | 2013/020167 | A1 |   | 2/2013  |            |
| WO | 2014/097068 | A1 |   | 6/2014  |            |
| WO | 2014/129913 | A1 |   | 8/2014  |            |
| WO | 2014/205513 | A1 |   | 12/2014 |            |
| WO | 2015/013761 | A1 |   | 2/2015  |            |
| WO | 2015/041545 | A1 |   | 3/2015  |            |
| WO | 2015/052681 | A1 |   | 4/2015  |            |
| WO | WO-2015073824 | A1 | * | 5/2015 | ............ A62B 18/10 |
| WO | 2016/041019 | A1 |   | 3/2016  |            |
| WO | 2016/141430 | A1 |   | 9/2016  |            |
| WO | WO-2017014647 | A1 | * | 1/2017 | ........ A61M 16/0816 |
| WO | WO-2017021836 | A1 | * | 2/2017 | ........ A61M 16/0825 |
| WO | 2017/049358 | A1 |   | 3/2017  |            |
| WO | 2018/052673 | A1 |   | 3/2018  |            |
| WO | 2018/053589 | A1 |   | 3/2018  |            |
| WO | 2018/126295 | A1 |   | 7/2018  |            |

OTHER PUBLICATIONS

"*Respiratory Physiology*", by John B. West, Lippincott Williams & Wilkins, $9^{th}$ edition published 2012 (8 pages).
International Search Report for PCT/AU2017/051028, dated Dec. 19, 2017, 5 pages.
Written Opinion of the ISA for PCT/AU2017/051028, dated Dec. 19, 2017, 5 pages.
International Preliminary Report on Patentability issued in related International Application No. PCT/AU2017/051028 (6 pages).
Extended European Search Report dated Aug. 14, 2019 issued in European Application No. 17851991.4 (9 pages).
Office Action dated Dec. 31, 2020 issued in Chinese Application No. 201780067393.X with English translation (15 pages).
Office Action dated Dec. 21, 2020 issued in Japanese Application No. 2019-515587 with English translation (13 pages).
First Examination Report dated Mar. 23, 2022 issued in Australian Application No. 2017329112 (3 pages).
Notice of Allowance dated Apr. 4, 2022 issued in Japanese Application No. 2019-515587 (3 pages).

* cited by examiner

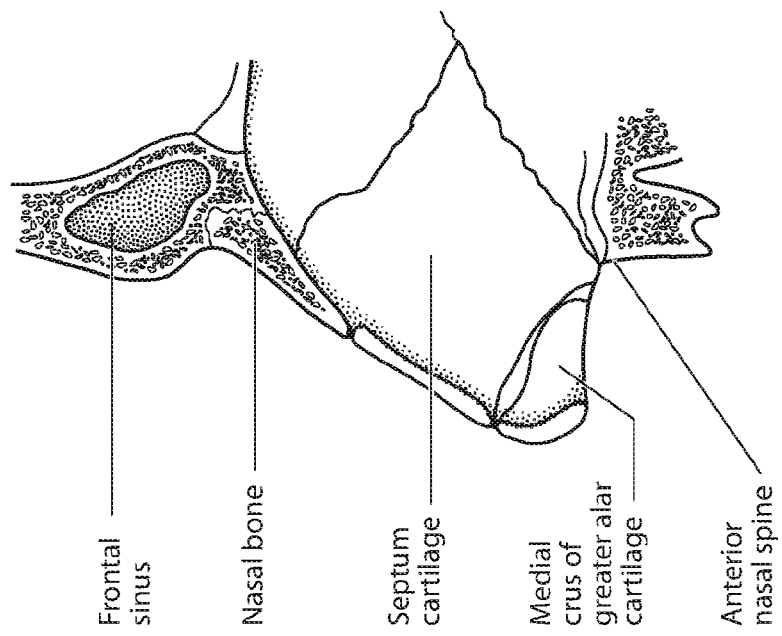
FIG. 2I
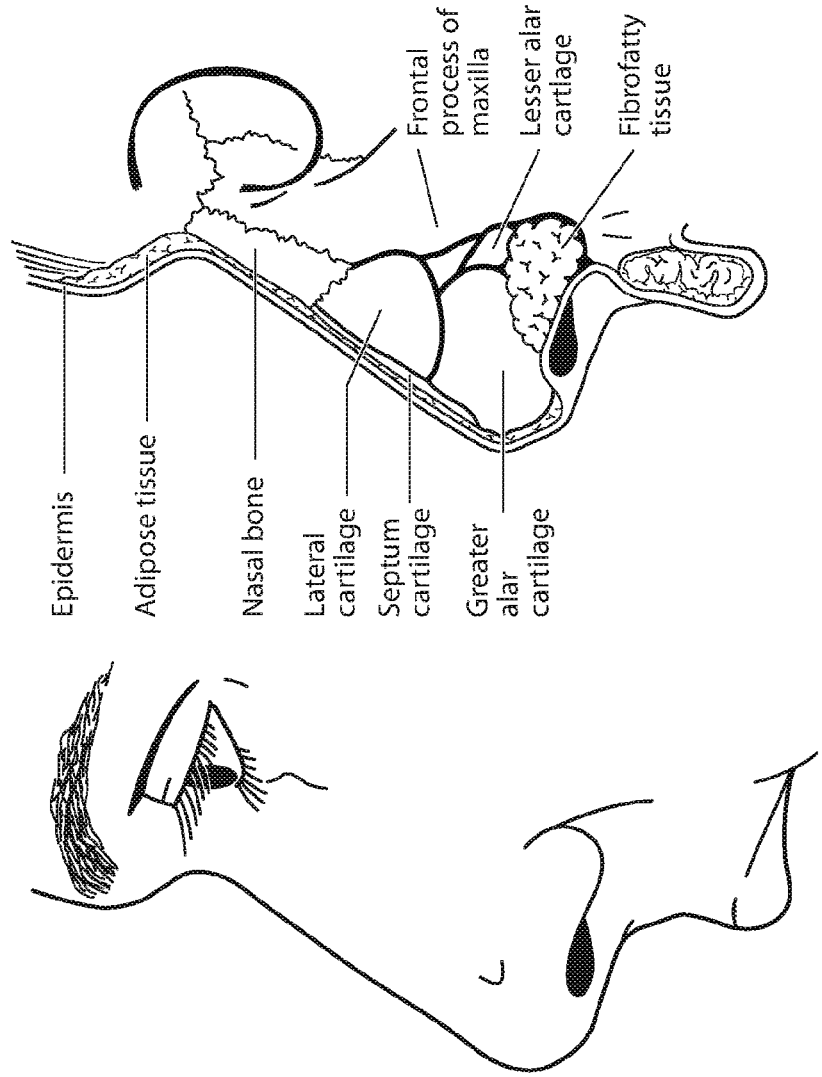
FIG. 2H
FIG. 2G

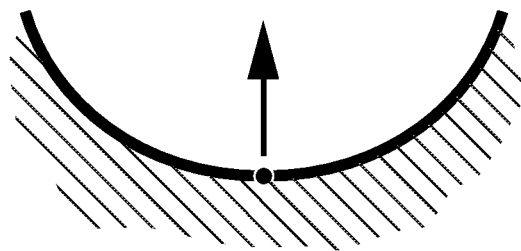
FIG. 3B — Relatively Large Positive Curvature
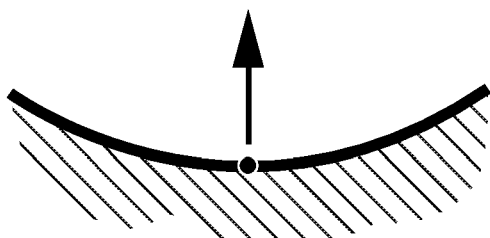
FIG. 3C — Relatively Small Positive Curvature
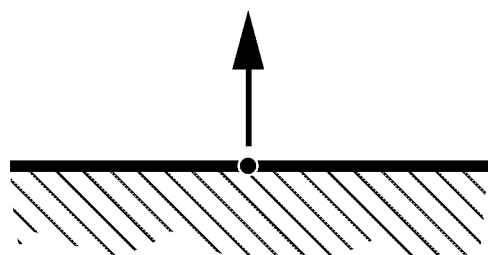
FIG. 3D — Zero Curvature
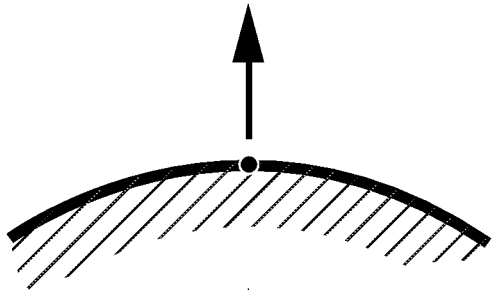
FIG. 3E — Relatively Small Negative Curvature
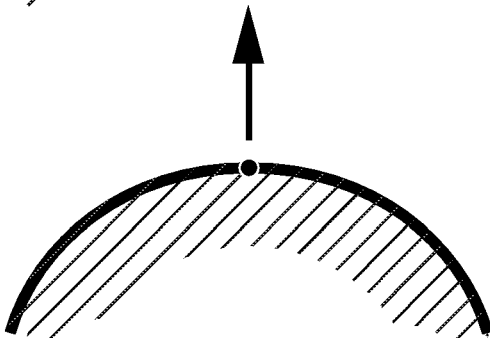
FIG. 3F — Relatively Large Negative Curvature

Left-hand rule
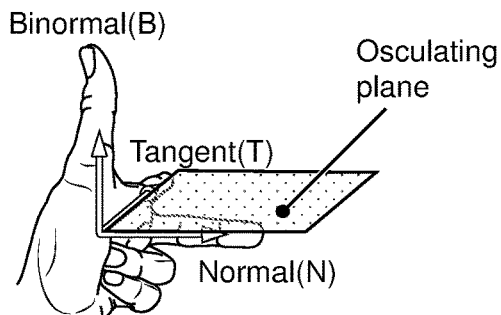
FIG. 3O
Right-hand rule
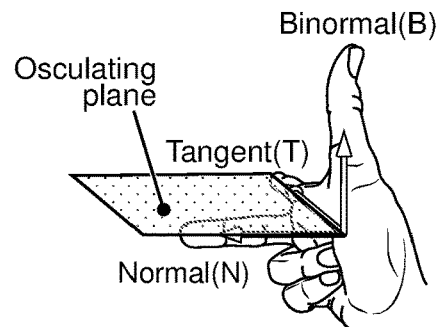
FIG. 3P
Left ear helix
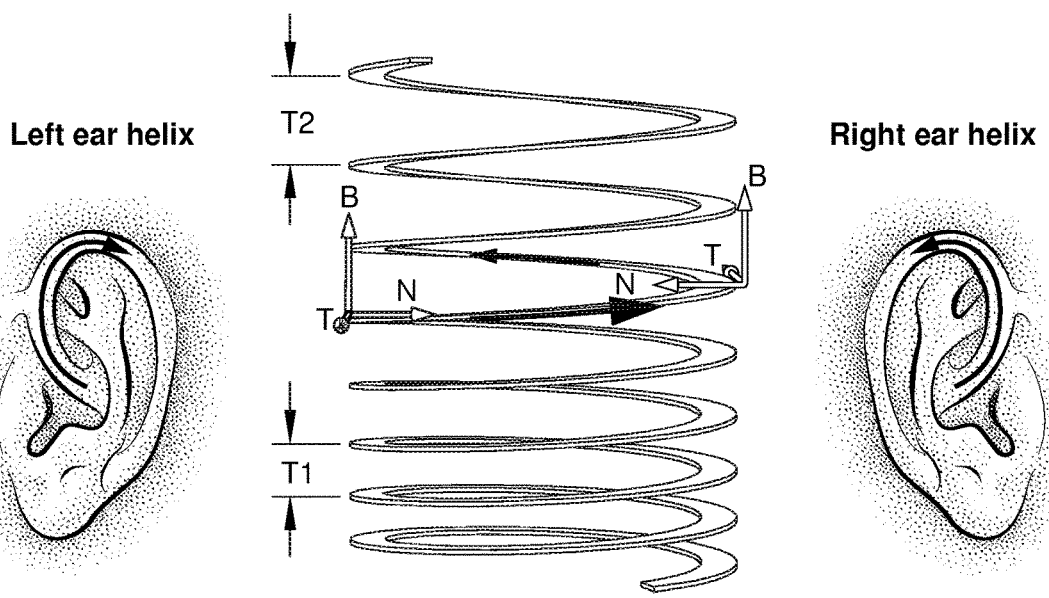
FIG. 3Q
Right-hand helix
Right-hand positive
FIG. 3S
Right ear helix
FIG. 3R
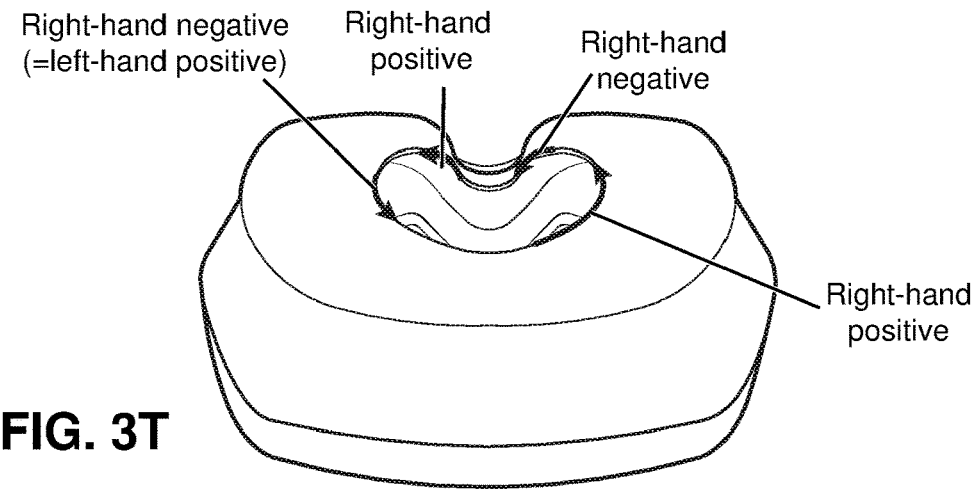
FIG. 3T

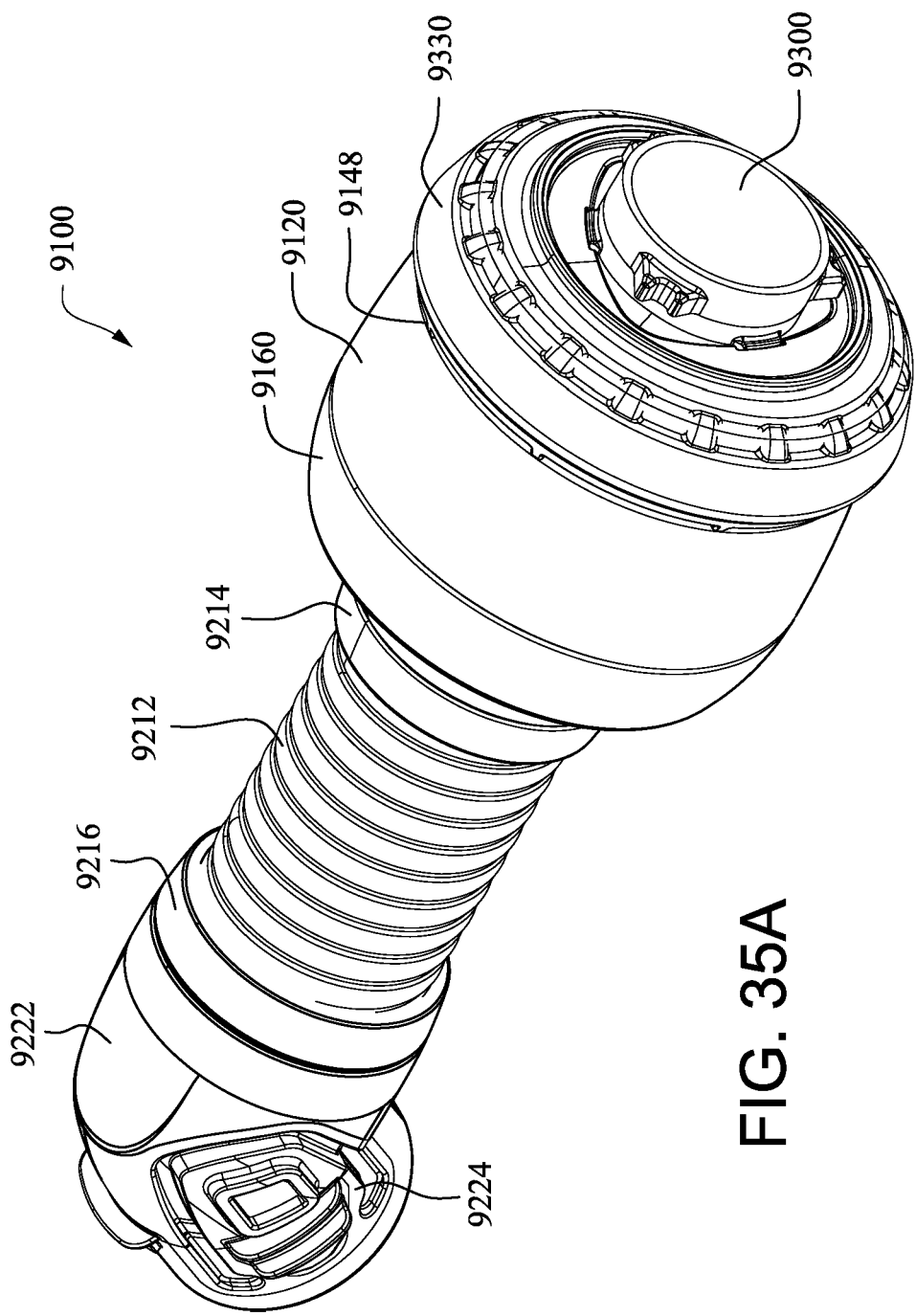

VENT AND VENT ADAPTOR FOR PATIENT INTERFACE

1 CROSS-REFERENCE TO RELATED APPLICATIONS

This application is the U.S. national phase of International Application No. PCT/AU2017/051028 filed Sep. 21, 2017, which designated the U.S. and claims the benefit of U.S. Provisional Application No. 62/397,544, filed Sep. 21, 2016, U.S. Provisional Application No. 62/443,305, filed Jan. 6, 2017, and claims priority to International Application No. PCT/AU2016/050893, filed Sep. 23, 2016, the entire contents of each of which are incorporated herein by reference.

2 BACKGROUND OF THE TECHNOLOGY

2.1 Field of the Technology

The present technology relates to one or more of the detection, diagnosis, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g., apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g., Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g., Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to diagnose a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology, e.g., if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g., for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g., filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g., aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g., by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g., because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g., for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used to deliver one or more of a number of therapies described above, such as by generating a flow of air for delivery to an entrance to the airways. The flow of air may be pressurised. Examples of RPT devices include a CPAP device and a ventilator.

Air pressure generators are known in a range of applications, e.g., industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH₂O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g., at a hospital). A medical humidifier for bedside placement may be small. A medical humidifier may be configured to only humidify and/or heat the flow of air delivered to the patient without humidifying and/or heating the patient's surroundings. Room-based systems (e.g., a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g., that the patient has used their RPT device according to certain a "compliance rule". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g., through noise or focussed airflow.

ResMed Limited has developed a number of improved mask vent technologies. See International Patent Application Publication No. WO 1998/034665; International Patent Application Publication No. WO 2000/078381; U.S. Pat. No. 6,581,594; US Patent Application Publication No. US 2009/0050156; US Patent Application Publication No. 2009/0044808.

| Table of noise of prior masks (ISO 17510-2: 2007, 10 cmH$_2$O pressure at 1 m) | | | |
|---|---|---|---|
| Mask name | Mask type | A-weighted sound power level dB(A) (uncertainty) | A-weighted sound pressure dB(A) (uncertainty) | Year (approx.) |
| Glue-on (*) | nasal | 50.9 | 42.9 | 1981 |
| ResCare standard (*) | nasal | 31.5 | 23.5 | 1993 |

-continued

Table of noise of prior masks (ISO 17510-2: 2007, 10 cmH₂O pressure at 1 m)

| Mask name | Mask type | A-weighted sound power level dB(A) (uncertainty) | A-weighted sound pressure dB(A) (uncertainty) | Year (approx.) |
|---|---|---|---|---|
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH₂O)

Sound pressure values of a variety of objects are listed below

| Object | A-weighted sound pressure dB(A) | Notes |
|---|---|---|
| Vacuum cleaner: Nilfisk Walter Broadly Litter Hog: B + Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Diagnosis and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home sleep testing.

Clinical experts may be able to diagnose or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

An aspect of certain forms of the present technology is to provide methods and/or apparatus that improve the compliance of patients with respiratory therapy.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g., by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

An aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing comprising a base having an inlet for the therapy flow of gas extending through the base and at least one first orifice extending through the base to allow gas to be discharged to atmosphere from the pressurized volume; at least one second orifice to allow gas to be discharged to atmosphere from the pressurized volume; and a membrane positioned adjacent to the base.

An aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing comprising a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, and wherein the membrane is elastically deformable due to pressure within the pressurized volume to apportion the vent flow between the at least one first orifice and the at least one second orifice throughout the therapeutic pressure.

In examples, (a) the vent housing may comprise an outer wall and an inner wall, the inner wall defining an inlet for the therapy flow of gas, and the base may be positioned between the outer wall and the inner wall, (b) the base the base may comprise an inner base and an outer base, (c) the outer base may be adjacent to the outer wall, the inner base may be adjacent to the outer base, and the inner base may be adjacent to the inner wall, (d) the at least one first orifice may comprise a plurality of first orifices and the at least one second orifice may comprise a plurality of second orifices, (e) the plurality of second orifices may pass through the outer base and the plurality of first orifices may pass between the outer base and the inner base, (f) the vent system may comprise a plurality of base connectors to join the inner base and the outer base and to divide the plurality of first orifices, (g) the vent system may comprise a plurality of membrane spacers extending from the inner base, (h) the membrane may be supported over the plurality of first orifices on the outer base and the membrane spacers, (i) the vent housing may comprise a base divider between the inner base and the outer base and the membrane may be supported over the plurality of first orifices on the base divider and the membrane spacers, (j) the plurality of membrane spacers may define a plurality of membrane spacer gaps between adjacent ones of the plurality of membrane spacers, (k) the membrane may include an atmosphere-side surface adjacent to the inner base and the outer base of the vent housing and an inner surface defining a membrane opening and an inner base membrane passage for the washout flow may be defined between the atmosphere-side surface of the membrane and the inner base of the vent housing, (l) an inner wall membrane passage for the washout flow may be defined between the inner surface of the membrane and the inner wall of the vent housing, (m) the inner base may comprise a plurality of inner base slots between adjacent ones of the plurality of membrane spacers, (n) the outer base may comprise a plurality of lateral membrane supports that are configured to prevent the membrane from covering the plurality of second orifices, (o) the vent housing may comprise a plurality of recesses opposite the outer base and at least one of the plurality of second orifices may open into a corresponding one of the plurality of recesses, (p) the inner wall may extend above the inner base and the outer base, (q) the inner wall may extend below the inner base and the outer base, (r) the membrane may comprises an elastically deformable material, (s) the elastically deformable material may comprise silicone, (t) the vent housing may be formed from a single, homogeneous piece of a relatively rigid material, (u) the relatively rigid material may be polycarbonate, (v) the outer wall, the inner wall, the inner base, the outer base, and the membrane may be circular, (w) the outer wall, the inner wall, the inner base, the outer base, and the membrane may be concentric, (x) the vent housing may comprise a shaft extending from the base to receive the therapy flow of gas, the at least one first orifice passing through the base, and the at least one second orifice passing through the shaft, (y) the at least one first orifice and the at least one second orifice may be oriented such that the vent flow passing through the at least one first orifice and the at least one second orifice intersects outside of the vent housing, (z) the vent system may comprise a diffuser, the vent flow passing through the at least one first orifice and the at least one second orifice intersects within the diffuser, (aa) the at least one first orifice may comprise a plurality of first orifices and the at least one second orifice may comprise a plurality of second orifices, and/or (bb) the membrane may not be attached to the vent housing such that the membrane is freely movable towards and away from the base.

Another aspect of the present technology is directed to a patient interface comprising: a seal-forming structure; a plenum chamber joined to the seal-forming structure; a positioning and stabilising structure to secure the patient interface on the patient in use; and the vent system according to any of the aspects and/or examples disclosed in the two immediately preceding paragraphs. The patient interface may comprise a vent connector tube or a decoupling structure to fluidly connect the vent system to the plenum chamber.

Another aspect of the present technology is directed to a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy. The vent system comprises a vent housing a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, wherein the membrane is configured such that an increase in pressure within the pressurized volume causes the membrane to restrict a first vent flow through the at least one first orifice throughout the therapeutic pressure range, and wherein restriction of the first vent flow through the at least one first orifice causes an increase in a second vent flow through the at least one second orifice such that the vent flow through the at least one first orifice and the at least one second orifice is approximately constant throughout the therapeutic pressure range.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapy pressure increases above a threshold therapy pressure value, (e) the membrane may be configured to decrease the first vent flow such that the second vent flow increases as the membrane is deflected closer to the base due to increasing the therapy pressure above the threshold therapy pressure value, (f) the at least one first orifice may comprise a plurality of first orifices and the at least one second orifice may comprise a plurality of second orifices, (g) the base may comprise an inner base and an outer base, (h) the vent system may comprise a plurality of membrane spacers extending from the inner base, (i) the membrane may be supported over the plurality of first orifices on the outer base and the membrane spacers such that increasing the therapy pressure above a threshold therapy pressure value causes the membrane to deflect towards the inner base, (j) the membrane may be configured such that a membrane-inner base gap defined between the membrane and the inner base decreases as the therapy pressure is increased above the threshold therapy pressure value, (k) the membrane may be configured such that as the membrane-inner base gap decreases the first vent flow decreases and the second vent flow increases, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, (r) the vent housing may comprise a shaft extending from the base to receive the therapy flow of gas, the at least one first orifice passing through the base, and the at least one second orifice passing through the shaft, (s) the at least one first orifice and the at least one second orifice may be oriented such that the vent flow passing through the at least one first orifice and the at least one second orifice intersects outside of the vent housing, (t) the vent system may comprise a diffuser, the vent flow passing through the at least one first orifice and the at least one second orifice intersects within the diffuser, (u) the at least one first orifice may comprise a plurality of first orifices and the at least one second orifice may comprise a plurality of second orifices, and/or (v) the membrane may not be attached to the vent housing such that the membrane is freely movable towards and away from the base.

Another aspect of the present technology is directed to a patient interface comprising: a seal-forming structure; a plenum chamber joined to the seal-forming structure; a positioning and stabilising structure to secure the patient interface on the patient in use; and the vent system according to any of the aspects and/or examples disclosed in the two immediately preceding paragraphs. The patient interface may comprise a vent connector tube or a decoupling structure to fluidly connect the vent system to the plenum chamber.

Another aspect of the present technology is directed to a patient interface that may comprise: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, and a portion of the tie being dimensioned and structured to engage in use a portion of the patient's head in a region of a parietal bone, wherein the positioning and stabilising structure has a non-rigid decoupling portion; and a vent system for use with a patient interface during respiratory therapy of a patient with a therapy flow of gas pressurized above ambient pressure, the vent system providing a vent flow of gas to discharge gas exhaled by the patient from a pressurized volume, the vent flow being continuous during the respiratory therapy, the vent system comprising: a vent housing a base having at least one first orifice extending through the base to allow gas to be discharged to atmosphere from the pressurized volume; at least one second orifice to allow gas to be discharged to atmosphere from the pressurized volume; and a membrane positioned adjacent to the base, wherein the pressurized volume is in fluid communication with atmosphere through the at least one first orifice and the at least one second orifice throughout a therapeutic pressure range, wherein the membrane is configured such that an increase in pressure within the pressurized volume causes the membrane to restrict a first vent flow through the at least one first orifice throughout the therapeutic pressure range, and wherein restriction of the first vent flow through the at least one first orifice causes an increase in a second vent flow through the at least one second orifice such that the vent flow through the at least one first orifice and the at least one second orifice is approximately constant throughout the therapeutic pressure range, and wherein the patient interface is configured to allow the patient to breath from ambient through their mouth in the absence of a flow of pressurised air through the plenum chamber inlet port, or the patient interface is configured to leave the patient's mouth uncovered.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapeutic pressure increases above a threshold therapeutic pressure value, (e) the membrane may be configured to decrease the first vent flow such that the second vent flow increases as the membrane is deflected closer to the base due to increasing the therapeutic pressure above the threshold therapeutic pressure value, (f) the base may comprise an inner base and an outer base, (g) the at least one first orifice may comprise a plurality of first orifices and the at least one second orifice may comprise a plurality of second orifices, (h) the vent system may comprise a plurality of membrane spacers extending from the inner base, (i) the membrane may be supported over the plurality of first orifices on the outer base and the membrane spacers, (j) the vent housing may comprise a base divider between the inner base and the outer base and the membrane may be supported over the plurality of first orifices on the base divider and the membrane spacers, (k) the outer base may comprise a plurality of lateral membrane supports that are configured to prevent the membrane from covering the plurality of second orifices, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, (r) the membrane may not be attached to the vent housing such that the membrane is freely movable towards and away from the base, (s) the vent housing may comprise a shaft extending from the base to receive the therapy flow of gas, the at least one first orifice passing through the base, and the at least one second orifice passing through the shaft, (t) the at least one first orifice and the at least one second orifice may be oriented such that the vent flow passing through the at least one first orifice and the at least one second orifice intersects outside of the vent housing, (u) the vent system may comprise a diffuser, the vent flow passing through the at least one first orifice and the at least one second orifice intersects within the diffuser, (v) the at least one first orifice may comprise a plurality of first orifices and the at least one second orifice may comprise a plurality of second orifices, and/or (w) the patient interface may comprise a vent connector tube or a decoupling structure to fluidly connect the vent system to the plenum chamber.

Another aspect of the present technology is directed to a patient interface that may comprise: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient; a seal-forming structure constructed and arranged to form a seal with a region of the patient's face surrounding an entrance to the patient's airways such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure to provide an elastic force to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use, and a portion of the tie being dimensioned and structured to engage in use a portion of the patient's head in a region of a parietal bone, wherein the positioning and stabilising structure has a non-rigid decoupling portion; and a vent system to provide a vent flow of gas to discharge gas exhaled by the patient from a pressurized volume, the vent flow being continuous during the respiratory therapy, the vent flow comprising a first vent flow and a second vent flow, the vent system comprising: a vent housing comprising a base having at least one first orifice extending through the base for the first vent flow; at least one second orifice for the second vent flow; and a membrane positioned adjacent to the base, wherein the pressurized volume is in fluid communication with atmosphere through the at least one first orifice and the at least one second orifice throughout a therapeutic pressure range, wherein the membrane is configured to be elastically deformed by pressure within the pressurized volume such that increased deformation due to increased pressure decreases the first vent flow through the at least one first orifice and increases the second vent flow through the at least one second orifice to maintain a substantially constant vent flow throughout the therapeutic pressure range, and wherein the patient interface is configured to allow the patient to breath from ambient through their mouth in the absence of a flow of pressurised air through the plenum chamber inlet port, or the patient interface is configured to leave the patient's mouth uncovered.

In examples, (a) the vent housing may comprise an outer wall and an inner wall, the inner wall defining an inlet for the therapy flow of gas, and the base may be positioned between the outer wall and the inner wall, (b) the washout flow may be greater than or equal to the sum of the first vent flow and the second vent flow, (c) the membrane may be elastically deformable toward the base in use such that the first vent flow is restricted as the membrane is deflected towards the base, (d) the membrane may be configured to deflect closer to the base as the therapeutic pressure increases above a threshold therapeutic pressure value, (e) the membrane may be configured to decrease the first vent flow such that the second vent flow increases as the membrane is deflected closer to the base due to increasing the therapeutic pressure above the threshold therapeutic pressure value, (f) the base may comprise an inner base and an outer base, (g) the at least one first orifice may comprise a plurality of first orifices and the at least one second orifice may comprise a plurality of second orifices, (h) the vent system may comprise a plurality of membrane spacers extending from the inner base, (i) the membrane may be supported over the plurality of first orifices on the outer base and the membrane spacers, (j) the vent housing may comprise a base divider between the inner base and the outer base and the membrane may be supported over the plurality of first orifices on the base divider and the membrane spacers, (k) the outer base may comprise a plurality of lateral membrane supports that are configured to prevent the membrane from covering the plurality of second orifices, (l) the membrane may comprise an elastically deformable material, (m) the elastically deformable material may comprise silicone, (n) the vent housing may be formed from a single, homogeneous piece of a relatively rigid material, (o) the relatively rigid material may be polycarbonate, (p) the outer wall, the inner wall, the inner base, the outer base, and the membrane may be circular, (q) the outer wall, the inner wall, the inner base, the outer base, and the membrane may be concentric, (r) the membrane may not be attached to the vent housing such that the membrane is freely movable towards and away from the base, (s) the vent housing may comprise a shaft extending from the base to receive the therapy flow of gas, the at least one first orifice passing through the base, and the at least one second orifice passing through the shaft, (t) the at least one first orifice and the at least one second orifice may be oriented such that the vent flow passing through the at least one first orifice and the at least one second orifice intersects outside of the vent housing, (u) the vent system may comprise a diffuser, the vent flow passing through the at least one first orifice and the at least one second orifice intersects within the diffuser, (v) the at least one first orifice may comprise a plurality of first orifices and the at least one second orifice may comprise a plurality of second orifices, and/or (w) the patient interface may comprise a vent connector tube or a decoupling structure to fluidly connect the vent system to the plenum chamber.

The methods, systems, devices and apparatus described herein can provide improved functioning in a processor, such as of a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
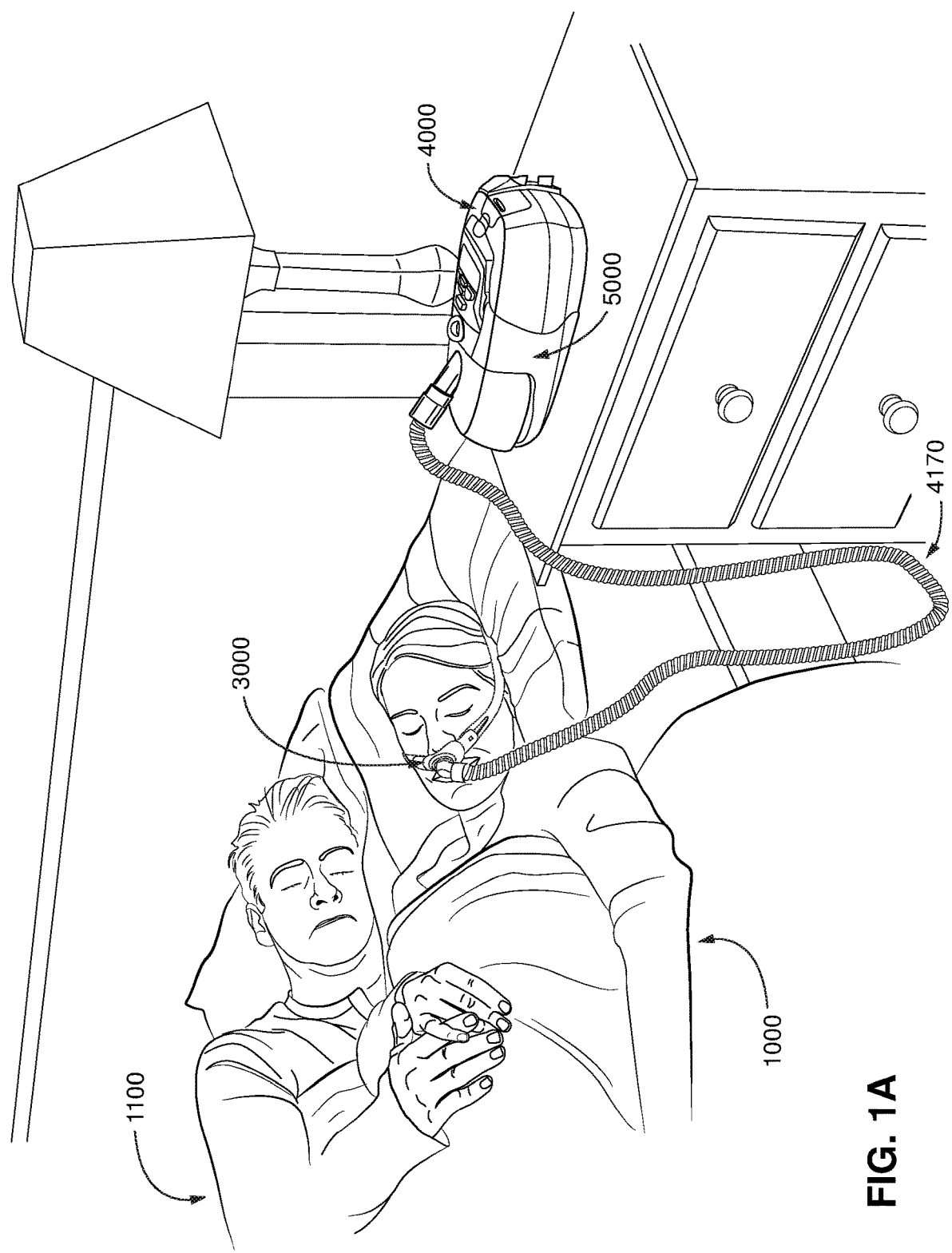
Figure 1B:
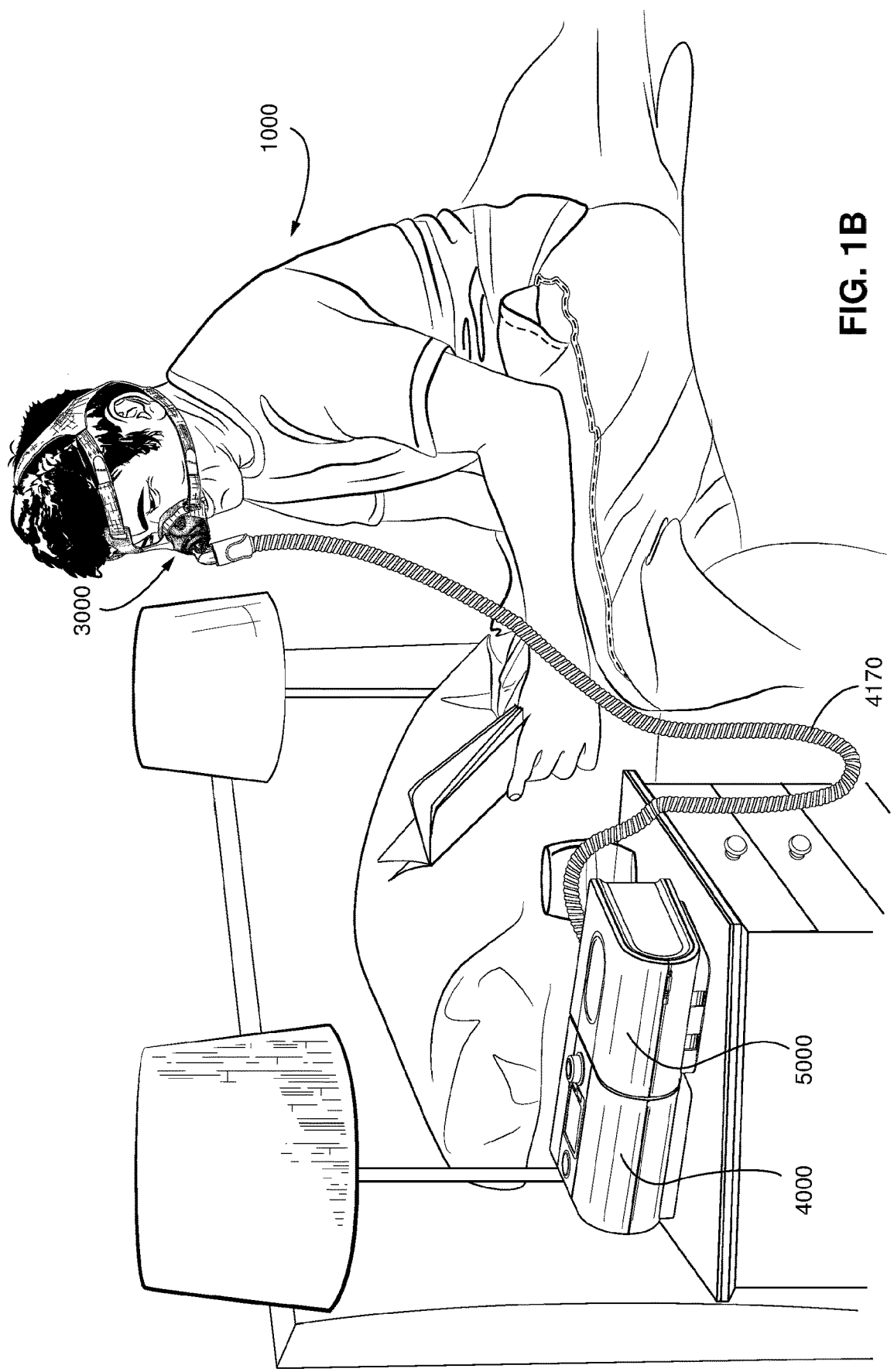
Figure 1C:
Figure 2A:
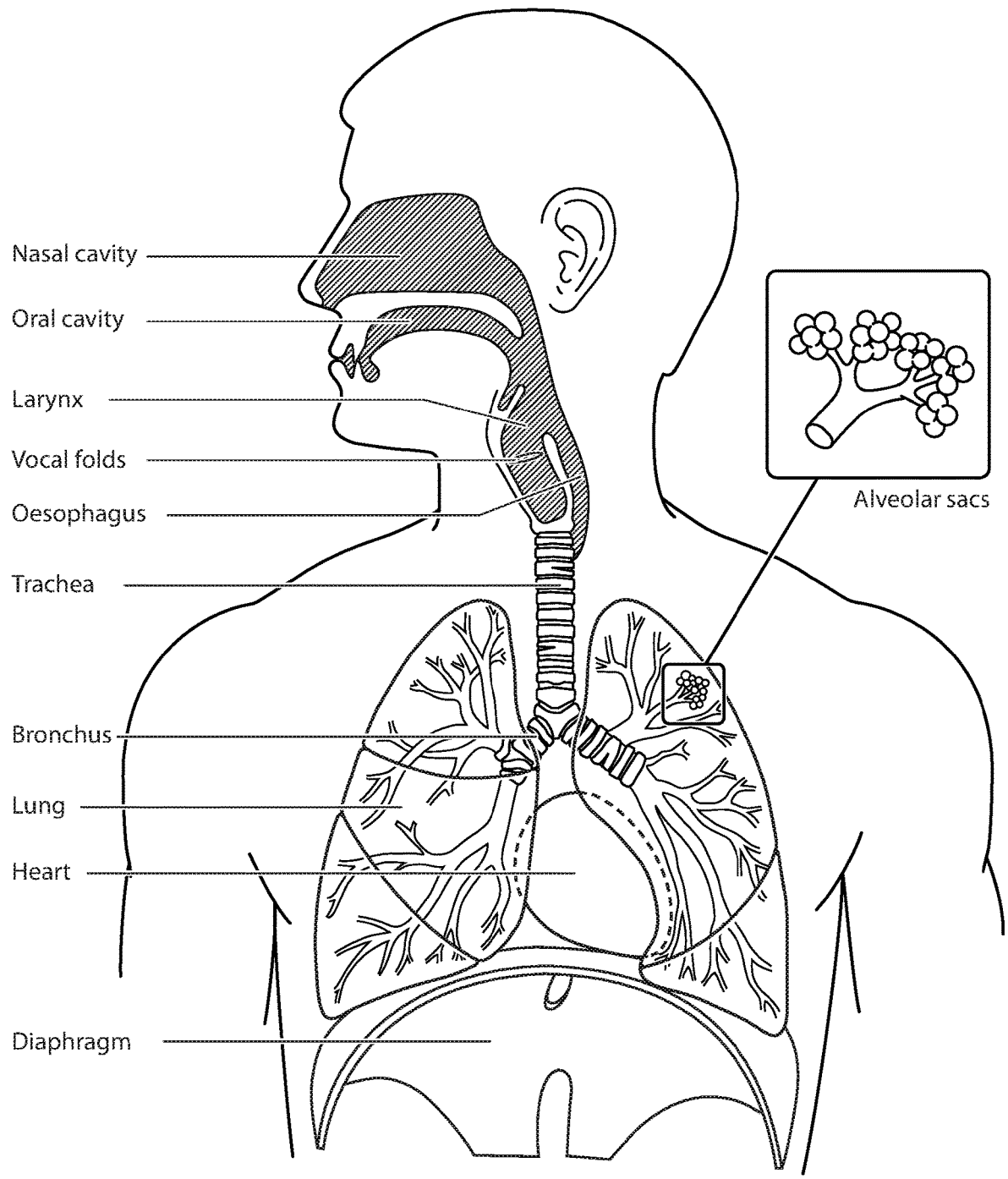
FIG. 2A shows an overview of a human respiratory system including the nasal and oral cavities, the larynx, vocal folds, oesophagus, trachea, bronchus, lung, alveolar sacs, heart and diaphragm.
Figure 2B:
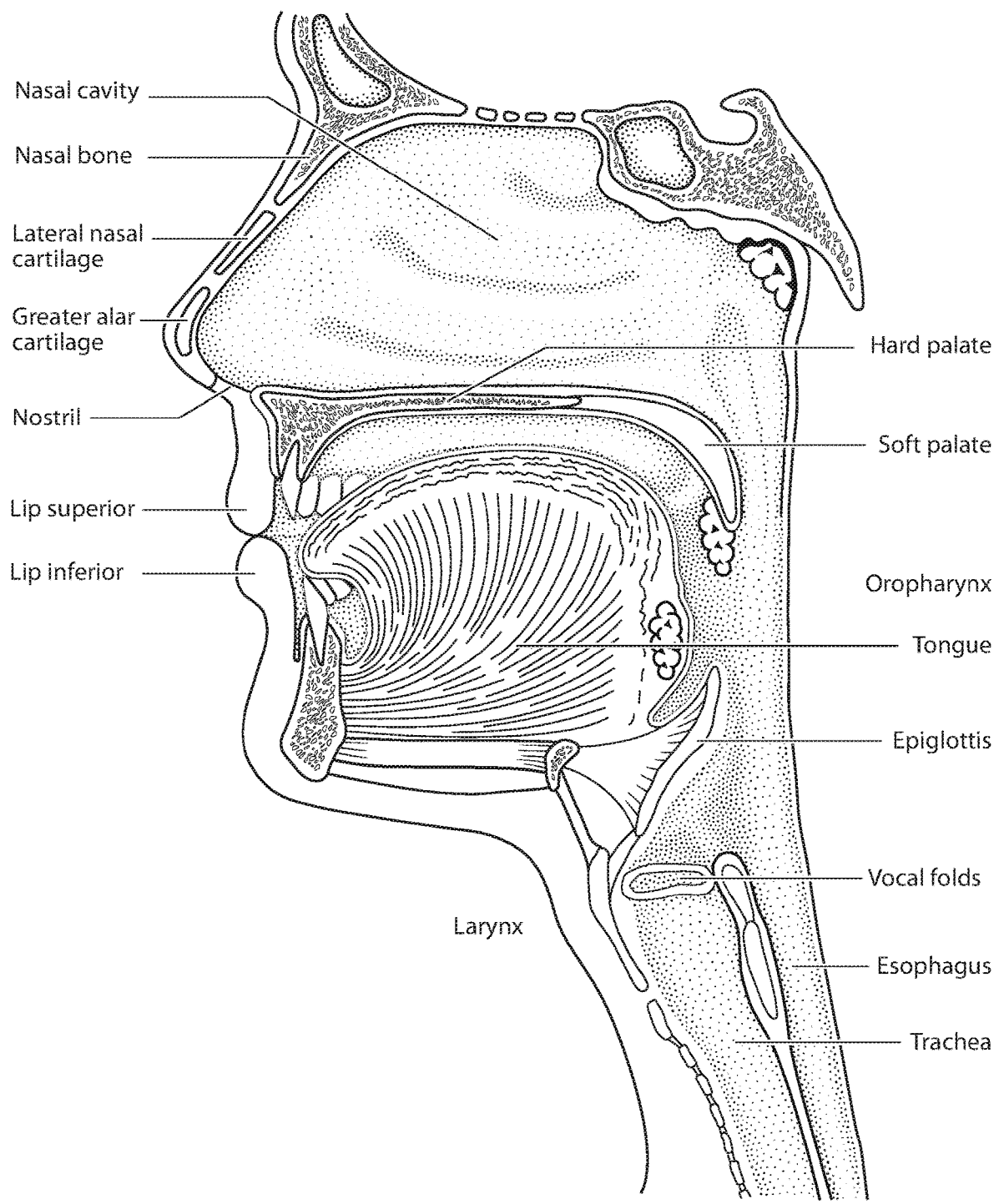
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
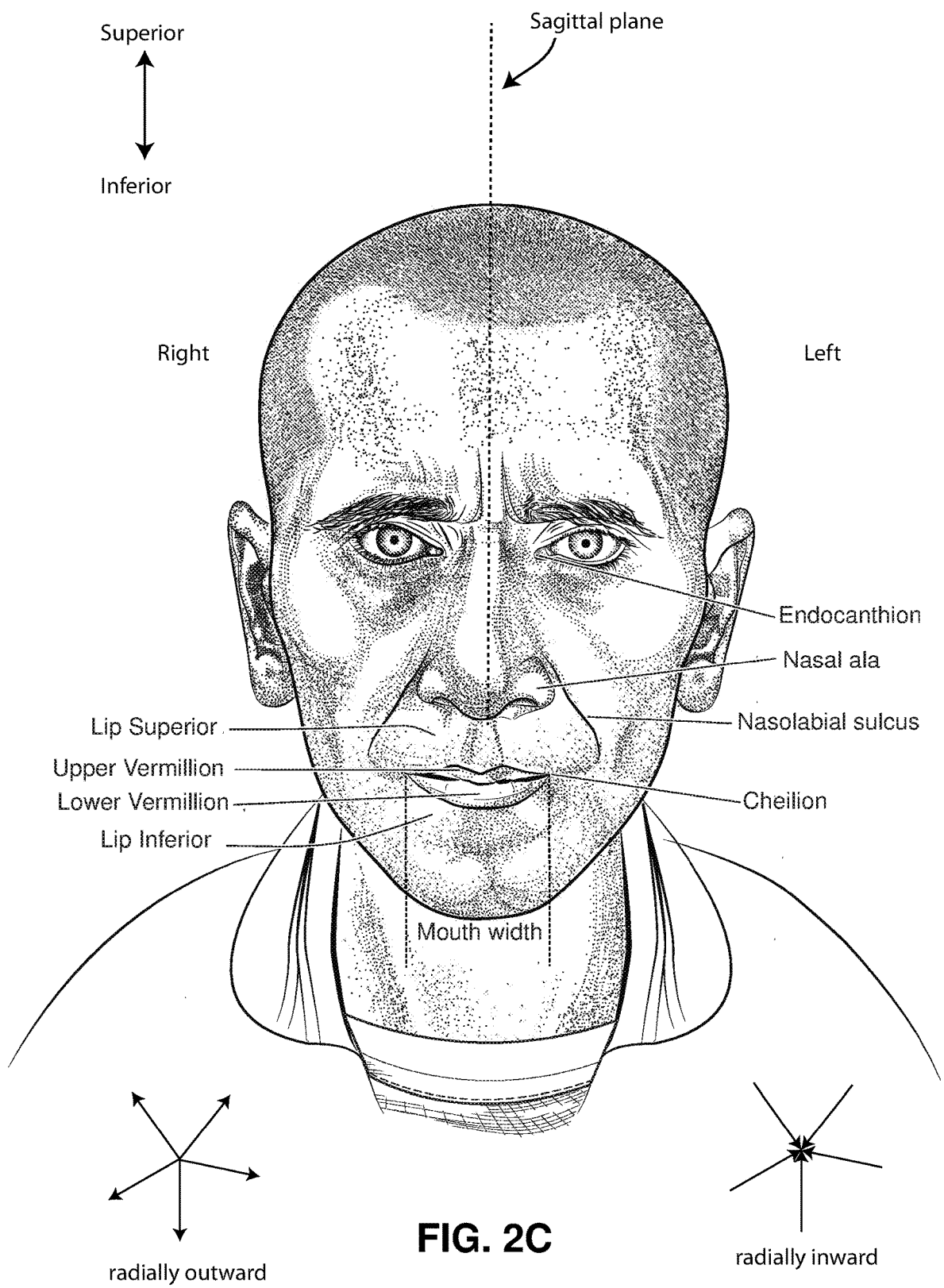
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
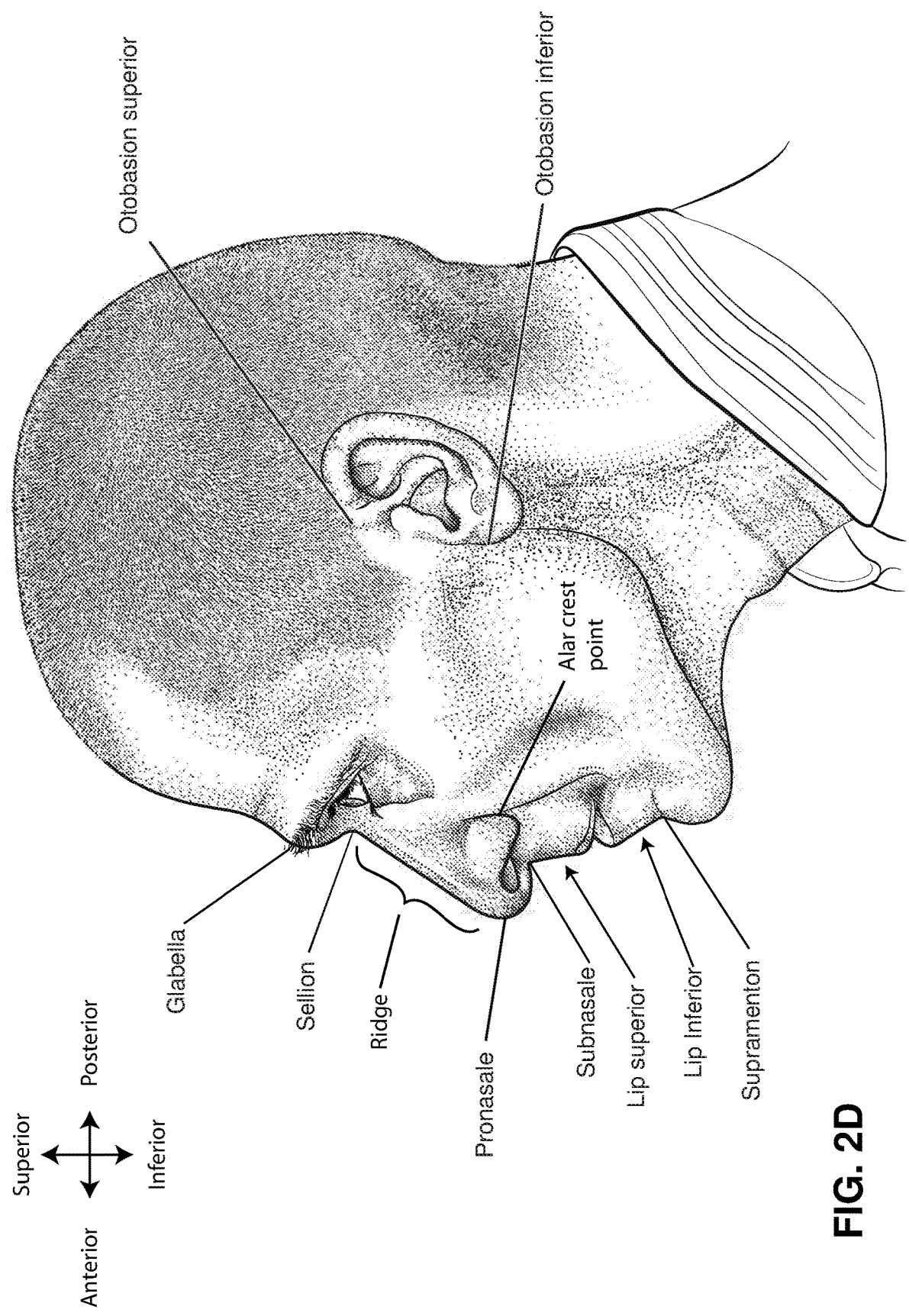
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
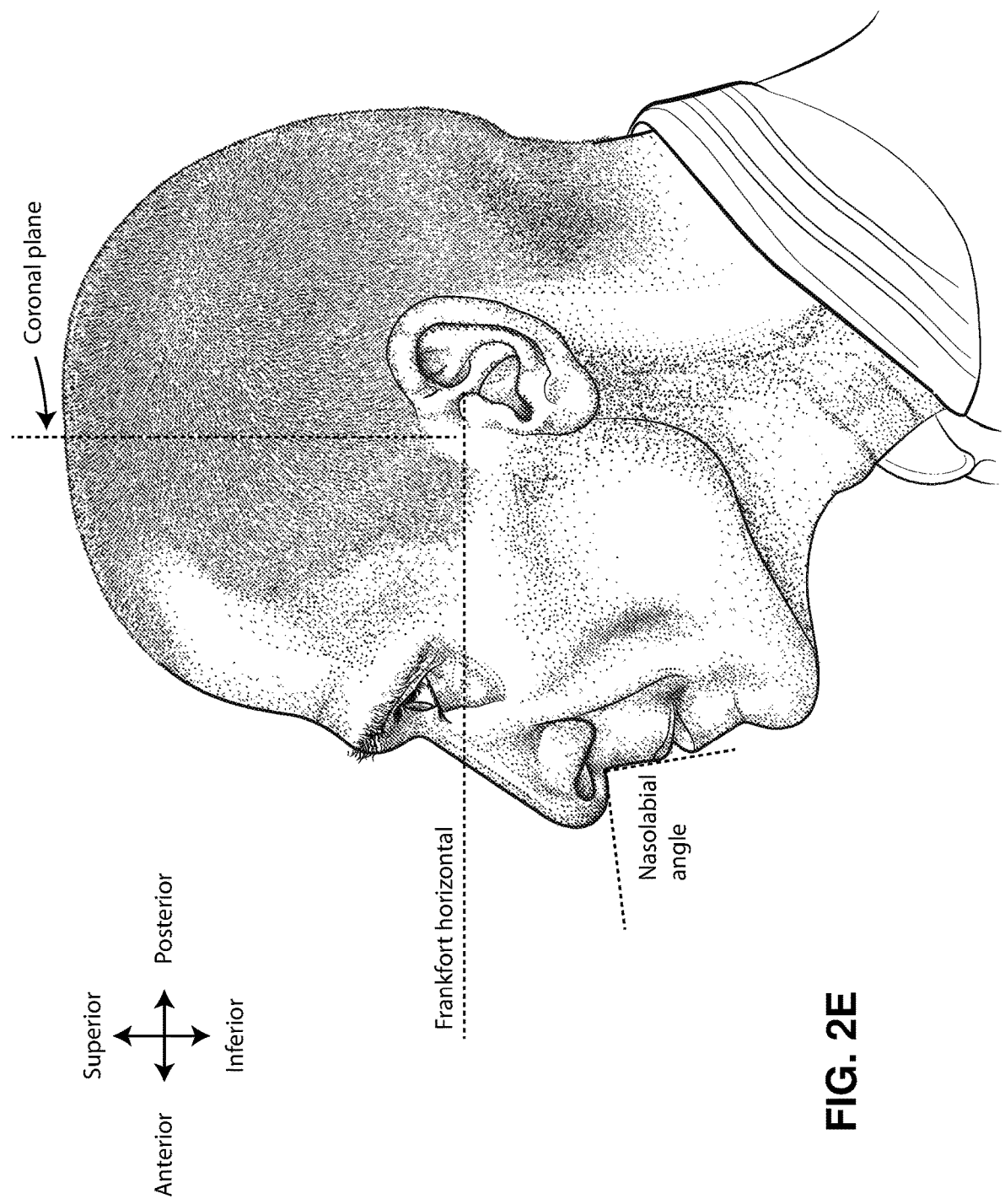

FIG. 2E is a further side view of a head. The approximate locations of the Frankfort horizontal and nasolabial angle are indicated. The coronal plane is also indicated.

Figure 2F:
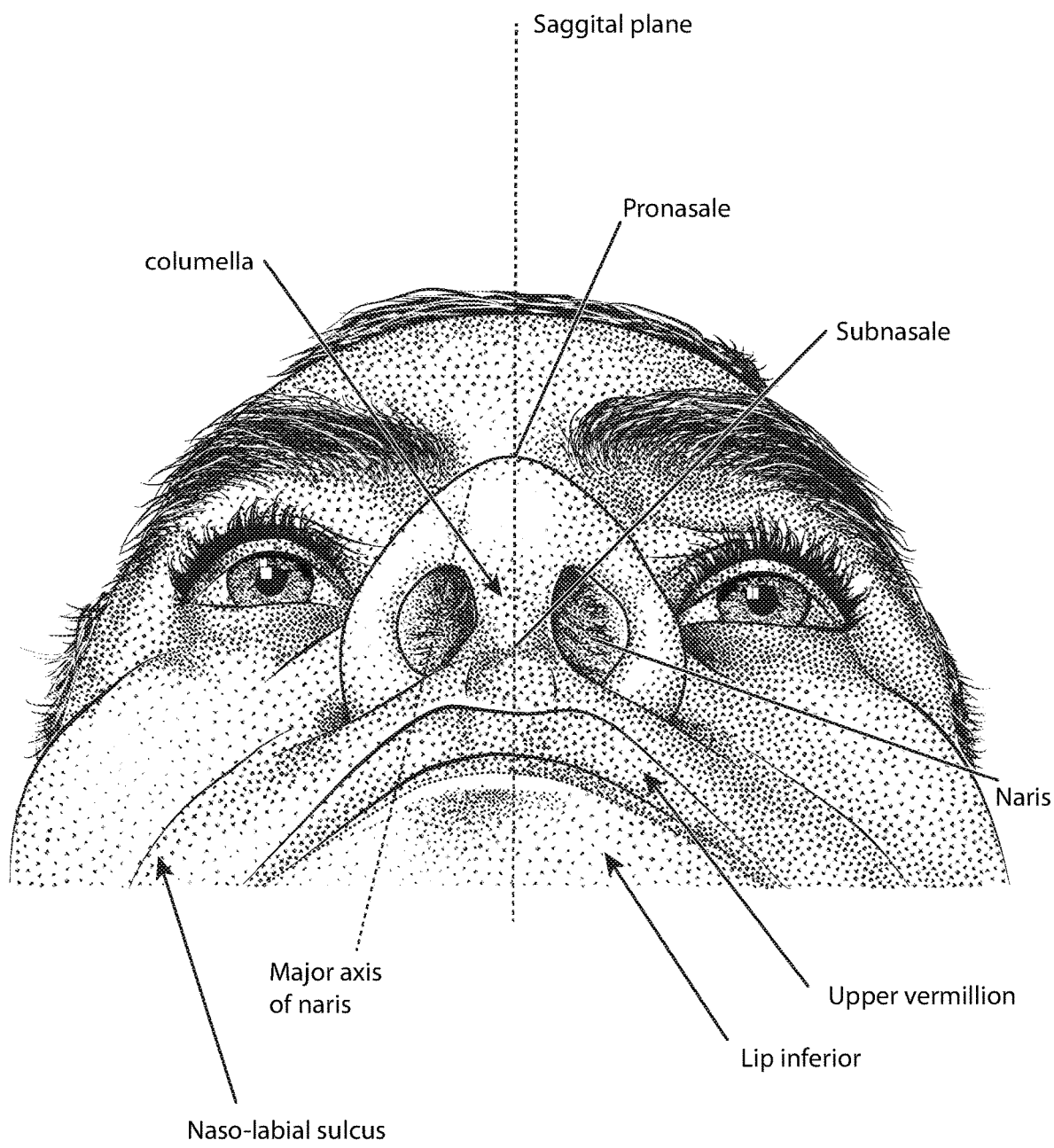

FIG. 2F shows a base view of a nose with several features identified including naso-labial sulcus, lip inferior, upper Vermilion, naris, subnasale, columella, pronasale, the major axis of a naris and the sagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from a sagittal plane, amongst other things showing the septum cartilage and medial crus of greater alar cartilage.

Figures 2J, 2K:
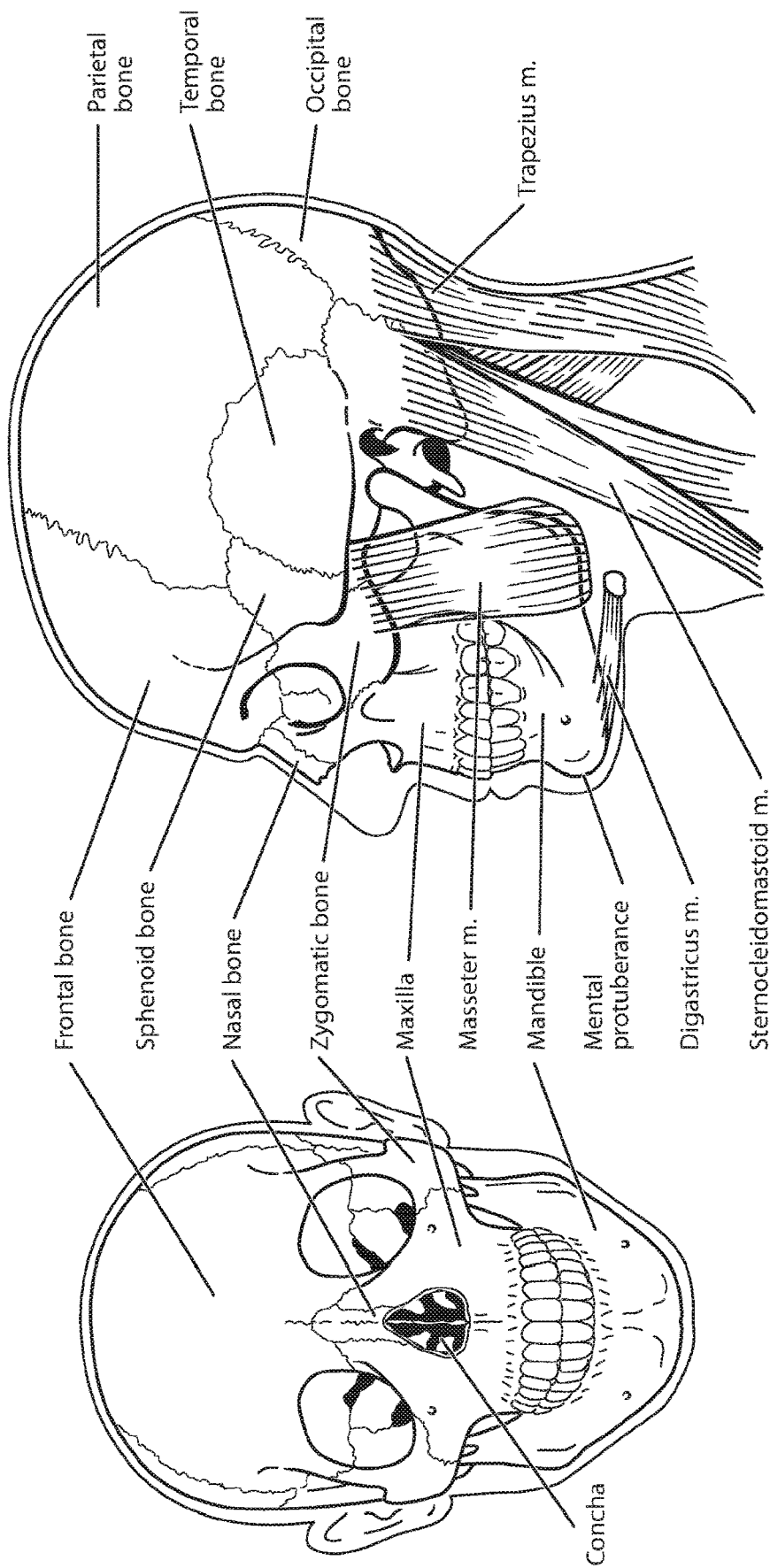

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
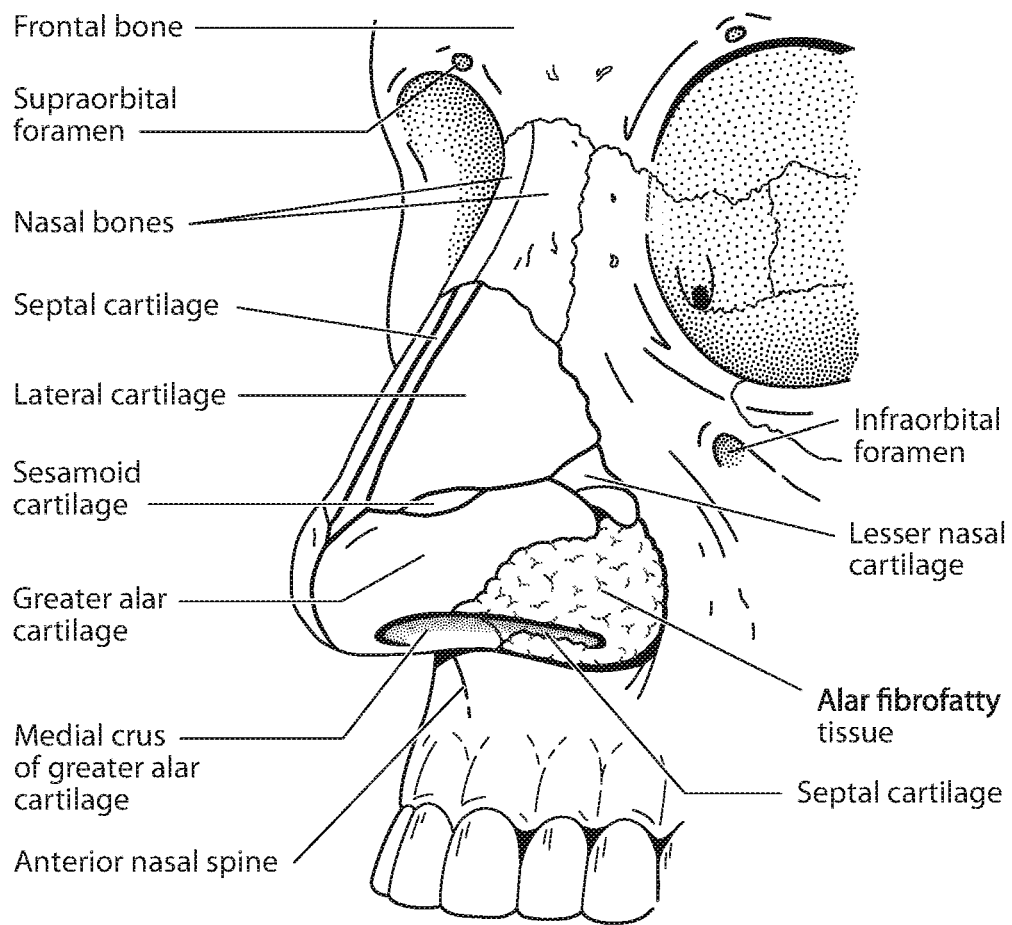

FIG. 2L shows an anterolateral view of a nose.

4.3 Patient Interface

Figure 3A:
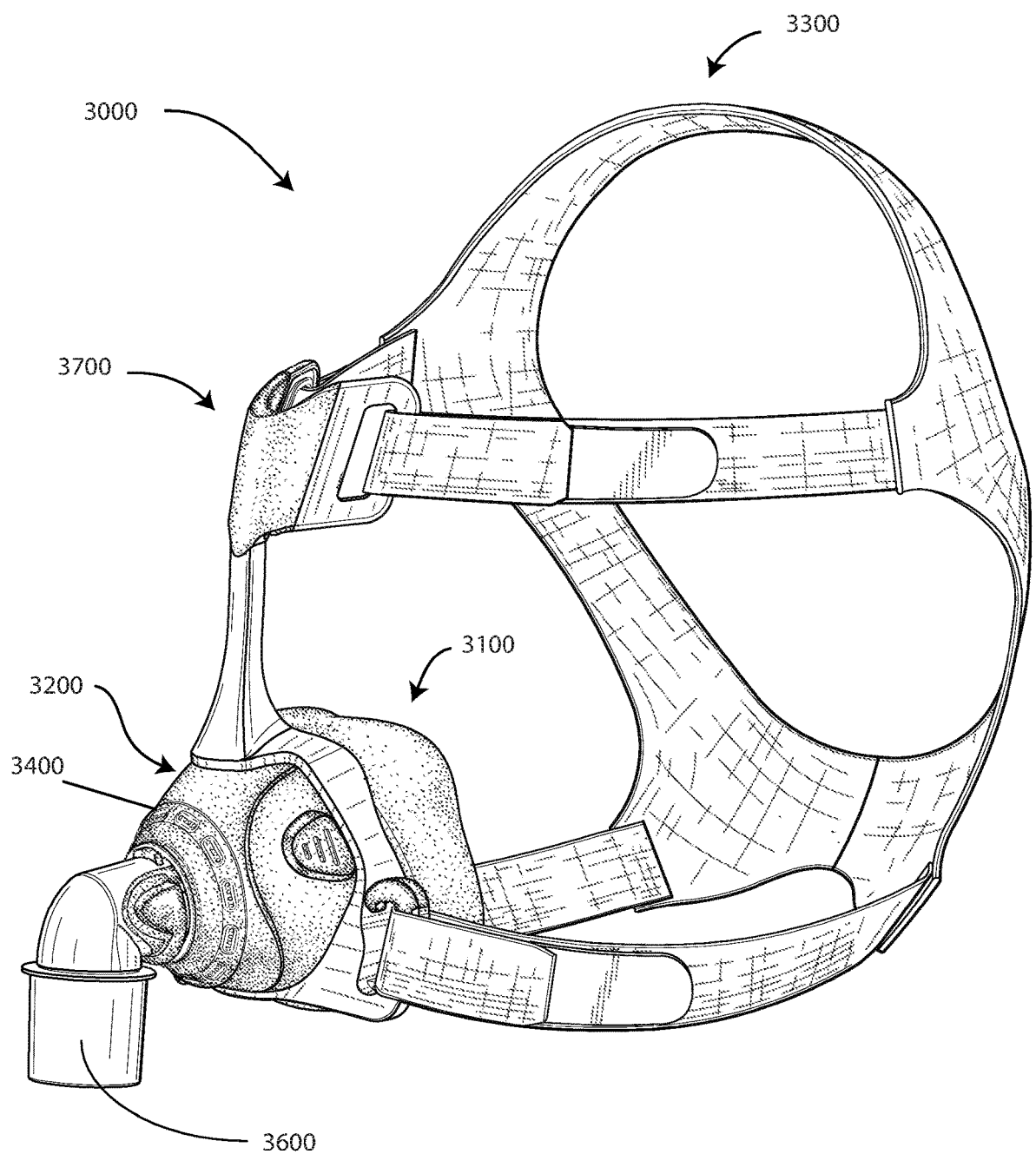

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
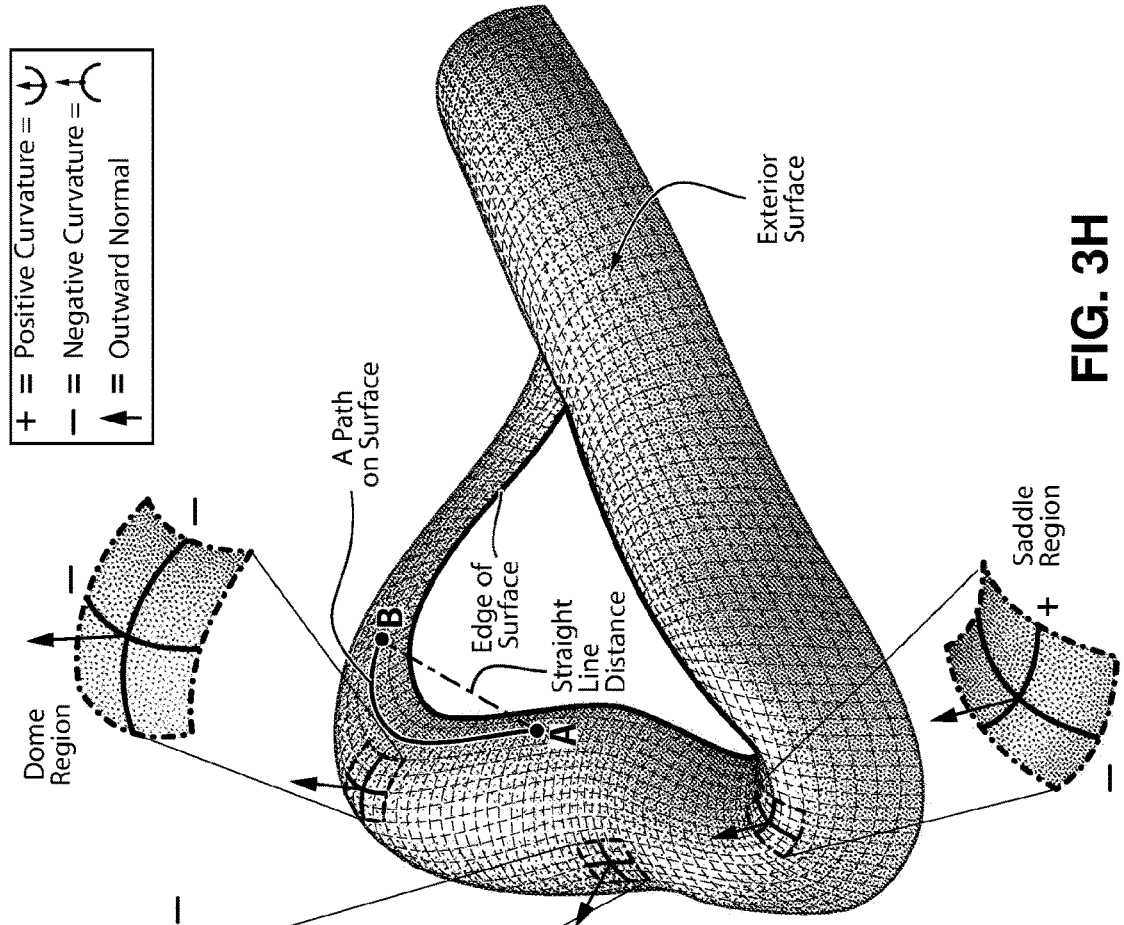
Figure 3G:
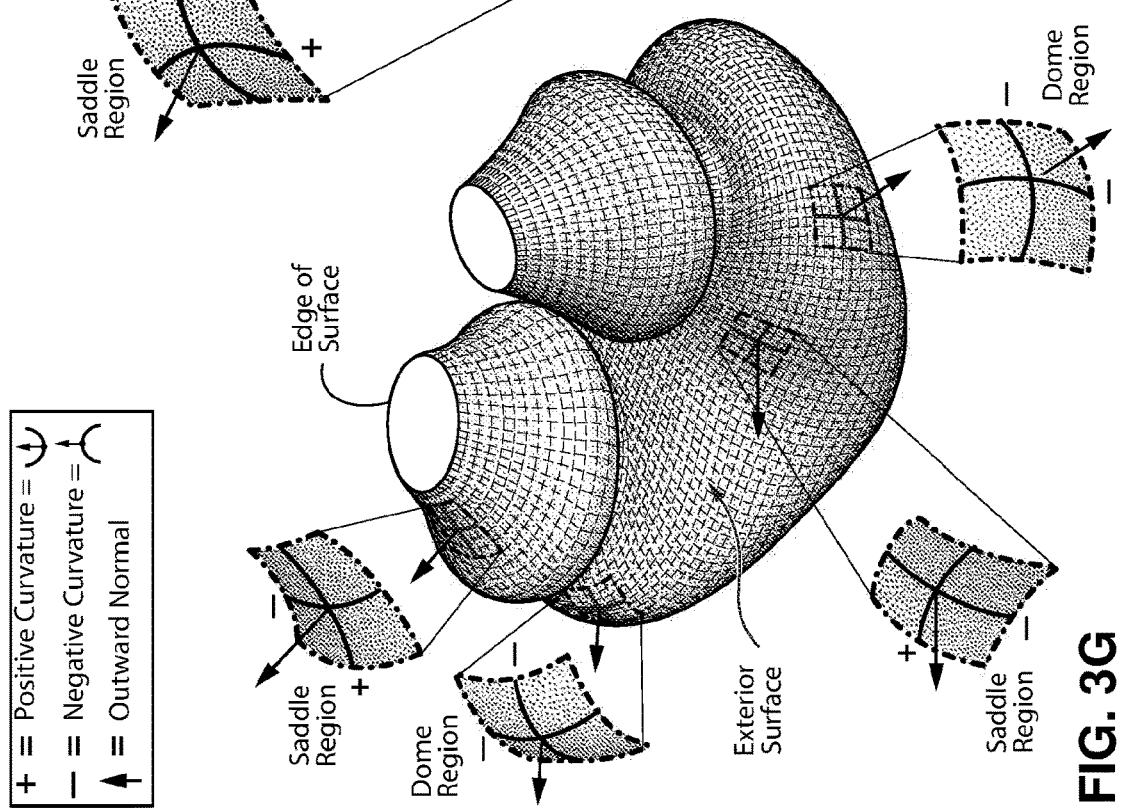

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

Figure 3I:
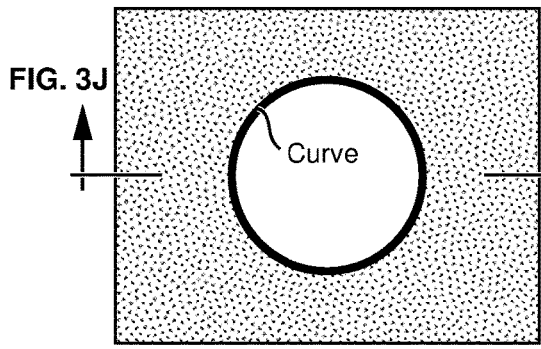

FIG. 3I shows the surface of a structure, with a one dimensional hole in the surface. The illustrated plane curve forms the boundary of a one dimensional hole.

Figure 3K:
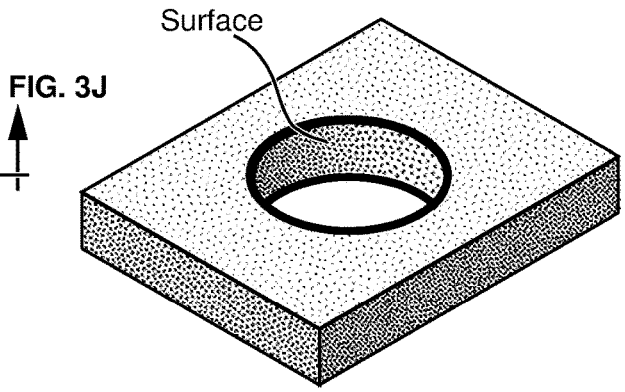
Figure 3J:
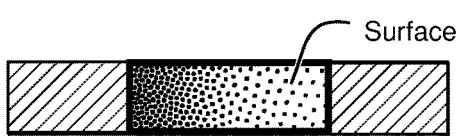

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

Figure 3L:
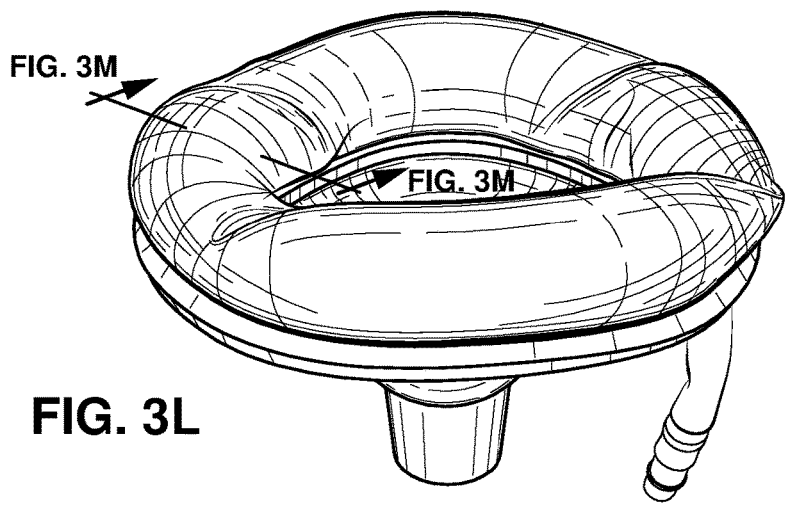

FIG. 3L shows a mask having an inflatable bladder as a cushion.

Figure 3M:
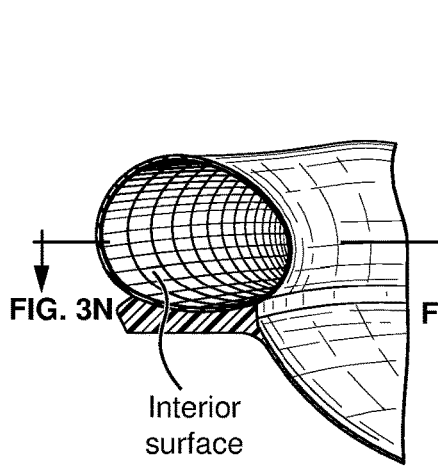

FIG. 3M shows a cross-section through the mask of FIG. 3L, and shows the interior surface of the bladder. The interior surface bounds the two dimensional hole in the mask.

Figure 3N:
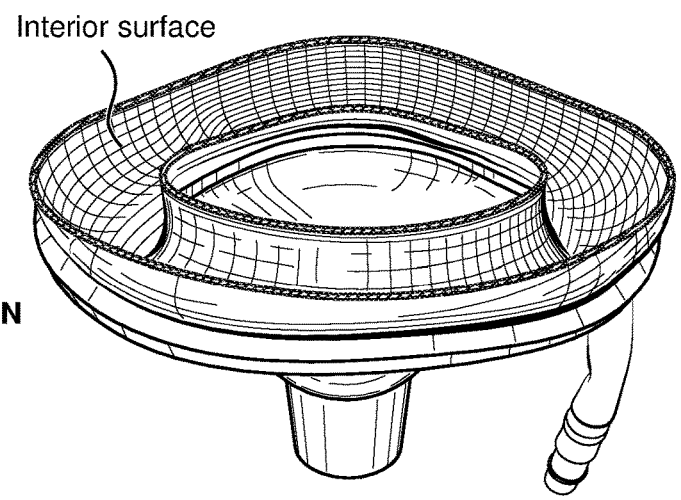

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

4.4 Breathing Waveforms

Figure 4:
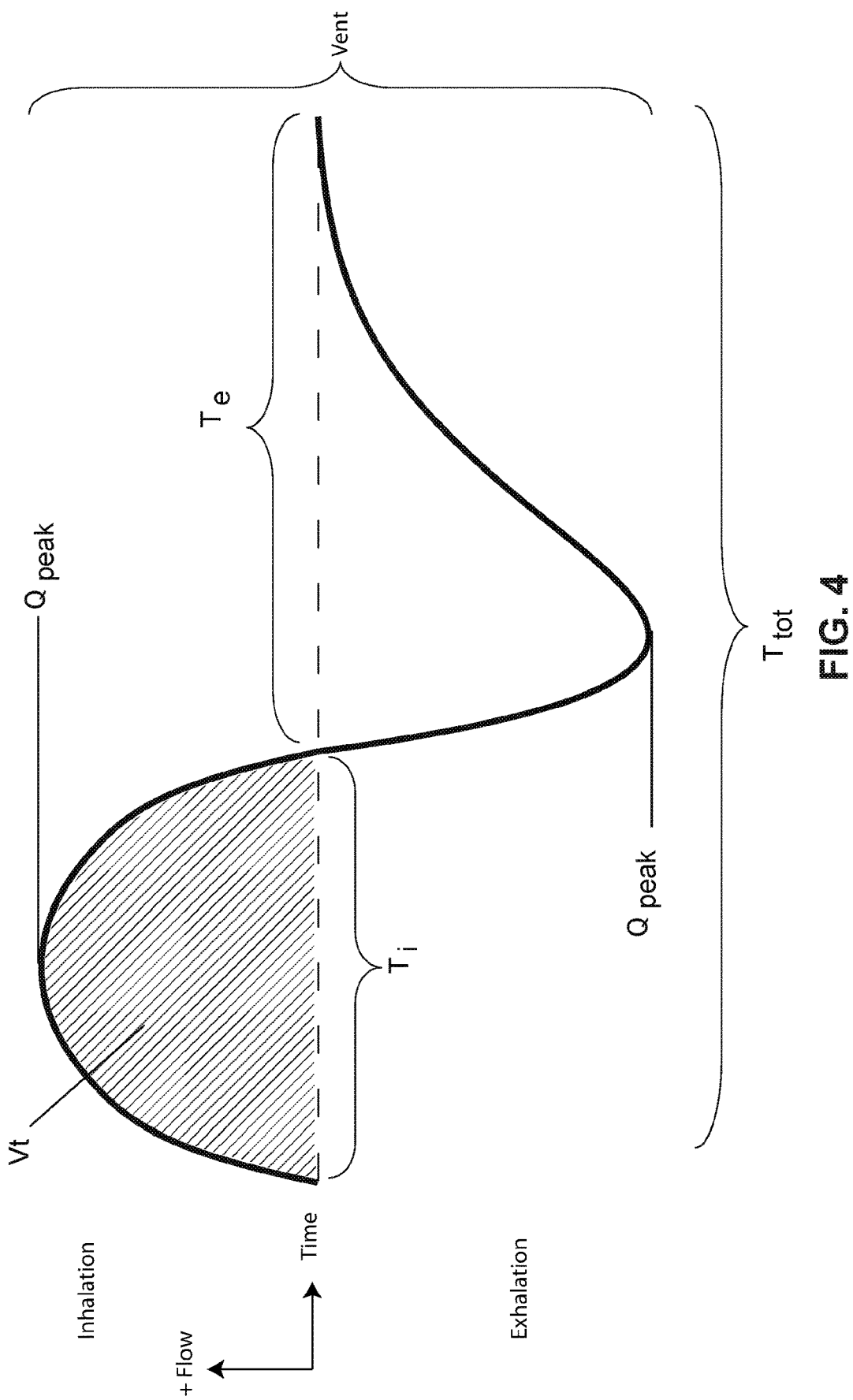

FIG. 4 shows a model typical breath waveform of a person while sleeping.

4.5 Vent System

Figure 5A:
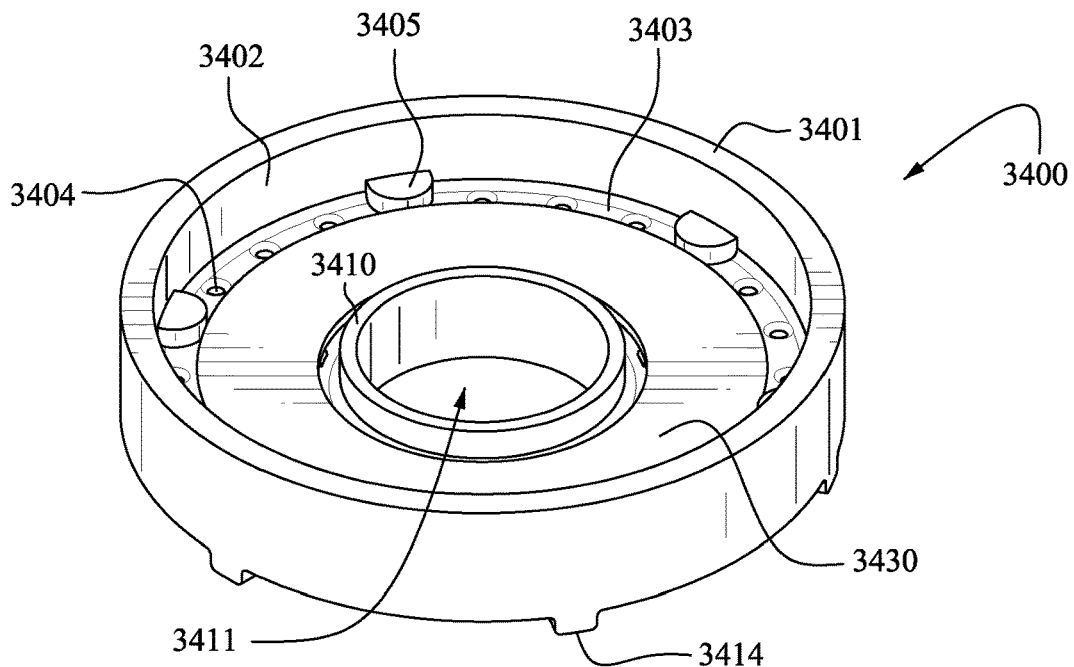

FIG. 5A shows a top perspective view of a vent system according to an example of the present technology.

Figure 5B:
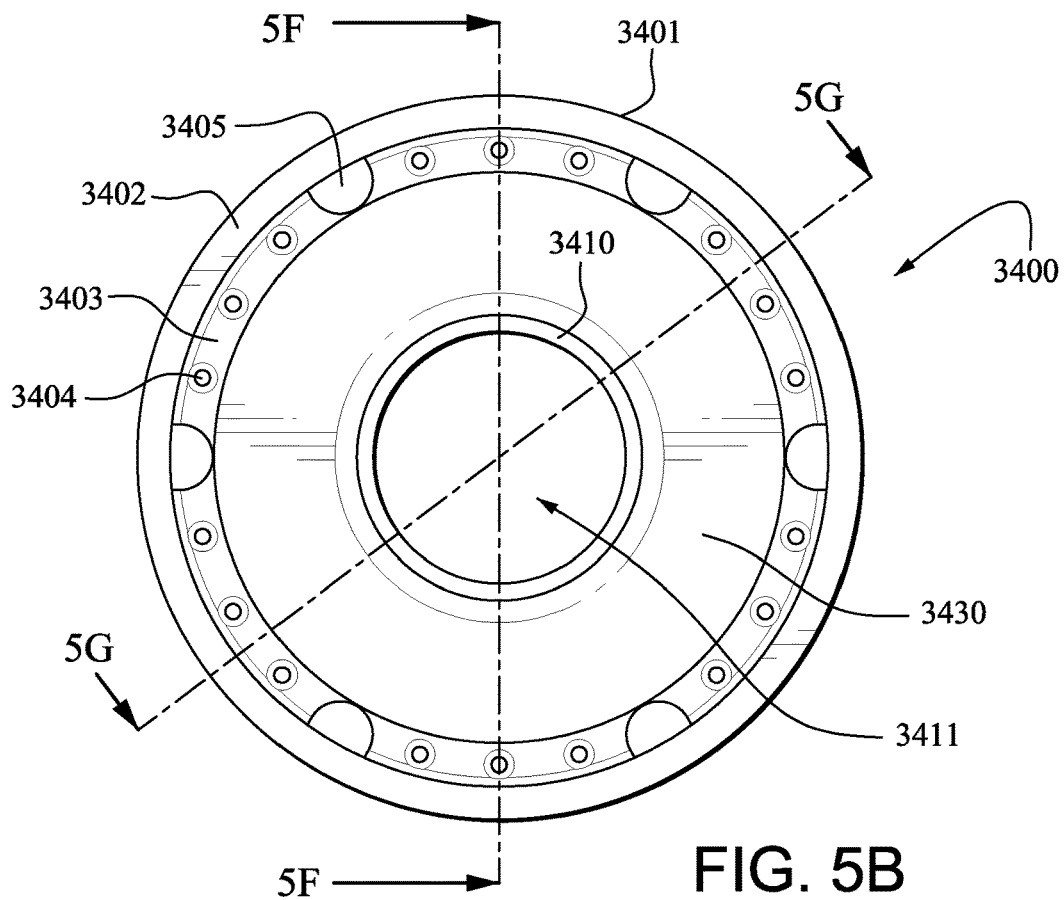

FIG. 5B shows a top view of a vent system according to an example of the present technology.

Figure 5C:
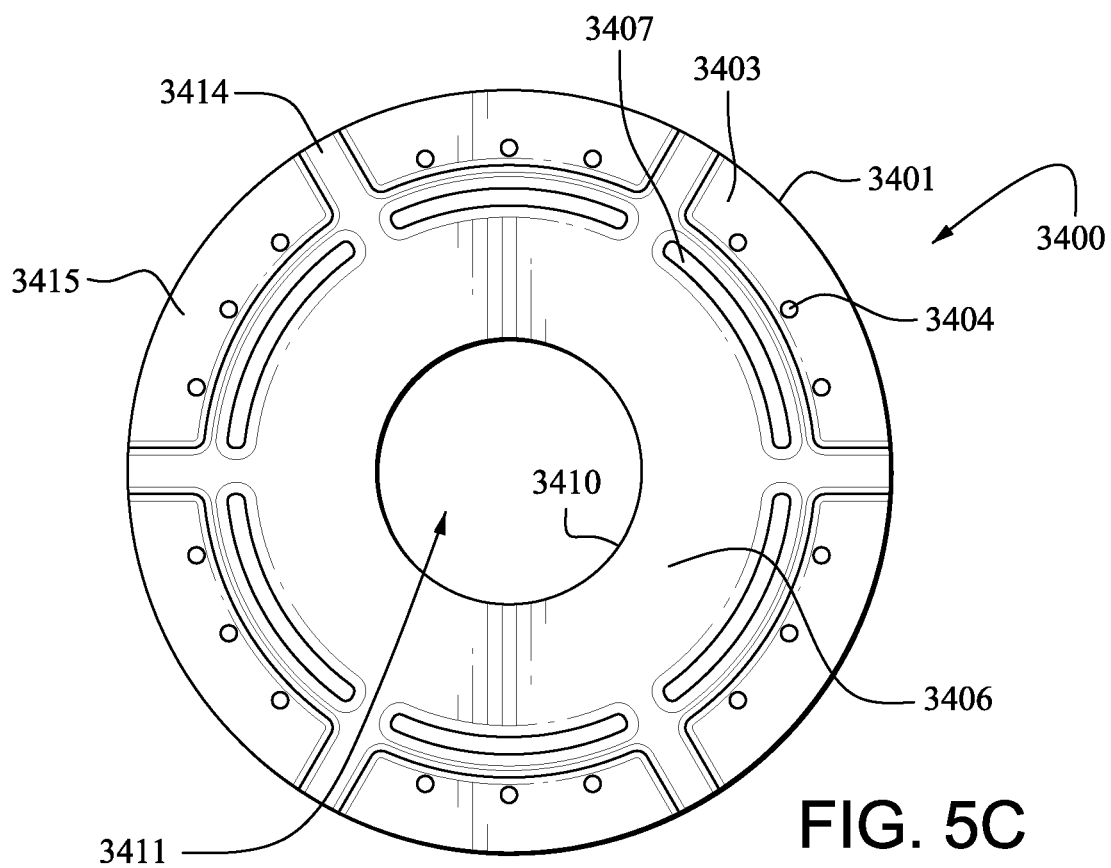

FIG. 5C shows a bottom view of a vent system according to an example of the present technology.

Figure 5D:
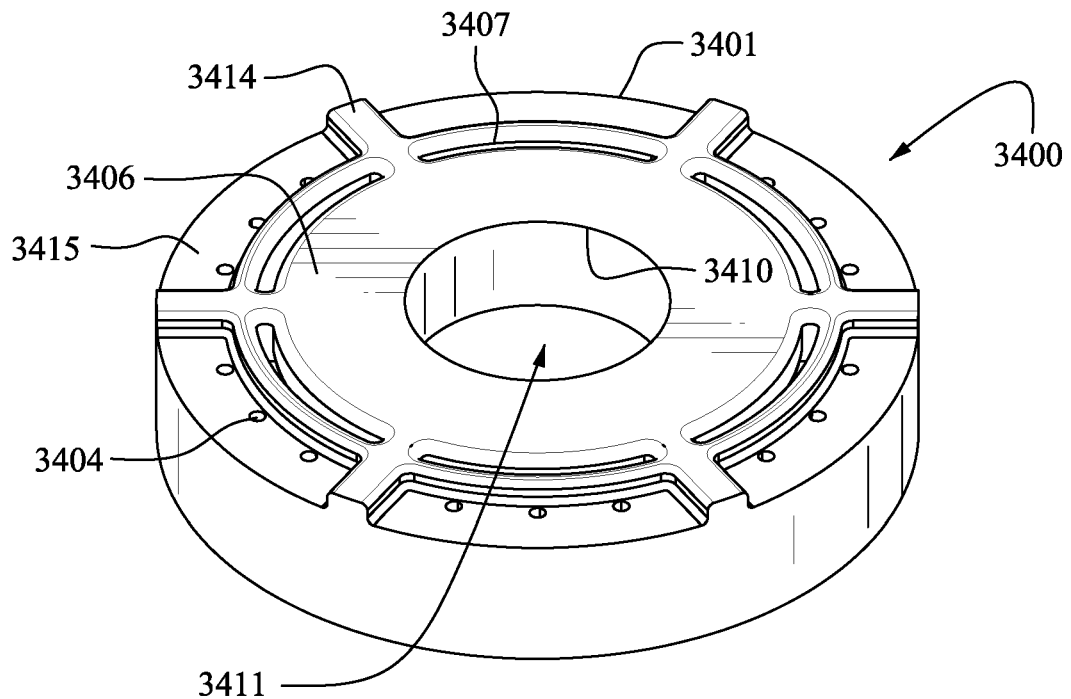

FIG. 5D shows a bottom perspective view of a vent system according to an example of the present technology.

Figure 5E:
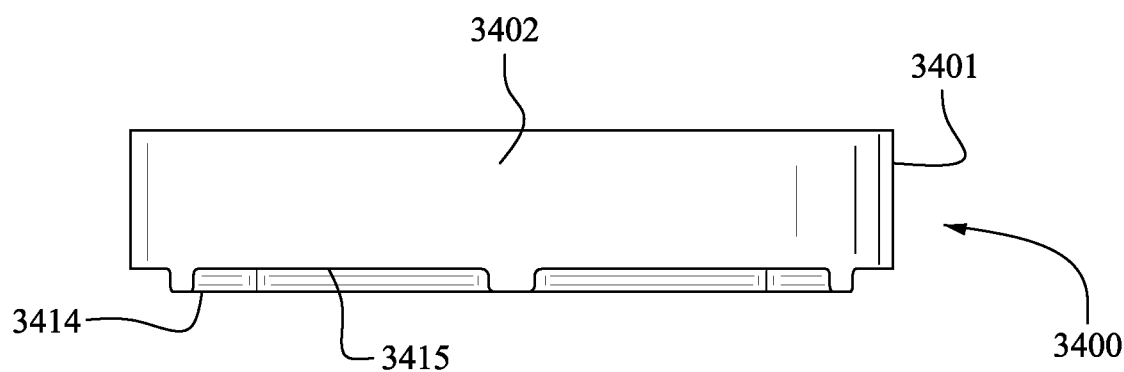

FIG. 5E shows a side view of a vent system according to an example of the present technology.

Figure 5F:
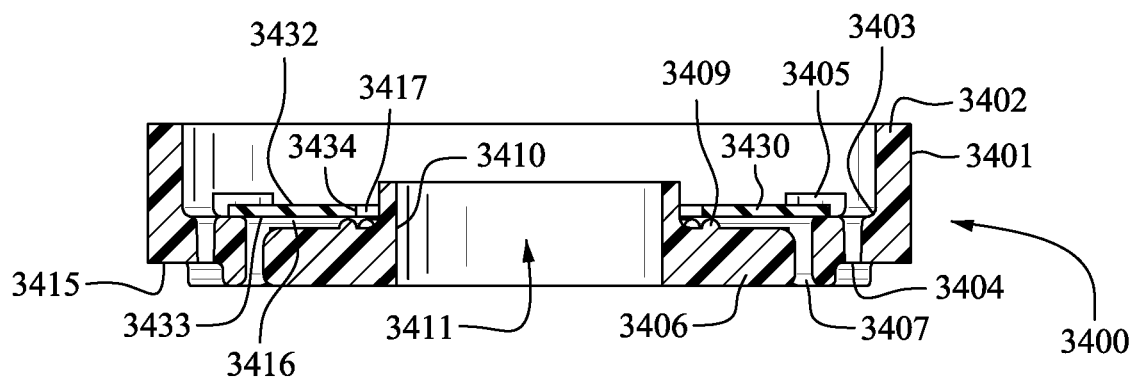

FIG. 5F shows a cross-sectional view of a vent system according to an example of the present technology taken through line 5F-5F of FIG. 5B.

Figure 5G:
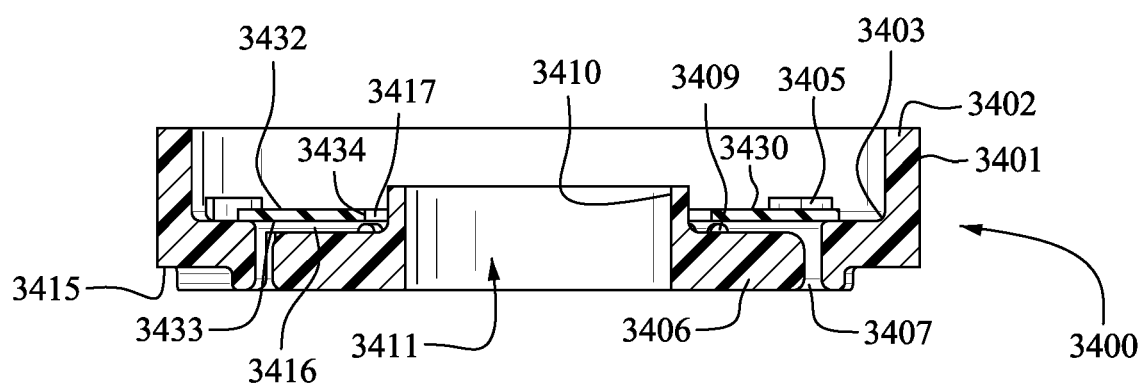

FIG. 5G shows a cross-sectional view of a vent system according to an example of the present technology taken through line 5G-5G of FIG. 5B.

Figure 6A:
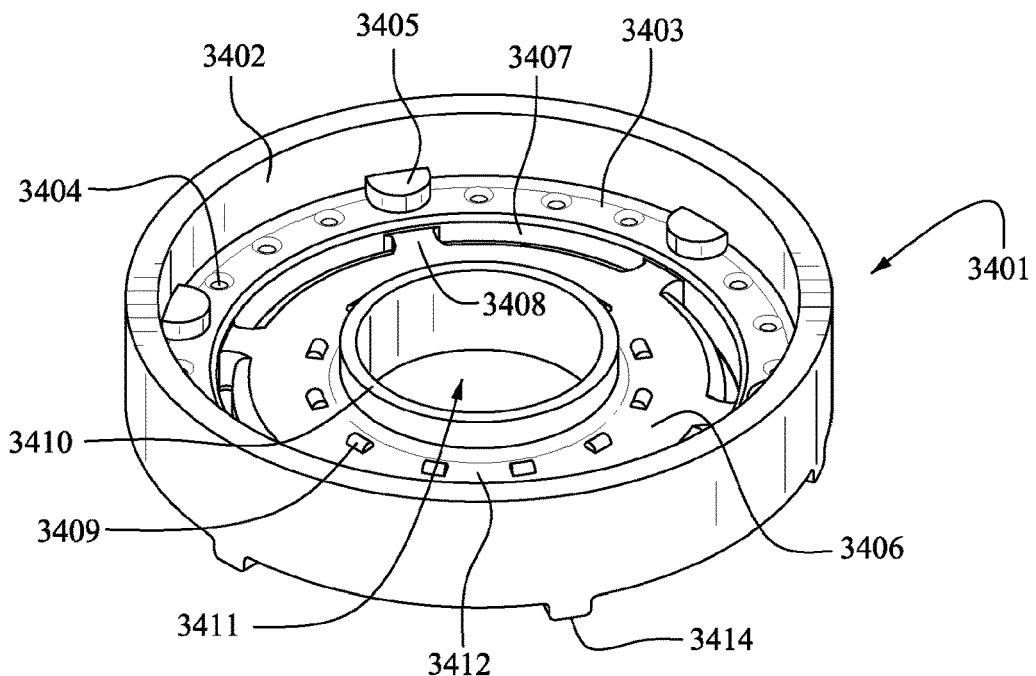

FIG. 6A shows a top perspective view of a vent housing according to an example of the present technology.

Figure 6B:
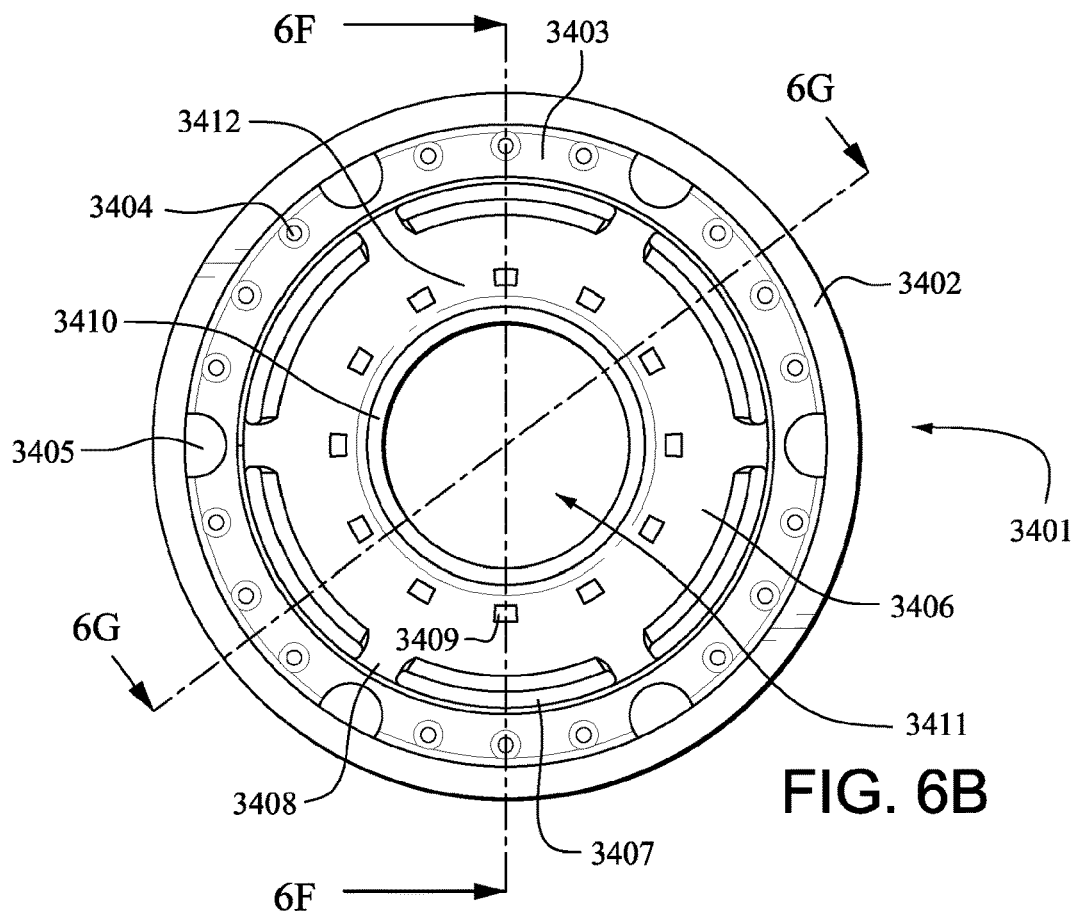

FIG. 6B shows a top view of a vent housing according to an example of the present technology.

Figure 6C:
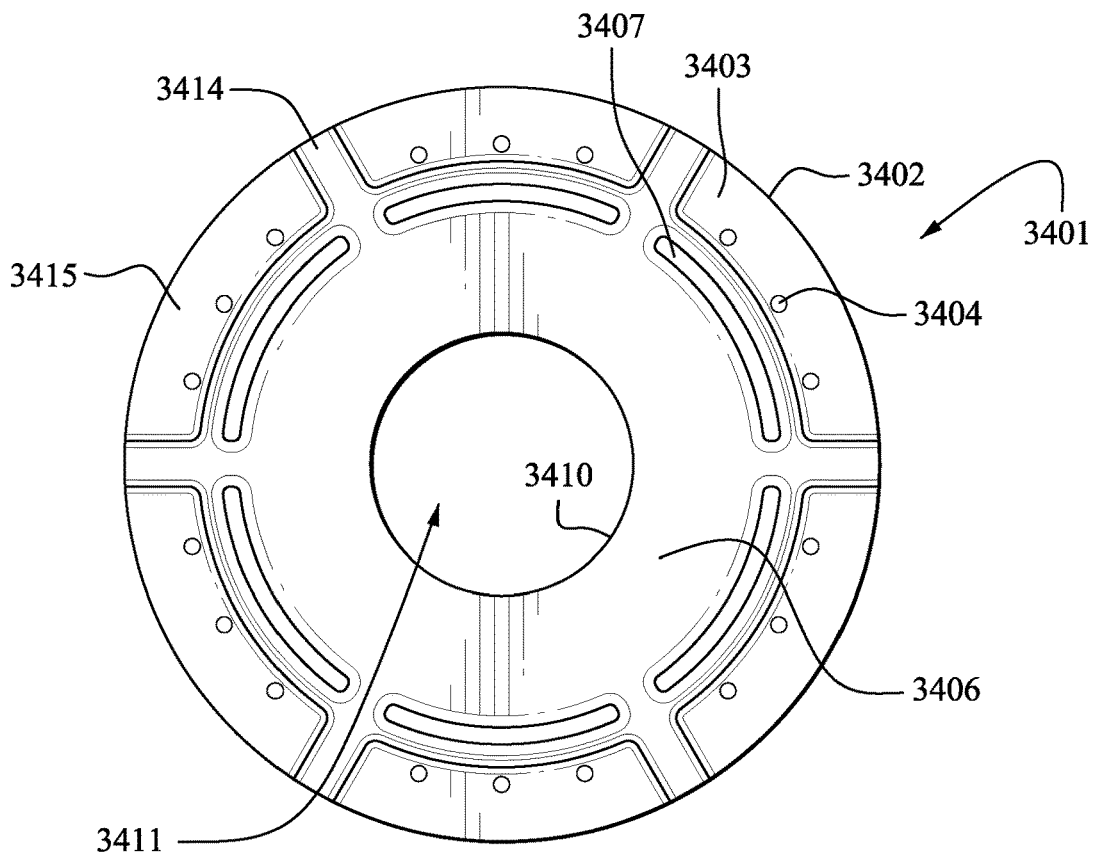

FIG. 6C shows a bottom view of a vent housing according to an example of the present technology.

Figure 6D:
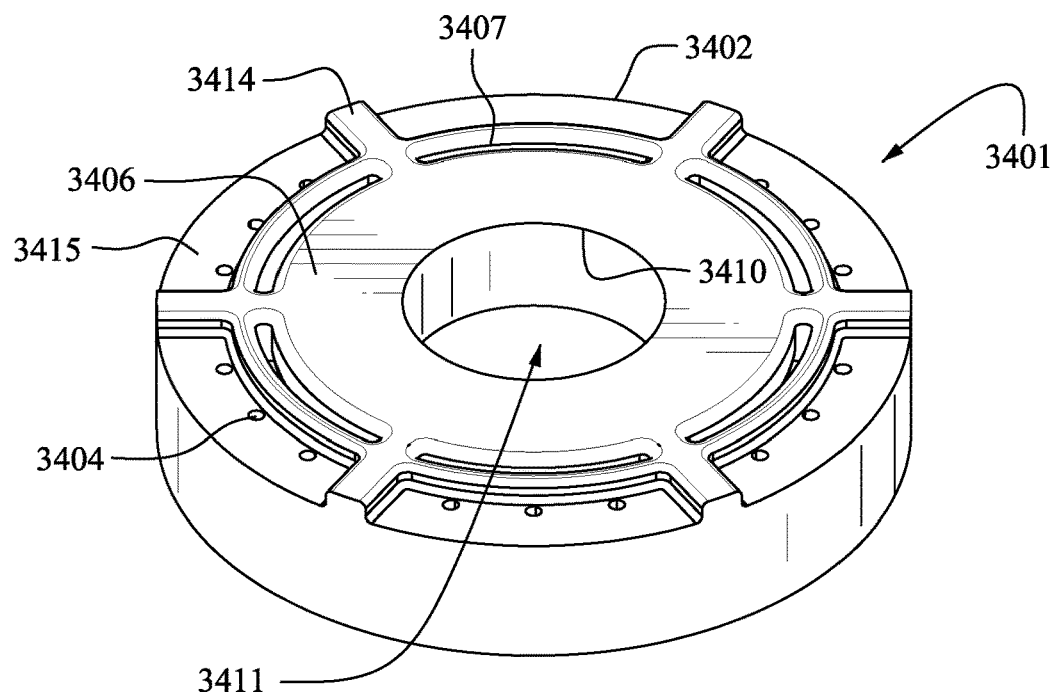

FIG. 6D shows a bottom perspective view of a vent housing according to an example of the present technology.

Figure 6E:
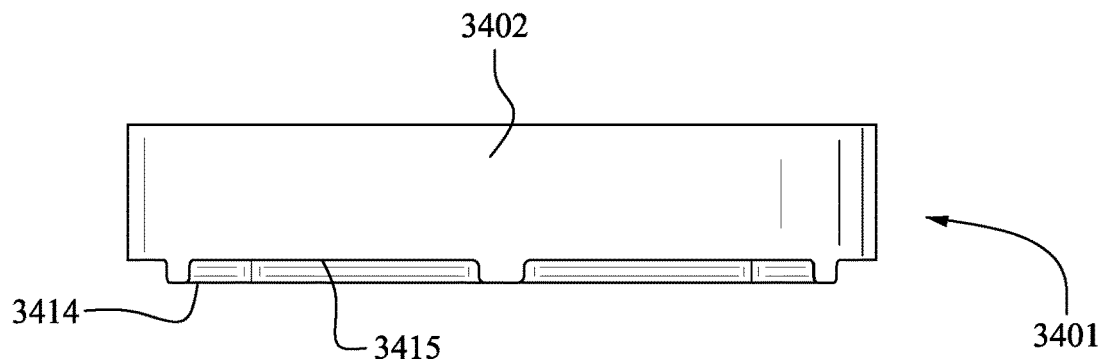

FIG. 6E shows a side view of a vent housing according to an example of the present technology.

Figure 6F:
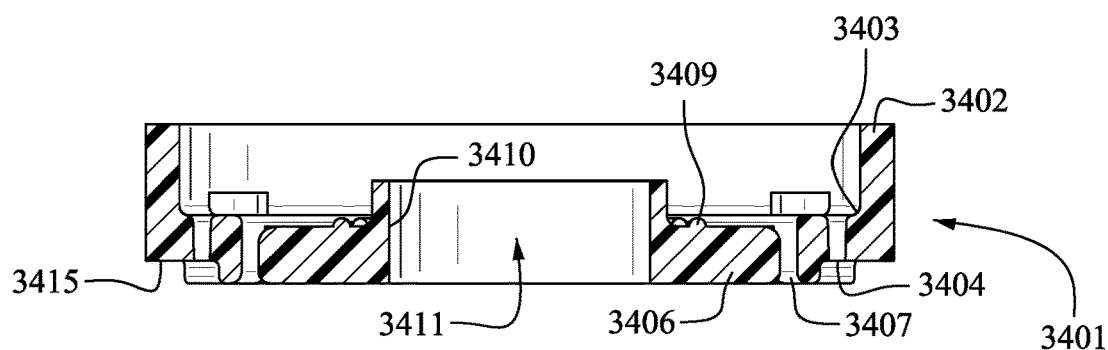

FIG. 6F shows a cross-sectional view of a vent housing according to an example of the present technology taken through line 6F-6F of FIG. 6B.

Figure 6G:
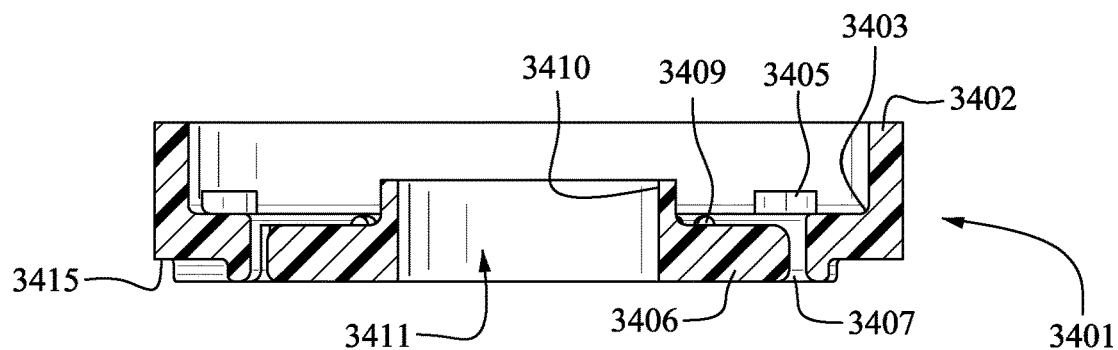

FIG. 6G shows a cross-sectional view of a vent housing according to an example of the present technology taken through line 6G-6G of FIG. 6B.

Figure 7A:
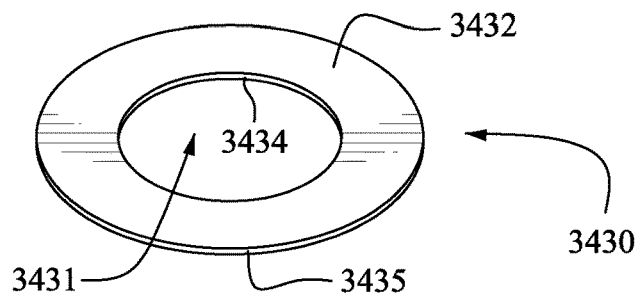

FIG. 7A shows a top perspective view of a membrane according to an example of the present technology.

Figure 7B:
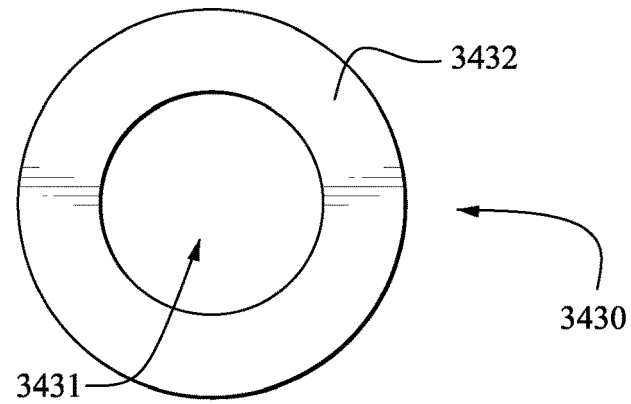

FIG. 7B shows a top view of a membrane according to an example of the present technology.

Figure 7C:
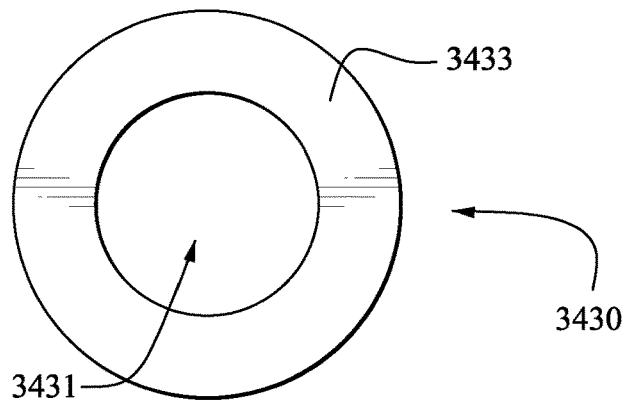

FIG. 7C shows a bottom view of a membrane according to an example of the present technology.

Figure 7D:
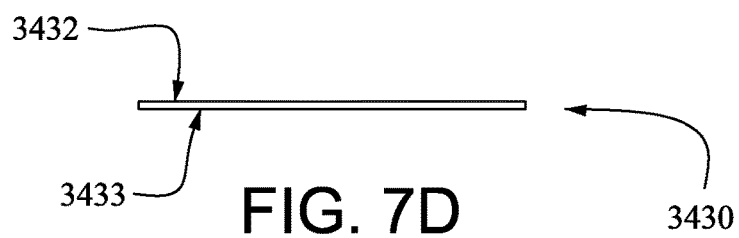

FIG. 7D shows a side view of a membrane according to an example of the present technology.

Figure 8A:
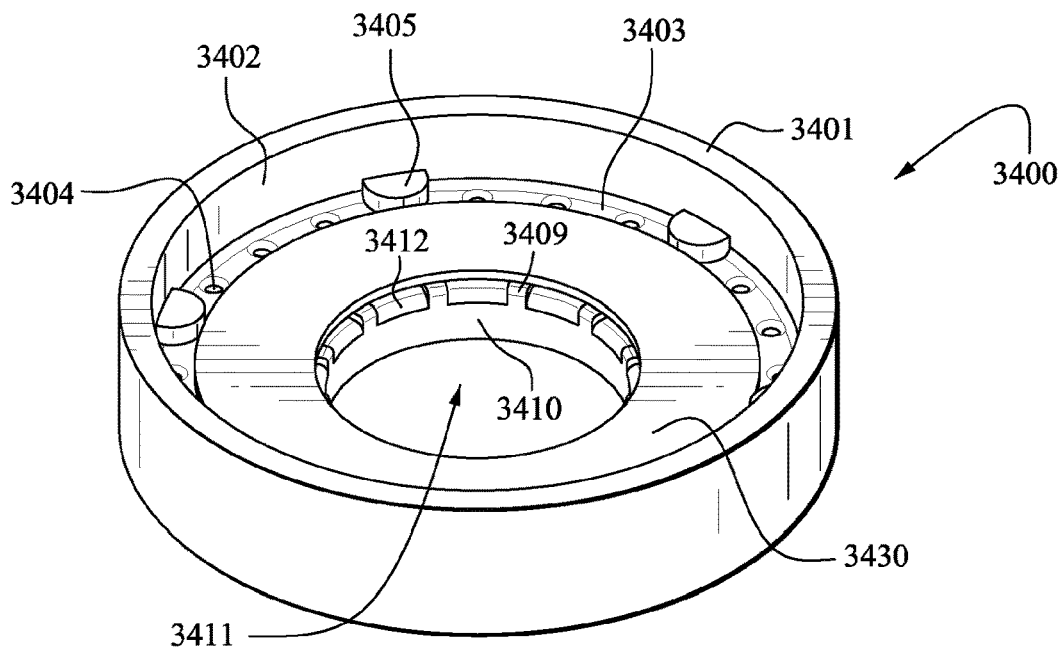

FIG. 8A shows a top perspective view of a vent system according to another example of the present technology.

Figure 8B:
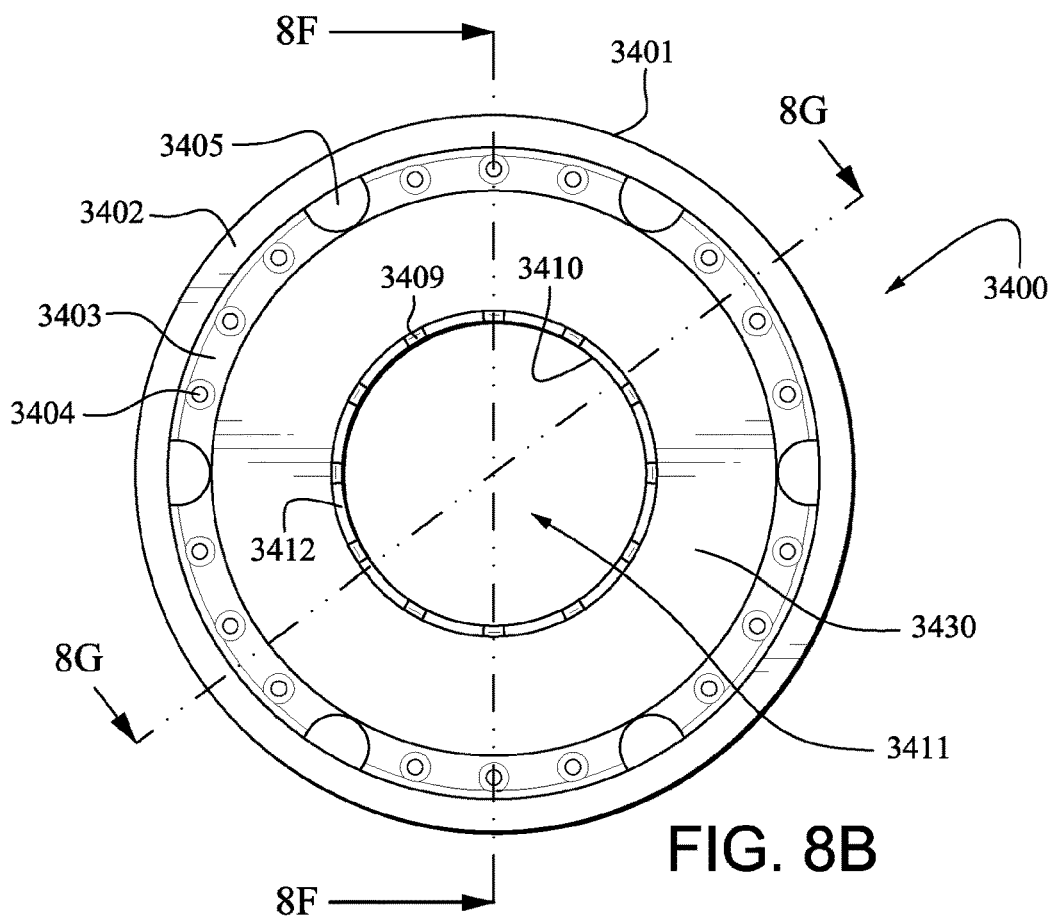

FIG. 8B shows a top view of a vent system according to another example of the present technology.

Figure 8C:
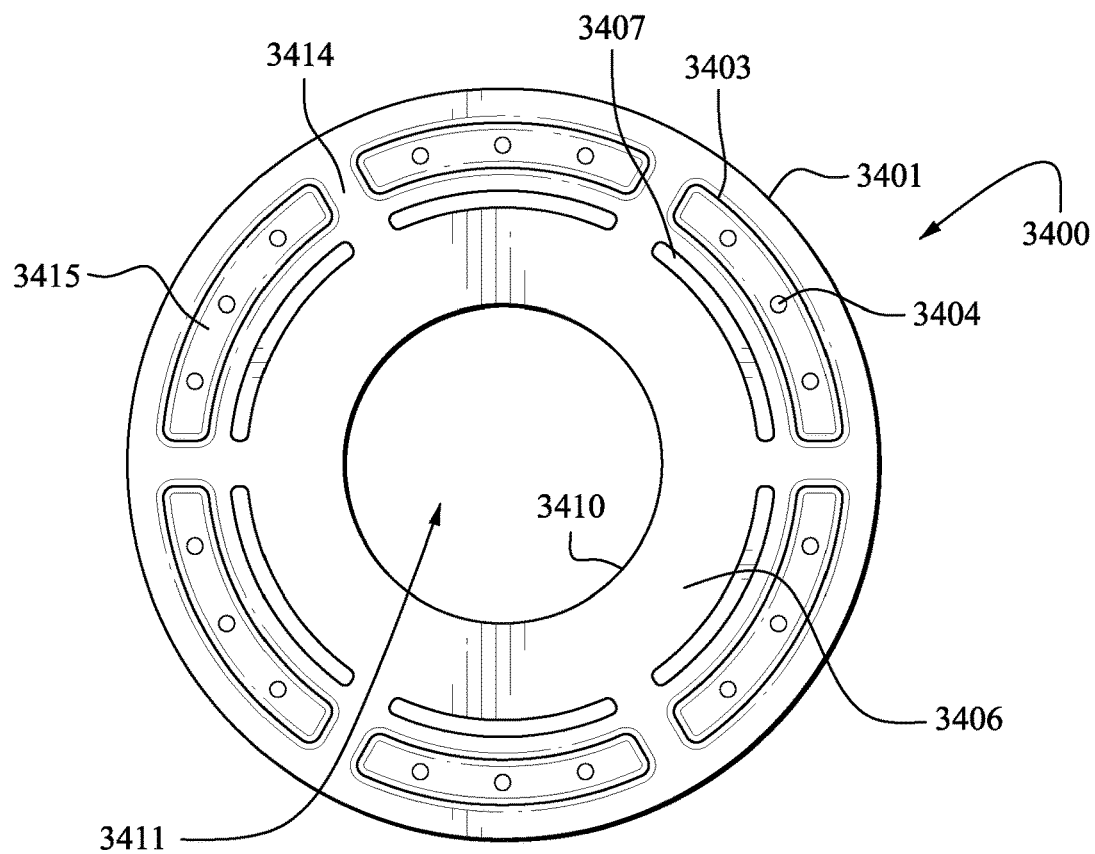

FIG. 8C shows a bottom view of a vent system according to another example of the present technology.

Figure 8D:
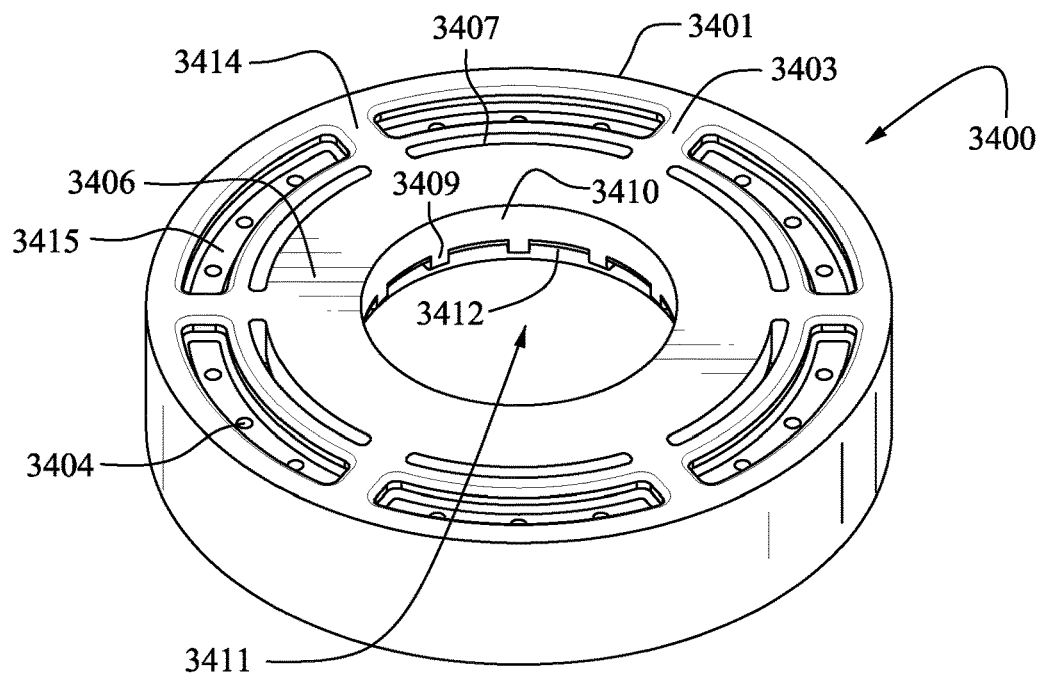

FIG. 8D shows a bottom perspective view of a vent system according to another example of the present technology.

Figure 8E:
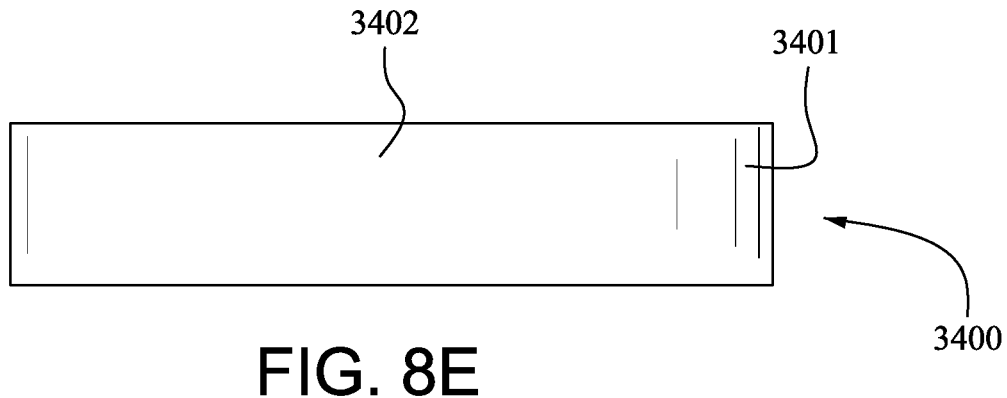

FIG. 8E shows a side view of a vent system according to another example of the present technology.

Figure 8F:
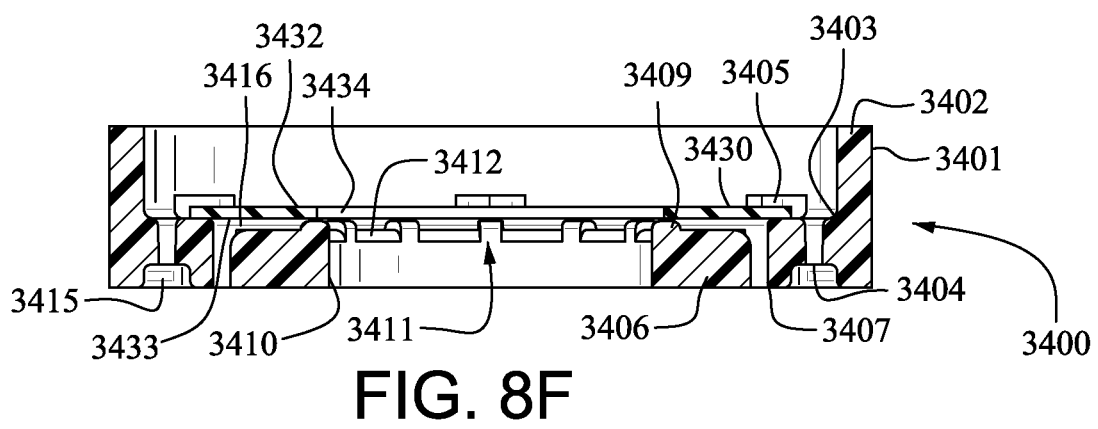

FIG. 8F shows a cross-sectional view of a vent system according to another example of the present technology taken through line 8F-8F of FIG. 8B.

Figure 8G:
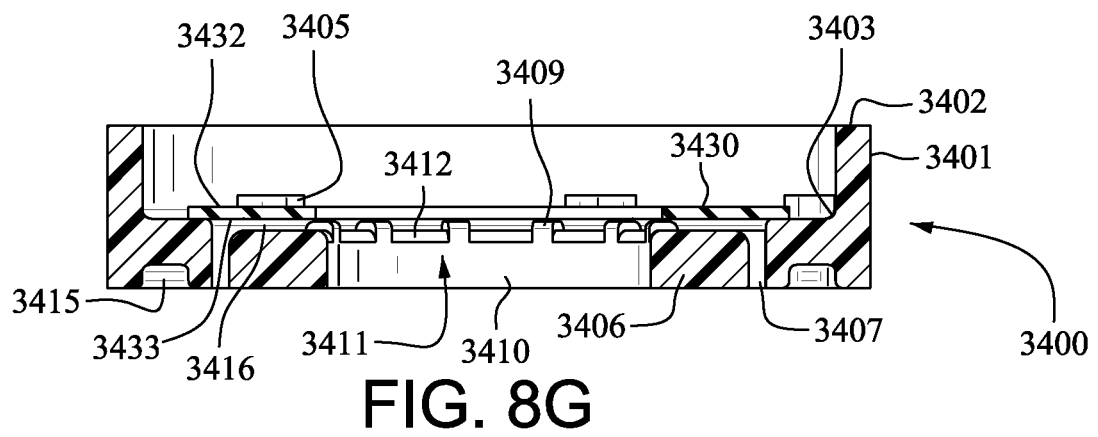

FIG. 8G shows a cross-sectional view of a vent system according to an example of the present technology taken through line 8G-8G of FIG. 8B.

Figure 9A:
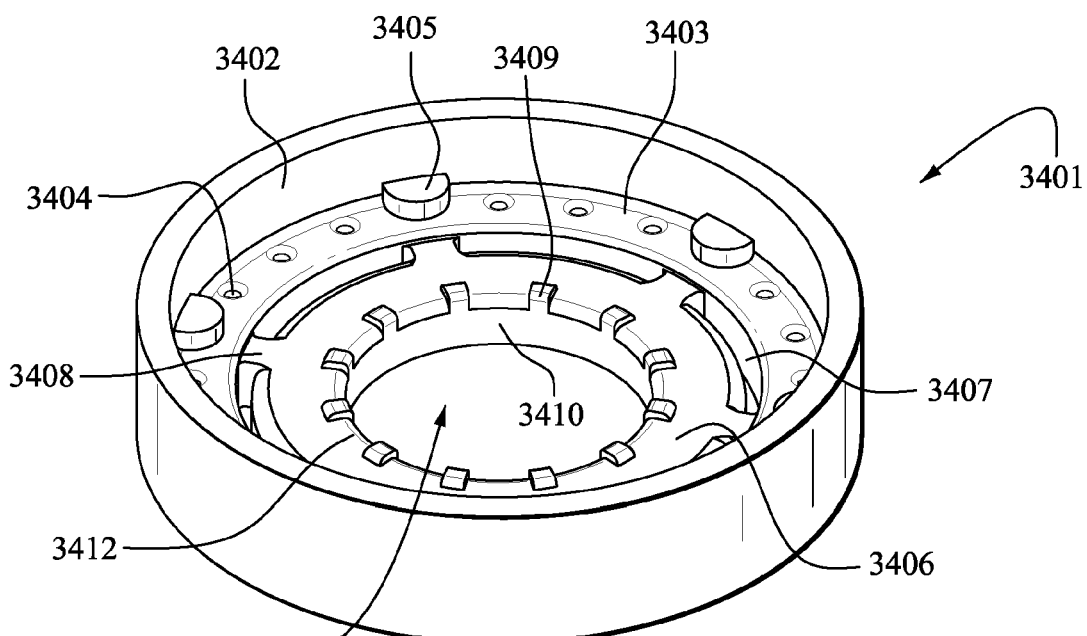

FIG. 9A shows a top perspective view of a vent housing according to another example of the present technology.

Figure 9B:
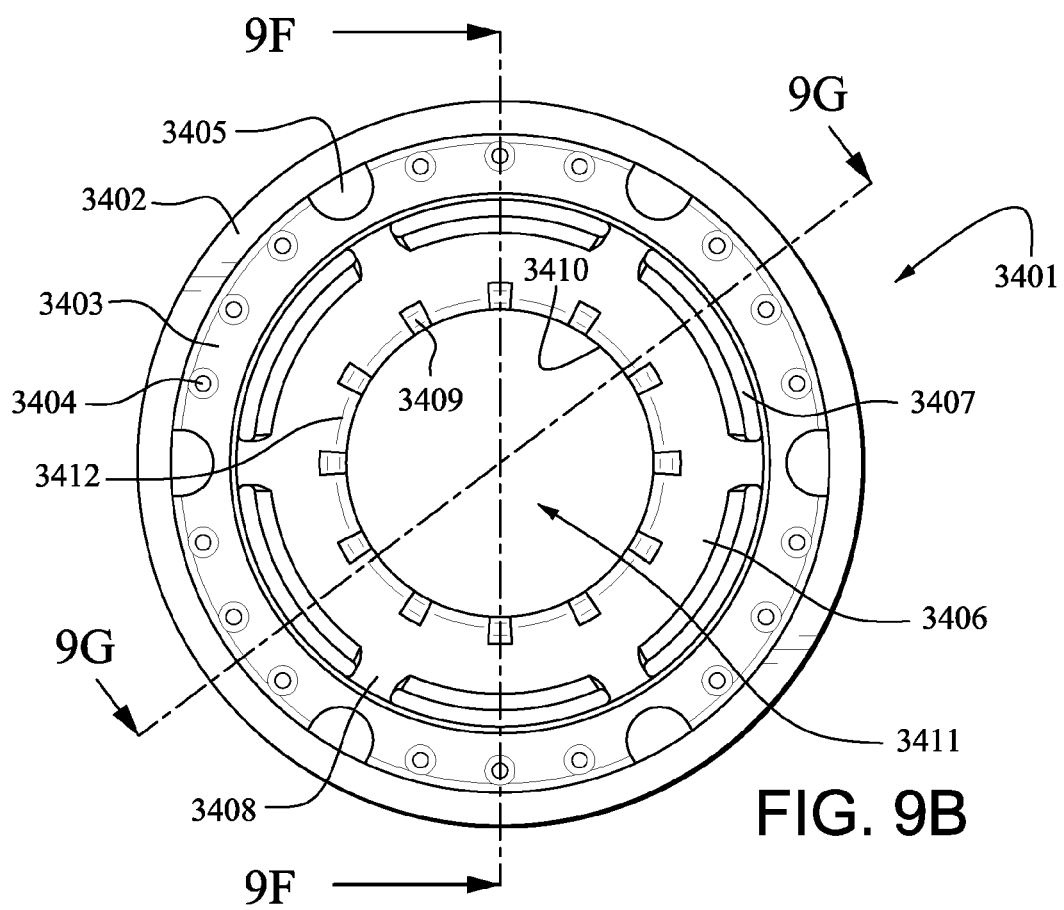

FIG. 9B shows a top view of a vent housing according to another example of the present technology.

Figure 9C:
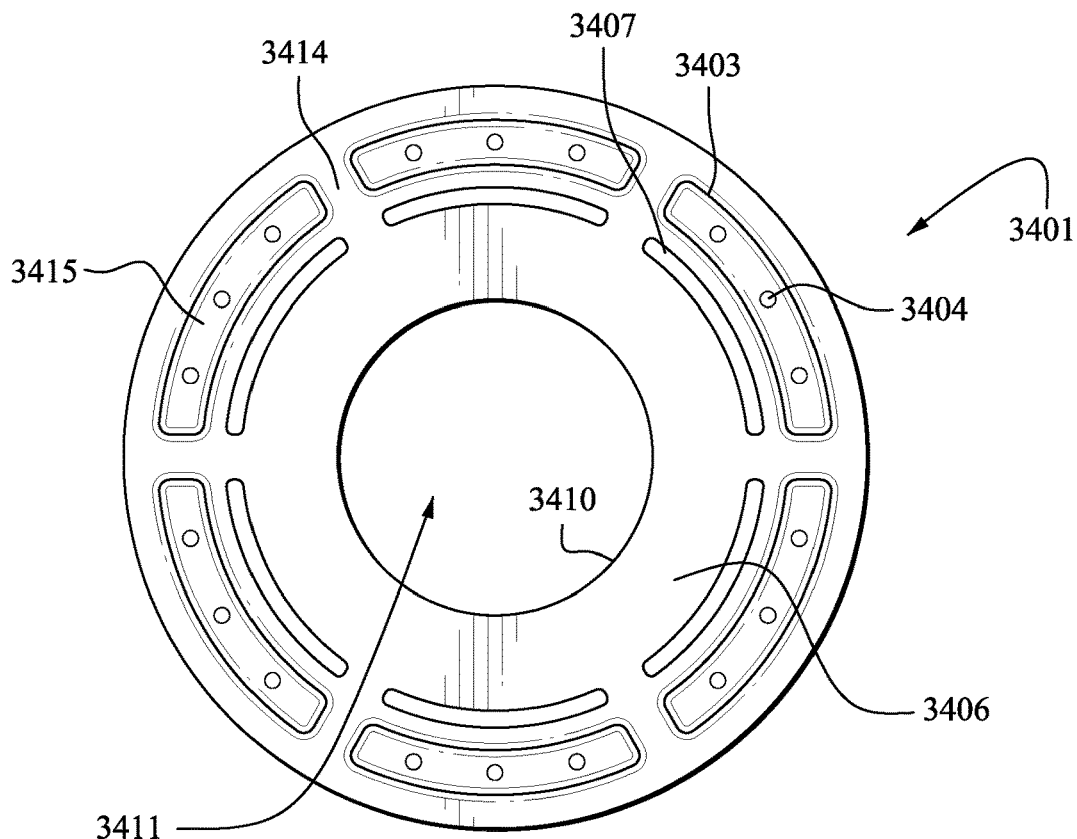

FIG. 9C shows a bottom view of a vent housing according to another example of the present technology.

Figure 9D:
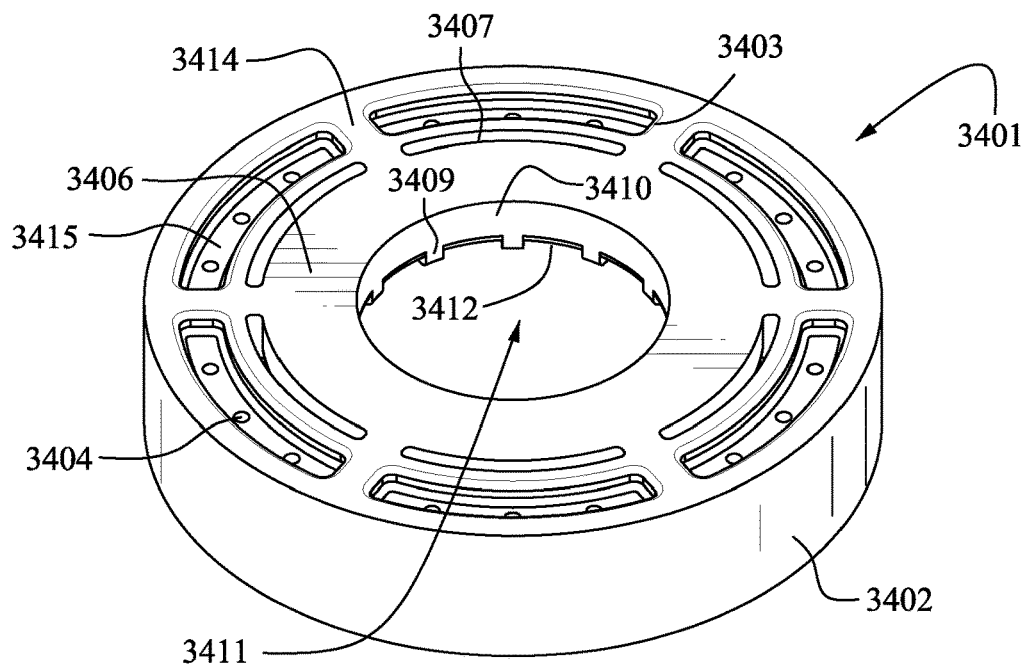

FIG. 9D shows a bottom perspective view of a vent housing according to another example of the present technology.

Figure 9E:
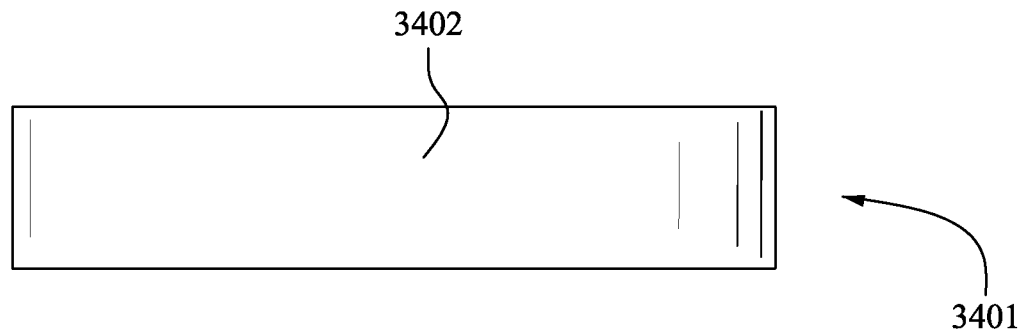

FIG. 9E shows a side view of a vent housing according to another example of the present technology.

Figure 9F:
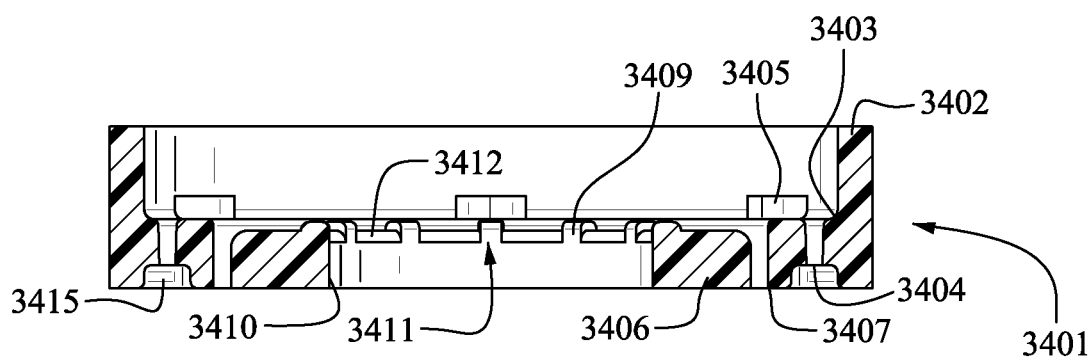

FIG. 9F shows a cross-sectional view of a vent housing according to another example of the present technology taken through line 9F-9F of FIG. 9B.

Figure 9G:
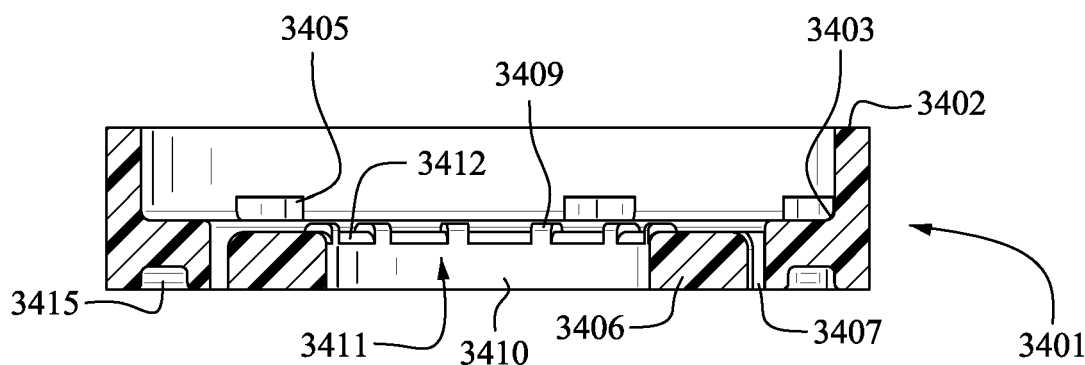

FIG. 9G shows a cross-sectional view of a vent housing according to another example of the present technology taken through line 9G-9G of FIG. 9B.

Figure 10A:
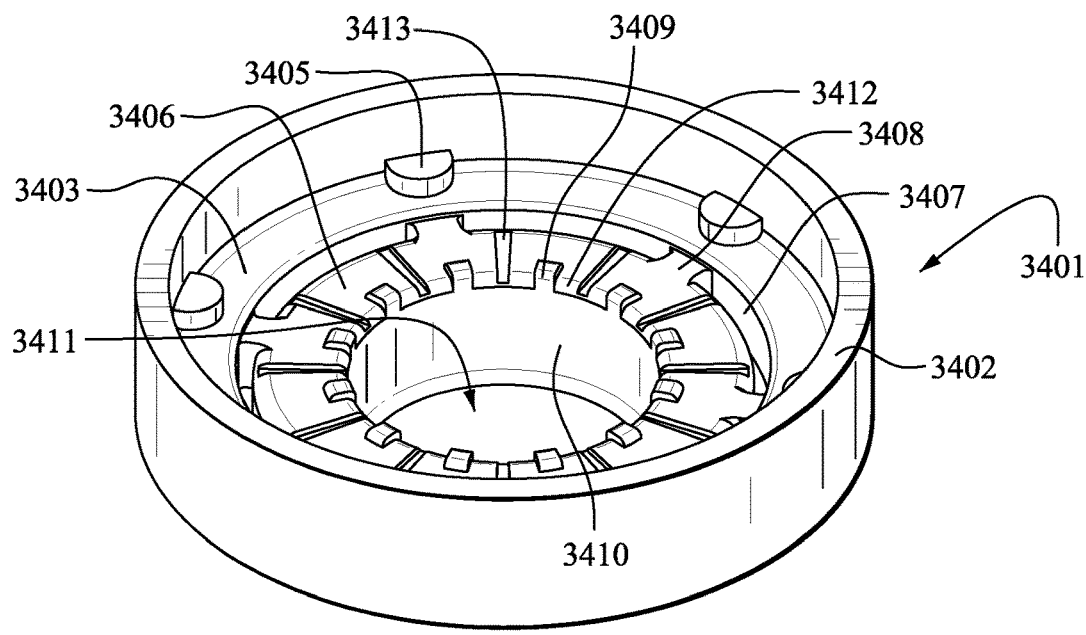

FIG. 10A shows a top perspective view of a vent housing according to another example of the present technology.

Figure 10B:
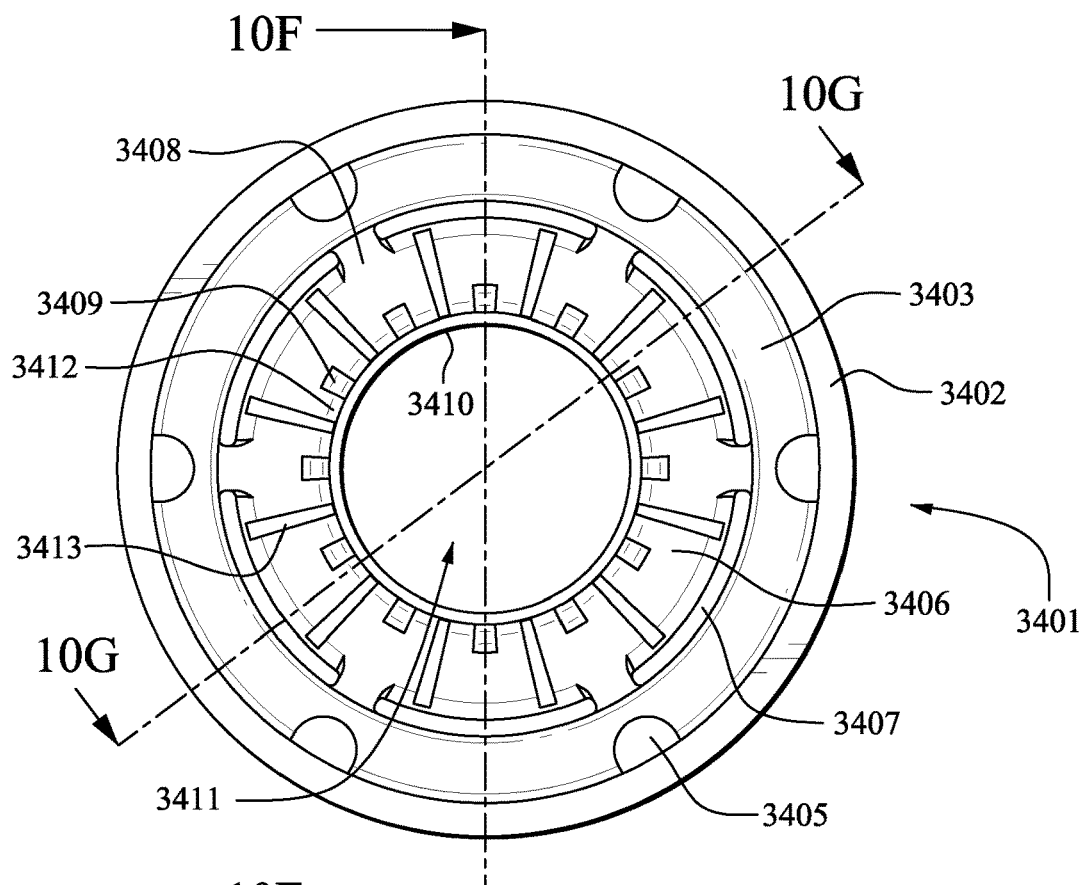

FIG. 10B shows a top view of a vent housing according to another example of the present technology.

Figure 10C:
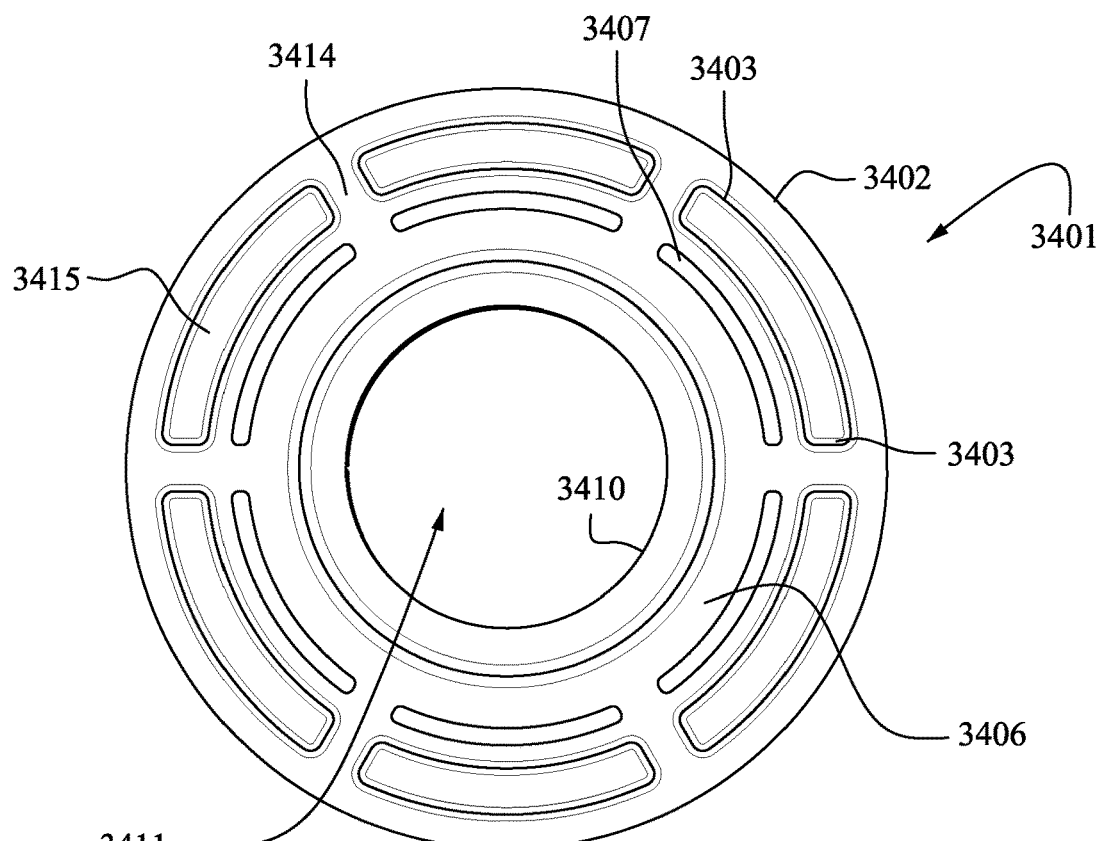

FIG. 10C shows a bottom view of a vent housing according to another example of the present technology.

Figure 10D:
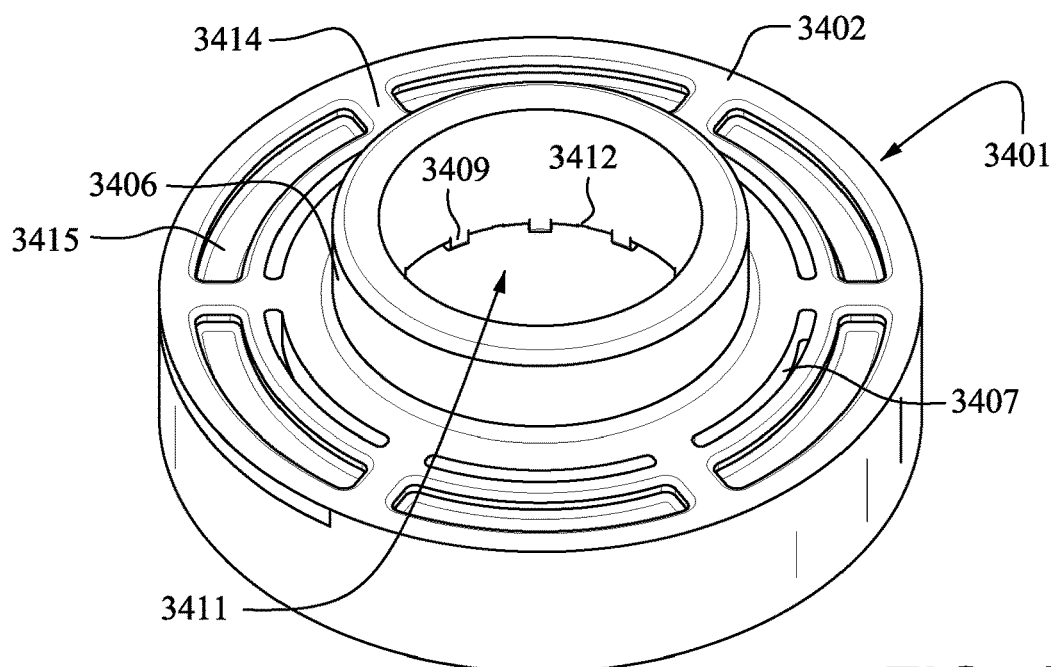

FIG. 10D shows a bottom perspective view of a vent housing according to another example of the present technology.

Figure 10E:
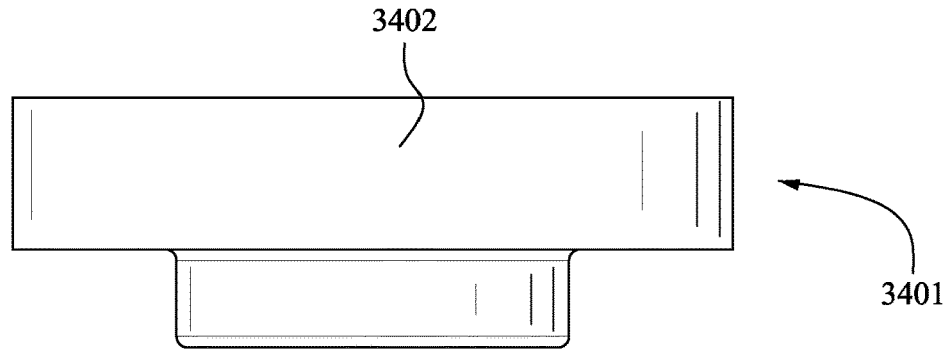

FIG. 10E shows a side view of a vent housing according to another example of the present technology.

Figure 10F:
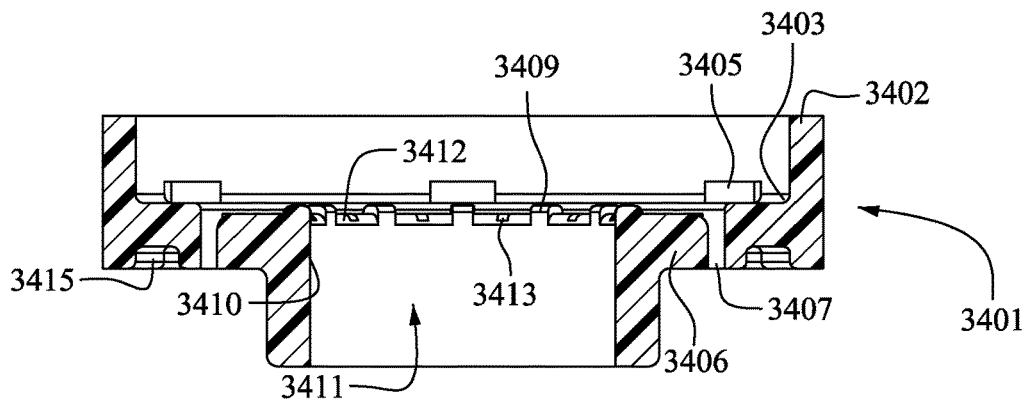

FIG. 10F shows a cross-sectional view of a vent housing according to another example of the present technology taken through line 10F-10F of FIG. 10B.

Figure 10G:
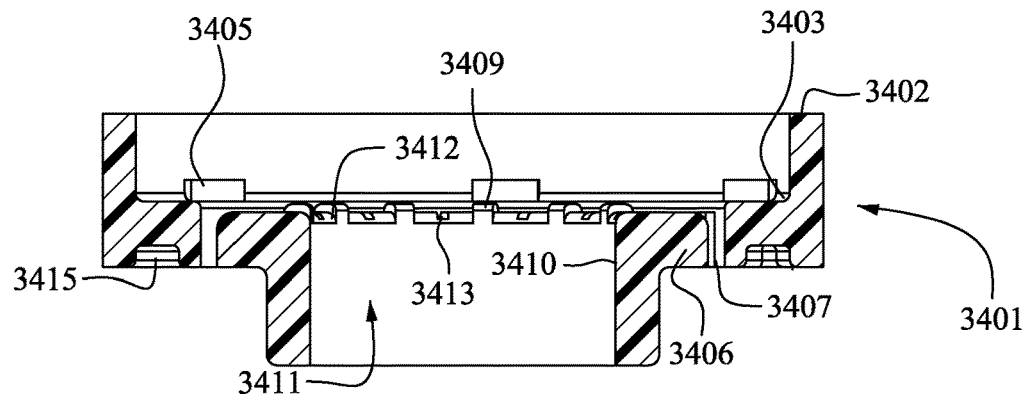

FIG. 10G shows a cross-sectional view of a vent housing according to another example of the present technology taken through line 10G-10G of FIG. 10B.

Figure 11A:
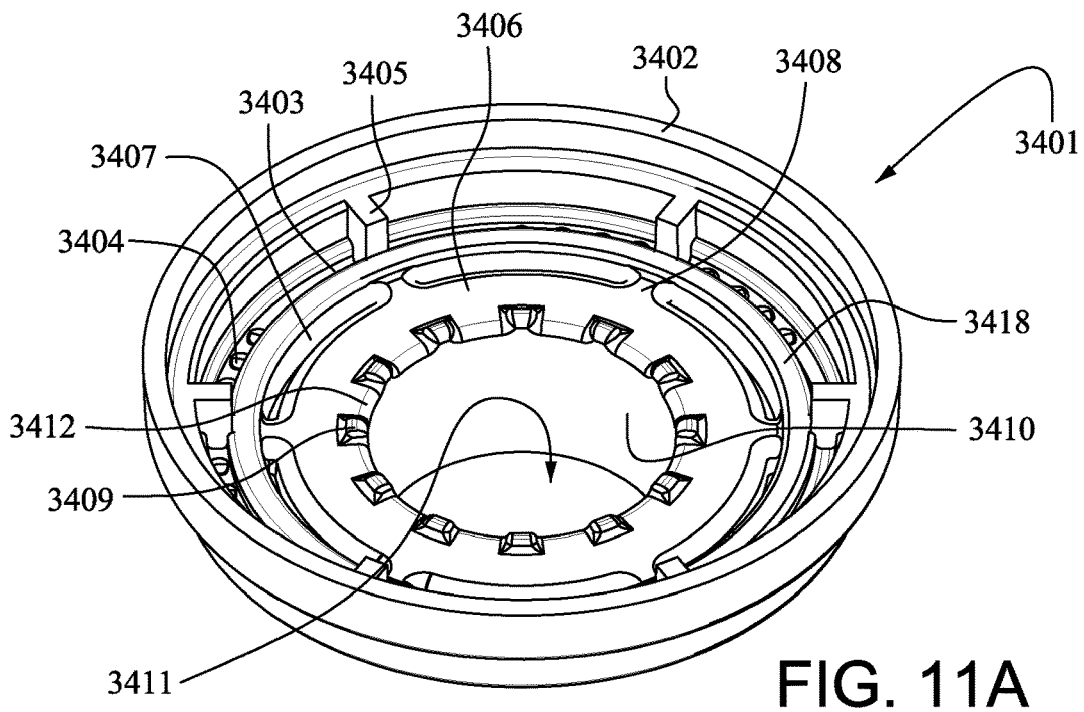

FIG. 11A shows a top perspective view of a vent housing according to another example of the present technology.

Figure 11B:
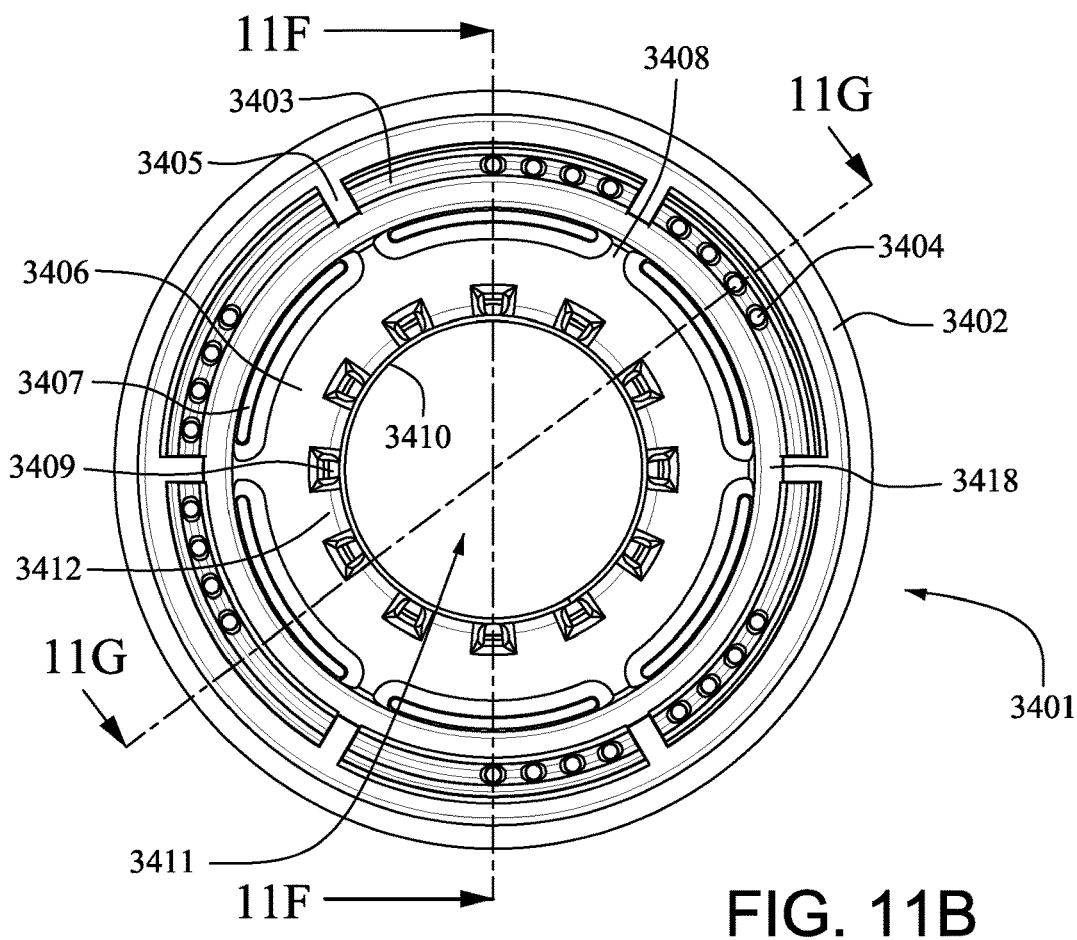

FIG. 11B shows a top view of a vent housing according to another example of the present technology.

Figure 11C:
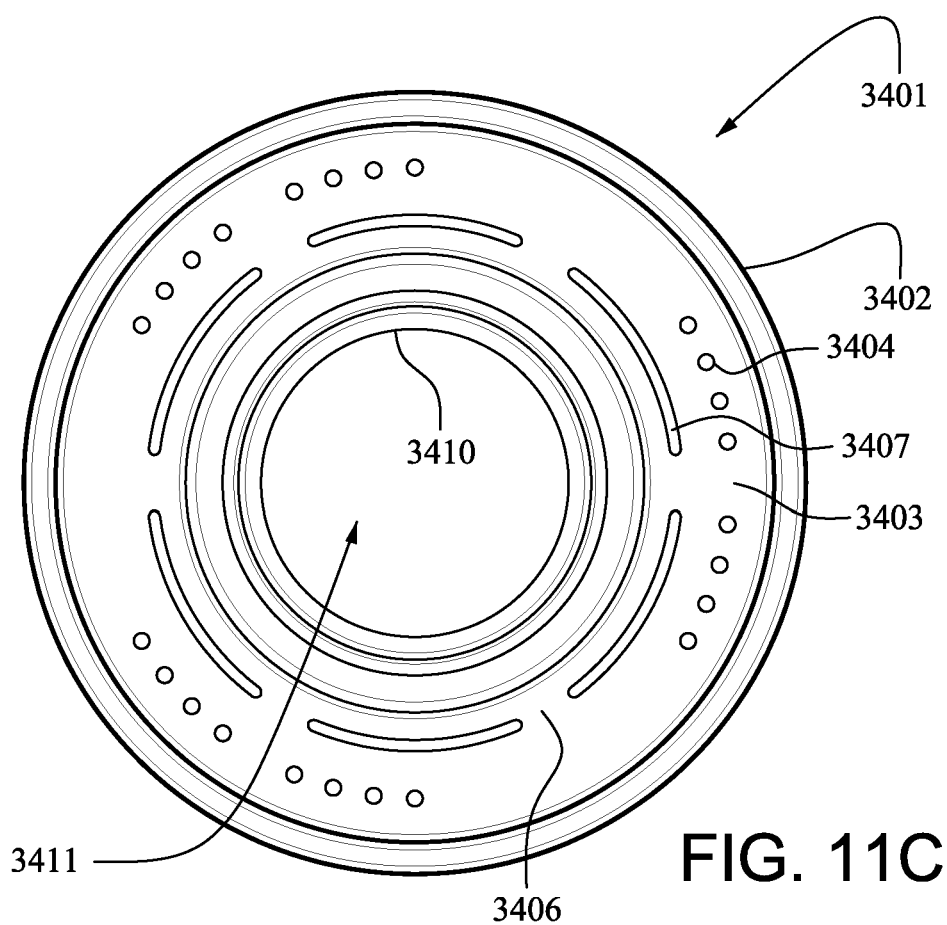

FIG. 11C shows a bottom view of a vent housing according to another example of the present technology.

Figure 11D:
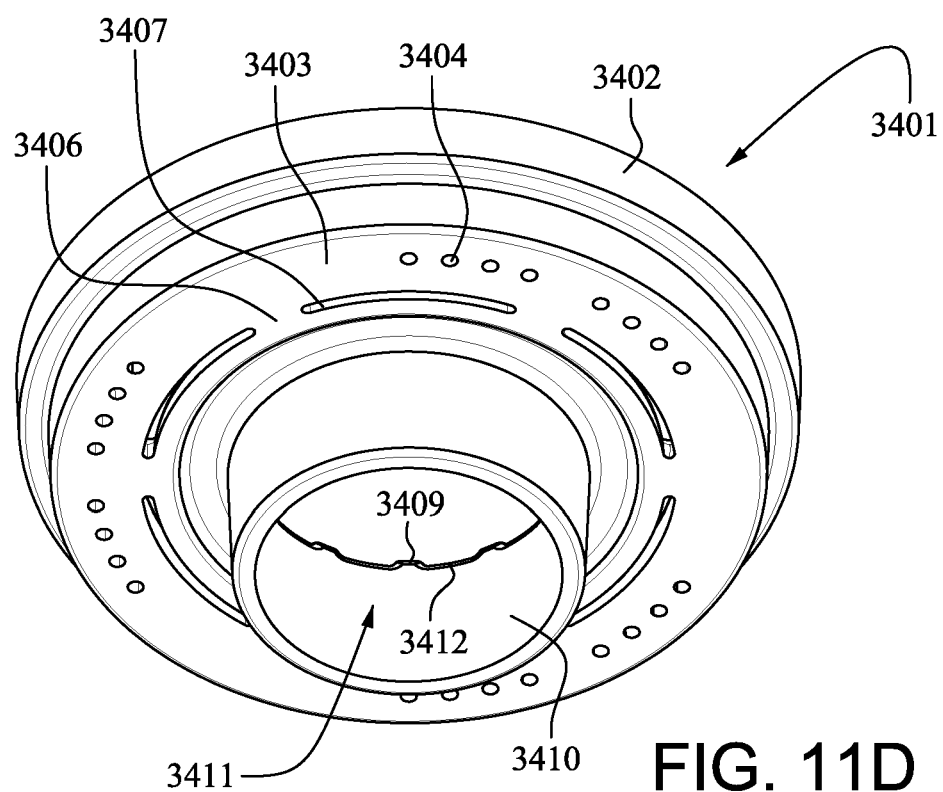

FIG. 11D shows a bottom perspective view of a vent housing according to another example of the present technology.

Figure 11E:
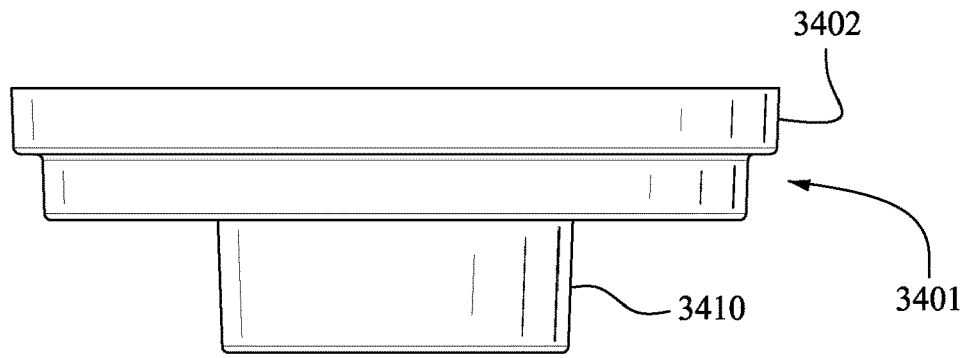

FIG. 11E shows a side view of a vent housing according to another example of the present technology.

Figure 11F:
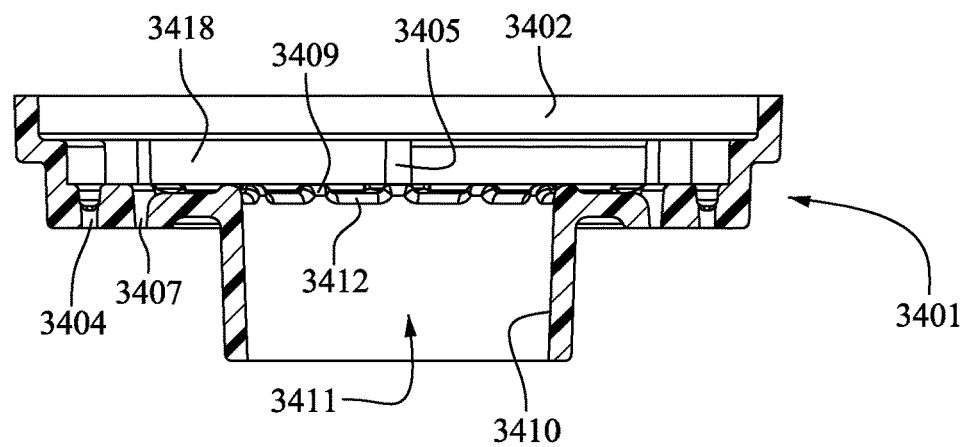

FIG. 11F shows a cross-sectional view of a vent housing according to another example of the present technology taken through line 11F-11F of FIG. 11B.

Figure 11G:
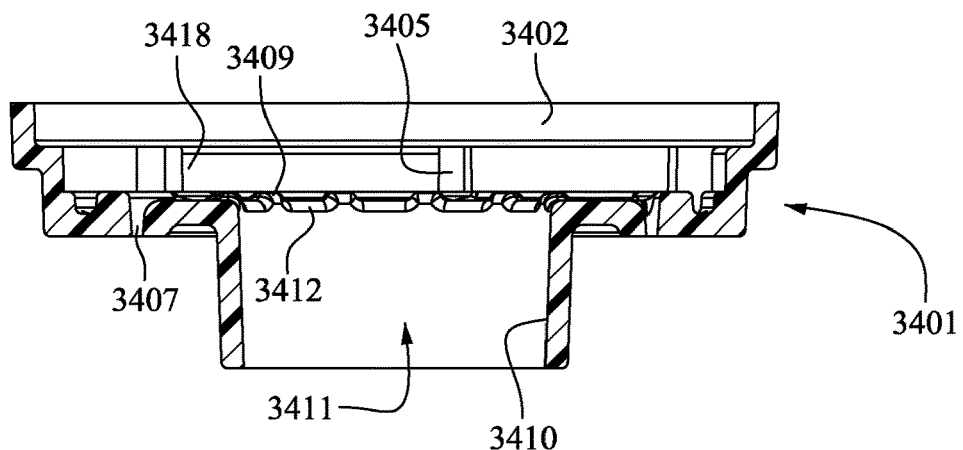

FIG. 11G shows a cross-sectional view of a vent housing according to another example of the present technology taken through line 11G-11G of FIG. 11B.

Figure 12A:
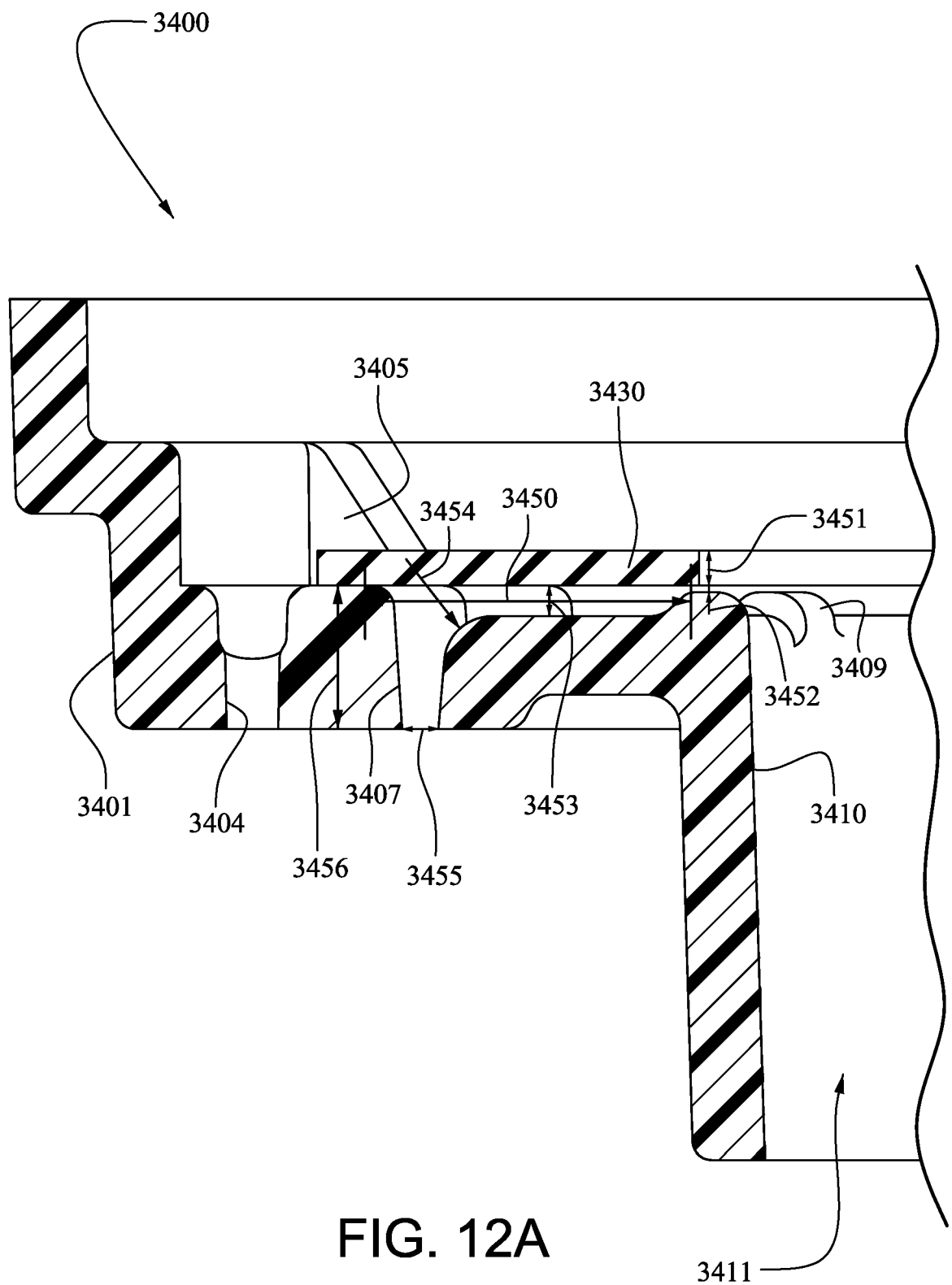

FIG. 12A depicts a partial cross-sectional view of a vent system according to an example of the present technology.

Figure 12B:
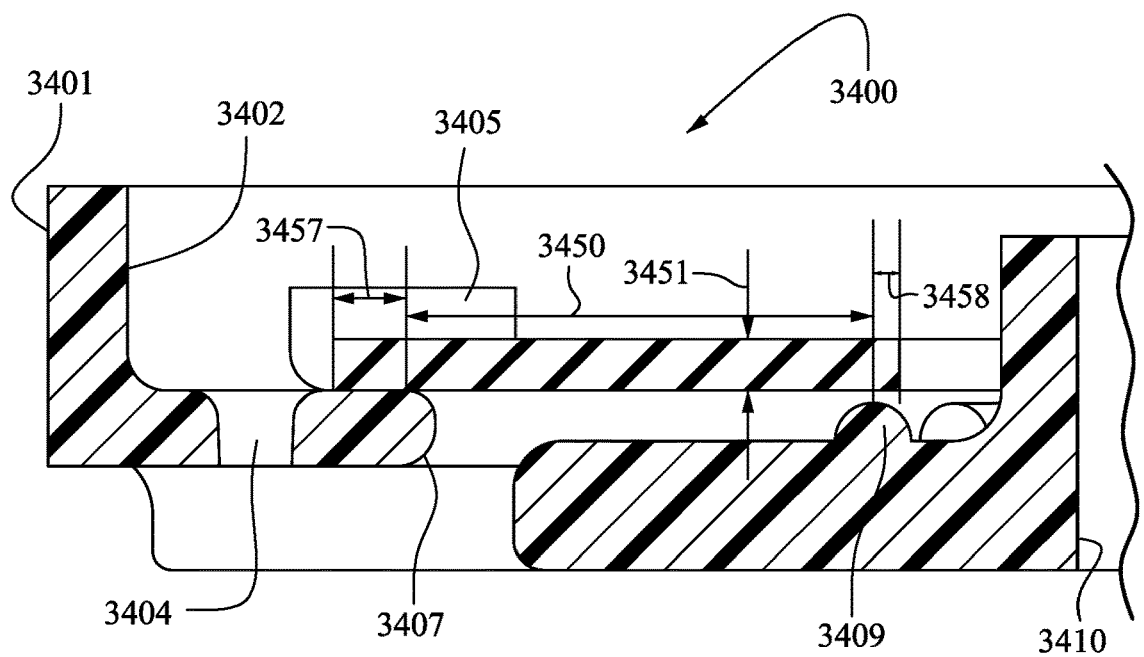

FIG. 12B depicts a partial cross-sectional view of a vent system according to an example of the present technology.

Figure 13:
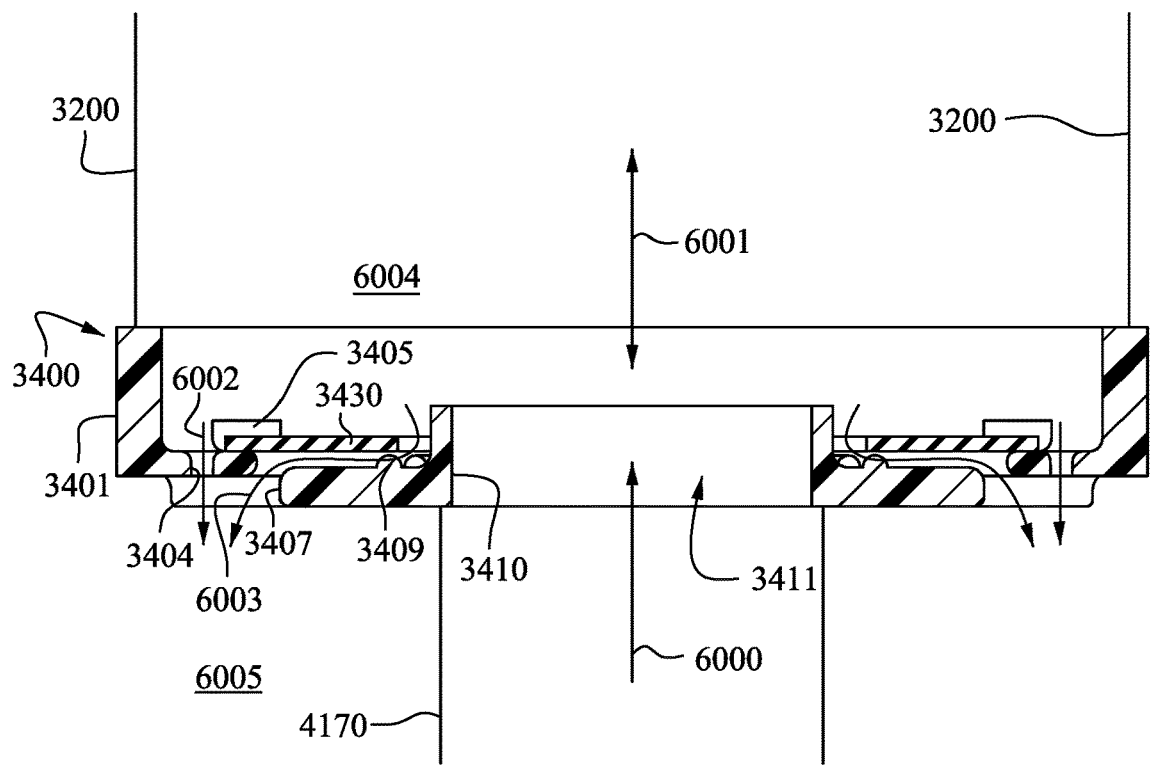

FIG. 13 depicts a cross-sectional view of a vent system according to an example of the present technology.

Figure 14A:
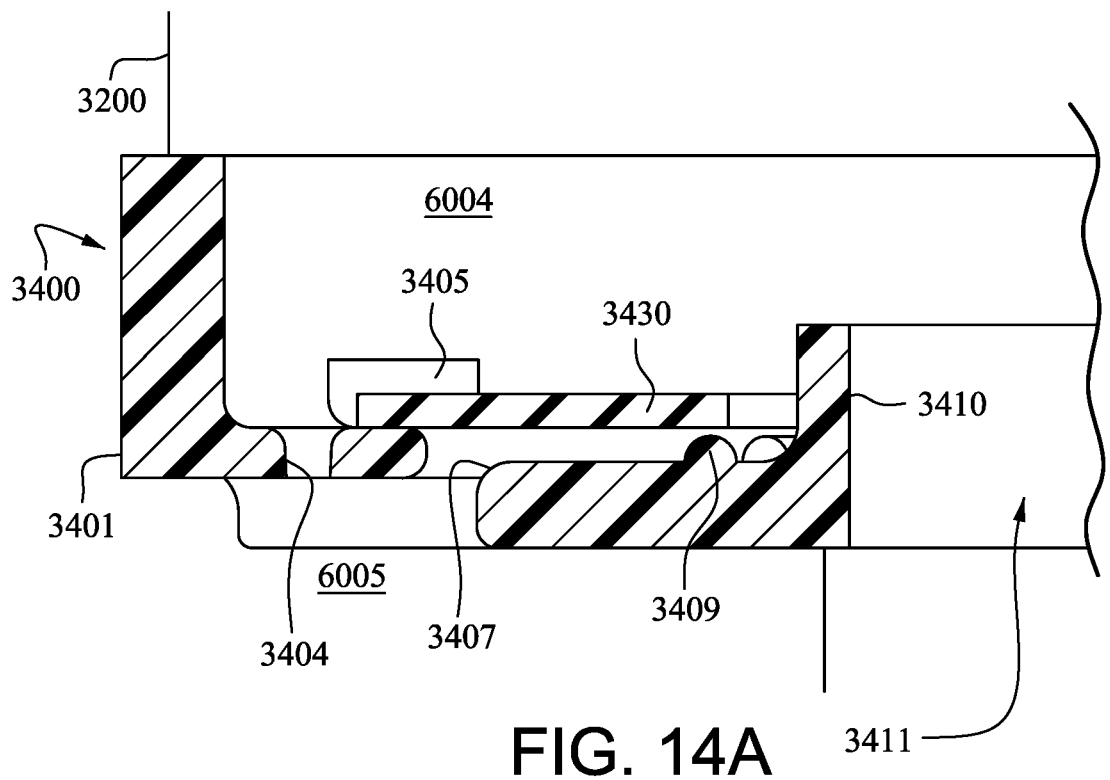

FIG. 14A depicts a partial cross-sectional view of a vent system according to an example of the present technology.

Figure 14B:
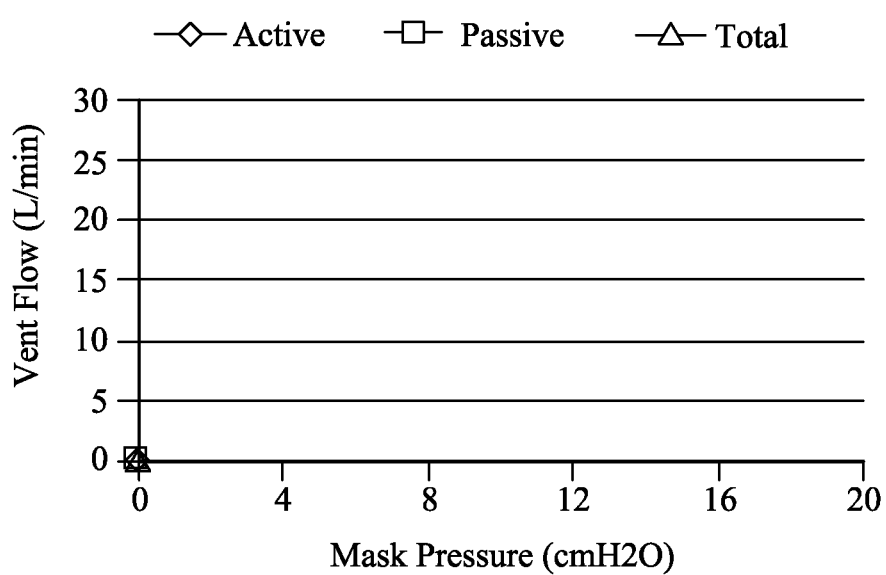

FIG. 14B depicts a graph of vent flow rates versus mask pressures for the vent system of FIG. 14A.

Figure 15A:
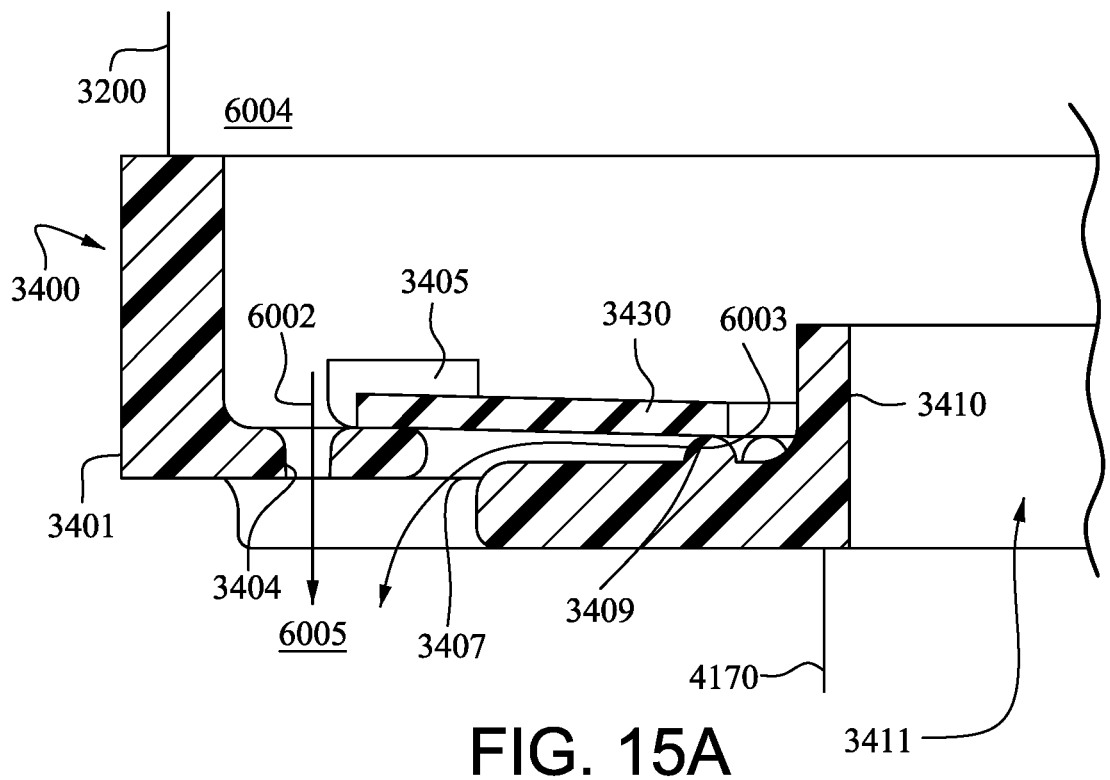

FIG. 15A depicts a partial cross-sectional view of a vent system according to an example of the present technology.

Figure 15B:
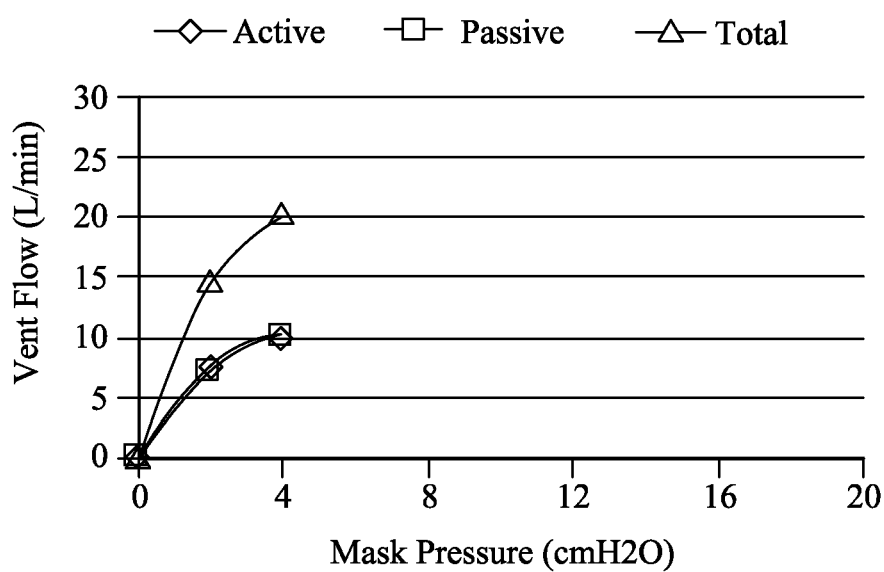

FIG. 15B depicts a graph of vent flow rates versus mask pressures for the vent system of FIG. 15A.

Figure 16A:
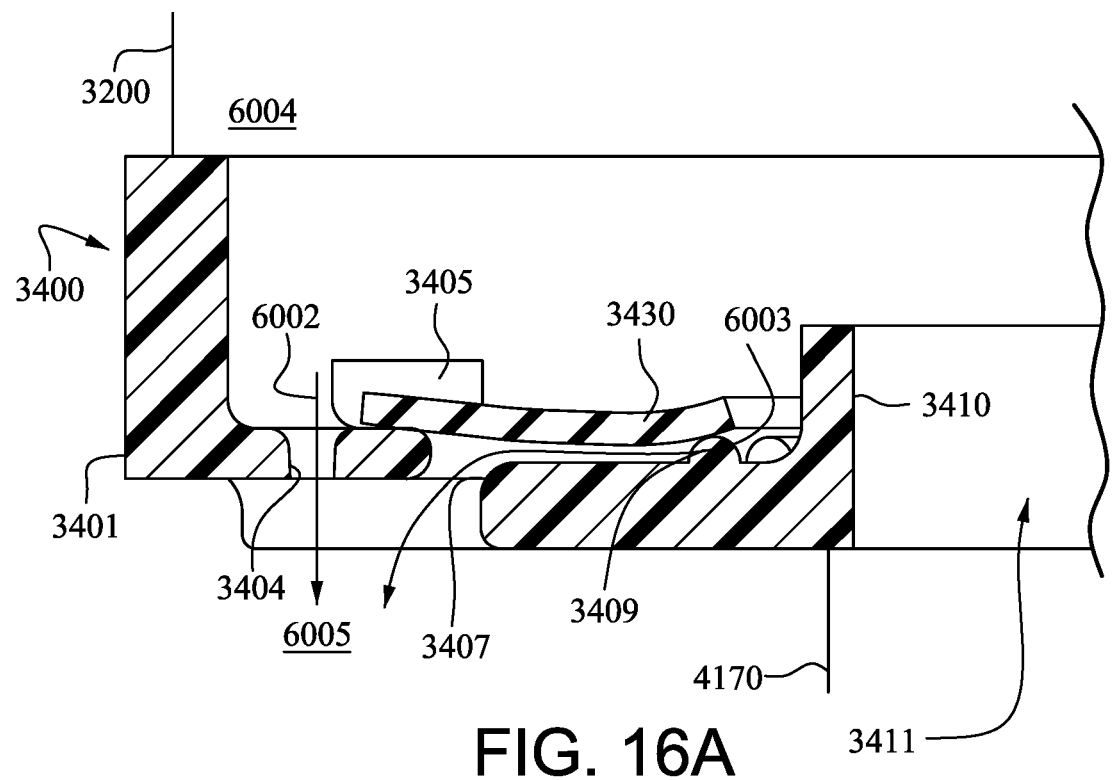

FIG. 16A depicts a partial cross-sectional view of a vent system according to an example of the present technology.

Figure 16B:
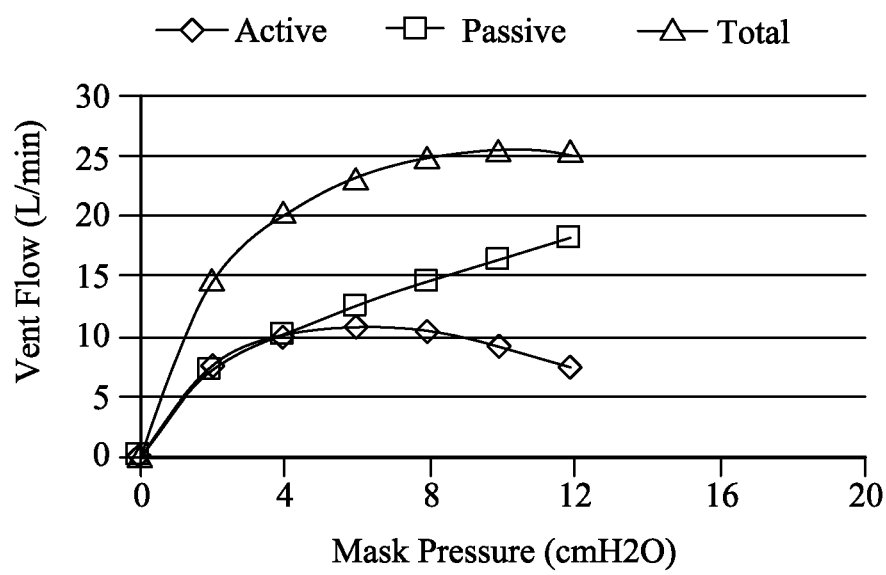

FIG. 16B depicts a graph of vent flow rates versus mask pressures for the vent system of FIG. 16A.

Figure 17A:
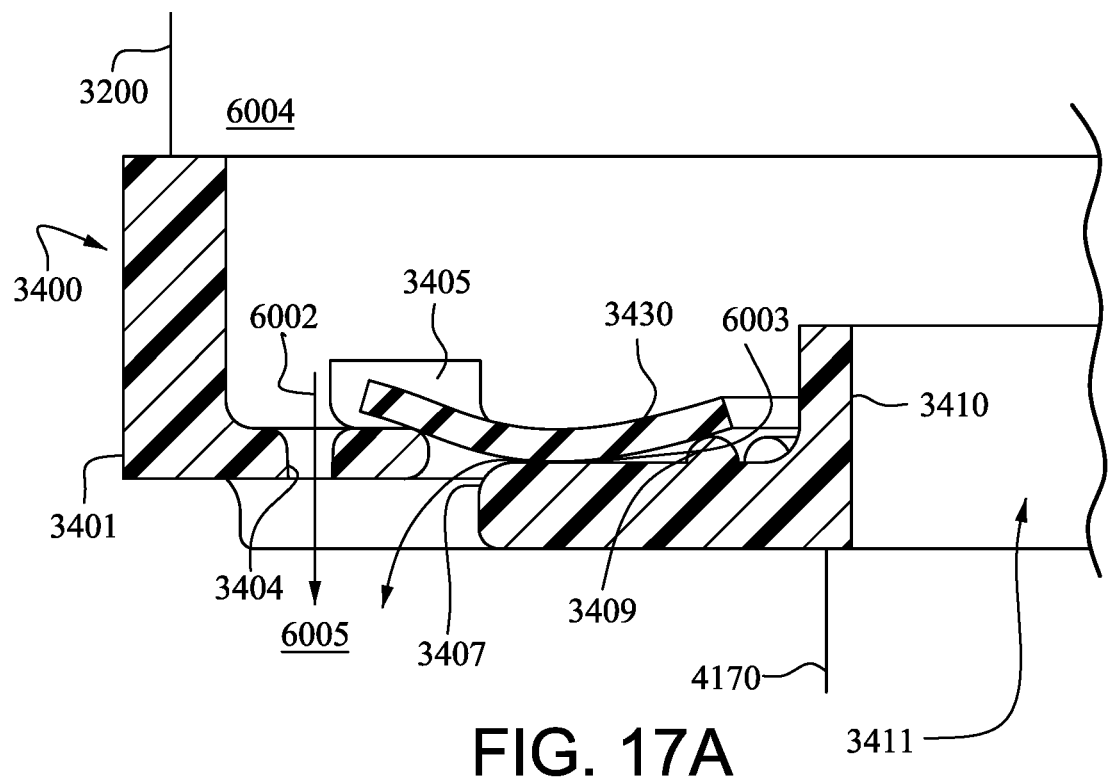

FIG. 17A depicts a partial cross-sectional view of a vent system according to an example of the present technology.

Figure 17B:
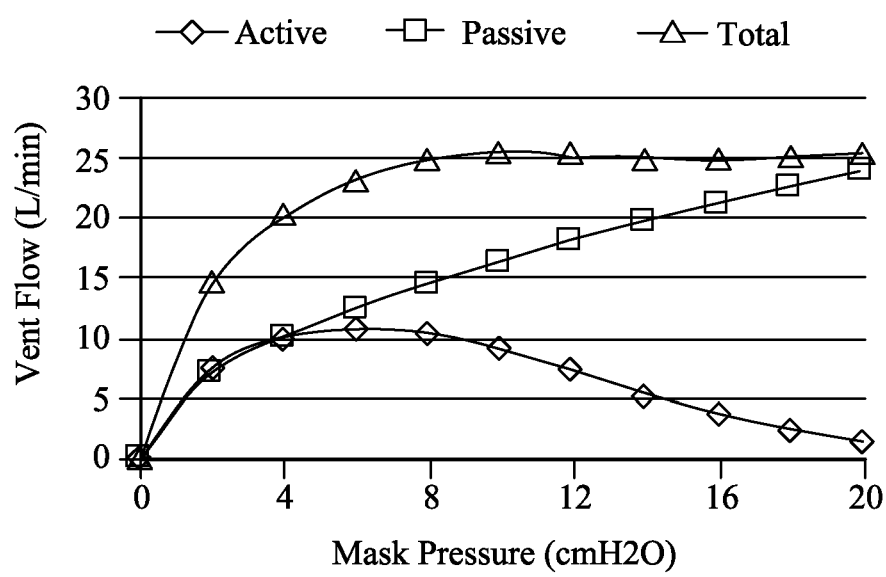

FIG. 17B depicts a graph of vent flow rates versus mask pressures for the vent system of FIG. 17A.

Figure 18:
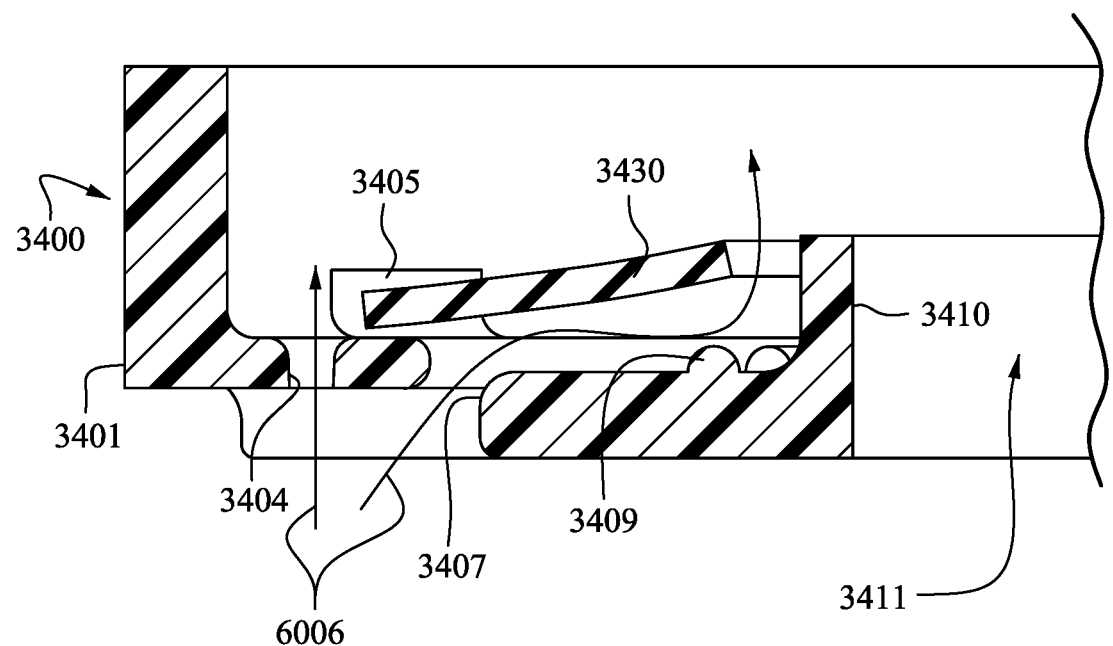

FIG. 18 depicts a partial cross-sectional view of a vent system according to an example of the present technology.

Figure 19:
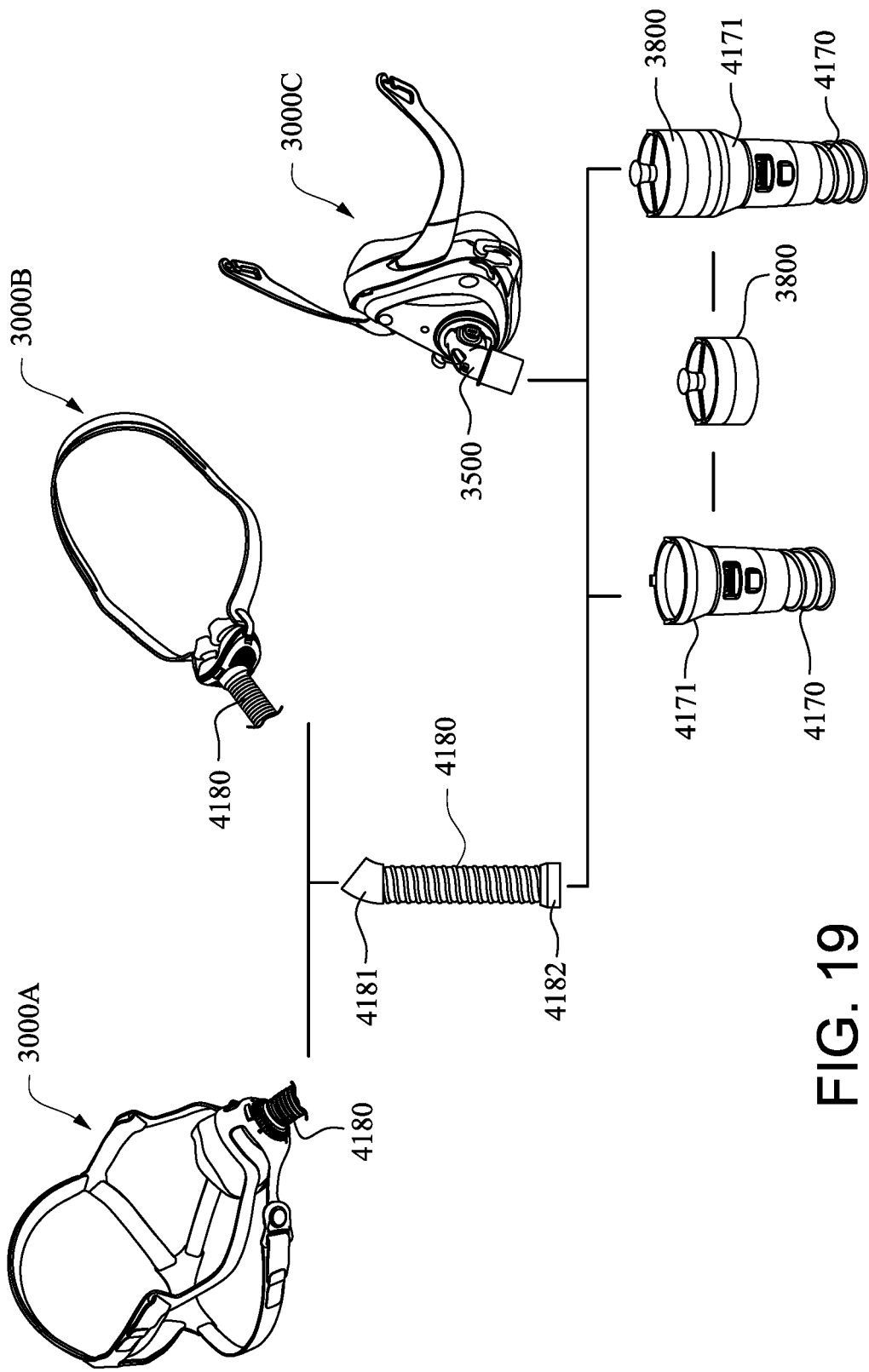

FIG. 19 depicts a schematic showing options for using vent systems of the present technology with various patient interfaces.

Figure 20A:
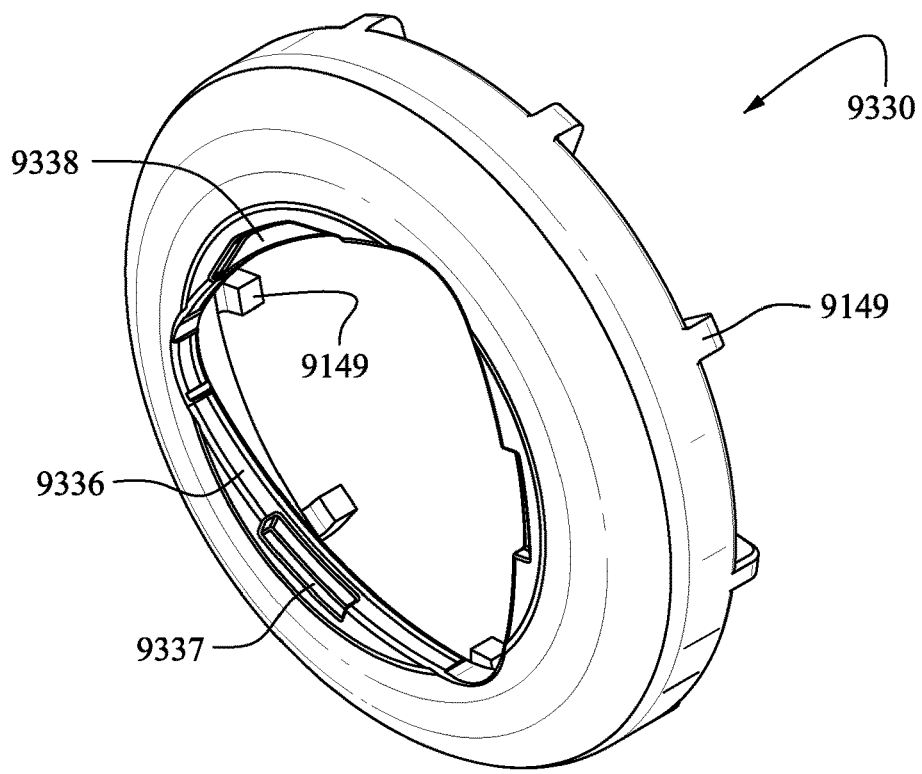

FIG. 20A depicts a front perspective view of a vent diffuser cover according to an example of the present technology.

Figure 20B:
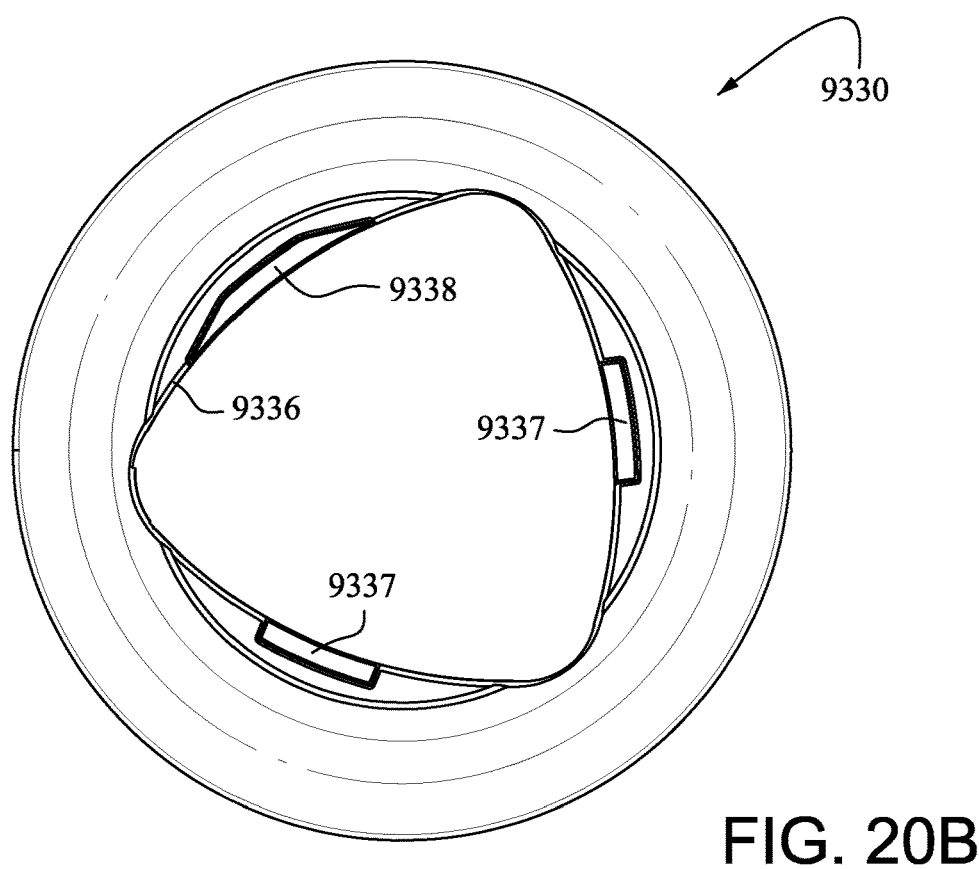

FIG. 20B depicts a front view of a vent diffuser cover according to an example of the present technology.

Figure 20C:
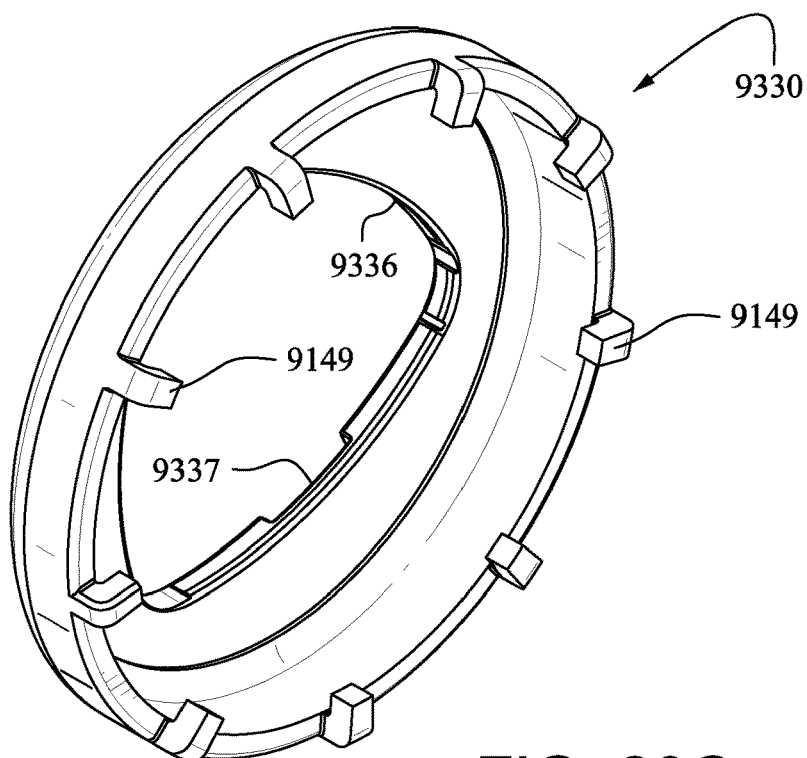

FIG. 20C depicts a rear perspective view of a vent diffuser cover according to an example of the present technology.

Figure 20D:
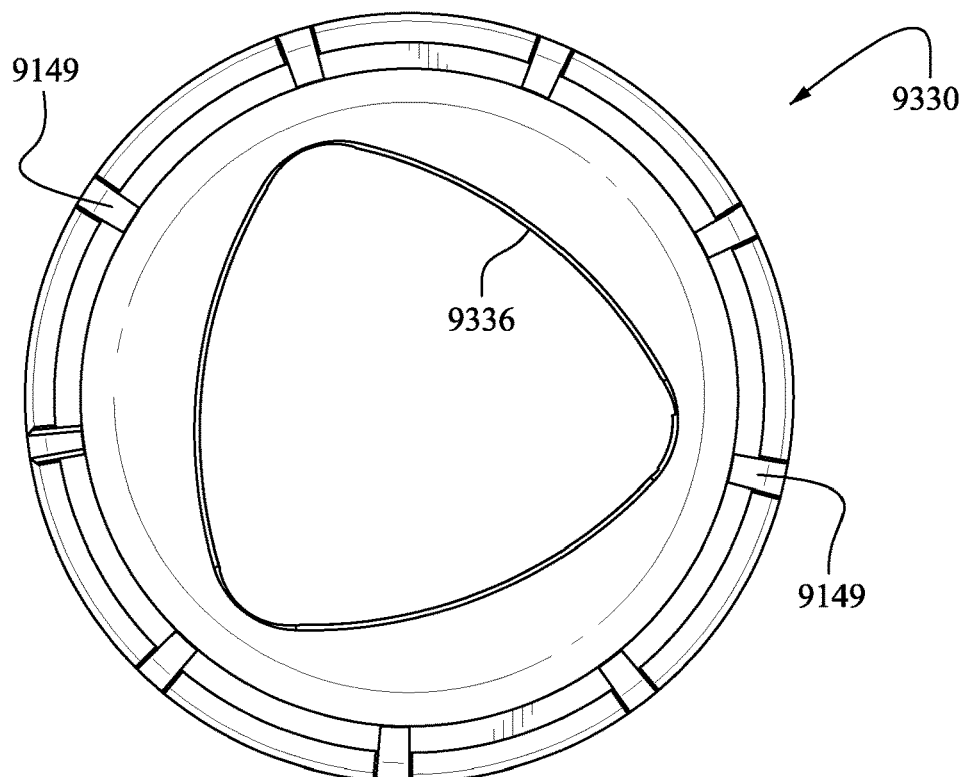

FIG. 20D depicts a rear view of a vent diffuser cover according to an example of the present technology.

Figure 20E:
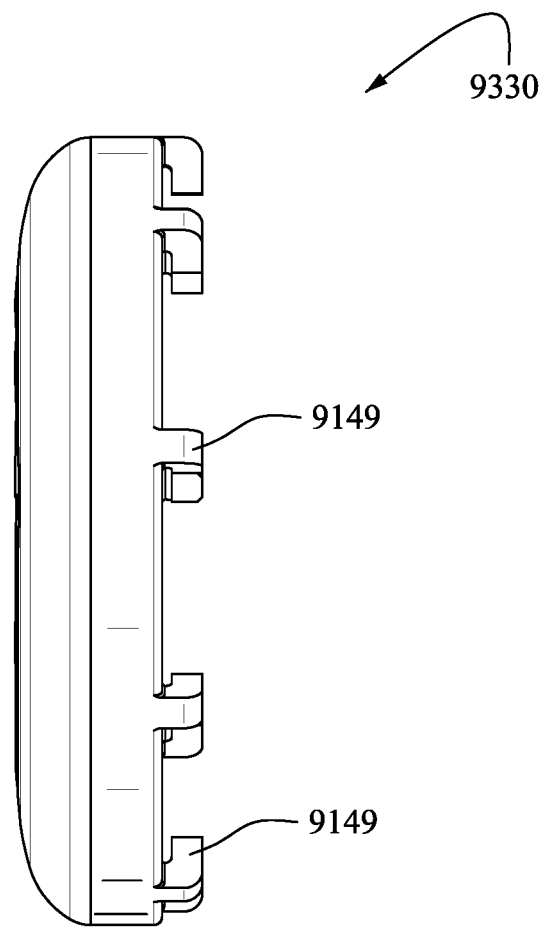

FIG. 20E depicts a side view of a vent diffuser cover according to an example of the present technology.

Figure 21A:
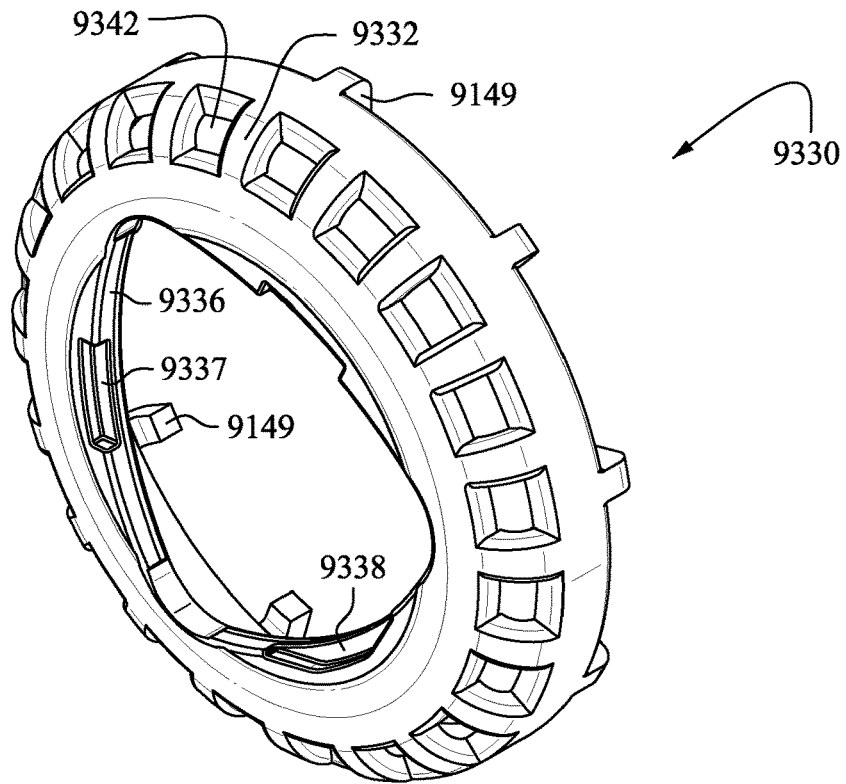

FIG. 21A depicts a front perspective view of a vent diffuser cover according to an example of the present technology.

Figure 21B:
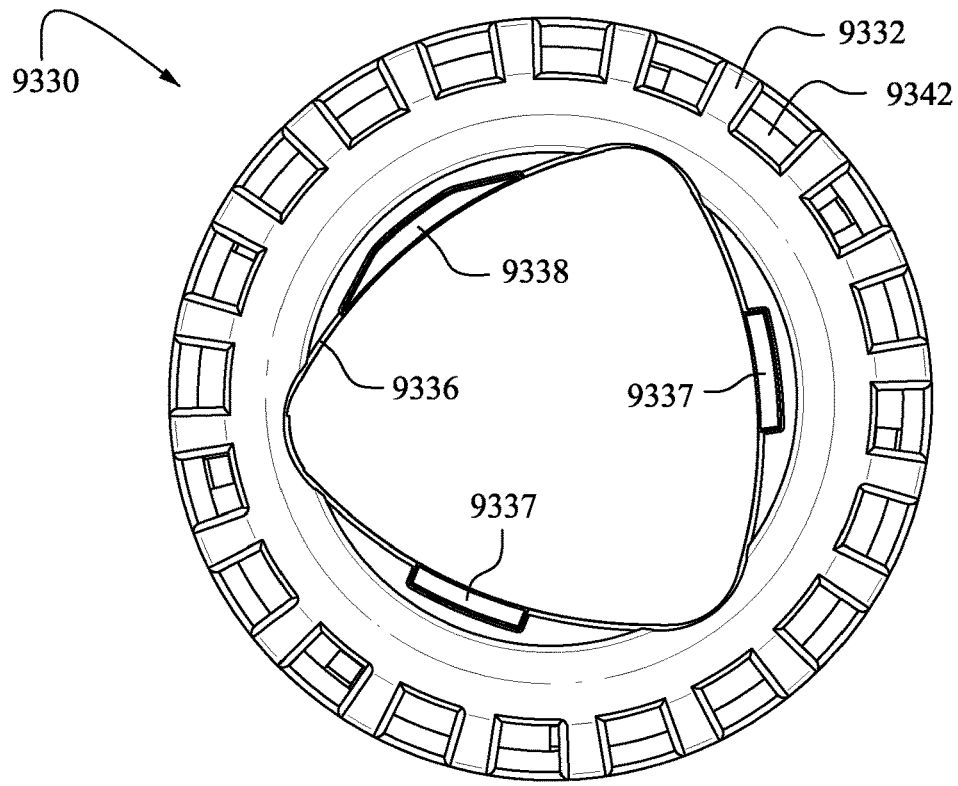

FIG. 21B depicts a front view of a vent diffuser cover according to an example of the present technology.

Figure 21C:
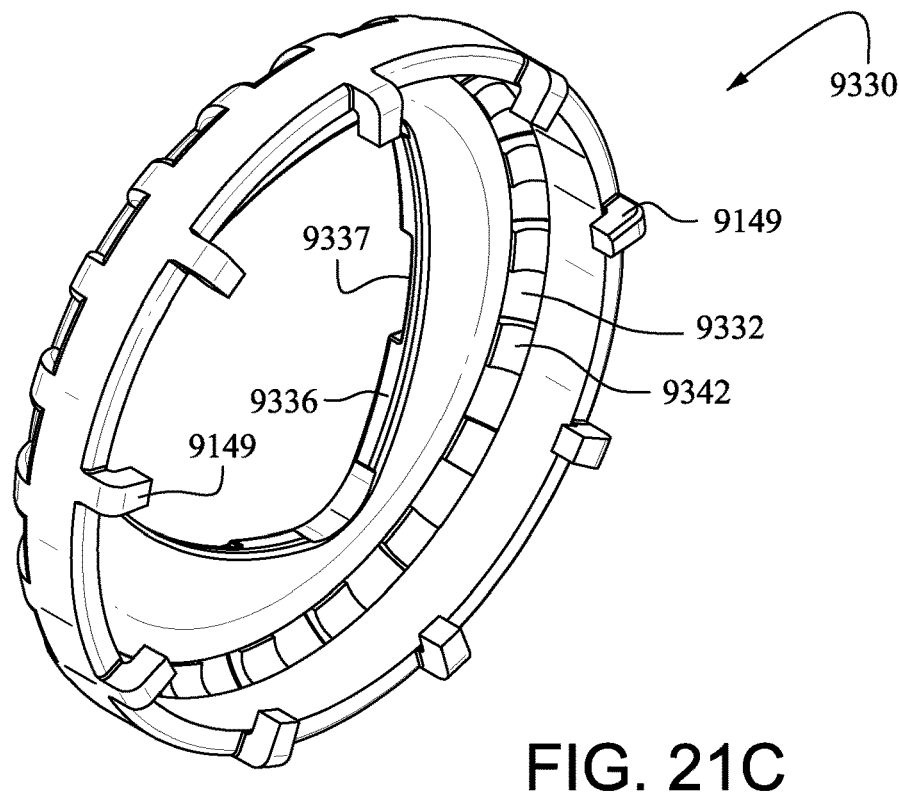

FIG. 21C depicts a rear perspective view of a vent diffuser cover according to an example of the present technology.

Figure 21D:
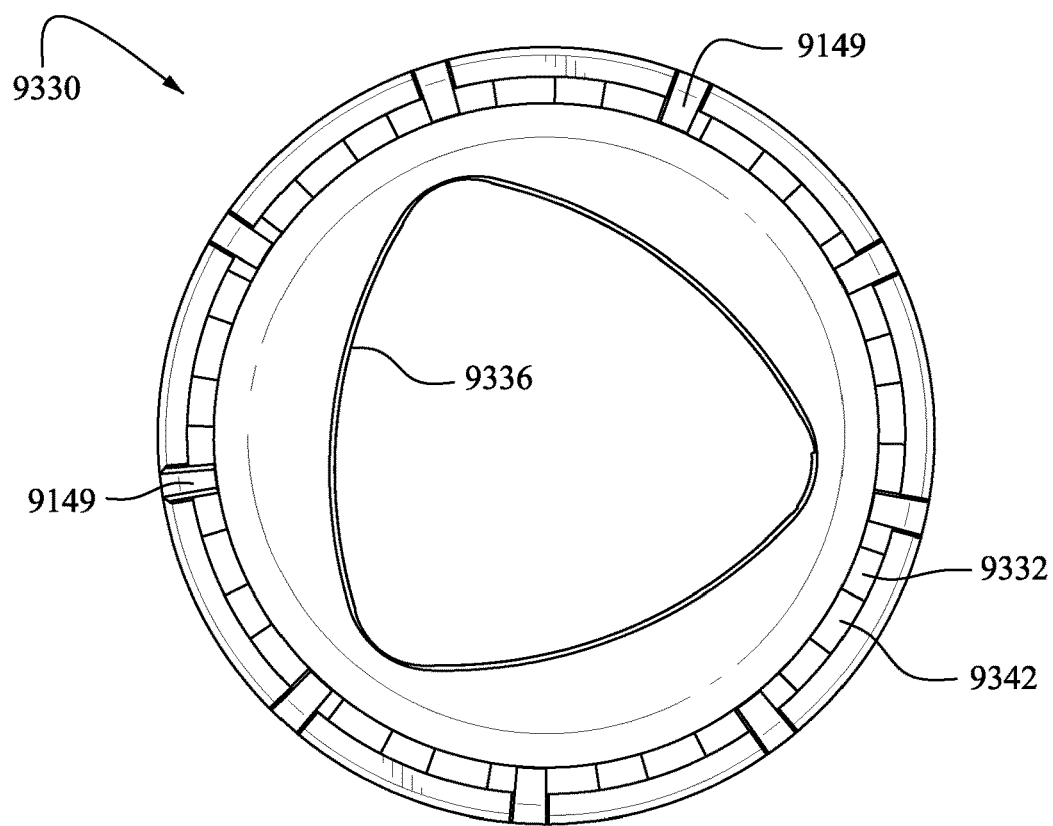

FIG. 21D depicts a rear view of a vent diffuser cover according to an example of the present technology.

Figure 21E:
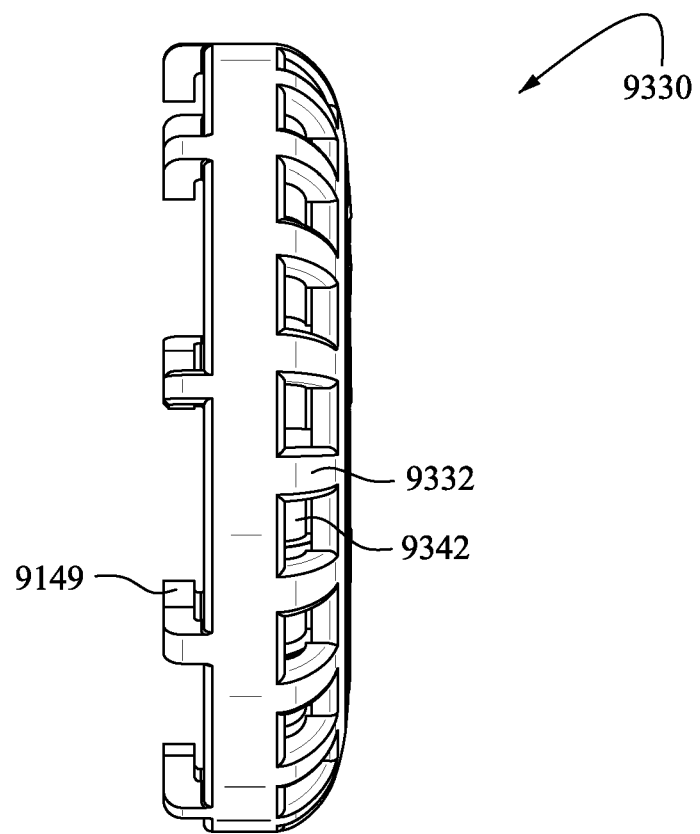

FIG. 21E depicts a side view of a vent diffuser cover according to an example of the present technology.

Figure 22A:
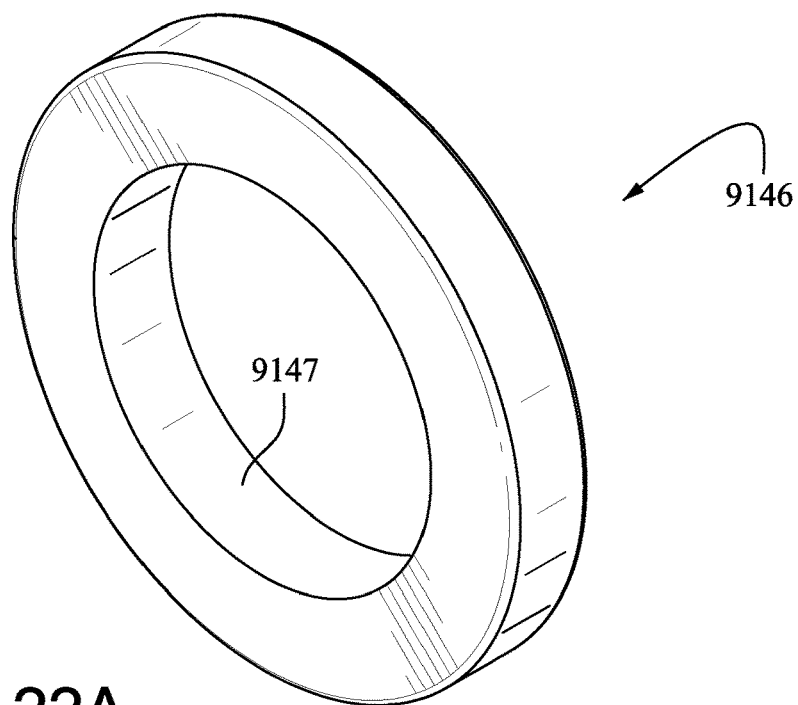

FIG. 22A depicts a front perspective view of a vent diffuser according to an example of the present technology.

Figure 22B:
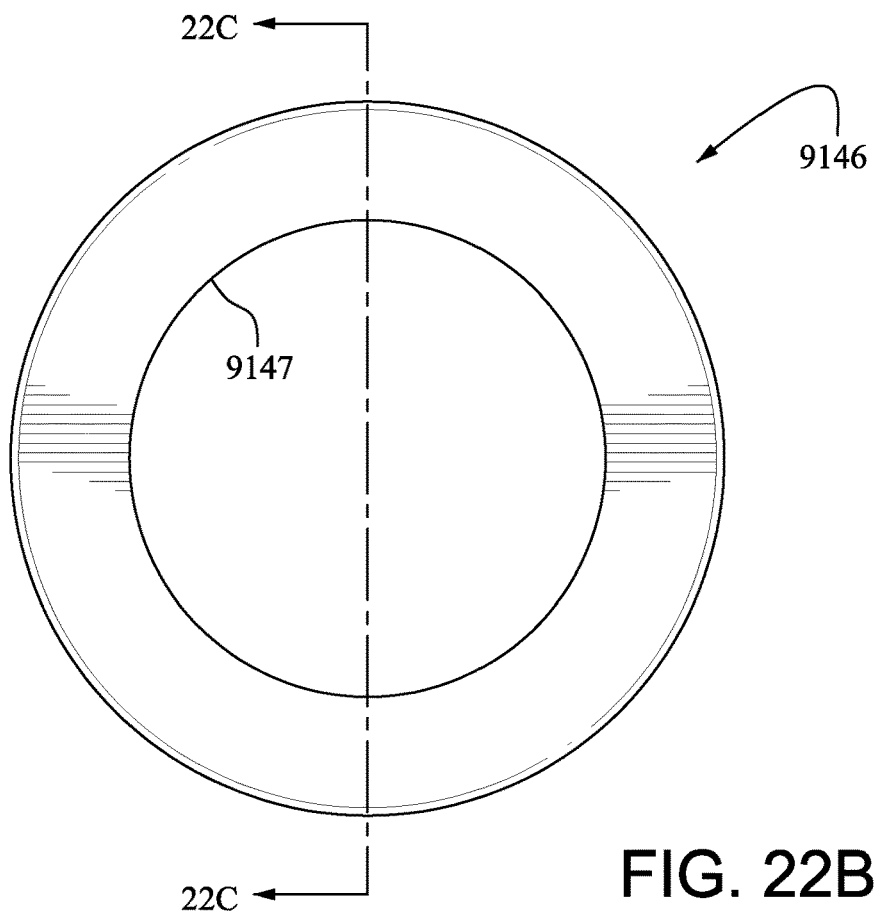

FIG. 22B depicts a front view of a vent diffuser according to an example of the present technology.

Figure 22C:
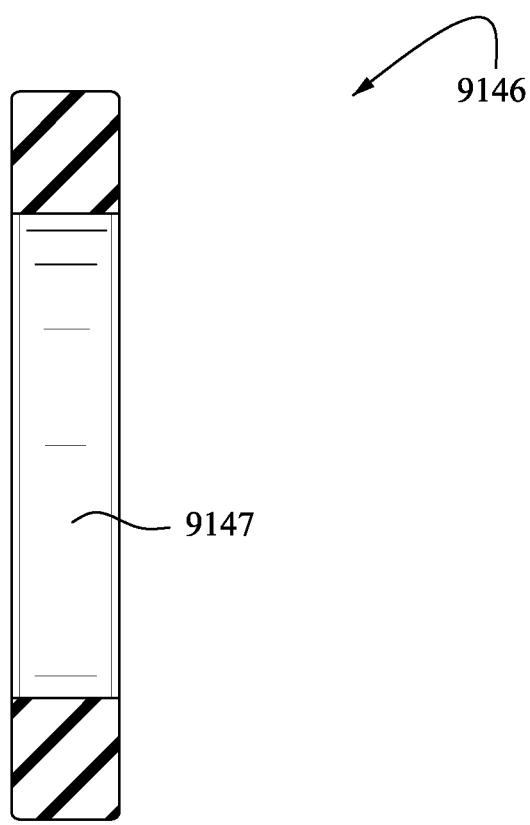

FIG. 22C depicts a cross-sectional view of a vent diffuser taken through line 22C-22C of FIG. 22B according to an example of the present technology.

Figure 23A:
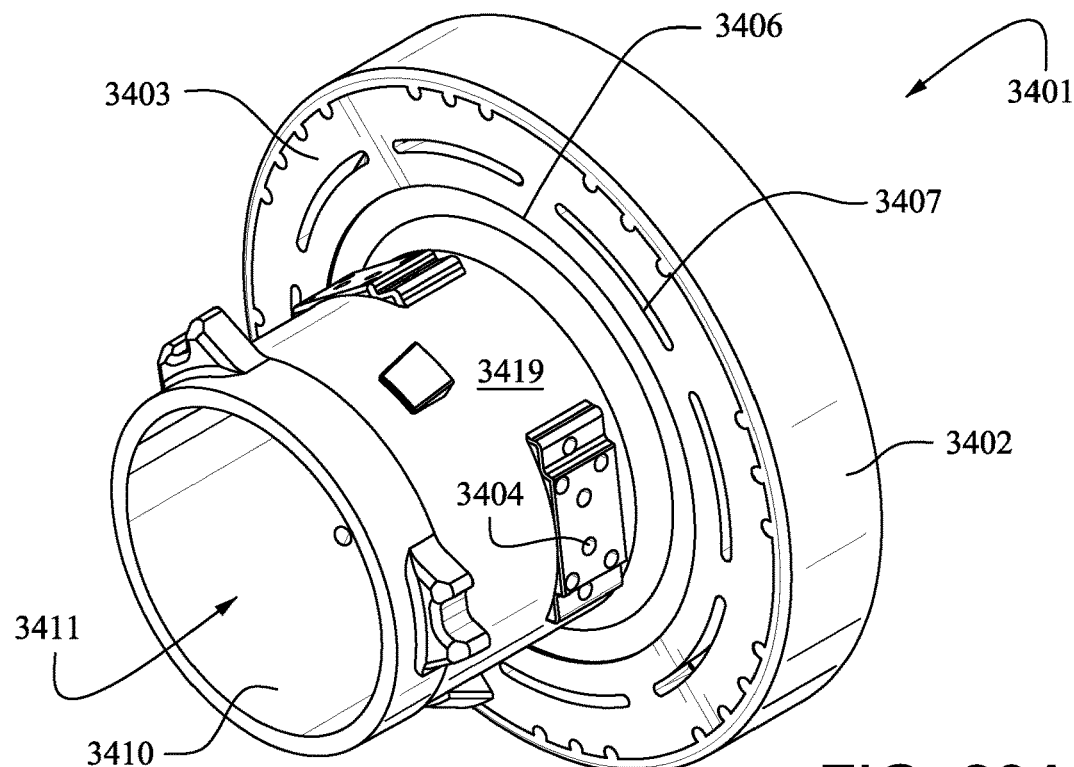

FIG. 23A depicts a front perspective view of a vent housing according to an example of the present technology.

Figure 23B:
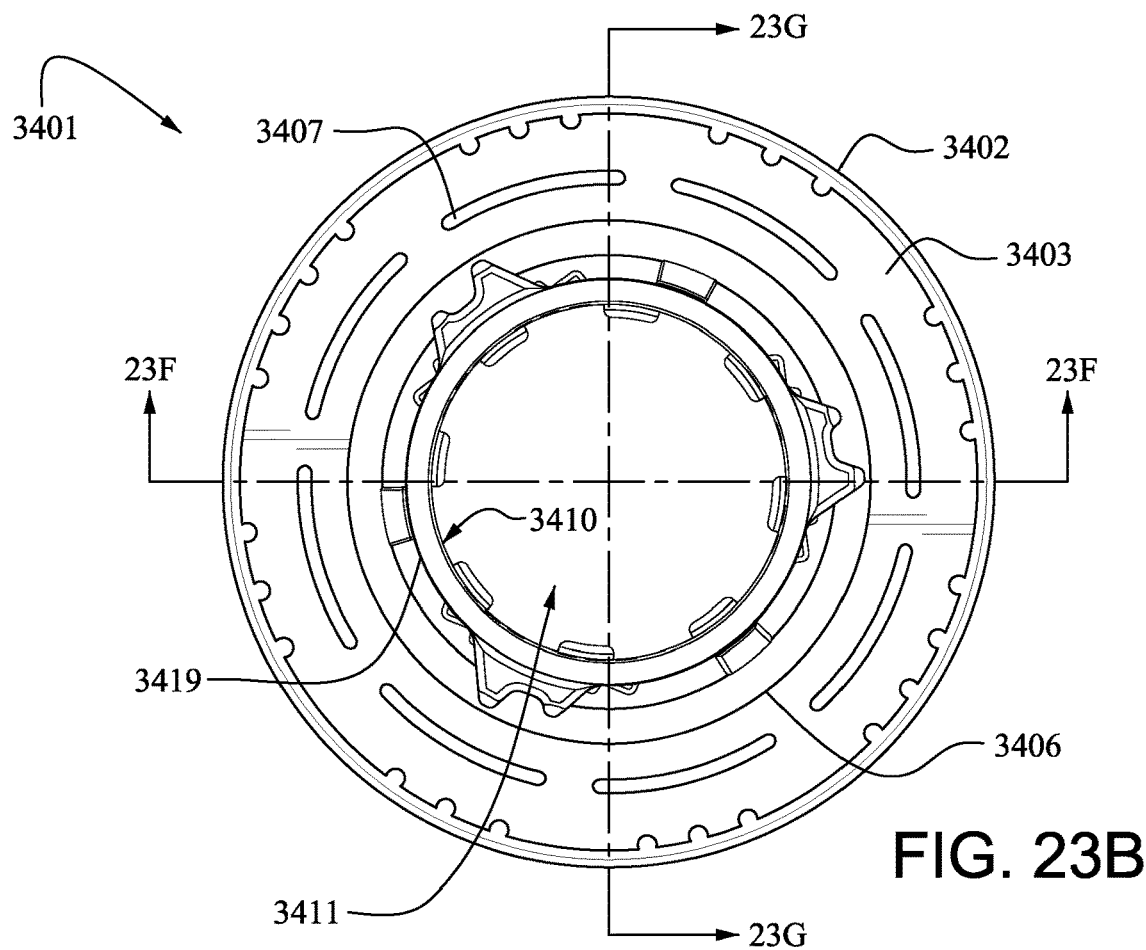

FIG. 23B depicts a front view of a vent housing according to an example of the present technology.

Figure 23C:
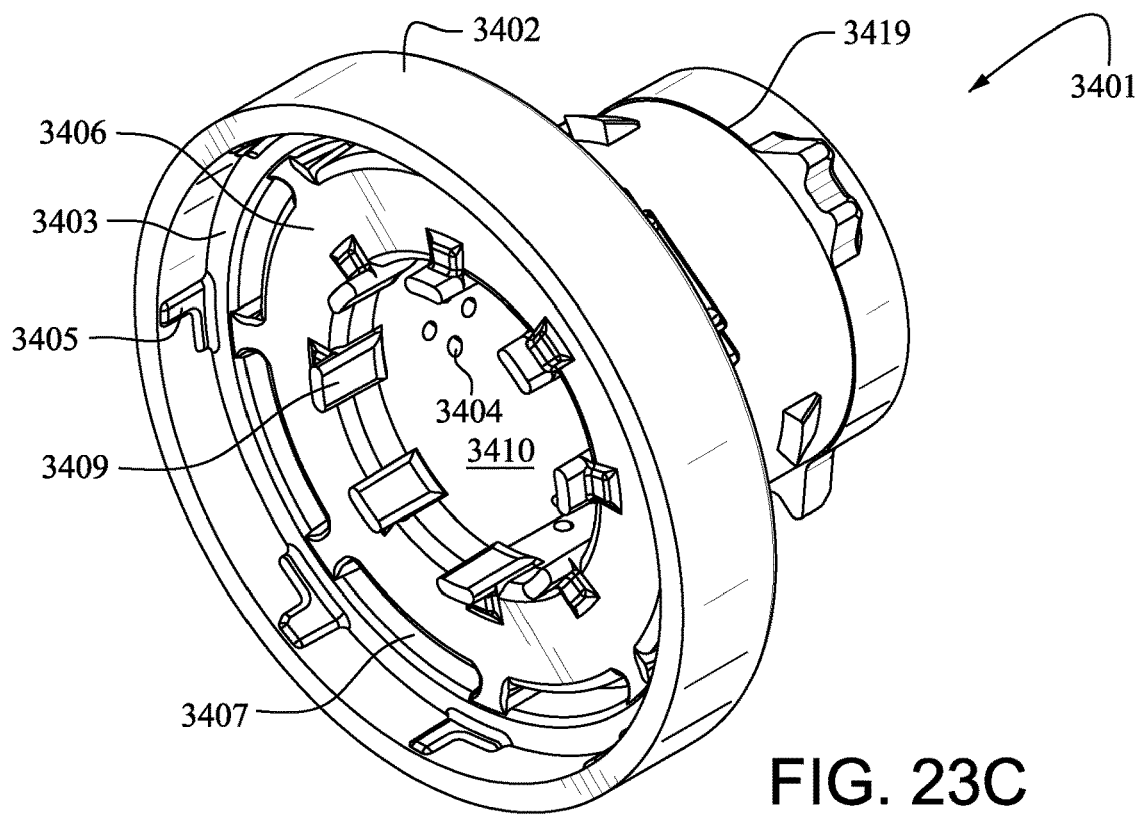

FIG. 23C depicts a rear perspective view of a vent housing according to an example of the present technology.

Figure 23D:
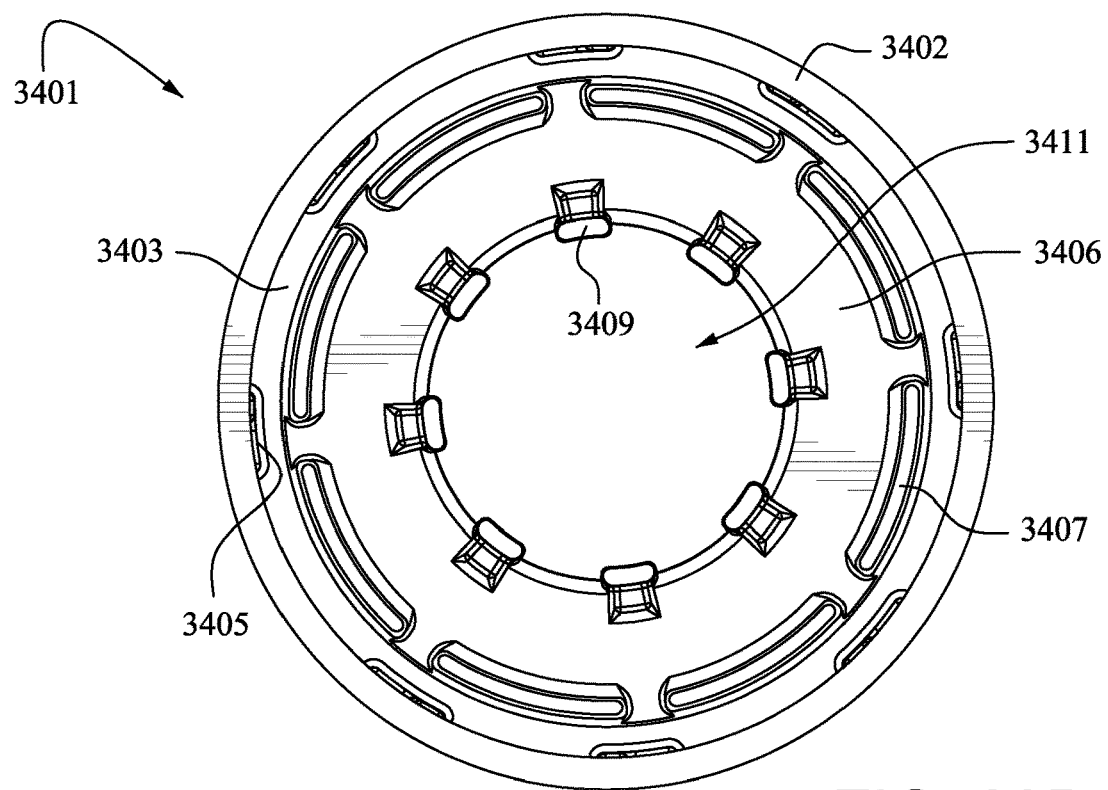

FIG. 23D depicts a rear view of a vent housing according to an example of the present technology.

Figure 23E:
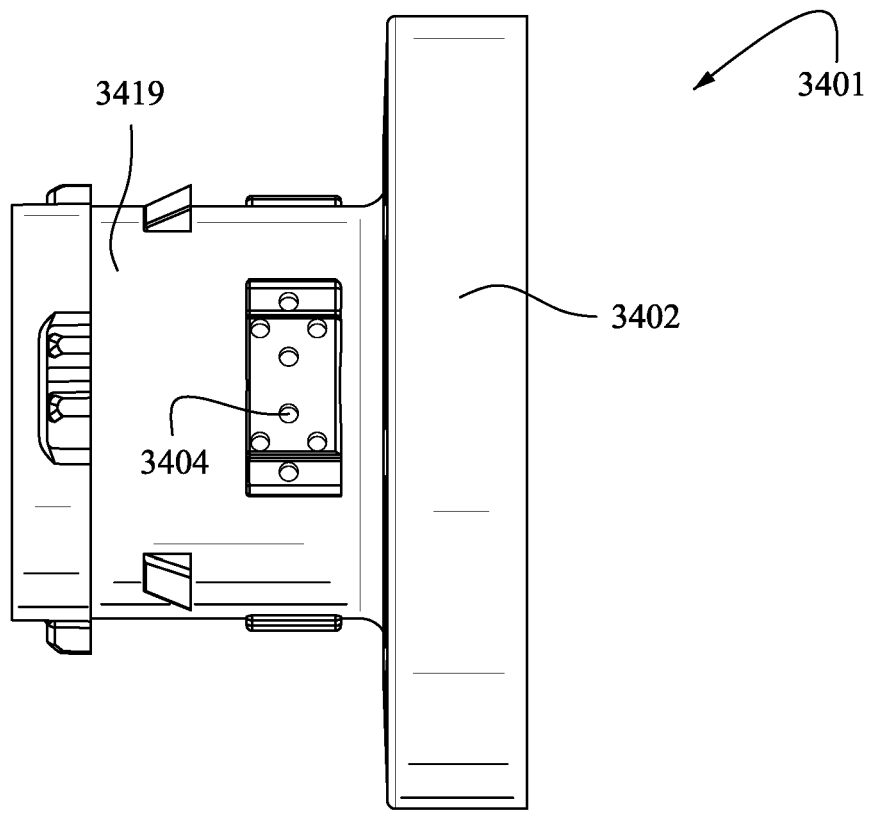

FIG. 23E depicts a side view of a vent housing according to an example of the present technology.

Figure 23F:
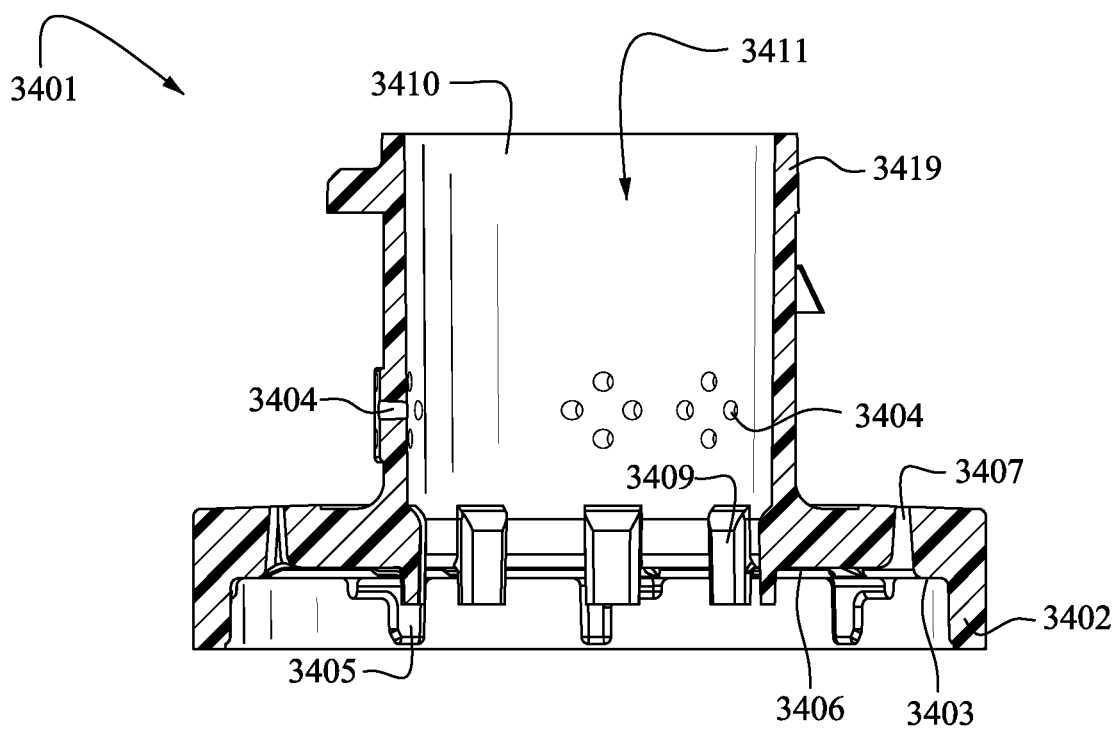

FIG. 23F depicts a cross-sectional view of a vent housing taken through line 23F-23F of FIG. 23B according to an example of the present technology.

Figure 23G:
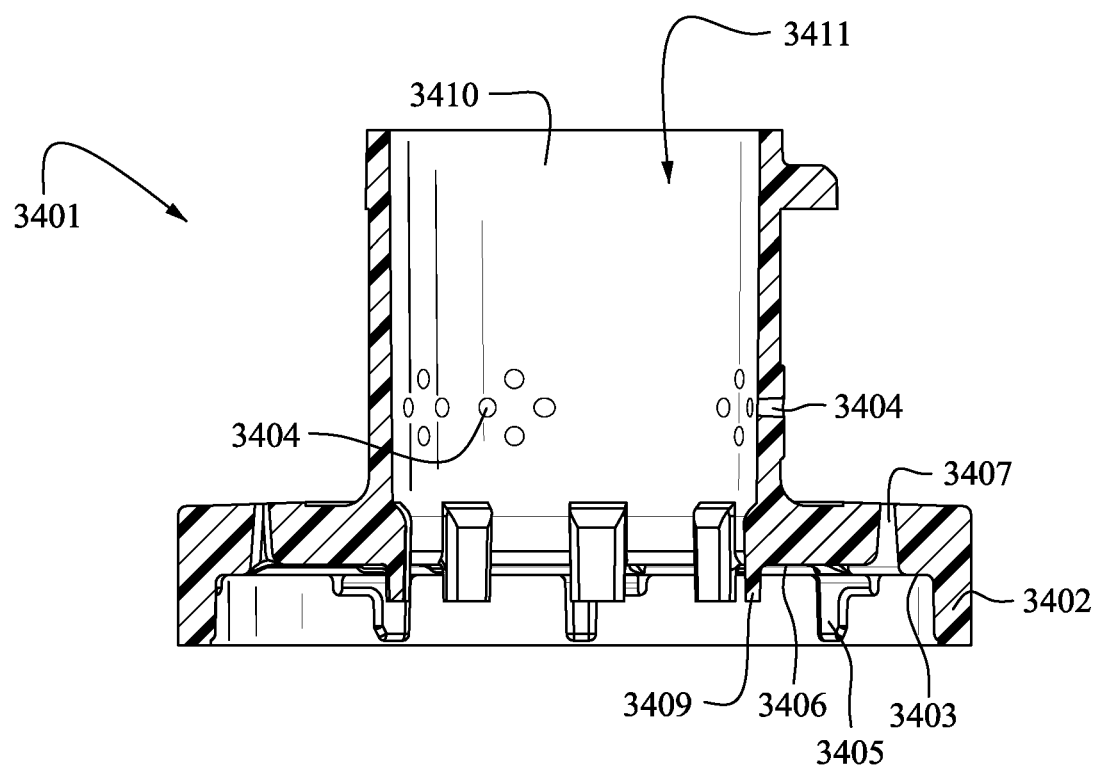

FIG. 23G depicts a cross-sectional view of a vent housing taken through line 23G-23G of FIG. 23B according to an example of the present technology.

Figure 24A:
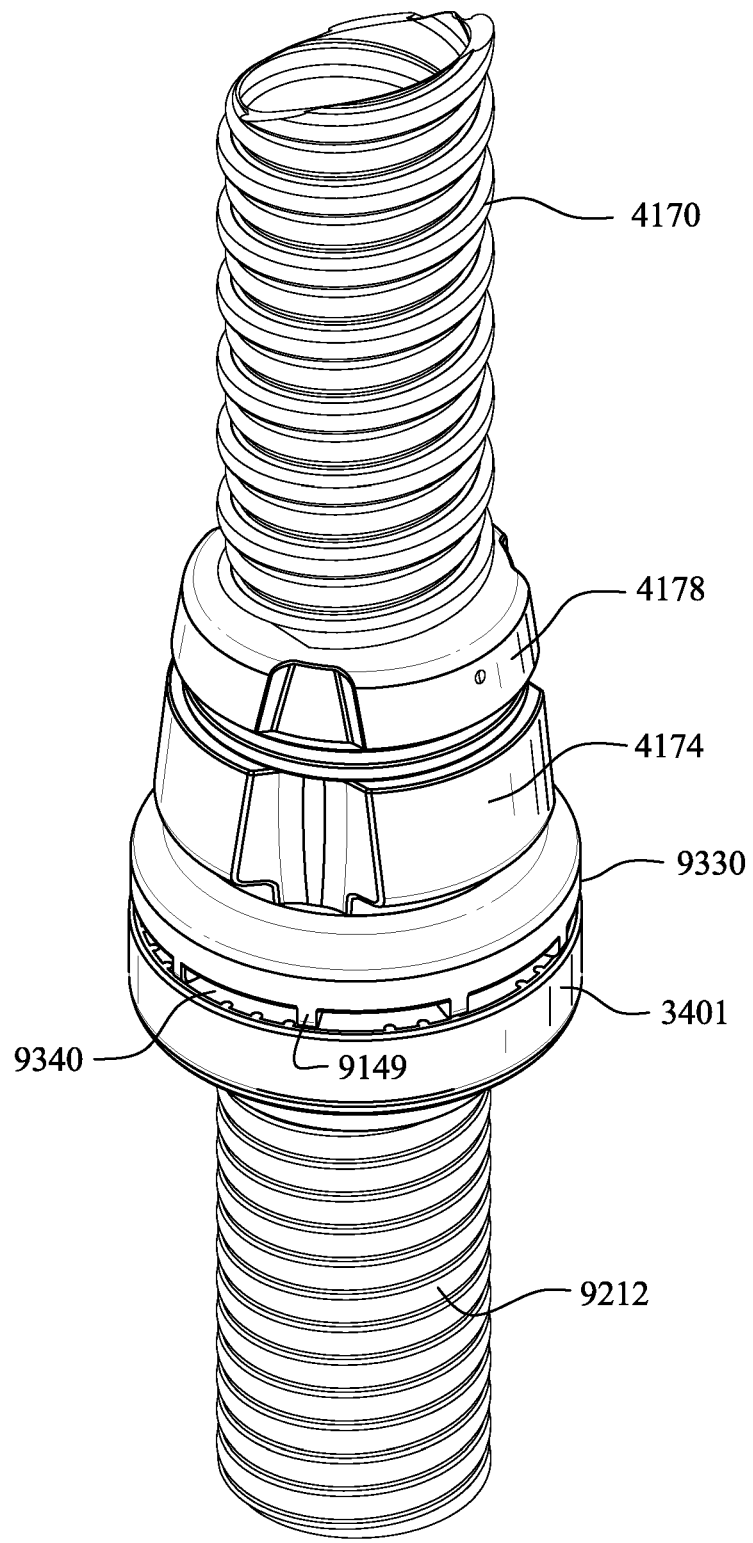

FIG. 24A depicts a perspective view of a vent adaptor assembly according to an example of the present technology.

Figure 24B:
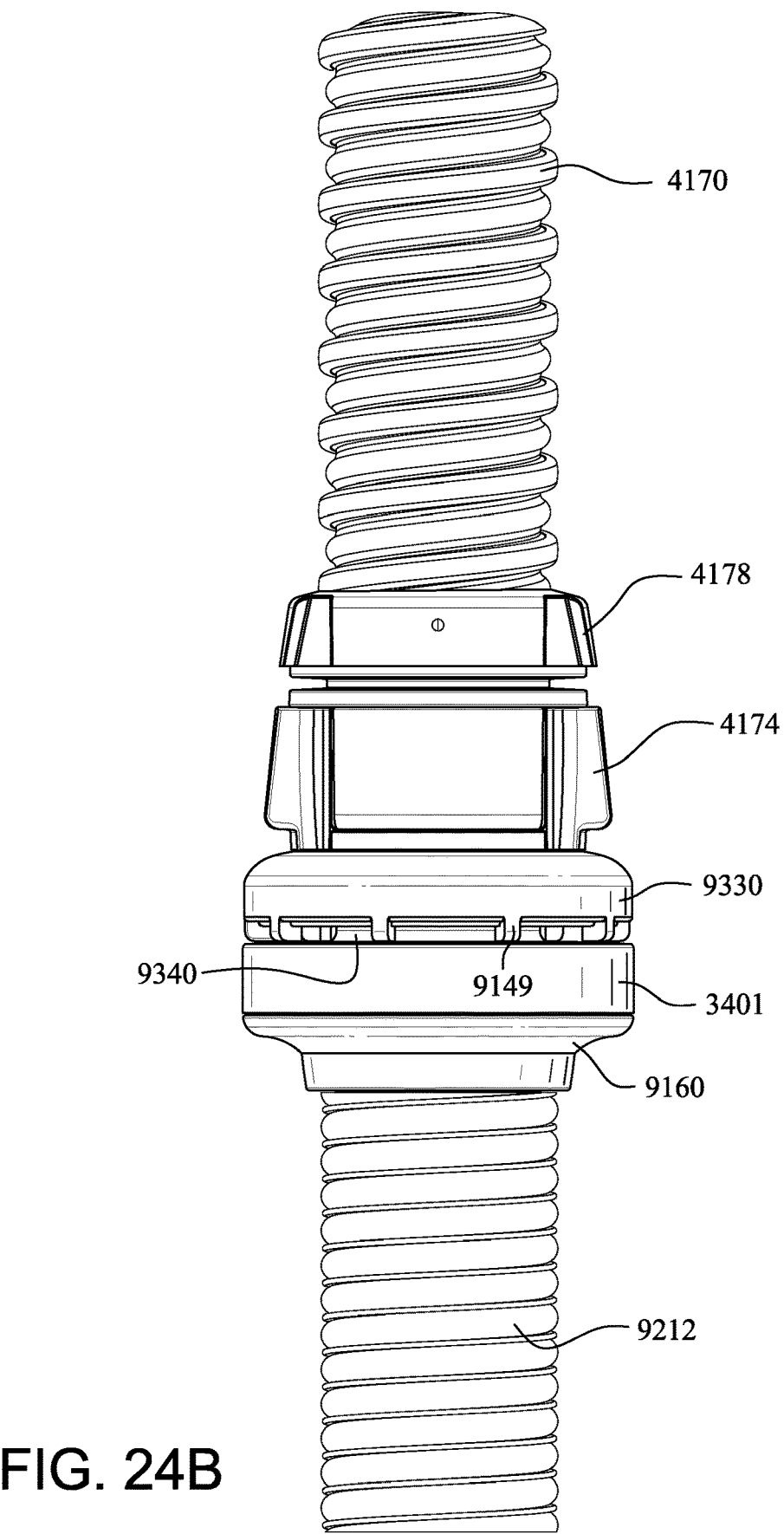

FIG. 24B depicts a side view of a vent adaptor assembly according to an example of the present technology.

Figure 24C:
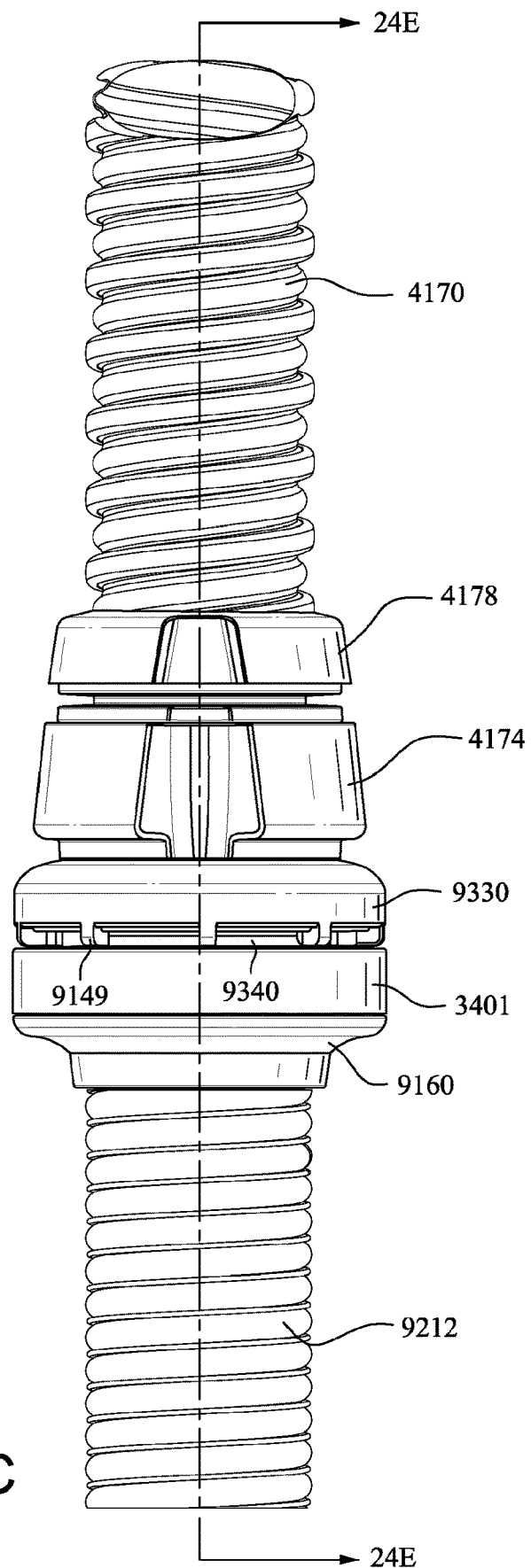

FIG. 24C depicts a side view of a vent adaptor assembly according to an example of the present technology.

Figure 24D:
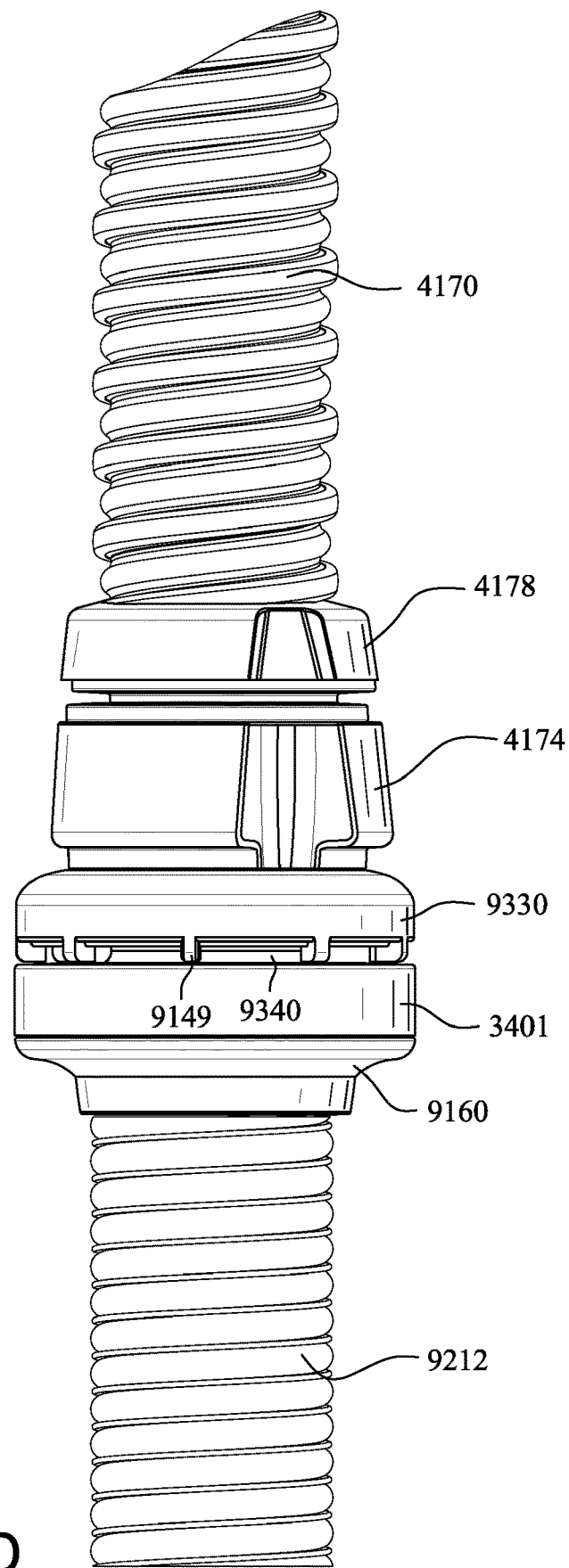

FIG. 24D depicts a side view of a vent adaptor assembly according to an example of the present technology.

Figure 24E:
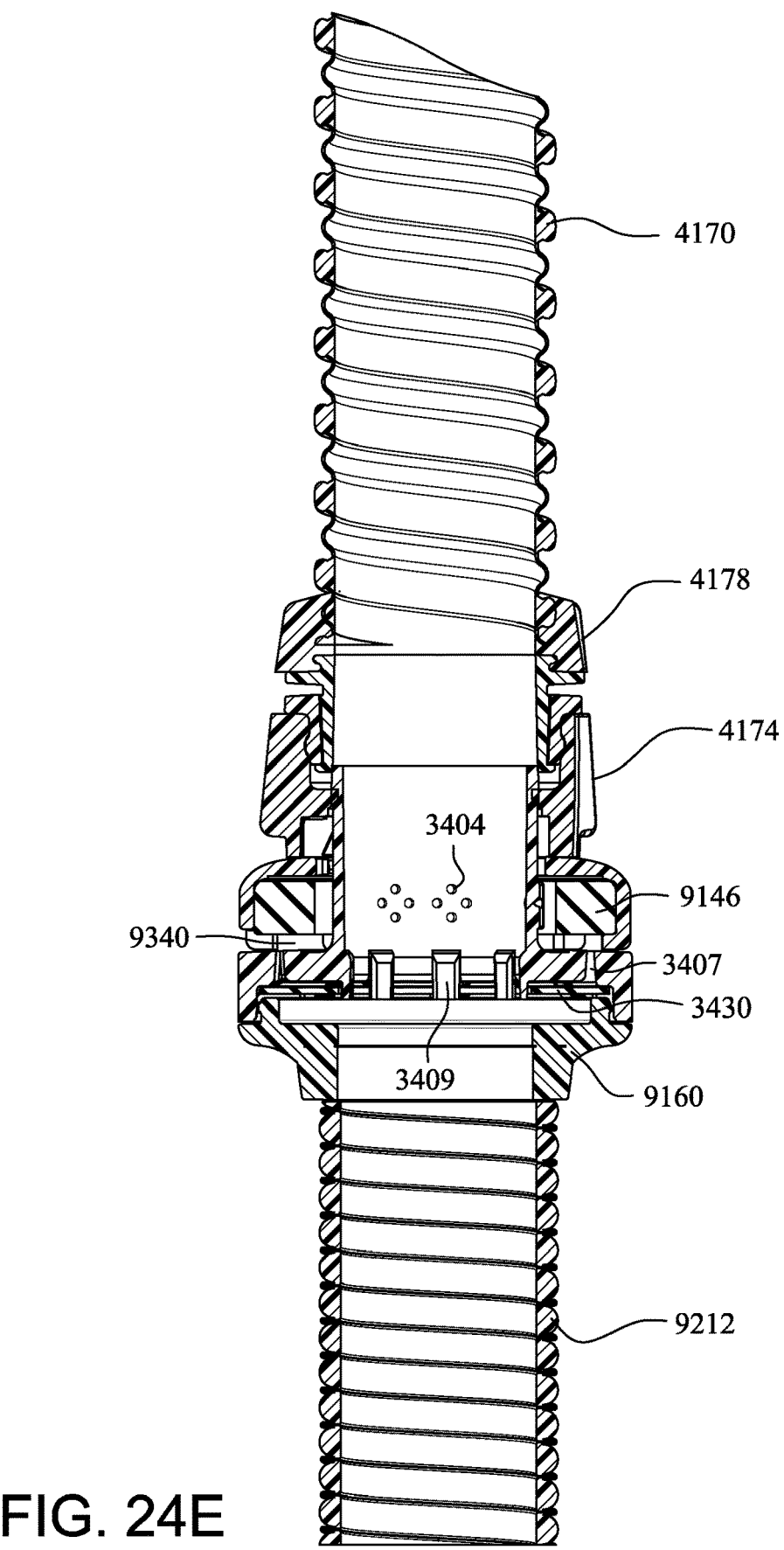

FIG. 24E depicts a cross-sectional view of a vent adaptor assembly taken through line 24E-24E of FIG. 24C according to an example of the present technology.

Figure 24F:
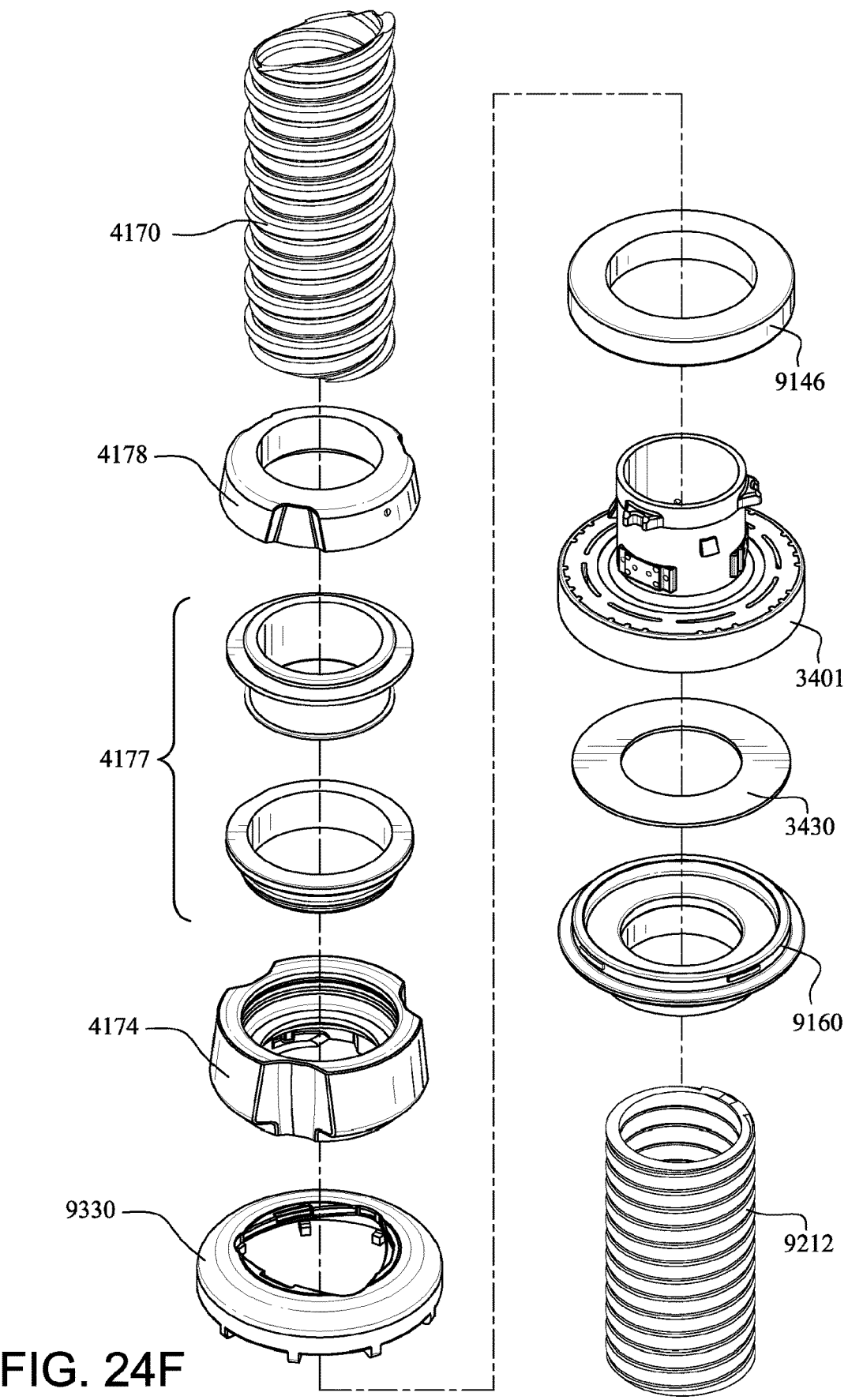

FIG. 24F depicts an exploded view of a vent adaptor assembly according to an example of the present technology.

Figure 25A:
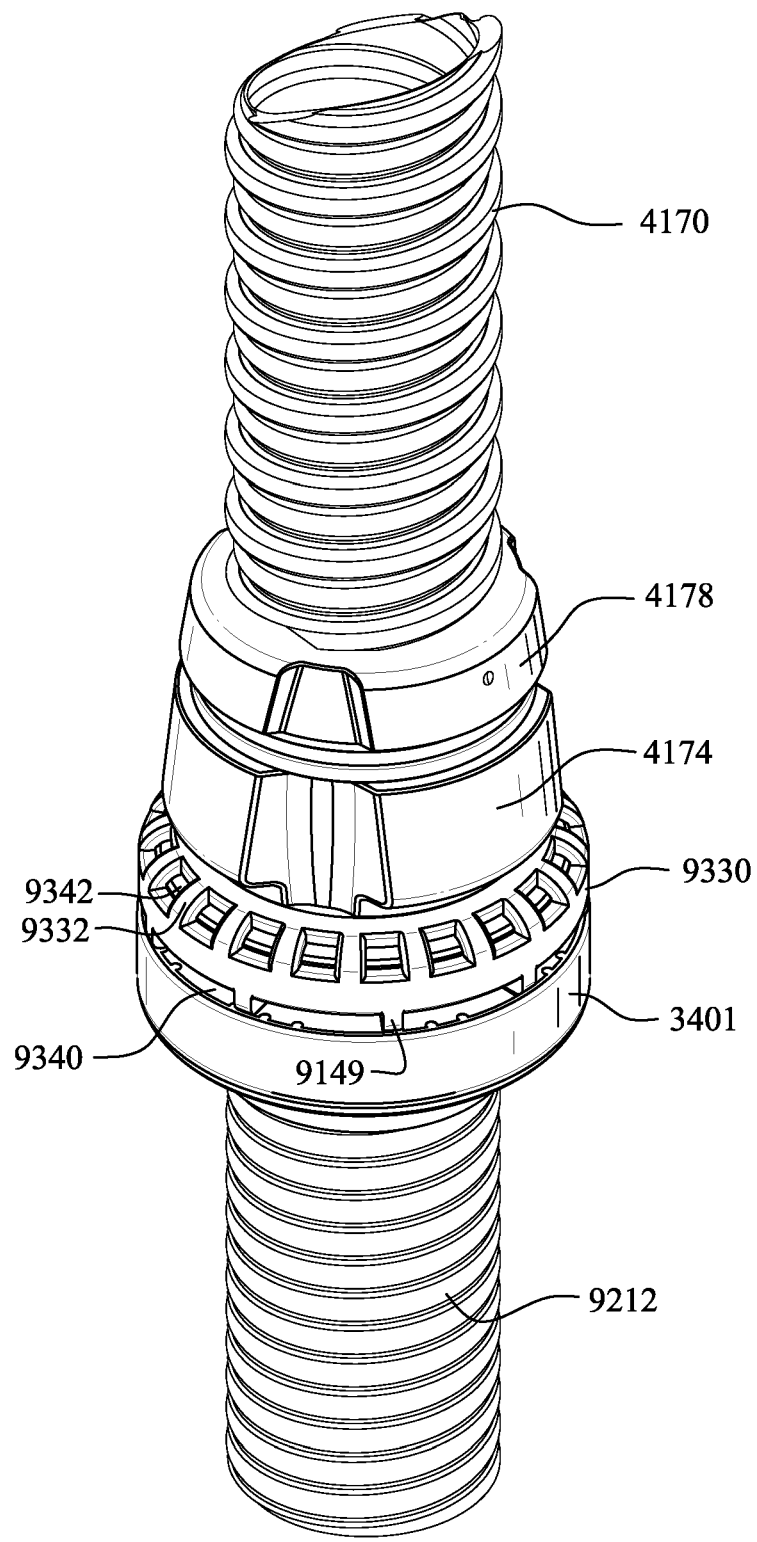

FIG. 25A depicts a perspective view of a vent adaptor assembly according to an example of the present technology.

Figure 25B:
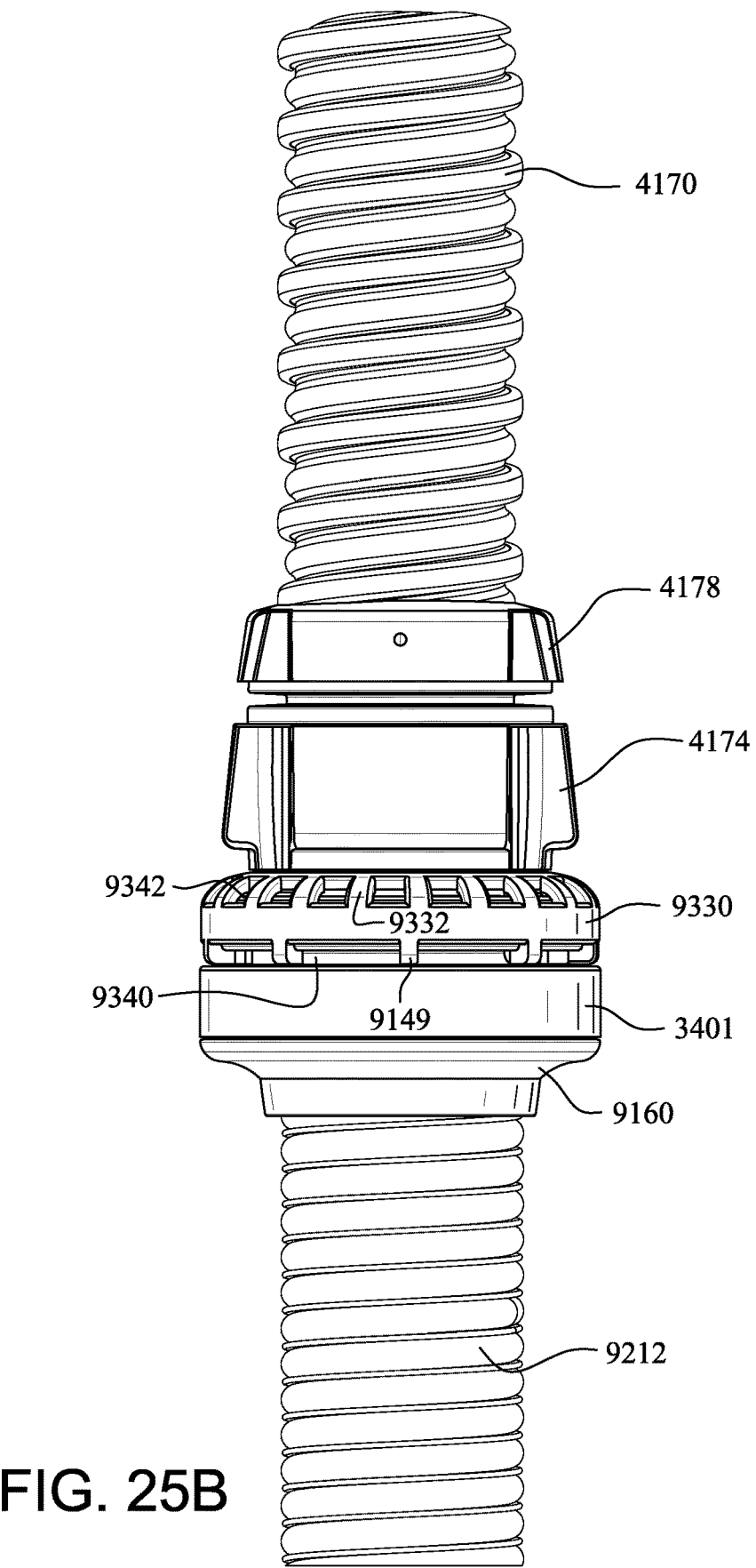

FIG. 25B depicts a side view of a vent adaptor assembly according to an example of the present technology.

Figure 25C:
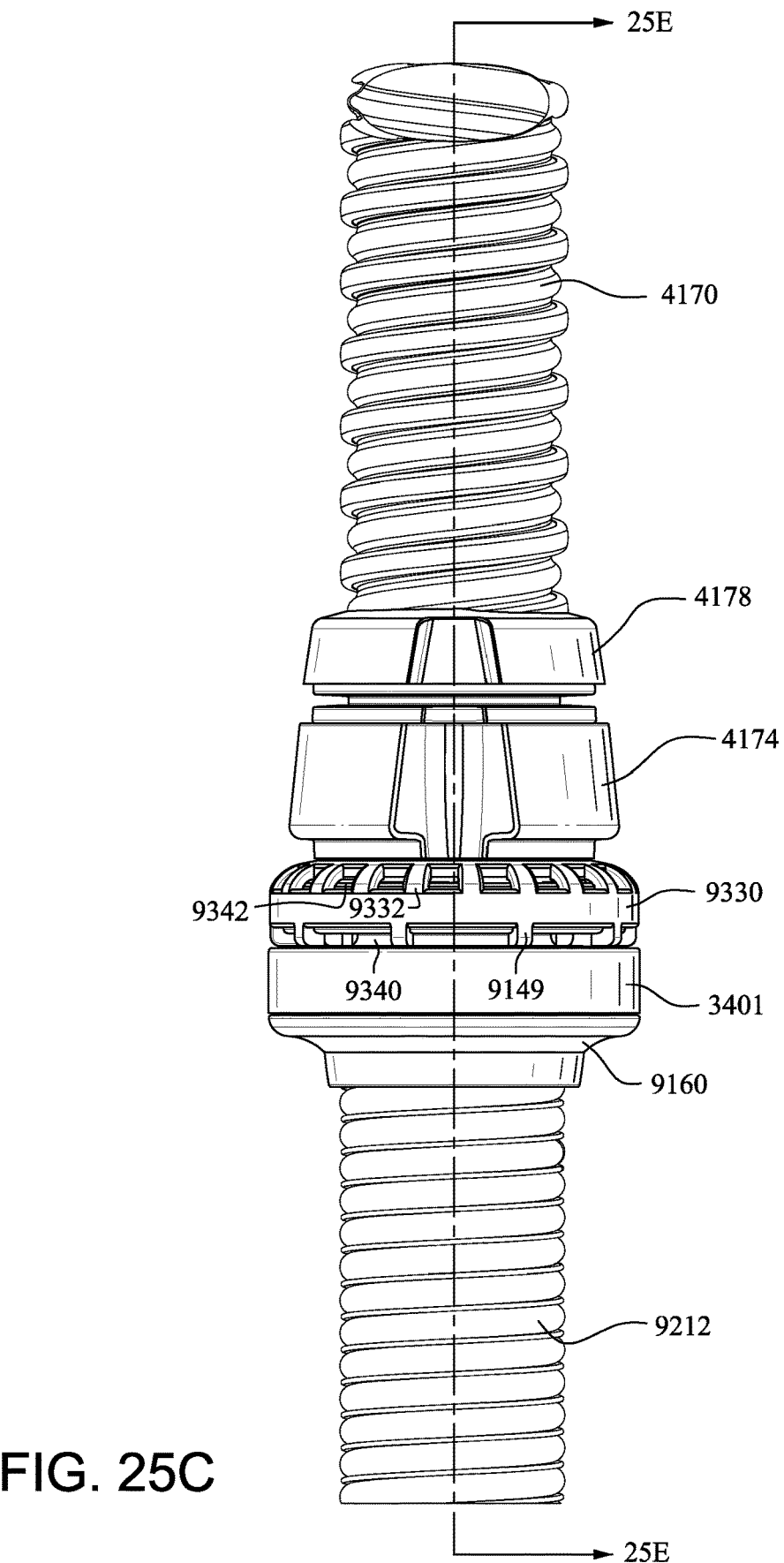

FIG. 25C depicts a side view of a vent adaptor assembly according to an example of the present technology.

Figure 25D:
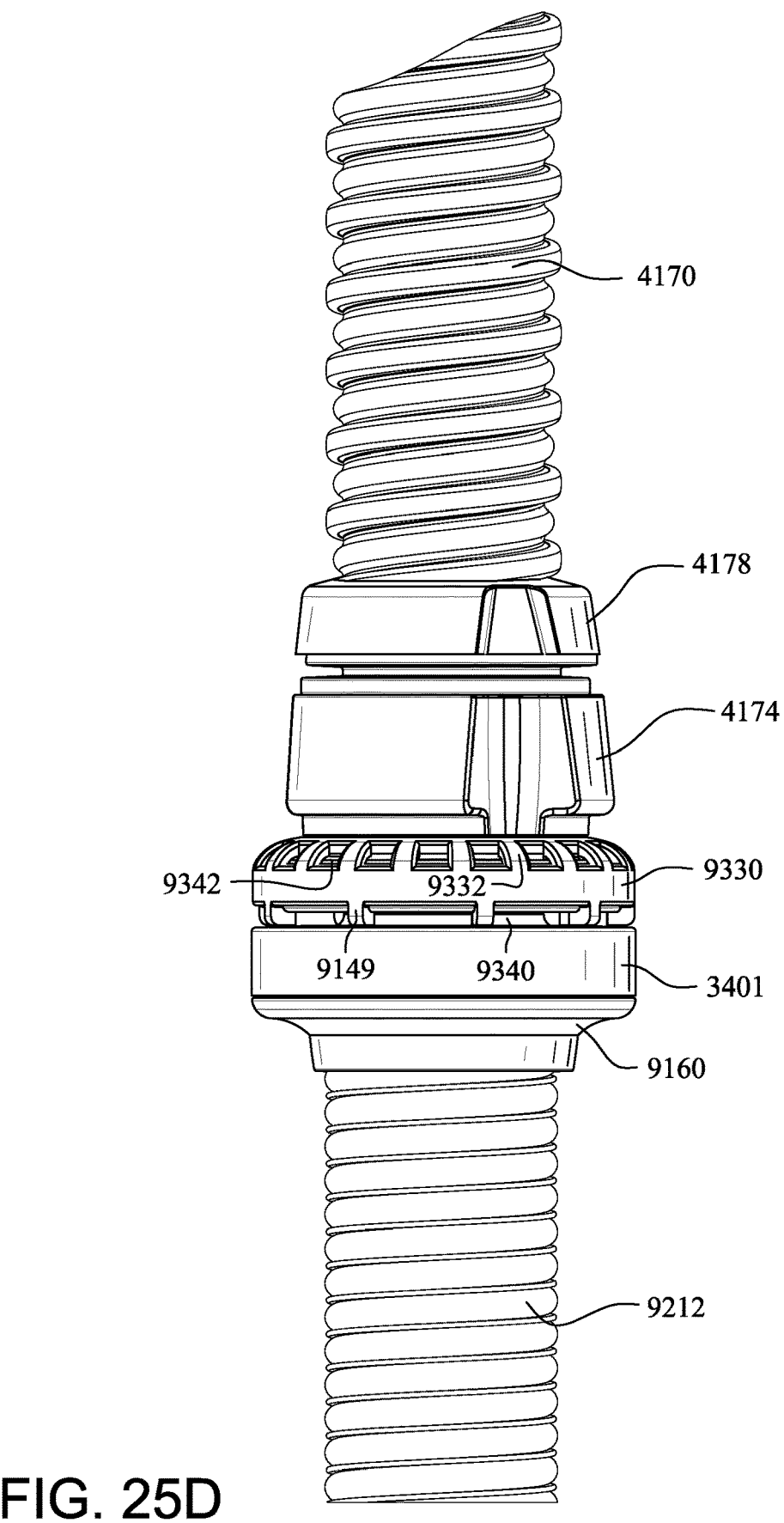

FIG. 25D depicts a side view of a vent adaptor assembly according to an example of the present technology.

Figure 25E:
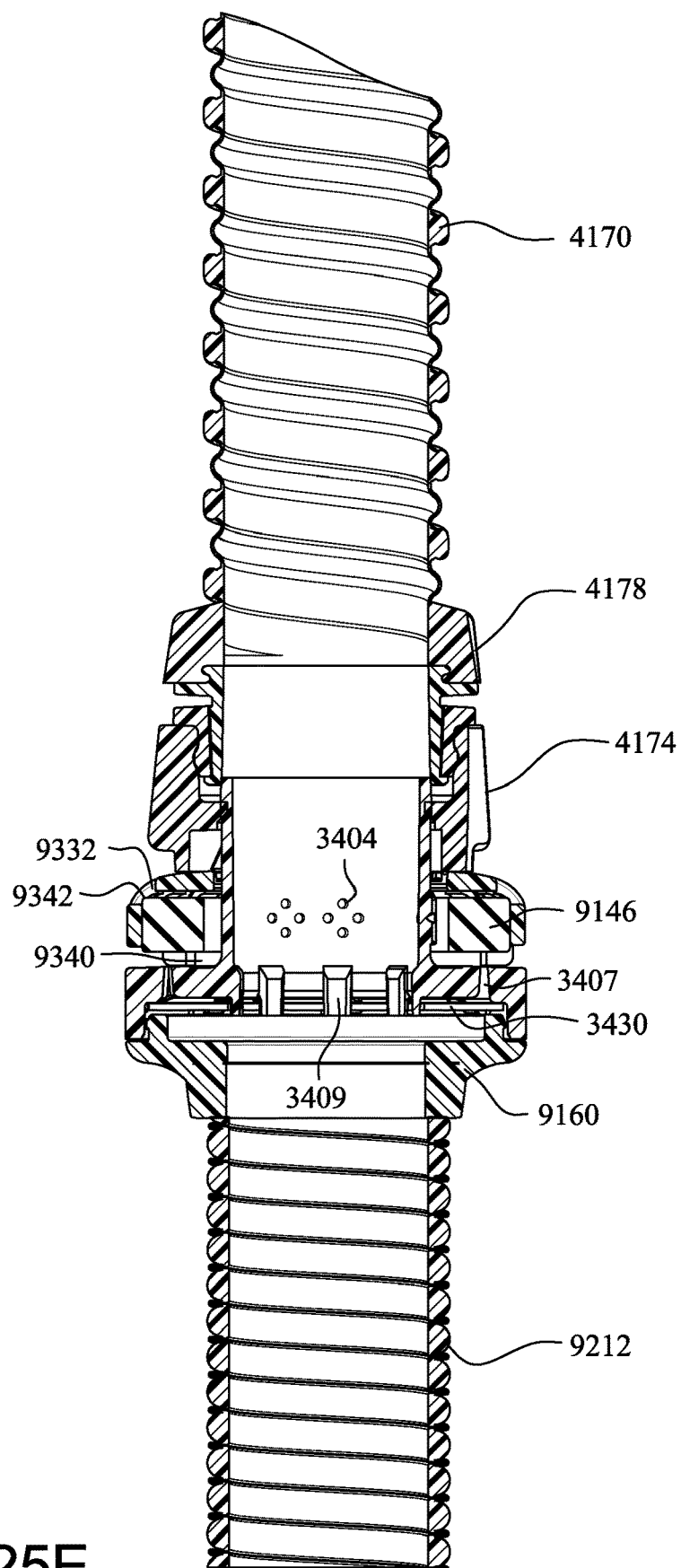

FIG. 25E depicts a cross-sectional view of a vent adaptor assembly taken through line 25E-25E of FIG. 25C according to an example of the present technology.

Figure 25F:
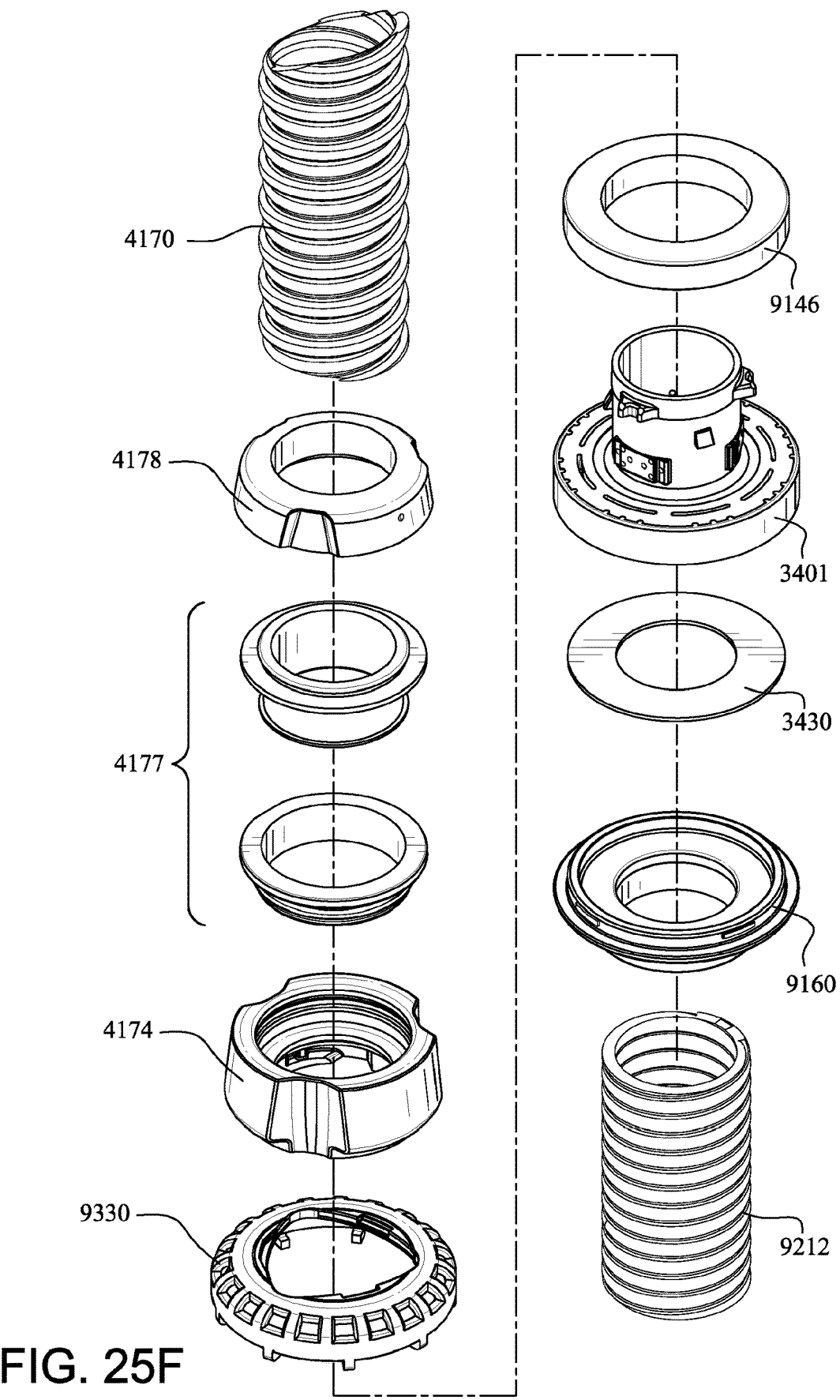

FIG. 25F depicts an exploded view of a vent adaptor assembly according to an example of the present technology.

Figure 26A:
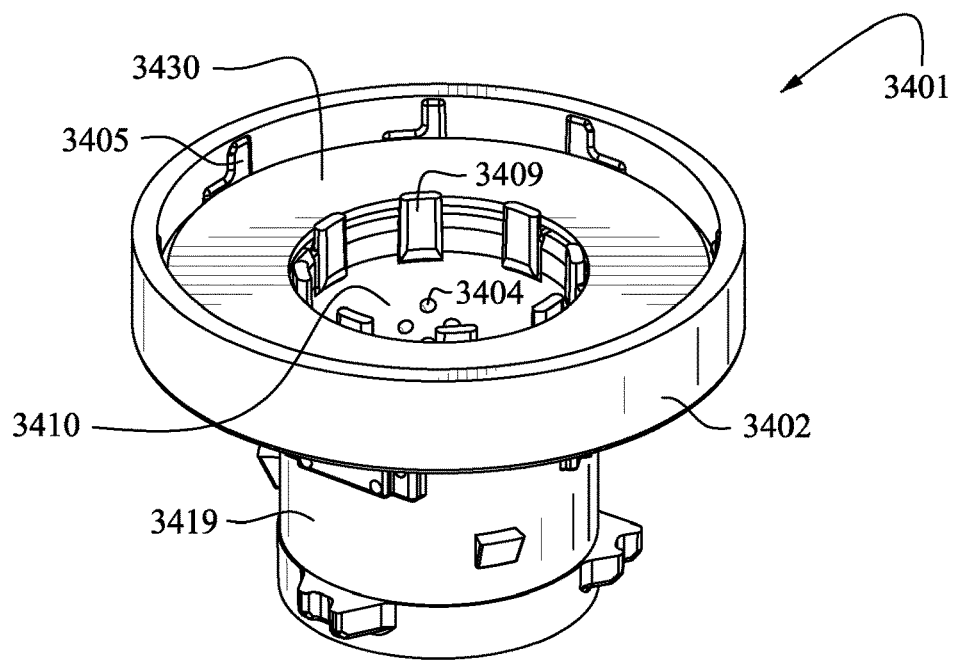

FIG. 26A depicts a rear perspective view of a vent housing according to an example of the present technology.

Figure 26B:
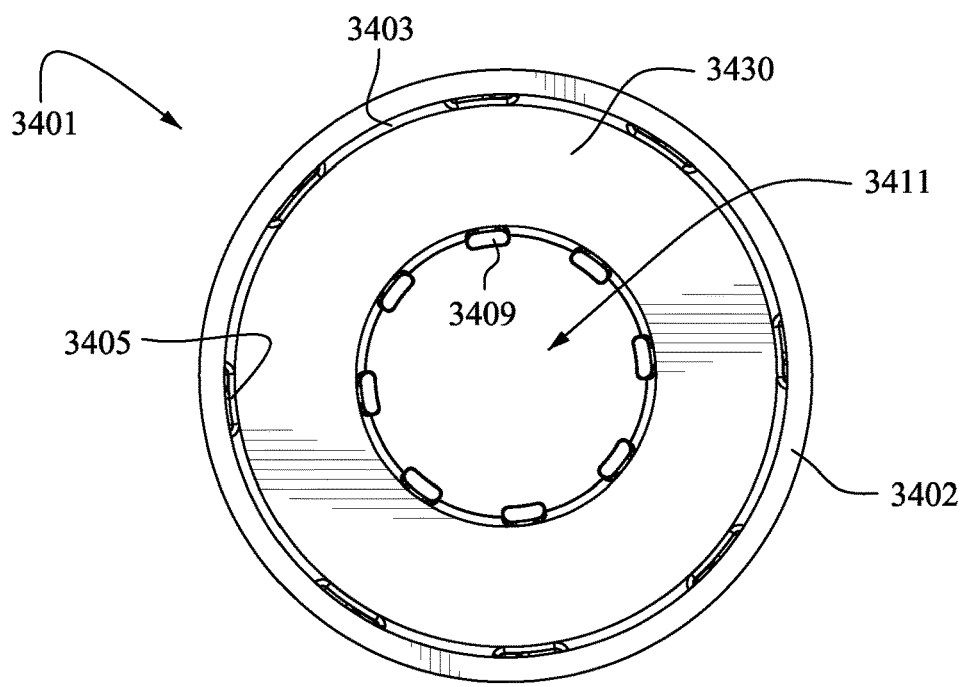

FIG. 26B depicts a rear view of a vent housing according to an example of the present technology.

Figure 26C:
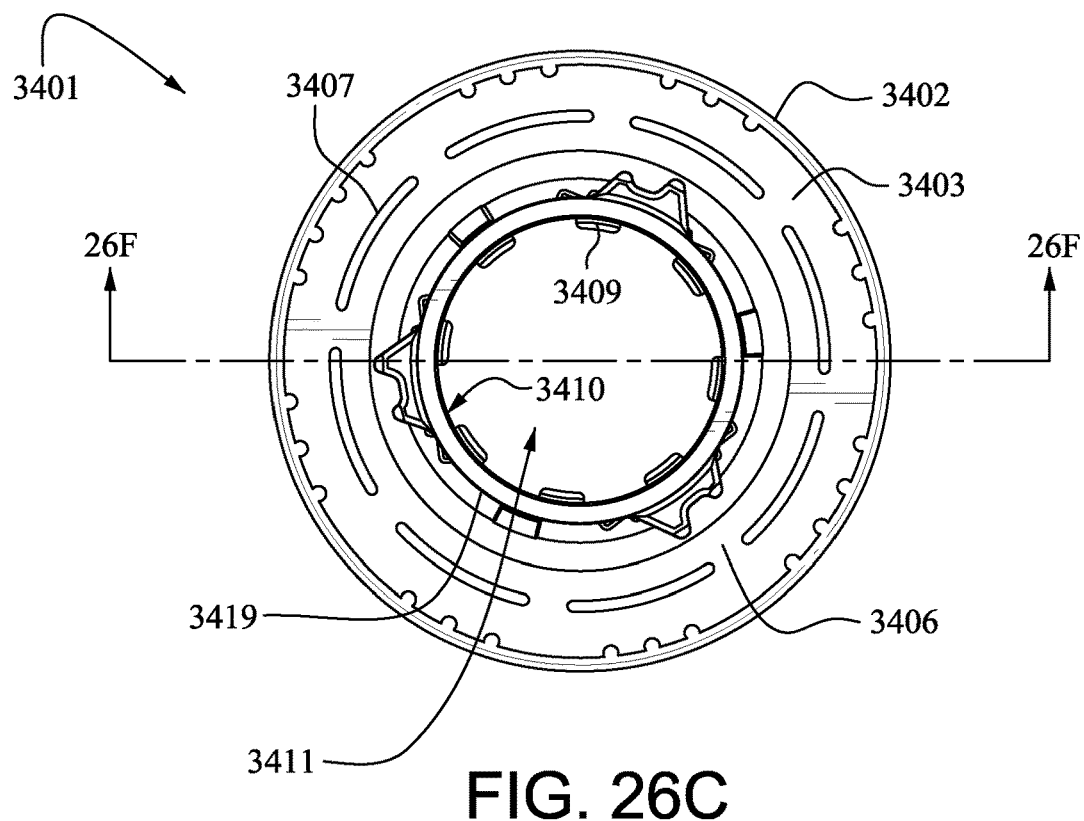

FIG. 26C depicts a front view of a vent housing according to an example of the present technology.

Figure 26D:
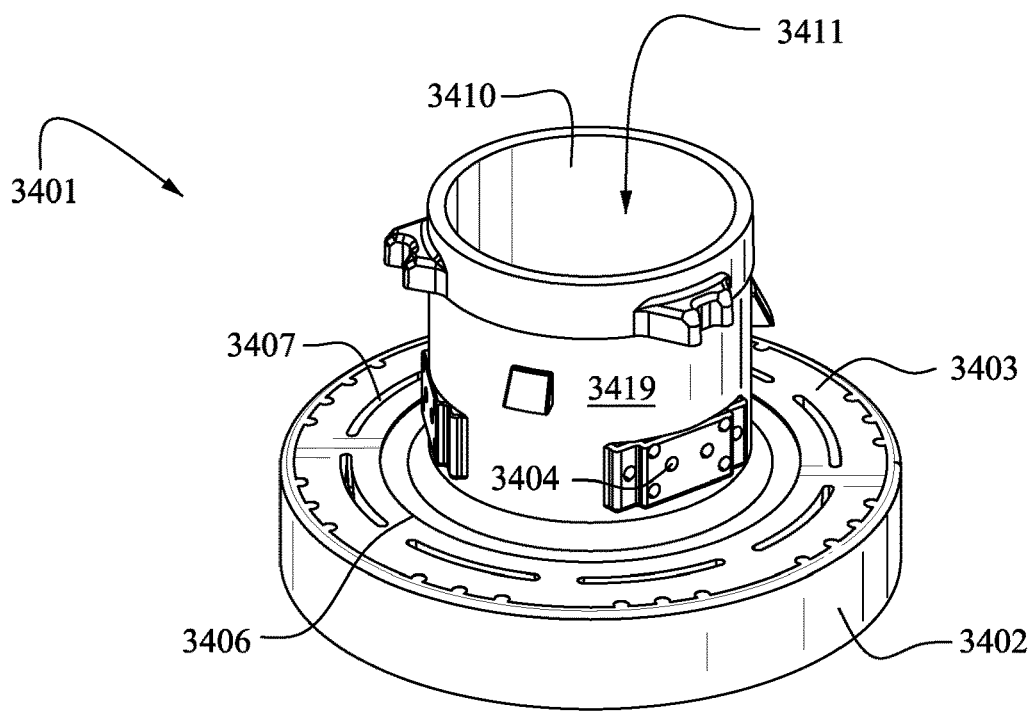

FIG. 26D depicts a front perspective view of a vent housing according to an example of the present technology.

Figure 26E:
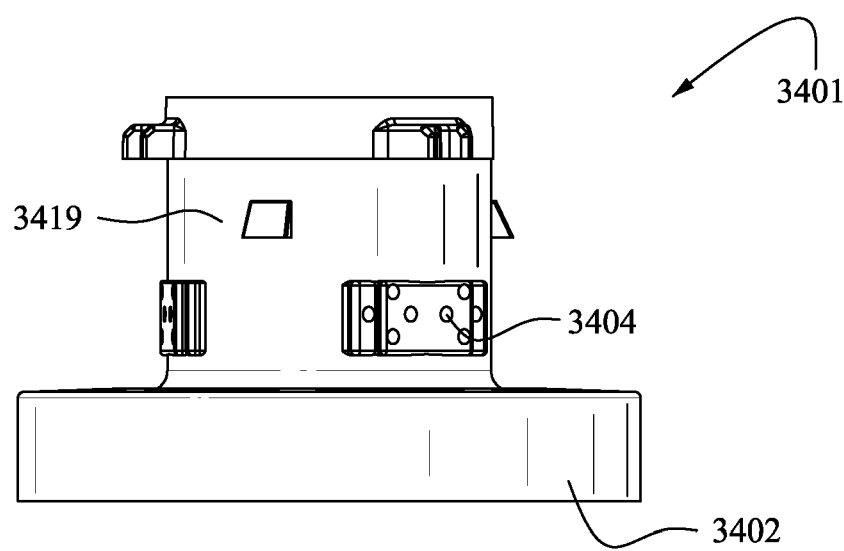

FIG. 26E depicts a side view of a vent housing according to an example of the present technology.

Figure 26F:
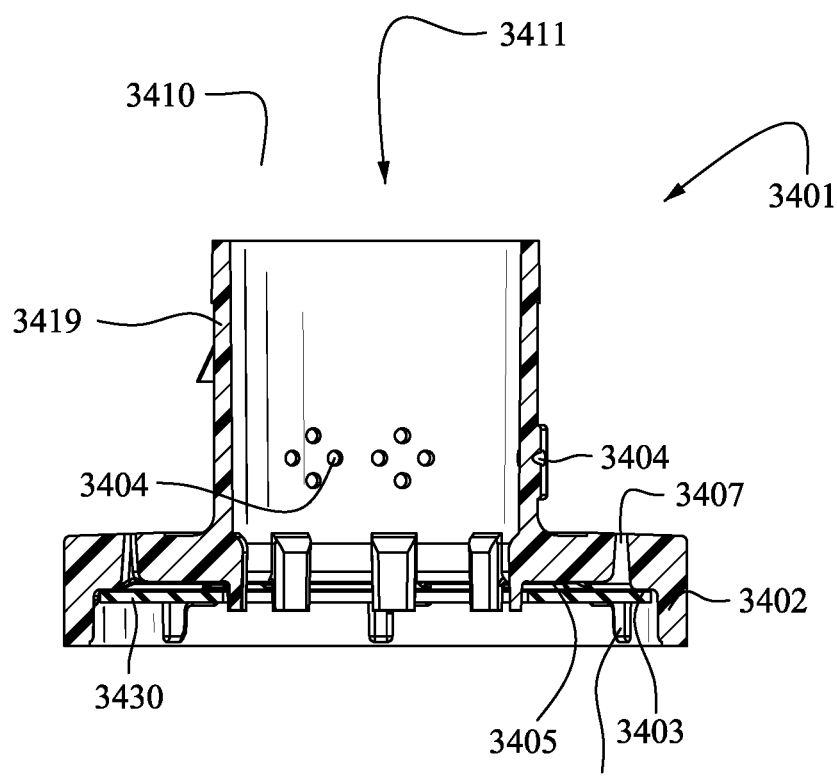

FIG. 26F depicts a cross-sectional view of a vent housing taken through line 26F-26F of FIG. 26C according to an example of the present technology.

Figure 27:
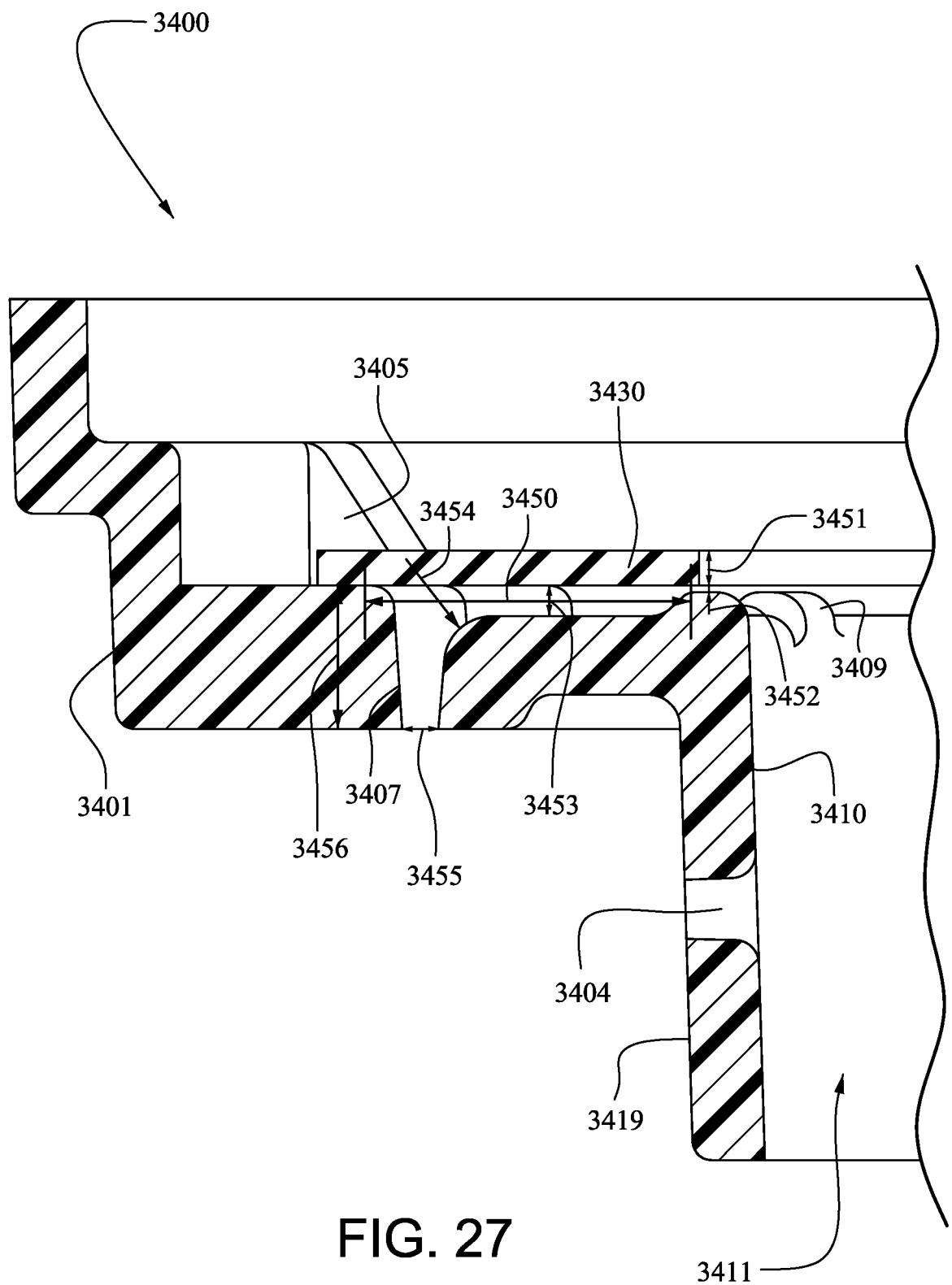

FIG. 27 depicts a partial cross-sectional view of a vent system according to an example of the present technology.

Figure 28:
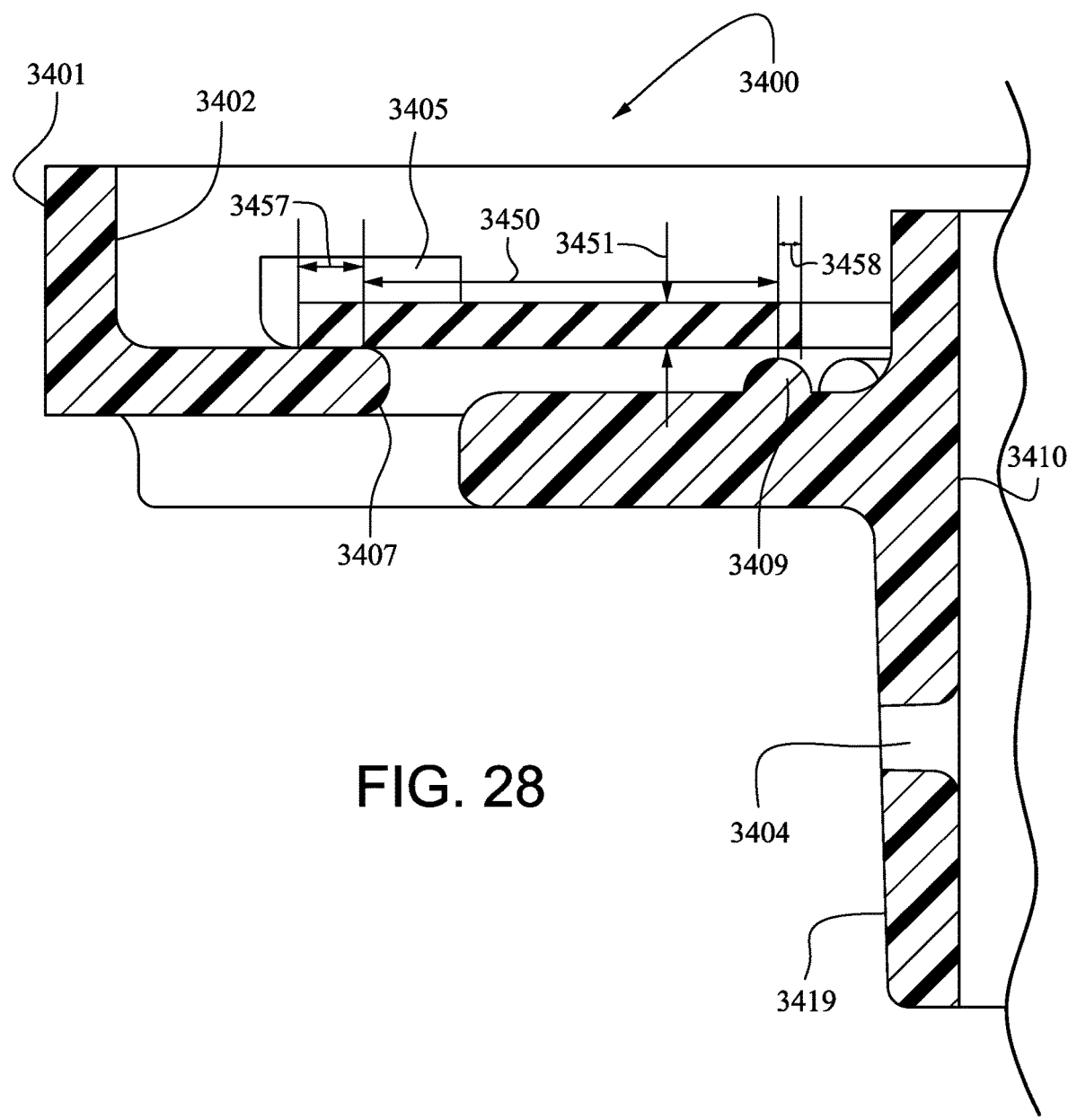

FIG. 28 depicts a partial cross-sectional view of a vent system according to an example of the present technology.

Figure 29:
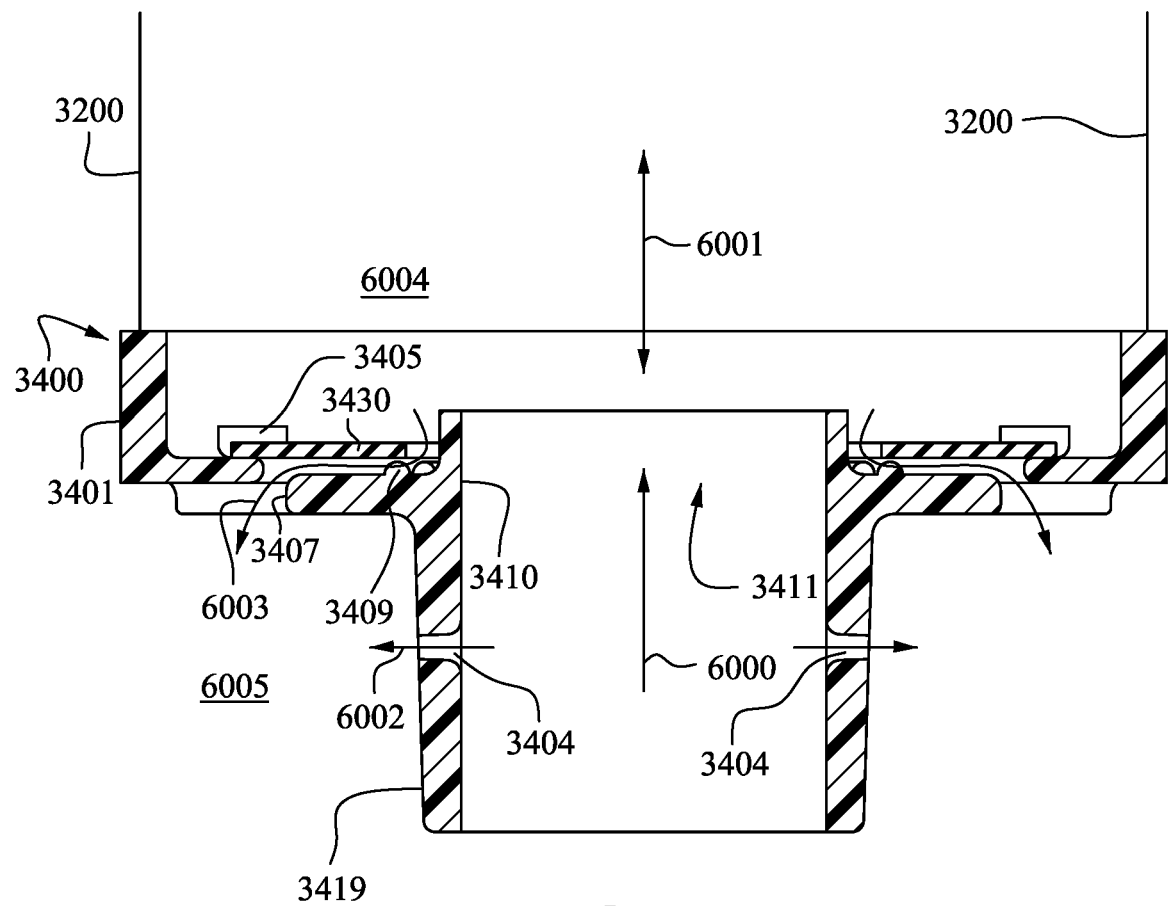

FIG. 29 depicts a cross-sectional view of a vent system according to an example of the present technology.

Figure 30A:
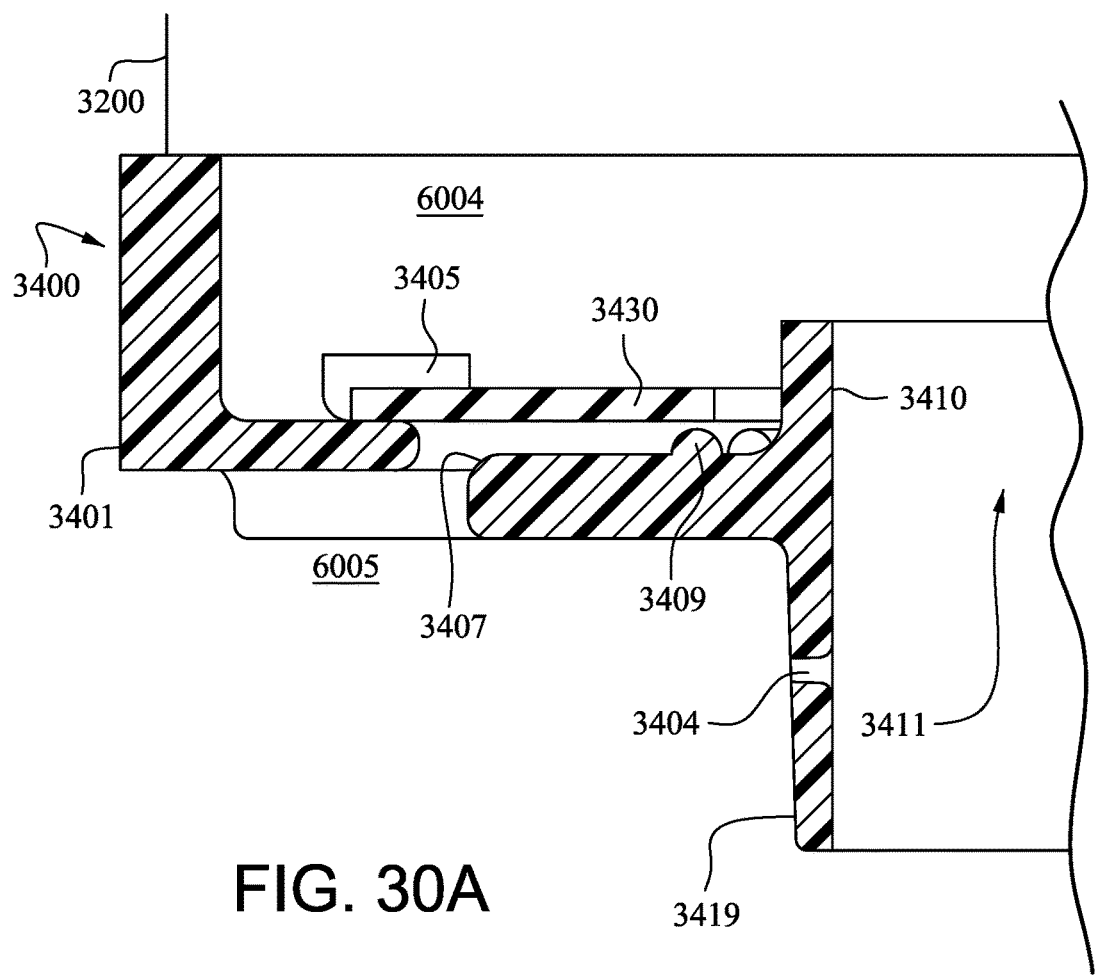

FIG. 30A depicts a partial cross-sectional view of a vent system according to an example of the present technology.

Figure 30B:
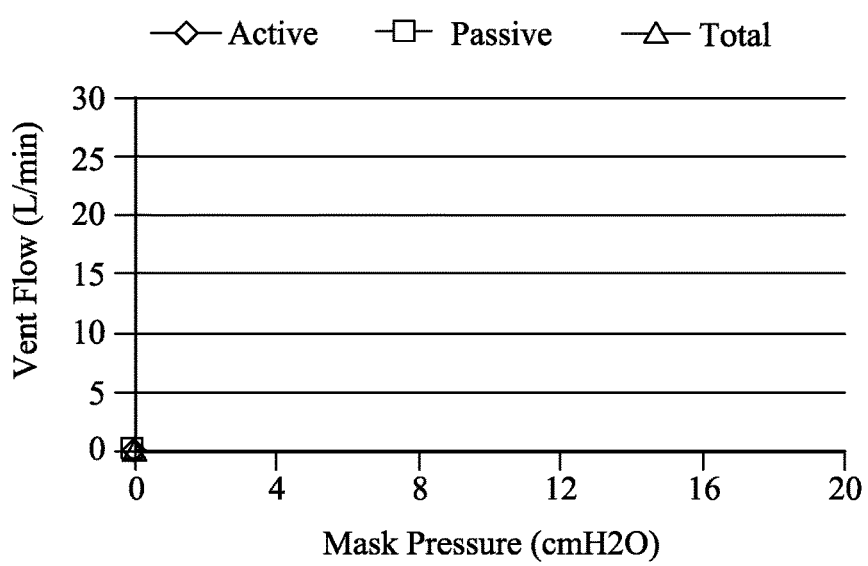

FIG. 30B depicts a graph of vent flow rates versus mask pressures for the vent system of FIG. 30A.

Figure 31A:
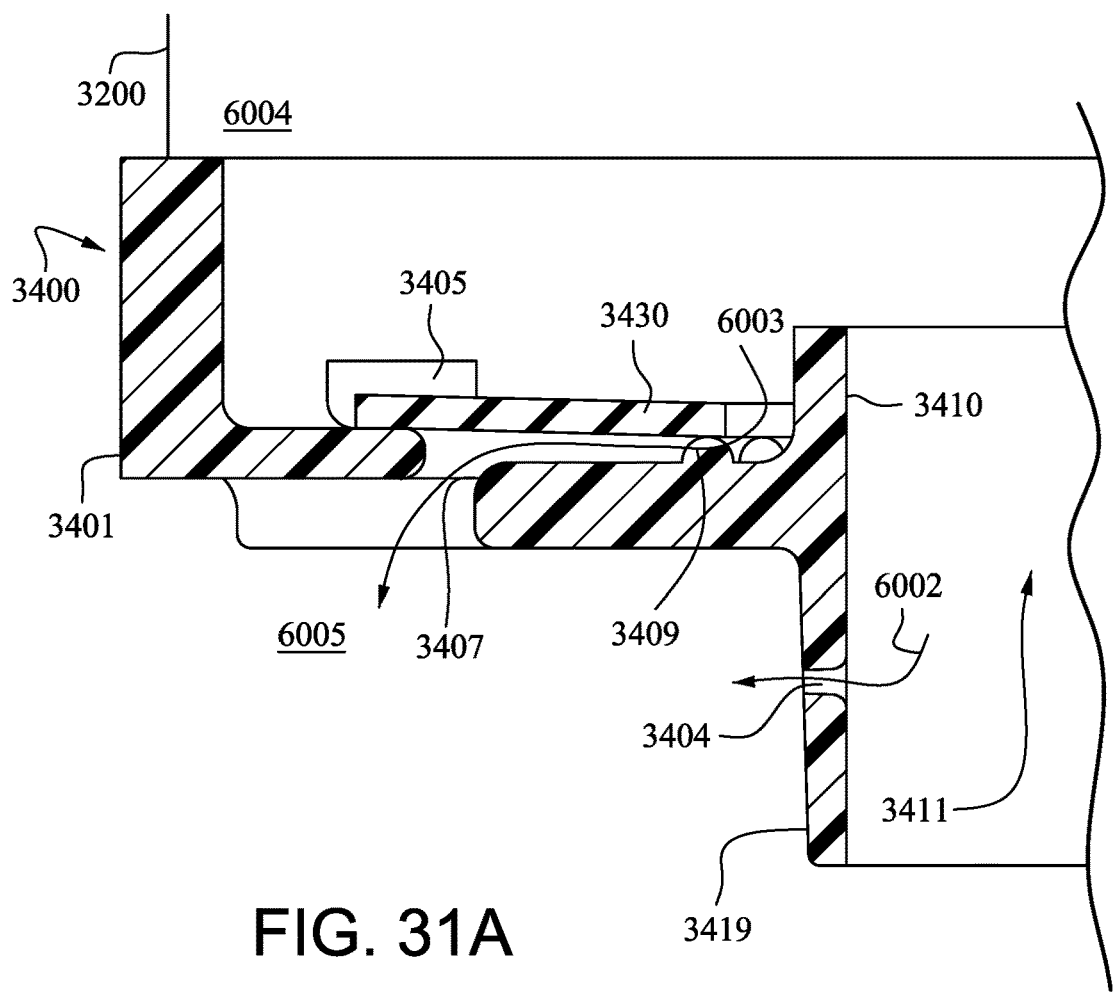

FIG. 31A depicts a partial cross-sectional view of a vent system according to an example of the present technology.

Figure 31B:
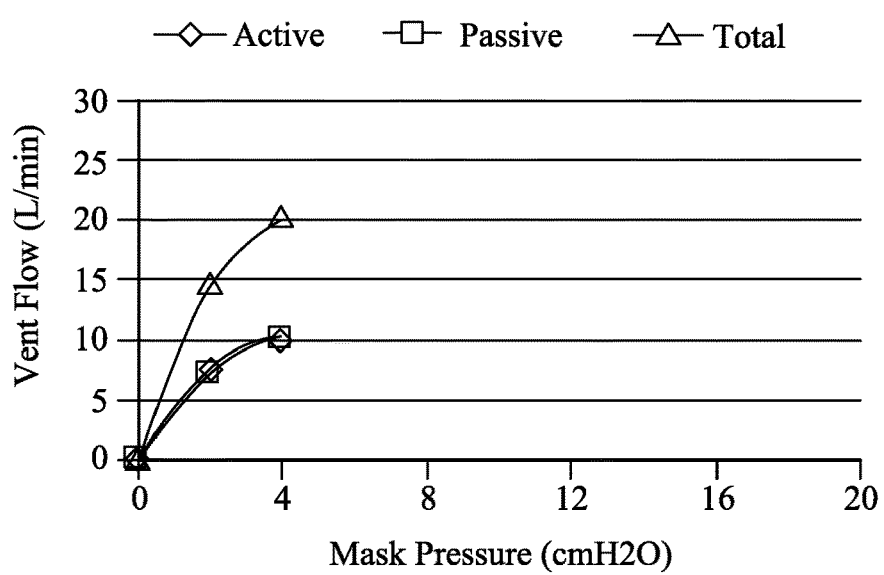

FIG. 31B depicts a graph of vent flow rates versus mask pressures for the vent system of FIG. 31A.

Figure 32A:
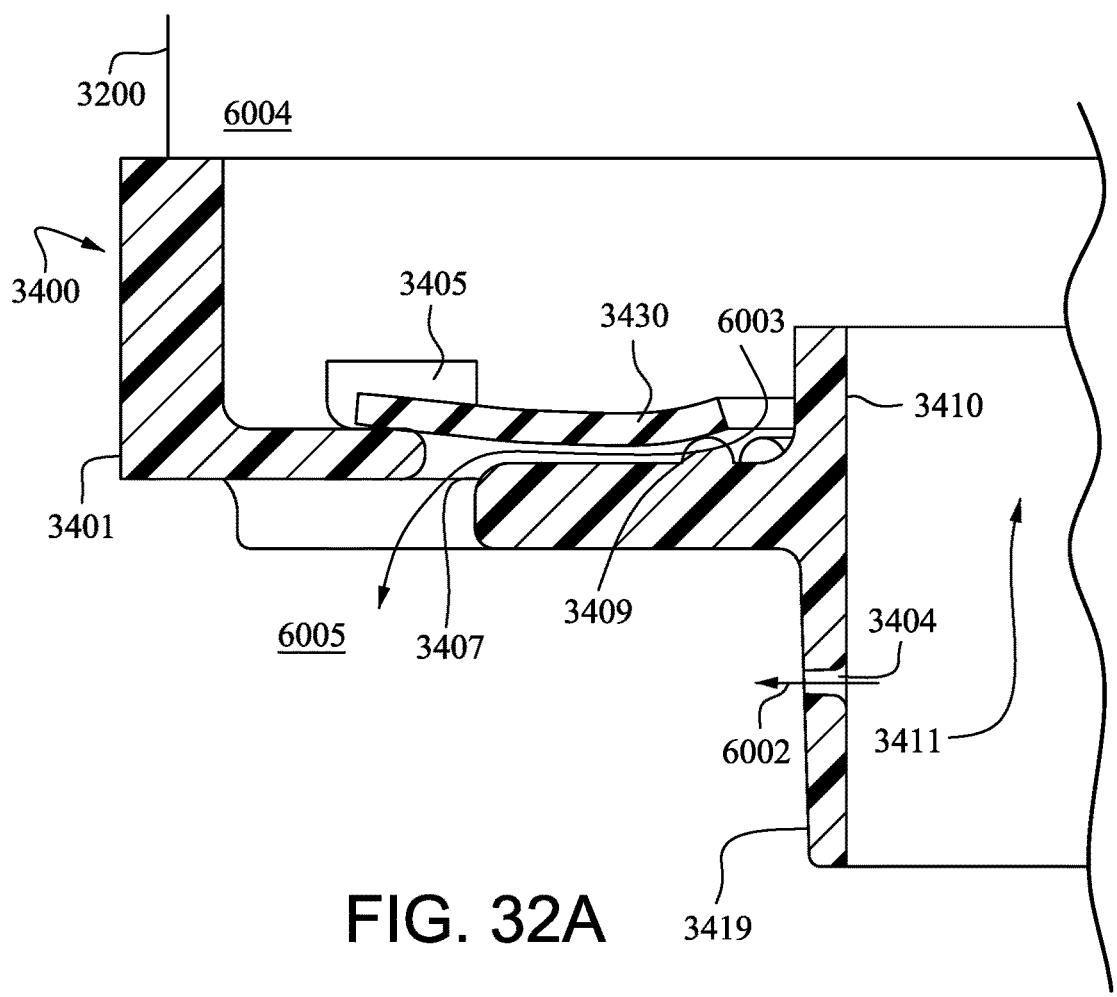

FIG. 32A depicts a partial cross-sectional view of a vent system according to an example of the present technology.

Figure 32B:
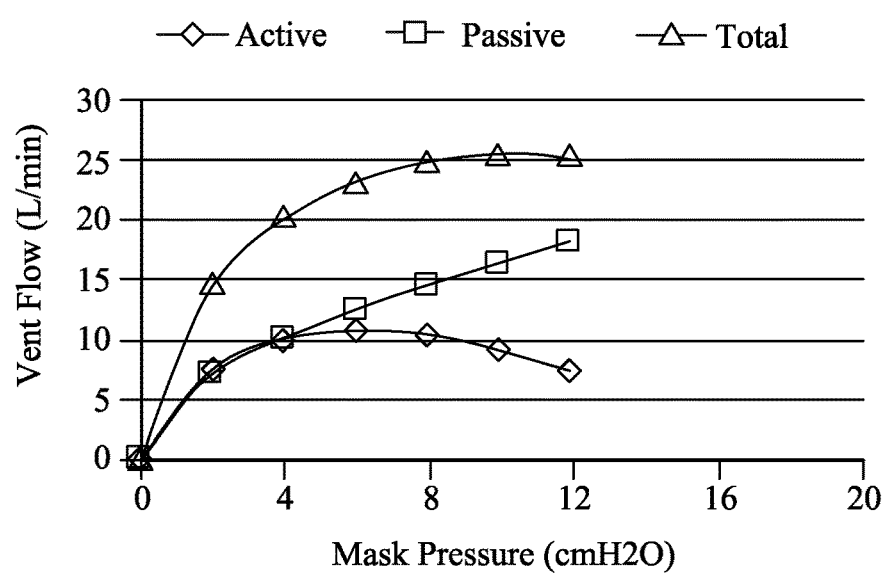

FIG. 32B depicts a graph of vent flow rates versus mask pressures for the vent system of FIG. 32A.

Figure 33A:
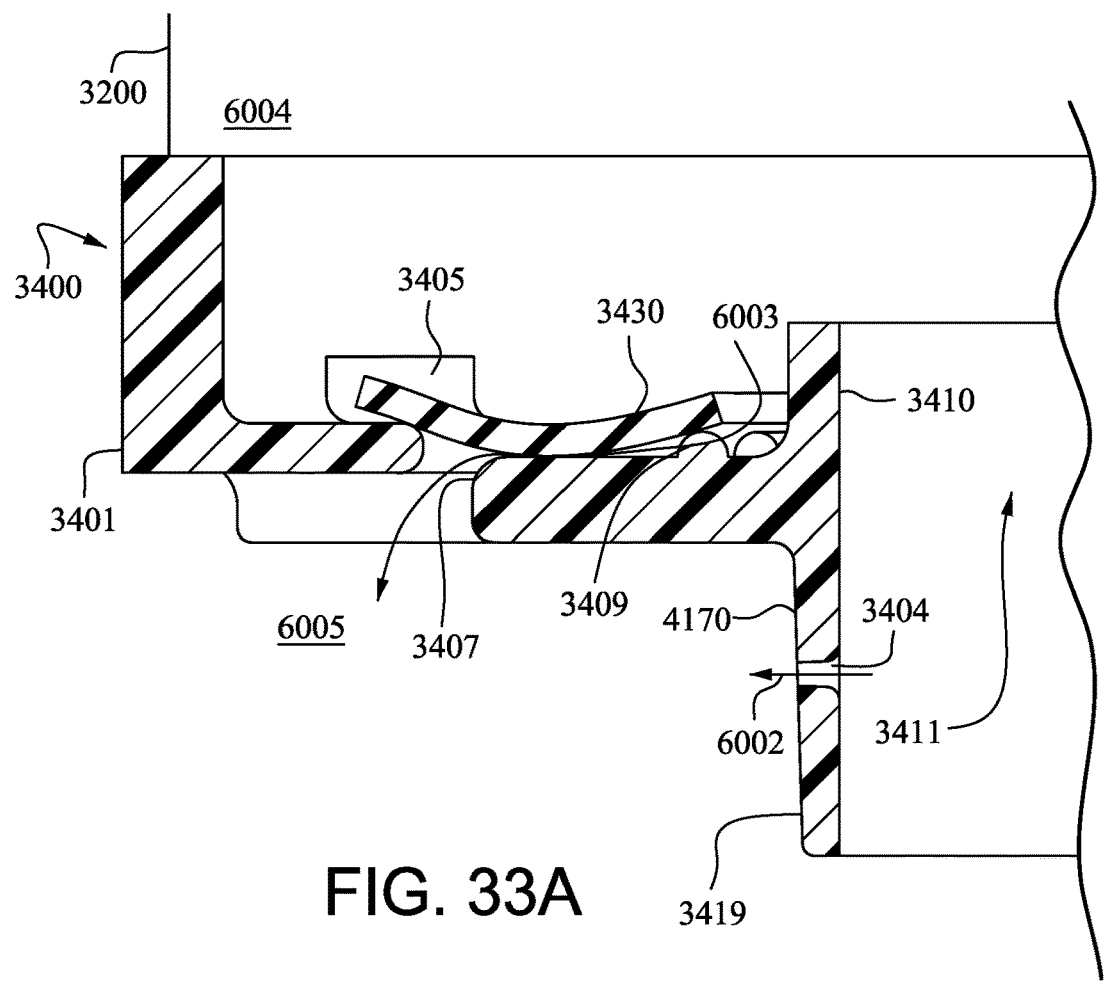

FIG. 33A depicts a partial cross-sectional view of a vent system according to an example of the present technology.

Figure 33B:
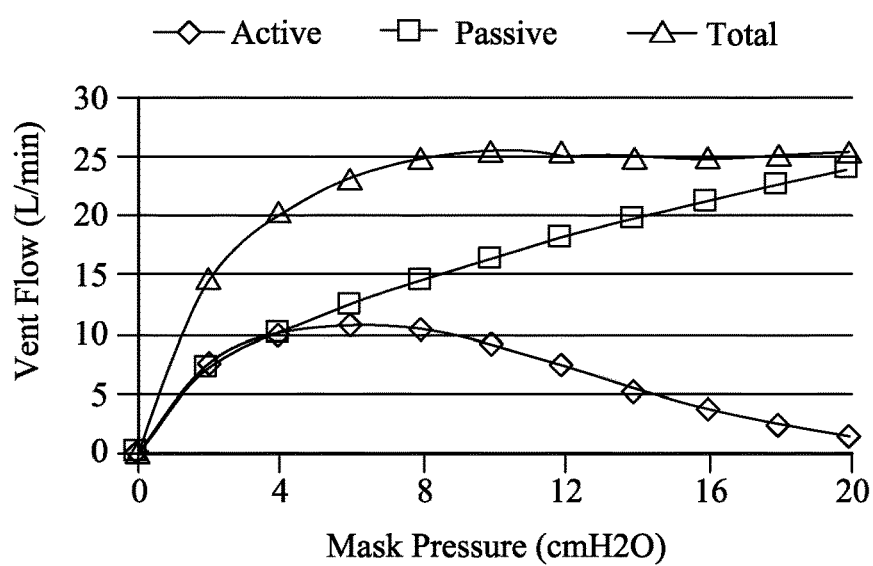

FIG. 33B depicts a graph of vent flow rates versus mask pressures for the vent system of FIG. 33A.

Figure 34:
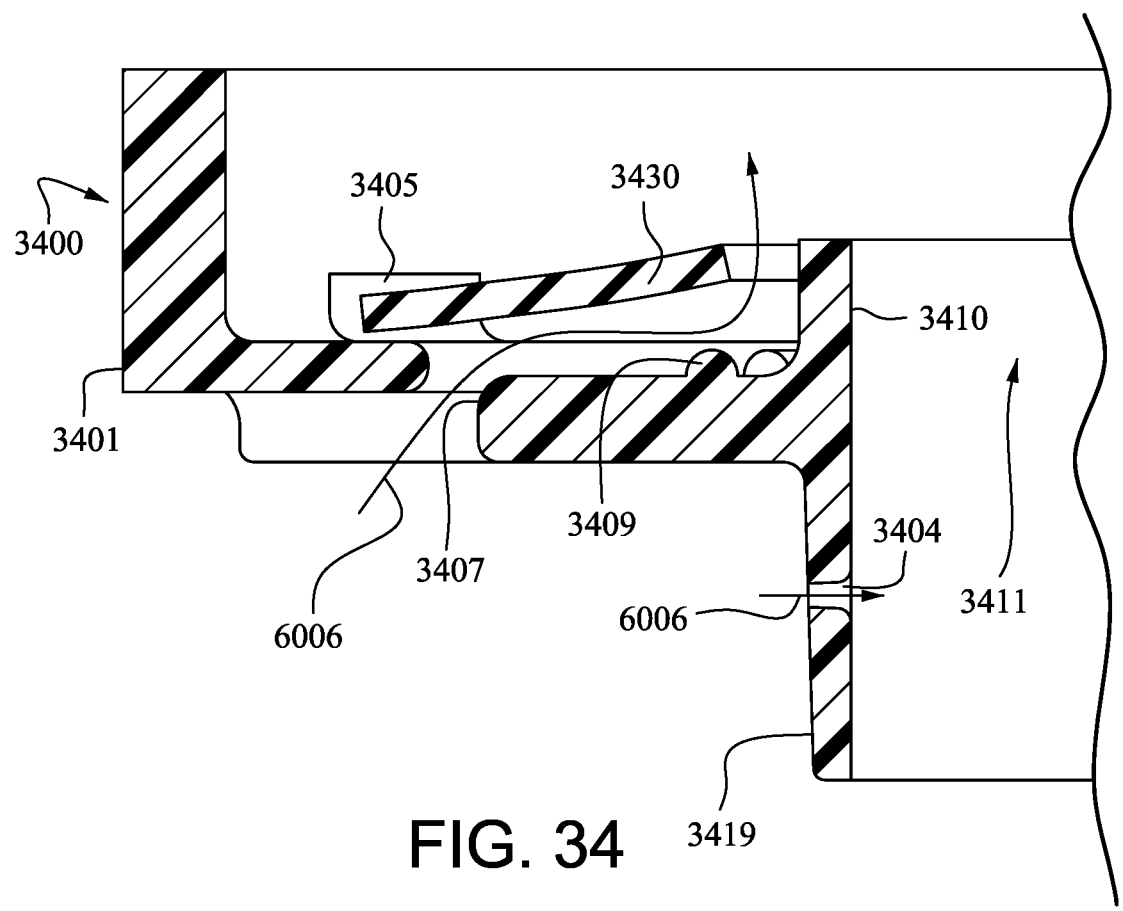

FIG. 34 depicts a partial cross-sectional view of a vent system according to an example of the present technology.

FIG. 35A depicts a perspective view of a vent adaptor according to an example of the present technology.

Figure 35B:
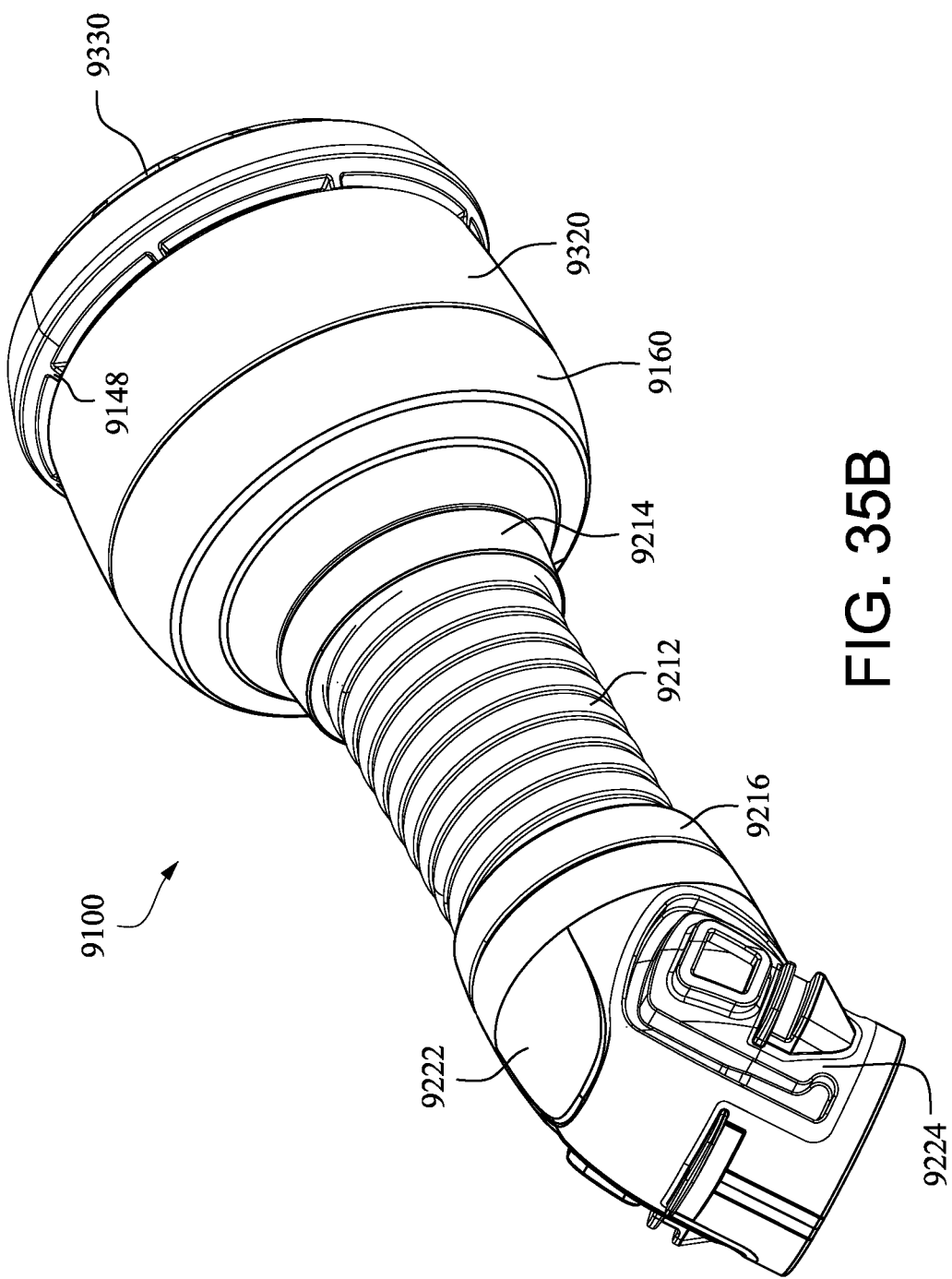

FIG. 35B depicts another perspective view of a vent adaptor according to an example of the present technology.

Figure 35C:
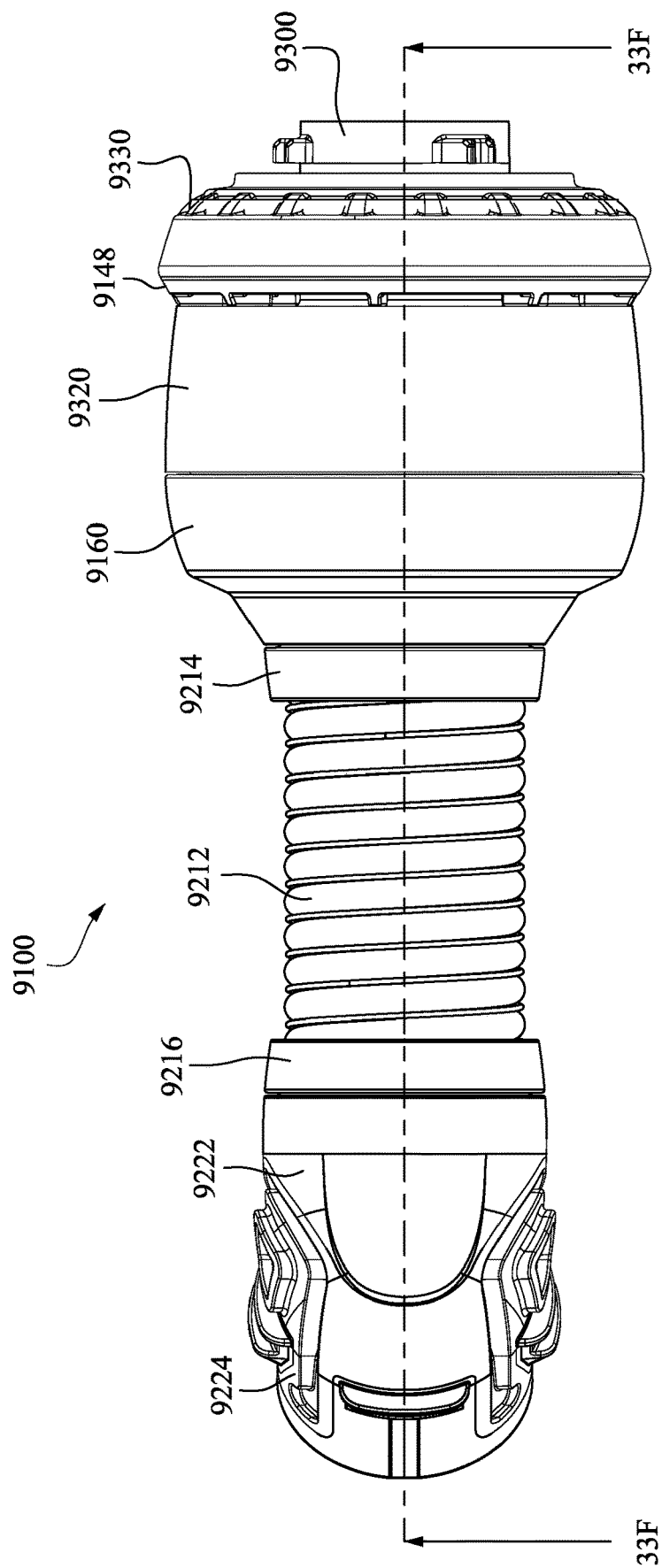

FIG. 35C depicts a superior view of a vent adaptor according to an example of the present technology.

Figure 35D:
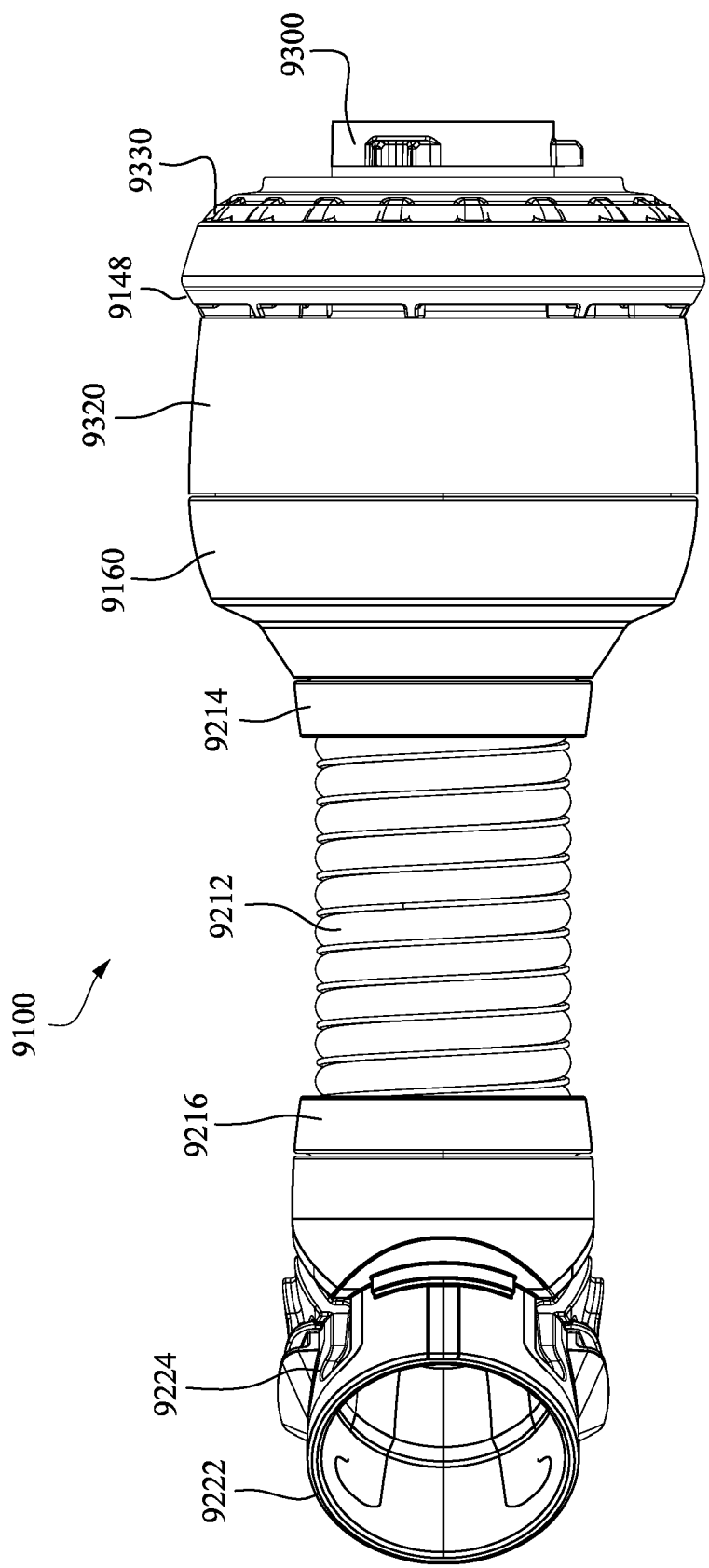

FIG. 35D depicts an inferior view of a vent adaptor according to an example of the present technology.

Figure 35E:
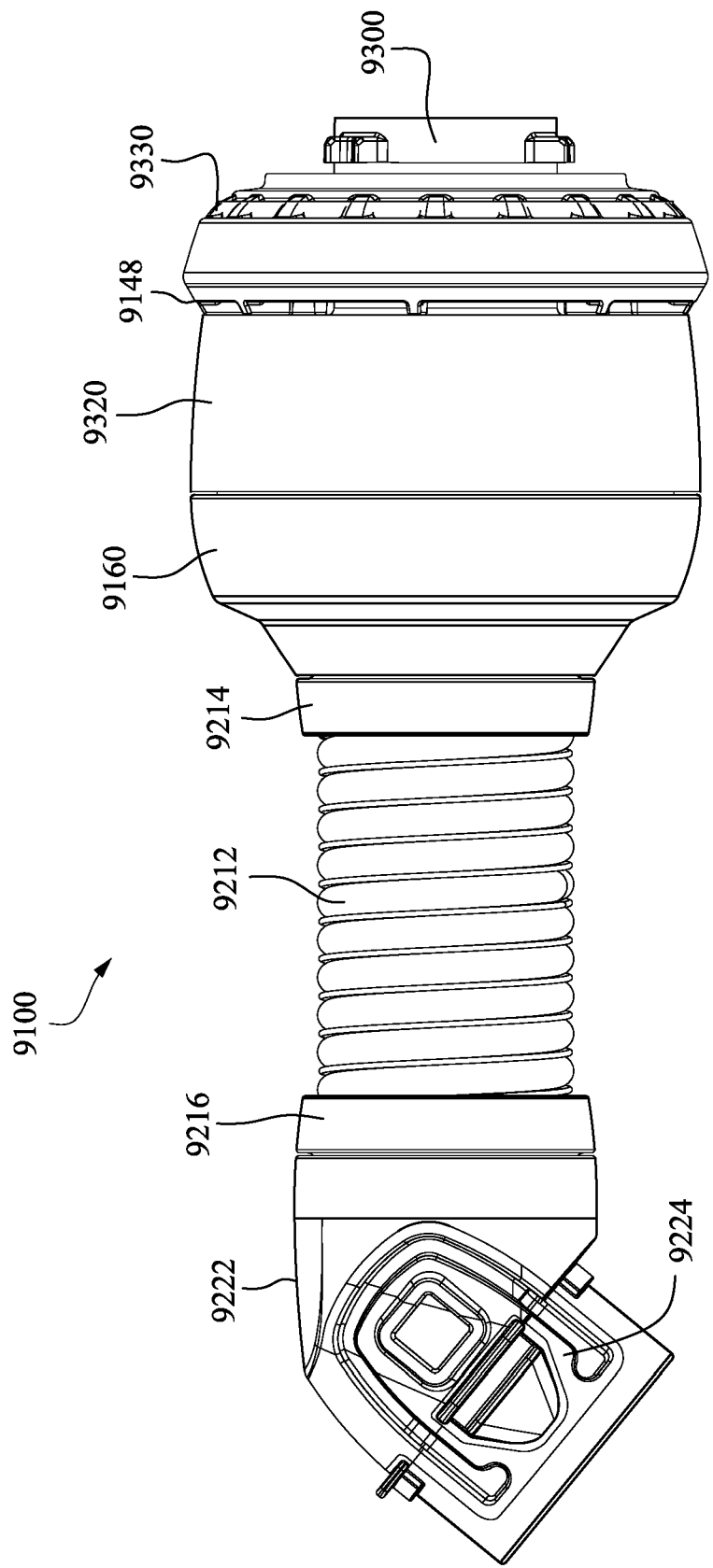

FIG. 35E depicts a lateral view of a vent adaptor according to an example of the present technology.

Figure 35F:
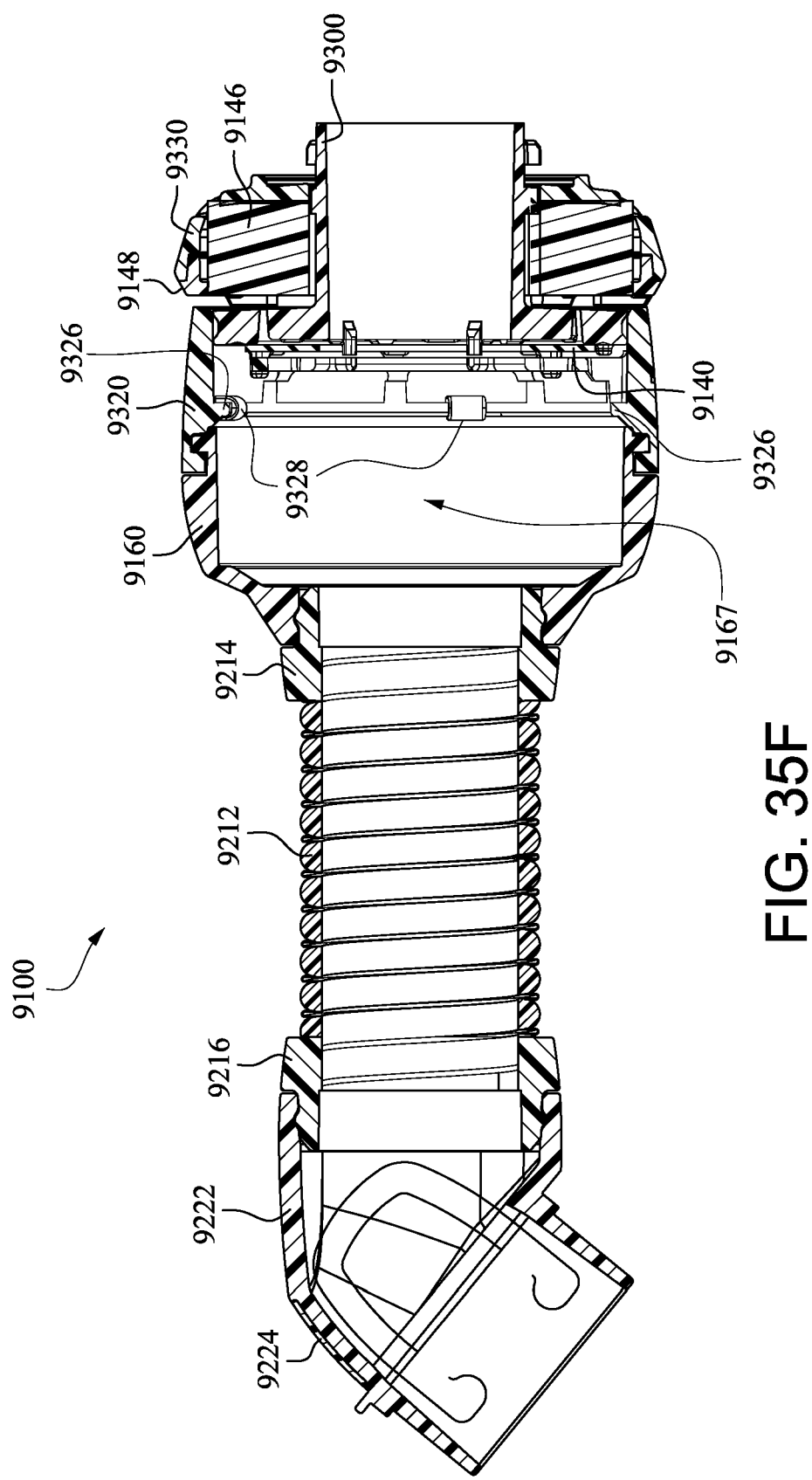

FIG. 35F depicts a cross-sectional view of a vent adaptor taken through line 35F-35F of FIG. 35C according to an example of the present technology.

Figure 35G:
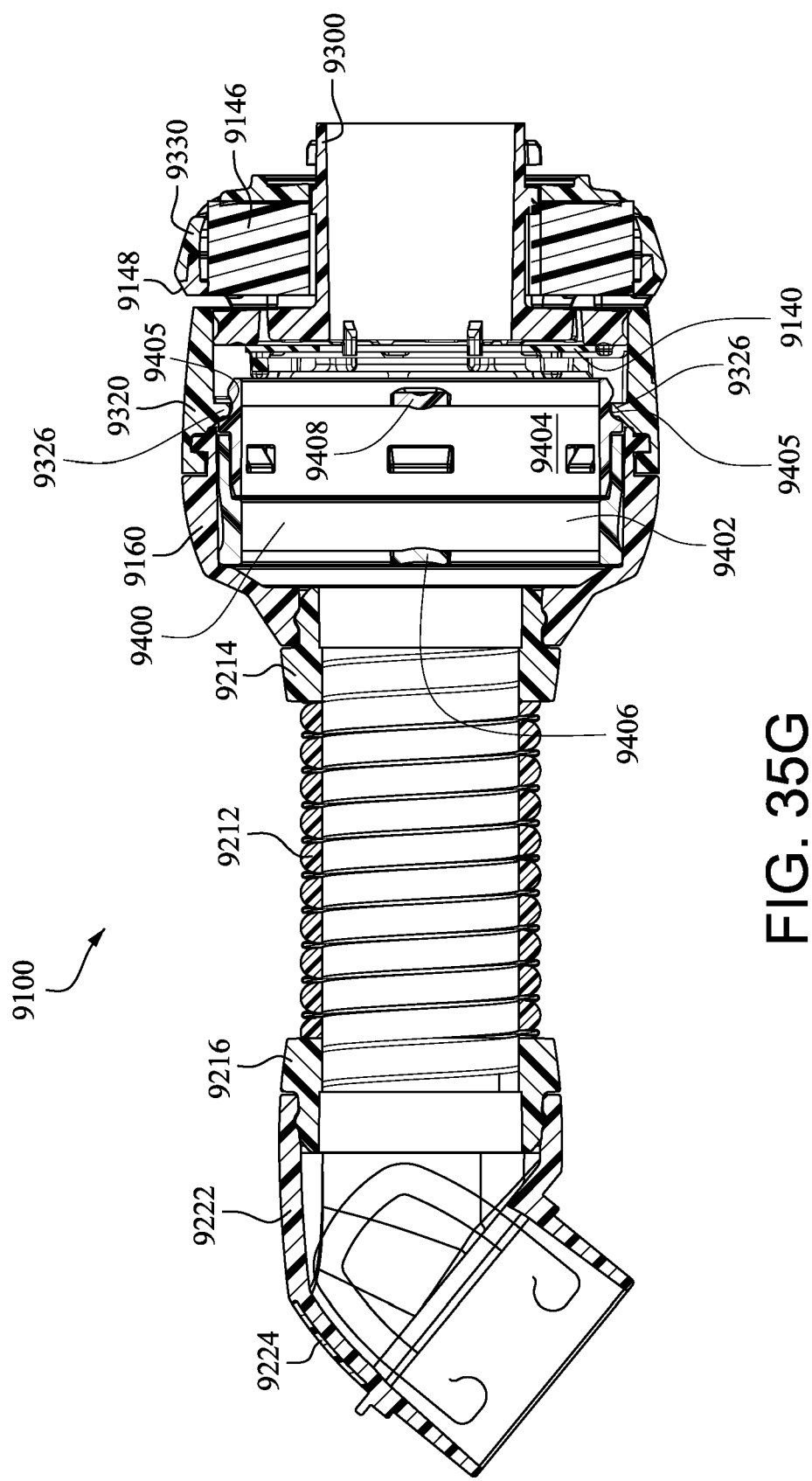

FIG. 35G depicts a cross-sectional view of a vent adaptor with a heat and moisture exchanger (HME) housing taken through line 35F-35F of FIG. 35C according to an example of the present technology.

Figure 35H:
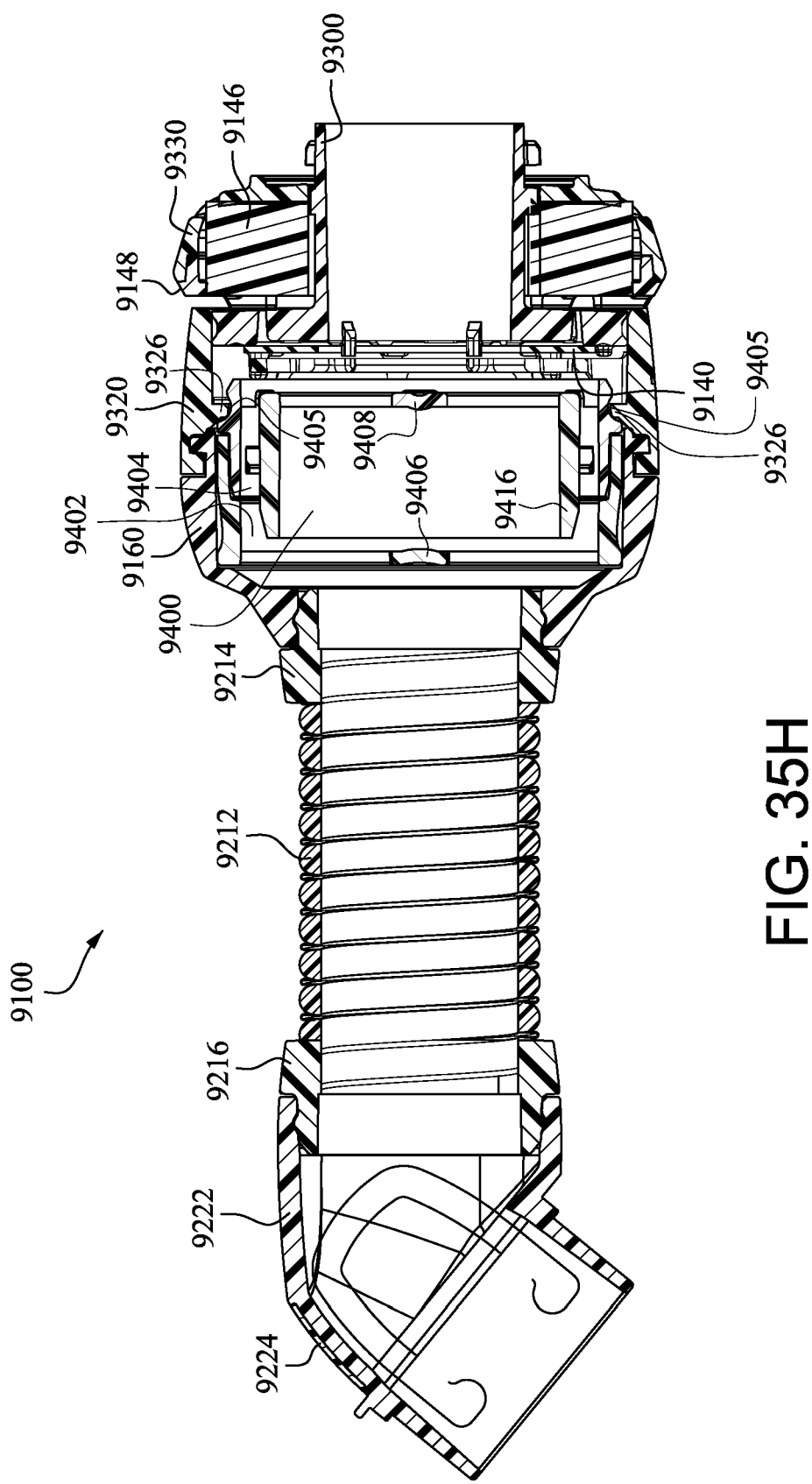

FIG. 35H depicts a cross-sectional view of a vent adaptor with a heat and moisture exchanger (HME) housing taken through line 35F-35F of FIG. 35C according to an example of the present technology.

Figure 35I:
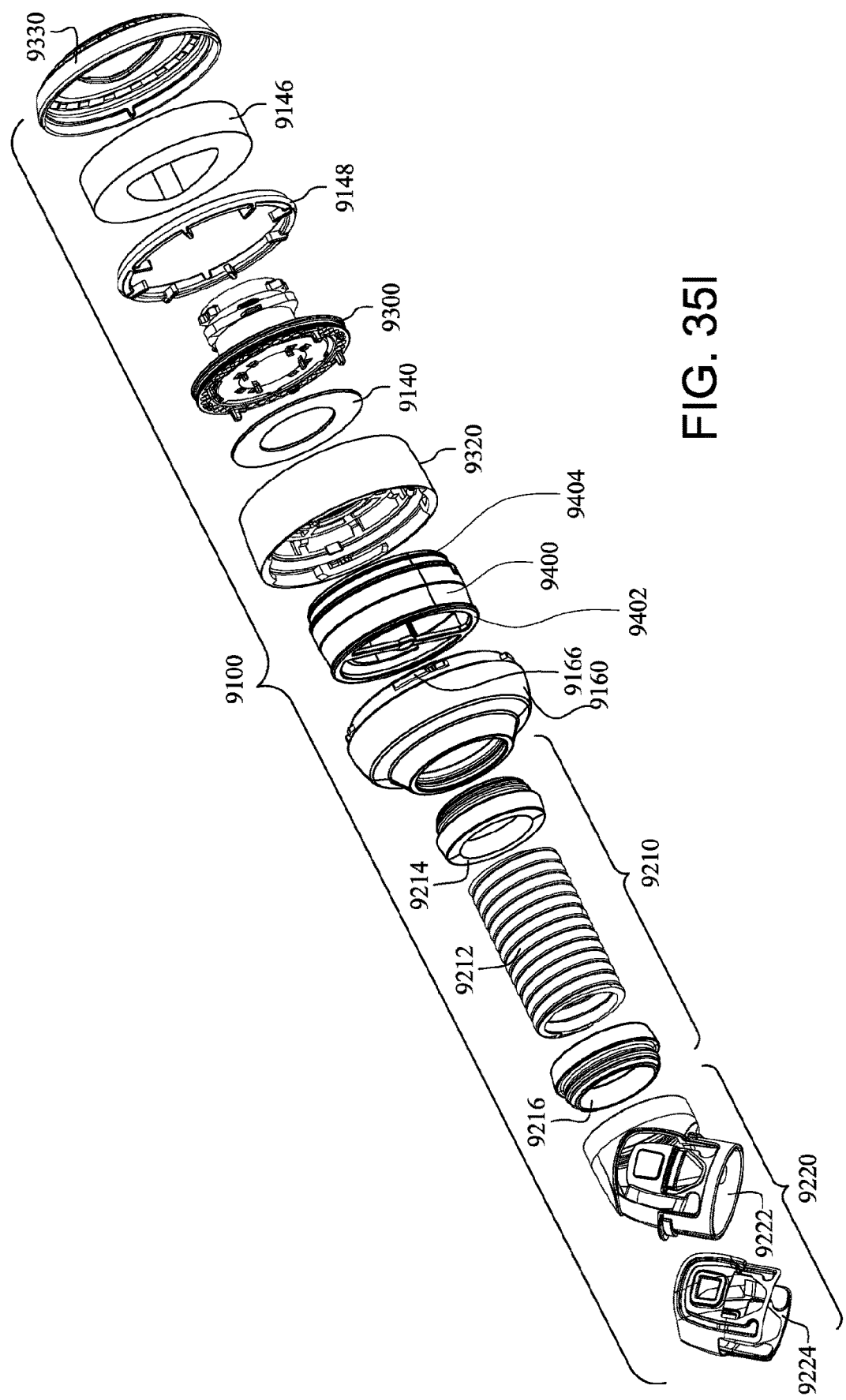

FIG. 35I depicts an exploded view of a vent adaptor according to an example of the present technology.

Figure 36A:
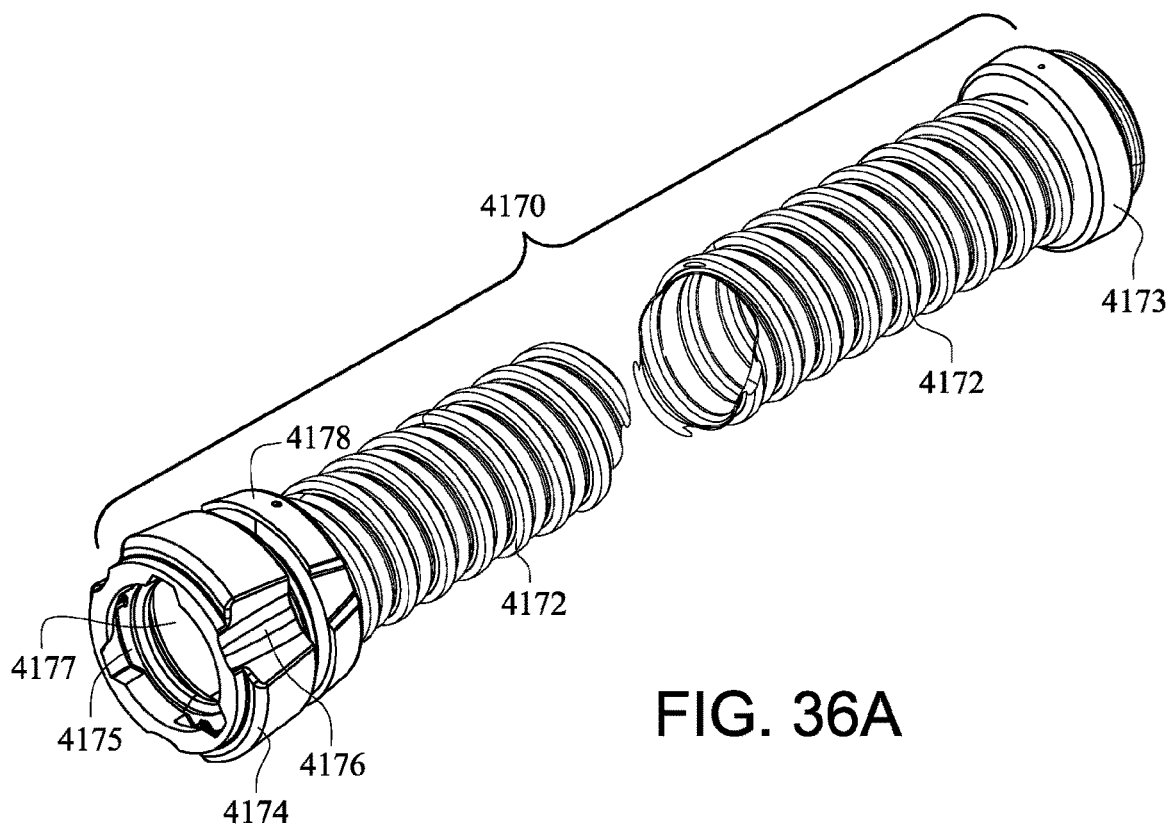

FIG. 36A depicts a perspective view of an air circuit according to an example of the present technology.

Figure 36B:
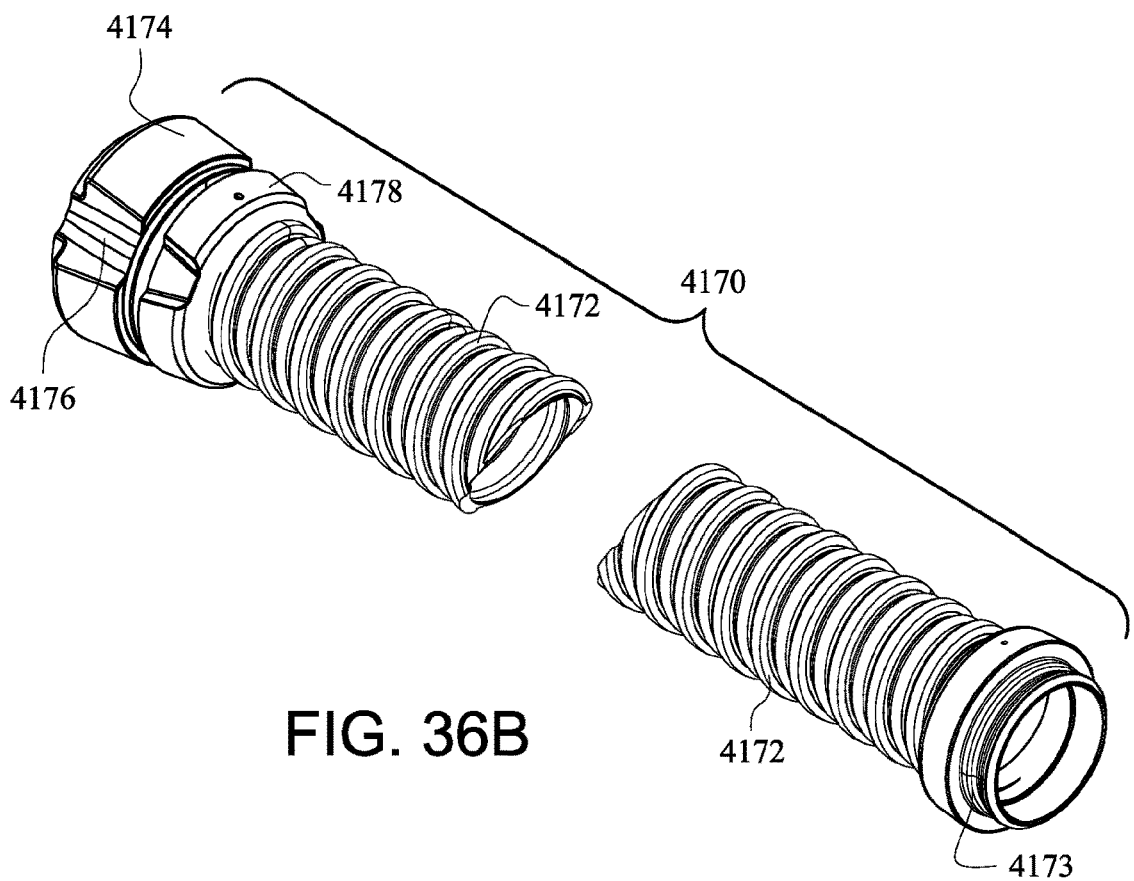

FIG. 36B depicts another perspective view of an air circuit according to an example of the present technology.

Figure 36C:
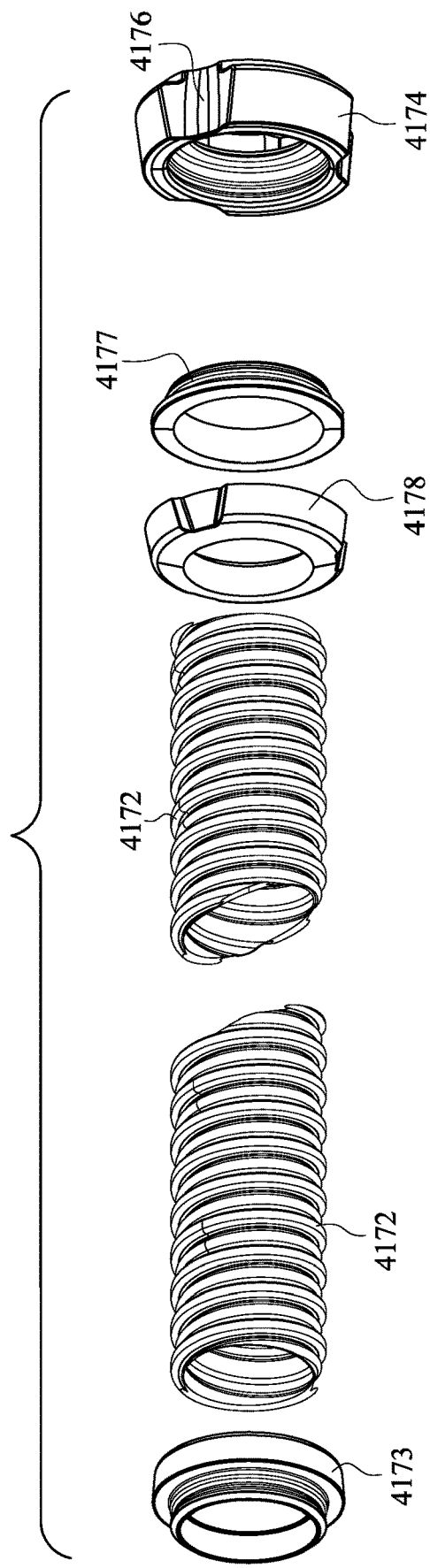

FIG. 36C depicts an exploded view of an air circuit according to an example of the present technology.

Figure 37A:
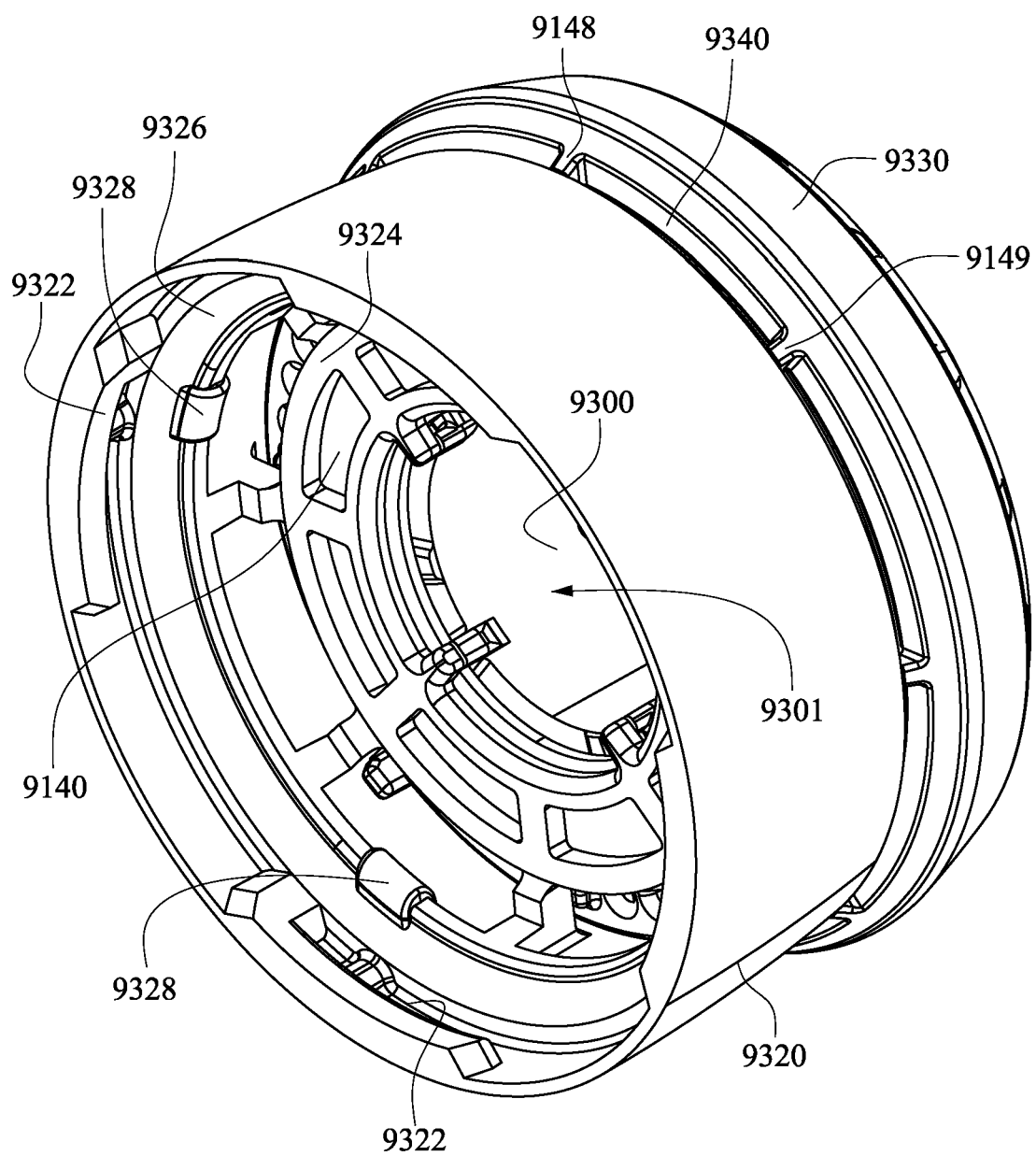

FIG. 37A depicts a perspective view of a vent assembly for a vent adaptor according to an example of the present technology.

Figure 37B:
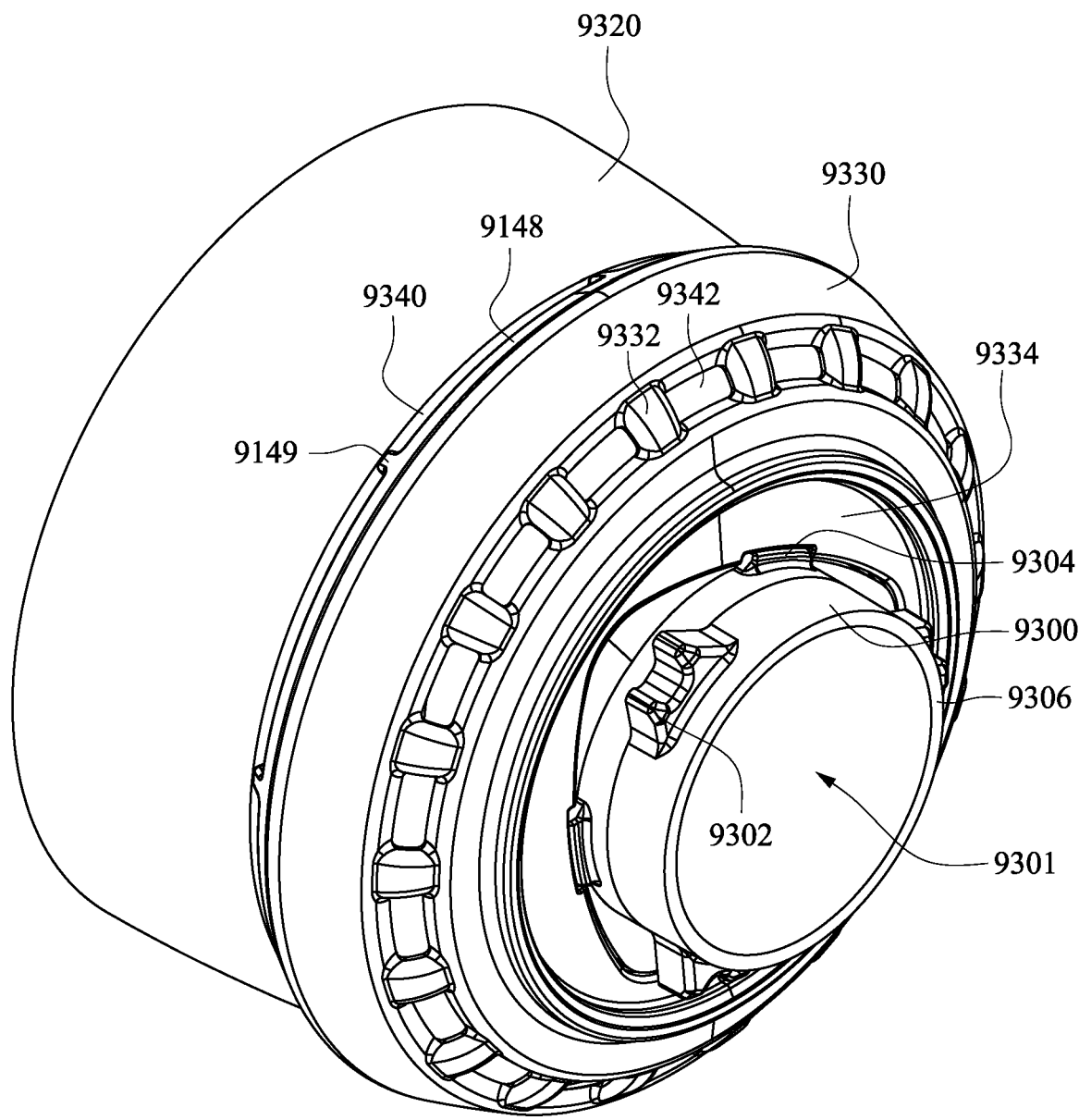

FIG. 37B depicts another perspective view of a vent assembly for a vent adaptor according to an example of the present technology.

Figure 37C:
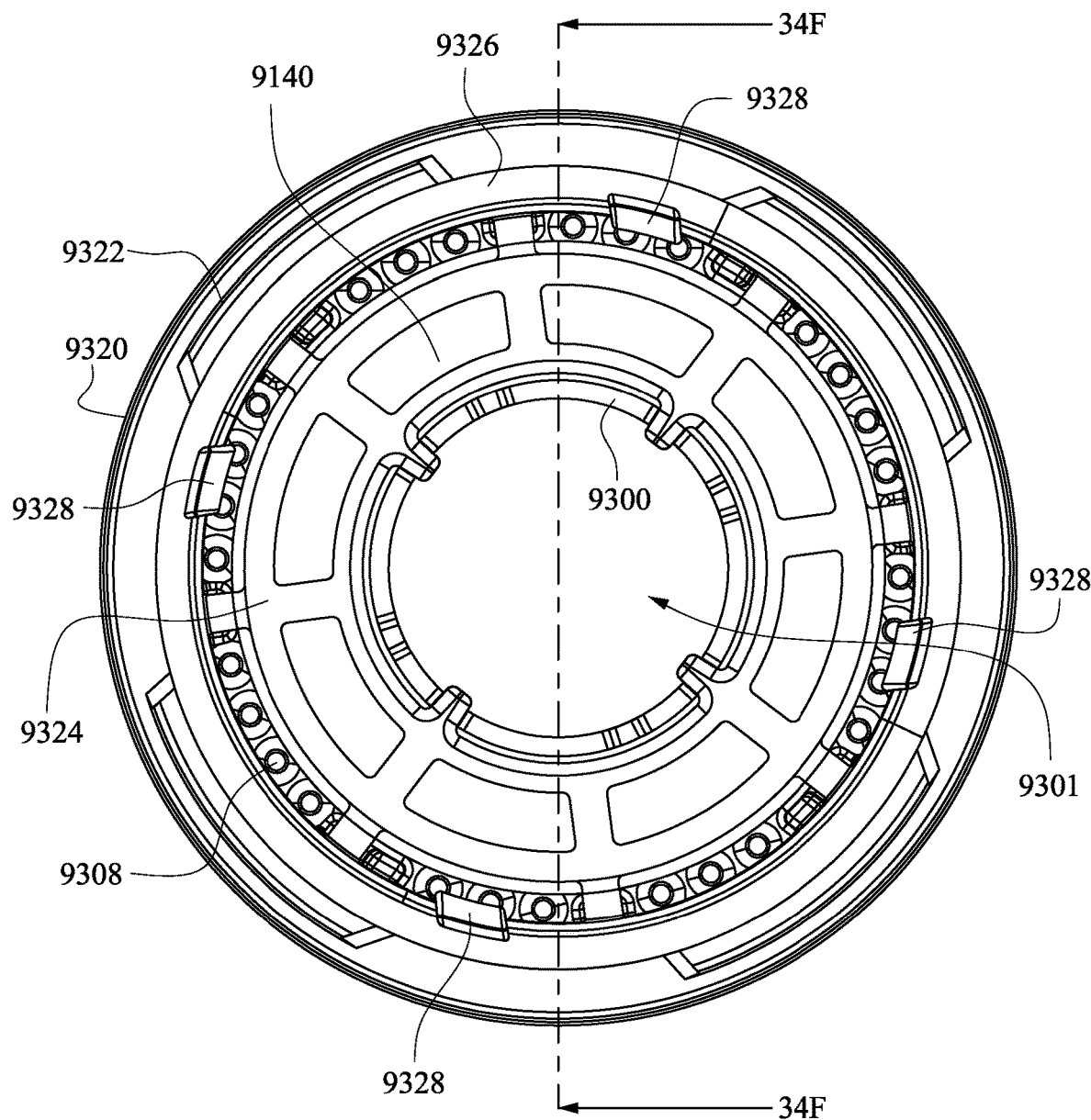

FIG. 37C depicts a posterior view of a vent assembly for a vent adaptor according to an example of the present technology.

Figure 37D:
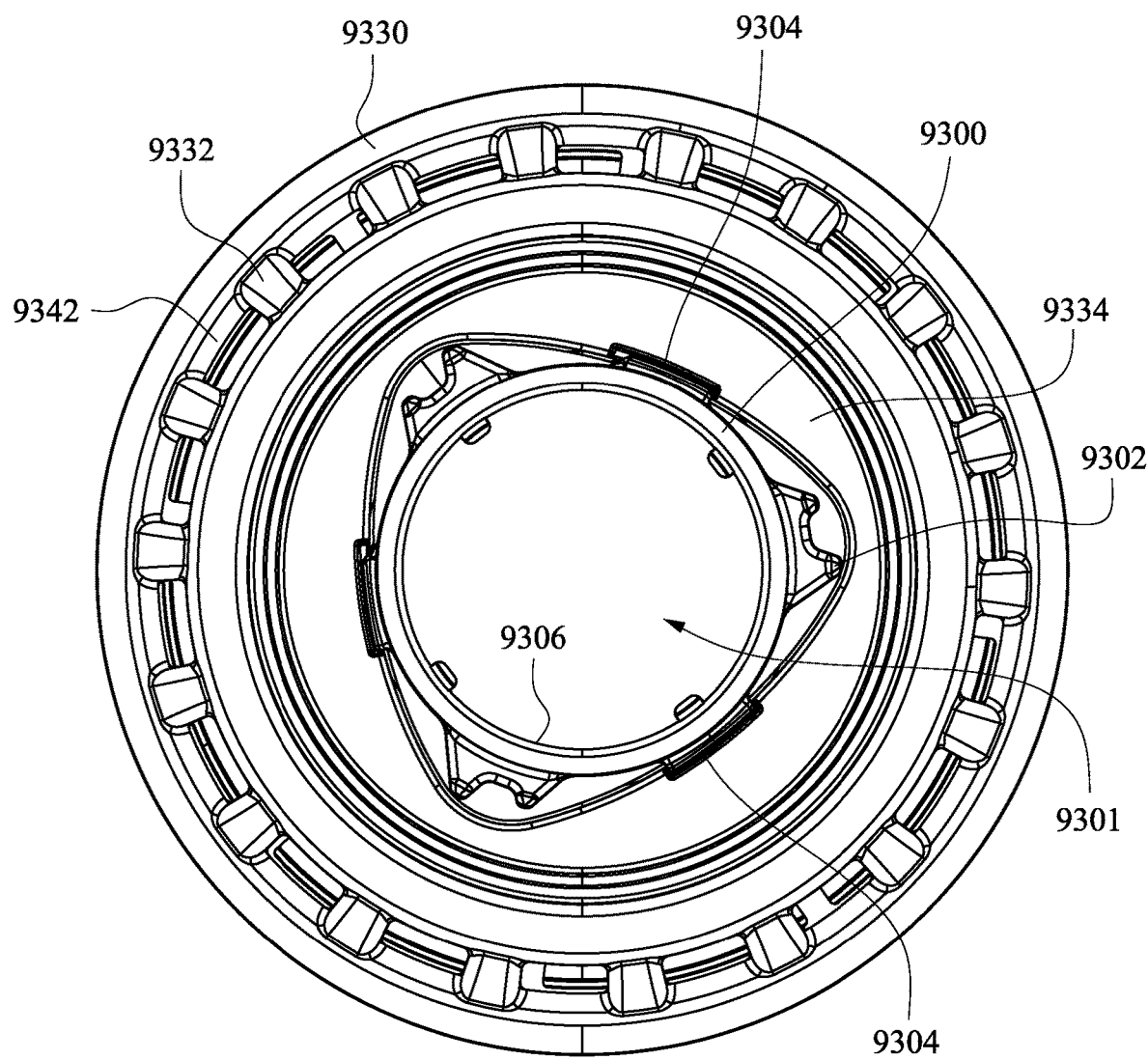

FIG. 37D depicts an anterior view of a vent assembly for a vent adaptor according to an example of the present technology.

Figure 37E:
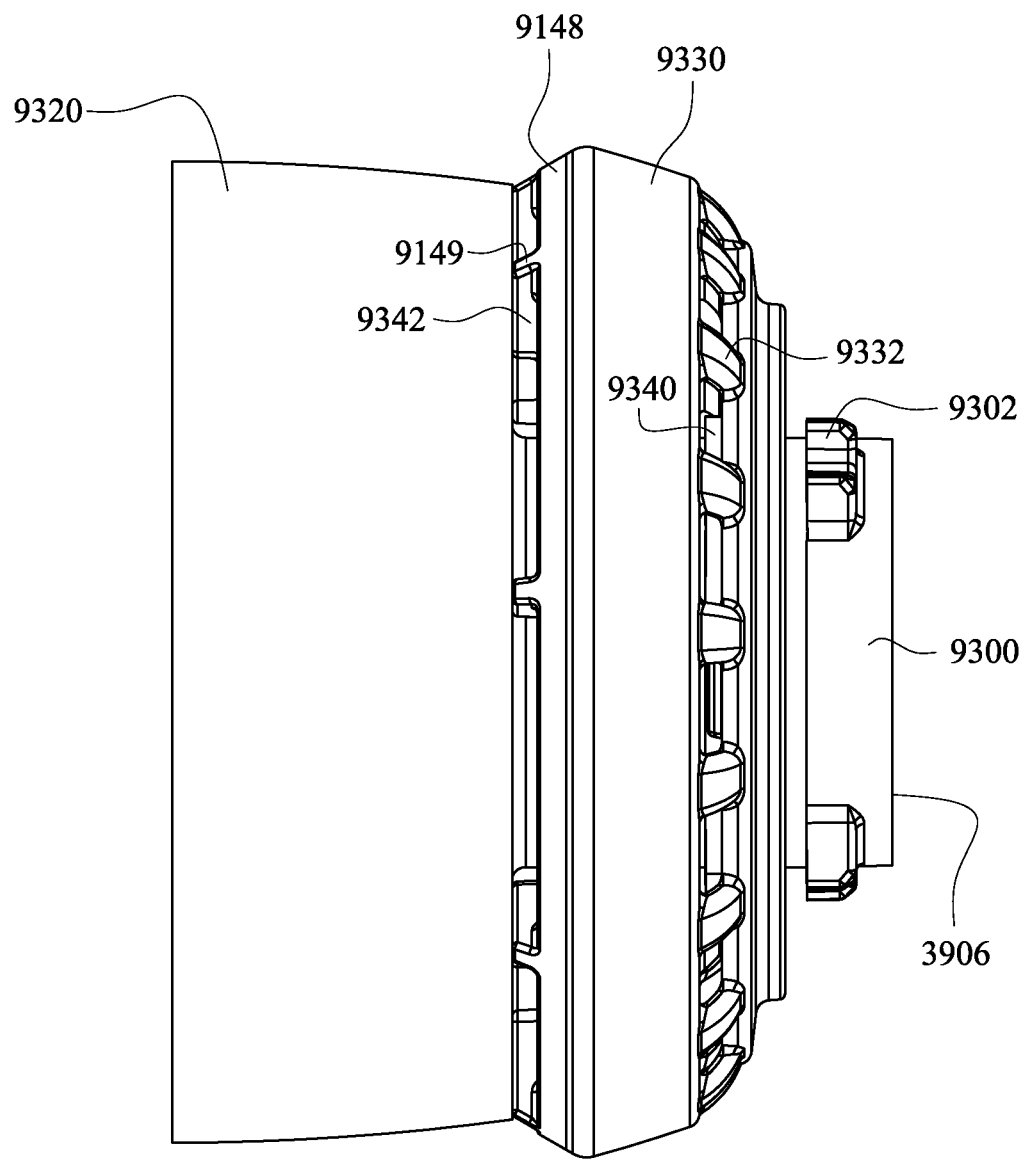

FIG. 37E depicts a lateral view of a vent assembly for a vent adaptor according to an example of the present technology.

Figure 37F:
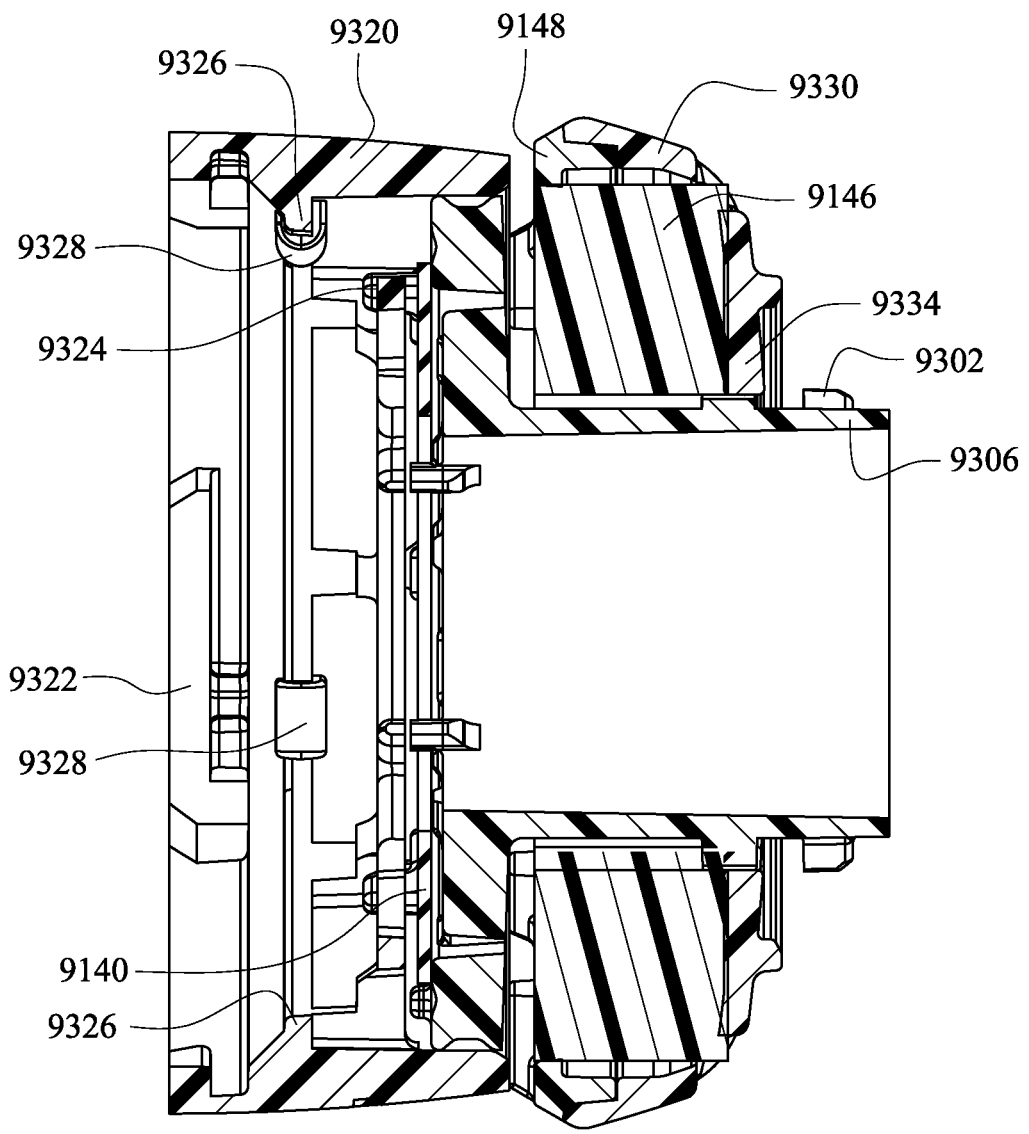

FIG. 37F depicts a cross-sectional view of a vent assembly for a vent adaptor taken through line 37F-37F of FIG. 37C according to an example of the present technology.

Figure 37G:
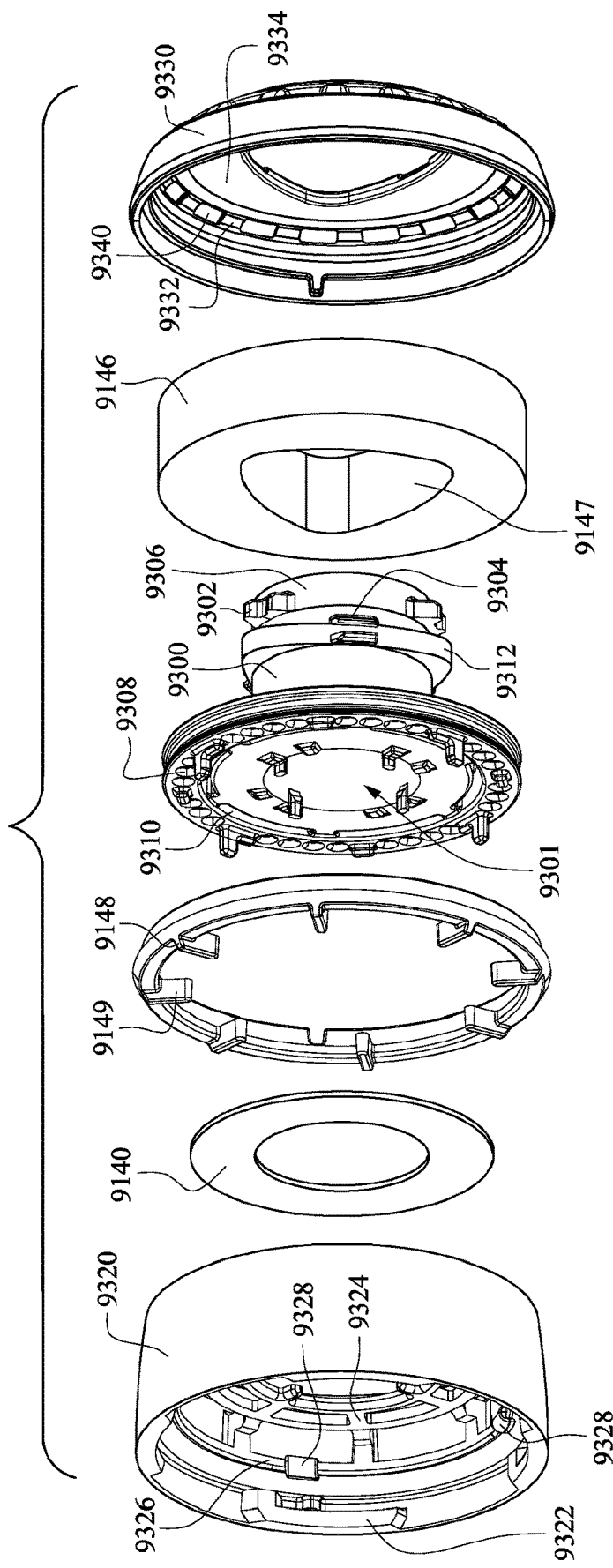

FIG. 37G depicts an exploded view of a vent assembly for a vent adaptor according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent system 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g., silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. The support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g., as a result of elastic tension in the positioning and stabilising structure.

In one form, the seal-forming structure comprises a tension portion. In use, the tension portion is held in tension, e.g., by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g., a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example, the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example, the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g., a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g., resiliently extensible. For example the strap may be configured in use to be in tension, and to direct a force to draw a seal-forming structure into sealing contact with a portion of a patient's face. In an example, the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of the parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and, e.g., non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another. suitable for a small sized head, but not a large sized head.

5.3.4 Vent System

In one form, the patient interface 3000 includes a vent system 3400 constructed and arranged to allow for the washout of exhaled gases, e.g., carbon dioxide.

In certain forms, the vent system 3400 is configured to allow a continuous vent flow from an interior of the plenum chamber 3200 to ambient whilst the pressure within the plenum chamber is positive with respect to ambient. The vent system 3400 is configured such that the vent flow rate has a magnitude sufficient to reduce rebreathing of exhaled $CO_2$ by the patient while maintaining the therapeutic pressure in the plenum chamber in use.

One form of vent system 3400 in accordance with the present technology comprises a plurality of holes, for example, about 20 to about 80 holes, or about 40 to about 60 holes, or about 45 to about 55 holes.

The vent system 3400 may be located in the plenum chamber 3200. Alternatively, the vent system 3400 is located in a decoupling structure, e.g., a swivel.

The vent system 3400 according to examples of the present technology may include a vent housing 3401 and a membrane 3430. The vent housing 3401 may be include a plurality of orifices and the membrane 3430 be deflected to restrict the vent flow or the washout flow through some of the orifices, but not others. By dynamically restricting the vent flow through certain orifices but not others, the combined vent flow may remain substantially constant over a large proportion of the range of typical therapeutic pressures. By structuring the vent system 3400 to maintain a constant rate of vent flow over a large proportion of the range of typical therapeutic pressures, the demands on the RPT device 4000 to provide a sufficient flow of air to maintain the desired therapeutic pressure within the plenum chamber 3200 despite losses, such as due to venting, are decreased. When the demands on the RPT device 4000 are decreased, it is possible to reduce costs because a less complex and powerful RPT device 4000 is required to provide the same level of therapy. A number of exemplary configurations of the vent system 3400 and a more detailed functional explanation follow below.

5.3.4.1 Vent Housing

FIGS. 6A to 6G, FIGS. 9A to 9G, FIGS. 10A to 10G, and FIGS. 11A to 11G depict examples of several different vent housing 3401 configurations. The vent housing 3401 may include an outer wall 3402 and the outer wall 3402 may define the outer periphery of the vent housing 3401. The vent housing 3401 may also include an inner wall 3410 that may define an inlet for the flow of gas generated by the RPT device 4000 and directed into the plenum chamber 3200 and toward the patient for therapy. As can be seen, the outer wall 3402 and the inner wall 3410 are formed as concentric circles in these examples.

Positioned between the outer wall 3402 and the inner wall 3410 is a base. The base may further comprise an outer base 3403 and an inner base 3406. The outer base 3403 may extend from the inner periphery of the outer wall 3402 and the inner base 3406 may extend from the outer periphery of the inner wall 3410. As can be seen, the outer base 3403 and the inner base 3406 are also formed as concentric circles in these examples. The inner wall 3410 may extend below the inner base 3406, as in FIGS. 10A to 10G and FIGS. 11A to 11G, or the inner wall 3410 may terminate at the bottom of the inner base 3406, as in FIGS. 6A to 6G, FIGS. 8A to 8G, and FIGS. 9A to 9G.

The outer base 3403 may include one or more second orifices 3404 distributed radially around the outer base 3403. These second orifices 3404 may extend entirely through the outer base 3403 to provide a flow path from the interior of the vent system 3400 to atmosphere. The second orifices 3404 may be straight, i.e., perpendicular to the outer base 3403, or the second orifices 3404 may pass through the outer base 3403 with a curved path or a slanted path. The diameter of the second orifices 3404 may be constant along their length or the diameter may be varied. The second orifices 3404 may all be identical or some may be different from others. The edges of the second orifices 3404 may have a chamfer or a fillet. The outer base 3403 may at least partially support the membrane 3430 to prevent the membrane 3430 from completely occluding the first orifices 3407. Accordingly, the outer base 3403 may extend higher up than the inner base 3406, as can be seen in FIGS. 6F, 6G, 9F, 9G, 10F, and 10G.

The vent housing 3401 may also include lateral membrane supports 3405 distributed about the outer base 3403 and the inner periphery of the outer wall 3402. The lateral membrane supports 3405 may abut and prevent the membrane 3430 from moving laterally during use, thereby covering the second orifices 3404. As will be explained below, it may be desirable not to obstruct the second orifices 3404 so that the vent system 3400 will be able to maintain a substantially constant vent flow rate over a large proportion of the range of typical therapeutic pressures. Therefore, the lateral membrane support 3405 may protrude radially inward beyond the edges of the second orifices 3404. The lateral membrane supports 3405 may be semi-circular, as in FIGS. 6A to 6G, FIGS. 9A to 9G, and FIGS. 10A to 10G, or the lateral membrane supports 3405 may be rectangular, as in FIGS. 11A to 11G.

In the examples depicted in FIGS. 6A to 6G and FIGS. 9A to 9G, the second orifices 3404 are distributed evenly in groups of three between adjacent lateral membrane supports 3405 about the circumference of the outer base 3403. In the example depicted in FIGS. 11A to 11G, the second orifices 3404 are concentrated into six groups of four with two of each of the six groups spaced closer to one adjacent lateral membrane support 3405 than the other adjacent lateral membrane supports 3405. In the example of FIGS. 10A to 10G, the second orifices 3404 are omitted.

The vent housing 3401 may also have a circular shape. However, the vent housing 3401 may also be shaped elliptically or the vent housing 3401 may have a polygonal shape, such as a triangle, a square, a rectangle, a pentagon, a hexagon, etc. In any of these configurations, the membrane 3430 may be shaped to correspond with the shape of the vent housing 3401.

The inner base 3406 may be positioned radially inward of the outer base 3403 and the inner base 3406 and the outer base 3403 may be joined by base connectors 3408 distributed radially therebetween. Between adjacent base connectors 3408 and between the inner base 3406 and the outer base 3403 there are one or more first orifices 3407. The first orifices 3407 in these examples are shaped as slots with an arc-shaped cross-section. However, it is envisioned that the first orifices 3407 may be circular holes, similar to the second orifices 3404. The first orifices 3407 extend completely through the vent housing 3401 between the inner base 3406 and the outer base 3403. As will be explained below, it may be desirable to allow the first orifices 3407 to be at least partially obstructed by the membrane 3430 to allow the vent system 3400 to maintain a substantially constant vent flow rate over a large proportion of the range of typical therapeutic pressures. The edges of the first orifices 3407 may have a chamfer or a fillet.

The inner base 3406 of the vent housing 3401 may also include several membrane spacers 3409. The membrane spacers 3409 may be evenly distributed radially about the inner base 3406. The membrane spacers 3409 may also be spaced closer to the inner wall 3410 than the outer base 3403, as shown in FIGS. 6A to 6G where the inner wall 3410 extends beyond the inner base 3406. Alternatively, where the inner wall 3410 does not extend beyond the inner base 3406, as in FIGS. 9A to 9G, FIGS. 10A to 10G, and FIGS. 11A to 11G, the membrane spacers 3409 may be located on the edge of the inner base 3406 so as to fade into the inner wall 3410. The membrane spacers 3409 are provided to at least partially support the membrane 3430, as will be described in greater detail below. The membrane spacers 3409 may extend from the inner base 3406 in a semi-cylindrical shape, as in FIGS. 6A to 6G, or in a rectangular shape, as in FIGS. 9A to 9G, FIGS. 10A to 10G, and FIGS. 11A to 11G. The edges of the membrane spacers 3409 may have a chamfer or a fillet.

The example depicted in FIGS. 10A to 10G includes inner base slots 3413 extending along the inner base 3406. The inner base slots 3413 are recessed below the inner base 3406 and extend between the inlet 3411 and the first orifices 3407. The inner base slots 3413 may have a rectangular profile, as shown in FIGS. 10A to 10G, or the inner base slots 3413 may have a circular or elliptical profile. The example depicted in FIGS. 10A to 10G also does not include second orifices 3404, because when the membrane 3430 is occluding the first orifices 3407, the inner base slots 3413 allow some vent flow to pass out the first orifices 3407 via the inner base slots 3413.

The vent housing 3401 may also include a base divider 3418, as shown in FIGS. 11A to 11B, between the outer base 3403 and the inner base 3406. The base divider 3418 may extend above the outer base 3403 and the inner base 3406. The base divider 3418 may at least partially support the membrane 3430, along with the membrane spacers 3409, to prevent the membrane 3430 from completely occluding the first orifices 3407.

The vent housing 3401 may also include one or more recesses 3415 spaced around the opposite side of the outer base, as can be seen in FIGS. 6A to 6G, FIGS. 9A to 9G, and FIGS. 10A to 10G. The recesses 3415 may be separated by recess dividers 3414. The second orifices 3404 may extend through the outer base 3403 and open into the corresponding recesses 3415 and multiple second orifices 3404 may open into a single recess 3415.

In an alternative example, the vent housing 3401 may only include one group of orifices that are analogous to the first orifices 3407 described above in that the vent flow passing therethrough can be restricted by the membrane's 3430 position. Accordingly, there may also be another group of orifices provided elsewhere on the patient interface 3000 that are analogous to the second orifices 3404 described above in that the vent flow passing therethrough is not restricted by the membrane 3430, regardless of the membrane's 3430 position. The latter group of orifices that are not restricted by the membrane 3430 may be placed on any of the plenum chamber 3200, the seal-forming structure 3100, the decoupling structure 3500, the vent connector tube 4180, or other component that is closer to the patient than the vent housing 3401. It is envisioned that the principles of operation of the vent systems 3400 described above will apply to such an alternative arrangement, but the ability to locate the orifices that are not restricted by the membrane 3430 closer to the patient may improve the discharge of exhaled $CO_2$.

The vent housing 3401 may be made from a single, homogeneous piece of material. The material of the vent housing 3401 may be relatively rigid. The material of the vent housing 3401 may be polycarbonate.

FIGS. 23A-23G depict another example of the vent housing 3401 according to the present technology. In this example, the second orifices 3404 are located on a shaft 3419. The shaft 3419 is shown with a cylindrical shape and the second orifices 3404 are distributed around the perimeter of the shaft 3419. The shaft 3419 may have other profiles, such as oval, triangular, square, rectangular, pentagonal, hexagonal, and octagonal.

The second orifices 3404 in this example take the form of holes having a cylindrical shape. The second orifices 3404 may have a constant diameter through the shaft 3419, or the diameter of the second orifices 3404 may increase or decrease from outside of the shaft 3419 to the inside.

The second orifices 3404 are shown in these examples distributed into three groups of eight, in which the second orifices 3404 of any given group are proximal to each other while each group is spaced further apart. In other examples, there may be one or more groups of second orifices 3404, and each group of second orifices 3404 may include one or more second orifices 3404.

As can be seen, the shaft 3419 is oriented approximately perpendicular to the inner base 3406 such that the first orifices 3407 and the second orifices 3404 are also oriented approximately perpendicular to each other. Accordingly, the flow path through each of the first orifices 3407 and the second orifices 3404 may be approximately perpendicular. Thus, vent flow out of the second orifices 3404 may pass radially outward from the shaft 3419, and vent flow of the first orifices 3407 may pass axially relative to the shaft 3419.

5.3.4.2 Membrane

FIGS. 7A to 7D depict views of an exemplary membrane 3430. The exemplary membrane 3430 may be used with any of the various vent housing 3401 configurations disclosed above. The membrane 3430 may be in the shape of a flat, circular disk. In other words, the thickness of the membrane 3430 (see FIG. 7D) may be small relative to its outer diameter. The thickness of the membrane 3430 may be uniform throughout, as shown in FIG. 7D. Alternatively, the thickness of the membrane 3430 may be variable in a radial direction.

The membrane 3430 includes a membrane opening 3431 such that when assembled onto the vent housing 3401, the flow of air through the inlet 3411 also passes through the membrane opening 3431 and along to the patient. The membrane 3430 also includes a patient-side surface 3432 that faces towards the patient in use and an atmosphere-side surface 3433 opposite the patient-side surface 3432 that faces towards the atmosphere in use. Additionally, the atmosphere-side surface 3433 faces towards the vent housing 3401 when assembled. The membrane 3430 also includes an inner surface 3434 that defines the membrane opening 3431 and an outer surface 3435 that is opposite the inner surface 3434.

The inner radius, i.e., the radius of the inner surface 3434, and the outer radius, i.e., the radius of the outer surface 3435, may be selected such that the membrane 3430 can be located over the first orifices 3407 in use without covering the second orifices 3404. Also, the inner radius and the outer radius may be selected such that the membrane 3430 covers a substantial portion of the inner base 3406 while being supported on the membrane spacers 3409 proximal to the inner surface 3434 and on the outer base 3403 or the base divider 3418 proximal to the outer surface.

The membrane 3430 may be made from a single piece of homogeneous material. The material may be elastically deformable such that the membrane 3430 can be deflected in use by the pressure from the flow of air. The material may be silicone. The membrane 3430 may be "tuned" to deform in a desired manner by altering one or more of its thickness, length, material, shape, inner radius, and/or outer radius.

5.3.4.3 Constant Flow Rate Vent System

FIGS. 5A to 5G and FIGS. 8A to 8G depict several views of exemplary vent systems 3400 with the membrane 3430 assembled with the vent housing 3401. In FIGS. 5A to 5G, the inner wall 3410 defining the inlet 3411 extends upward from the inner base 3406 and in FIGS. 8A to 8G, the inner wall 3410 does not extend above the inner base 3406. In the examples where the inner wall 3410 extends upward from the inner base 3406, the inner wall 3410 may provide a baffle function that separates the flow of gas traveling into the vent system 3400 via the inlet 3411 from the vent flow exiting the vent system 3400, which in turn may reduce the amount of flow traveling in from the inlet 3411 and then directly out of the vent system 3400.

In the examples of FIGS. 5A to 5G and FIGS. 8A to 8G, a portion of the membrane 3430 proximal to the outer surface 3435 can be seen supported on an inner portion of the outer base 3403. Also, a portion of the membrane 3430 proximal to the inner surface 3434 can be seen supported just above the membrane spacers 3409. However, the membrane 3430 may deform towards the membrane spacers 3409 by virtue of its own weight such that the membrane 3430 is also supported on the membrane spacers 3409 even though there may not be any air pressure causing the deformation.

FIGS. 5A to 5G and FIGS. 8A to 8G also show the membrane's 3430 location constrained by the lateral membrane supports 3405. As explained above, the membrane 3430 may be shaped and dimensioned to cover only the first orifices 3407 and not the second orifices 3404. However, the membrane 3430 may not be directly attached to the vent housing 3401 and, as such, may be free to move. Therefore, a sufficient number of lateral membrane supports 3405 can prevent lateral movement of the membrane 3430 so that the membrane 3430 cannot cover one or more of second orifices 3404 in use.

The inverse of these examples is also envisioned in which the second orifices 3404 may be covered by the membrane 3430 and the first orifices 3407 are not blocked by the membrane 3430. Accordingly, lateral membrane supports 3405 may be provided to prevent the membrane 3430 from covering the first orifices 3407.

FIGS. 5A to 5G also depict the inner base membrane passage 3416 and the inner wall membrane passage 3417. These are the passages through which the first vent flow 6003, which is described in greater detail below, must travel to exit the vent system 3400 during use. The inner base membrane passage 3416 is defined between the inner base

3406 and the atmosphere-side surface 3433 of the membrane 3430. The inner wall membrane passage 3417 is defined between the inner wall 3410 and the inner surface 3434 of the membrane 3430. It should be understood that other variations of the vent housing 3401 in which the inner wall 3410 does not extend above the inner base 3406, such as in FIGS. 8A to 8G, FIGS. 9A to 9G, FIGS. 10A to 10G, and FIGS. 11A to 11G, will not have the inner wall membrane passage 3417.

FIGS. 12A to 12B and 27 to 28 depict various dimensions and parameters of an exemplary vent system 3400 that may affect the performance characteristics of the vent system. Such performance characteristics may include noise, vent flow rate, and responsiveness to pressure changes.

FIGS. 12A and 27 depict the active length 3450 of the membrane 3430, which is the distance between the points where the membrane 3430 is supported by the outer base 3403 and the membrane spacers 3409. The membrane thickness 3451 is another dimension that is shown. The spacer height 3452, which is the height that the membrane spacer 3409 extends above the inner base 3406, is also shown. Another dimension that is shown is the membrane-inner base gap 3453, which is the distance between the inner base 3406 and the atmosphere-side surface 3433 of the membrane 3430. The first orifice radius 3454 is the radius of curvature of the fillet on the first orifice 3407. The first orifice width 3455 is the width of the first orifice 3407 in a radial direction. The first orifice length 3456 is the length of the first orifice 3407 from the outer base 3403 to the end of the first orifice 3407 that vents to atmosphere.

FIGS. 12B, 28 also depict the overlap length 3457, which is the length of the membrane 3430 that overlaps the outer base 3403. The overhang length 3458 is also shown and is the length of the membrane 3430 that hangs over the membrane spacer 3409.

FIG. 19 depicts various configurations for incorporating the exemplary vent systems 3400 with various patient interfaces. The outer wall 3402 may provide an interface for connecting the vent system 3400 to an air circuit connector 4171 to join the vent system 3400 with the air circuit 4170 and locate the vent system 3400 within the flow path. The outer wall 3402 of the vent housing 3401 may also provide an interface for connecting the vent system 3400 to a vent connector tube 4180 at a tube connector 4182. The vent connector tube 4180 may be connected to a nasal patient interface 3000A or a nasal pillows patient interface 3000B opposite the tube connector 4182 via an elbow 4181. The vent connector tube 4180 may be lighter and/or have a smaller diameter than the air circuit 4170, because such a configuration allows the vent system 3400 to be spaced away from the patient interface 3000A/3000B to reduce tube drag. In the case of a full-face patient interface 3000C, the vent connector tube 4180 may be excluded and the outer wall 3402 of the vent housing 3401 may be joined to the decoupling structure 3500. In any of these configurations, a heat and moisture exchanger (HMX) 3800 may also be included.

FIGS. 20A to 26F depict further features of exemplary vent systems 3400 according to the present technology. These examples include a vent housing 3401 in which the second orifices 3404 are on a shaft 3419 that forms the inlet 3411. As will be discussed below, the operation of these vent systems 3400 is similar to what is described in FIGS. 14A-18. However, locating the second orifices 3404 on the shaft 3419 allows the diameter of the vent housing 3401, as well as the overall vent system 3400, to be reduced. Moreover, the flow path through the first orifices 3407 and the second orifices 3404 are not parallel, but are directed at the same space (i.e., the vent diffuser 9146) to promote a cross-flow relationship that can enhance diffusion of the flow and reduce noise production.

5.3.4.4 Operation of the Vent System

FIGS. 13 to 18 and 29 to 34 depict views of exemplary vent systems 3400 with gas flow, i.e., in use. As explained above, the exemplary vent systems 3400 may include a membrane 3430 positioned over the first orifices 3407 to at least partially restrict the flow of gas through the first orifices 3407, while the vent flow through the second orifices 3404 is not restricted by the membrane 3430.

FIGS. 13 and 29 show the various flow paths relevant to the operational sequence depicted in subsequent drawings. FIGS. 13 and 29 show the RPT device flow 6000, which is the flow of pressurized gas generated by the RPT device 4000 for providing respiratory therapy in accordance with the therapies described above in section 2.2.2, for example. Typically, the RPT device flow 6000 is unidirectional toward the patient and, therefore, is indicated with a single-headed arrow. However, there may be certain therapies in which the RPT device flow 6000 travels away from the patient, at least relatively briefly. The patient-generated flow 6001 is shown with a double-headed arrow to indicate that the flow may travel towards or away from the patient depending on whether the patient is inhaling or exhaling. It should be understood that the deflection of the membrane 3430 described below is not dependent on the direction of any flow of gas, but is dependent on the pressure within the pressurized volume 6004. In other words, it is not necessary for there to be a flow of gas in direction opposition to the membrane 3430 to cause deflection, rather the pressure within the pressurized volume 6004 can be relied upon to cause the deflection.

The components of the vent flow are also shown, which include the first vent flow 6003 and the second vent flow 6002. The second vent flow 6002 represents the flow passing through the second orifices 3404 that is unobstructed by the membrane 3430. The first vent flow 6003 represents the flow passing through the first orifices 3407 that is restricted by the membrane 3430, the magnitude of the restriction depending on the position of the membrane 3430. The second vent flow 6002 is described as being passive, because its magnitude may vary but any such variation is inversely related to the magnitude of the first vent flow 6003, at least above a therapy pressure threshold, which is in turn varied by the position of the membrane 3430. It should be understood that the vent flow or the washout flow provided by the vent system 3400 is equal to or greater than the sum of the second vent flow 6002 and the first vent flow 6003. If the total vent flow or washout flow from the vent system 3400 and/or the patient interface 3000 exceeds the sum of the second vent flow 6002 and the first vent flow 6003, other sources of flow may be the cause such as leak from other components, e.g., through the decoupling structure 3500, around the seal-forming structure 3100, and/or at the junction between various components of the patient interface 3000.

FIGS. 13 and 29 show the pressurized volume 6004. The pressurized volume 6004 may represent any volume of therapy flow path that is pressurized by the flow of gas and is downstream of the vent system 3400 relative to the RPT device flow 6000. In these examples, the vent system 3400 is shown schematically joined directly to the plenum chamber 3200 of the patient interface 3000. However, in accordance with the examples depicted in FIG. 19, the pressurized volume 6004 may also include the vent connector tube 4180 or a decoupling structure 3500, which are in turn connected to the plenum chamber 3200.

FIGS. 13 and 29 show the atmosphere 6005 that is external to the pressurized volume 6004. The atmosphere 6005 is generally understood to be at ambient pressure and the vent flow is directed to the atmosphere 6005.

FIGS. 14A and 14B and FIGS. 30A and 30B show an example of the vent system 3400 in which no therapy is being provided. In other words, the RPT device flow 6000 is zero and, thus, the mask pressure, i.e., the pressure of the pressurized volume 6004 relative to atmosphere is zero. Since there is no flow provided by the RPT device flow 6000 and the patient is not breathing such that the patient-generated flow 6001 is also zero, there is also no vent flow. Furthermore, the membrane 3430 can be seen in an undeformed position and supported on the outer base 3403.

FIGS. 15A and 15B and FIGS. 31A and 31B show an example where the RPT device flow 6000 has been increased such that the pressure within the pressurized volume 6004 is at approximately 4 cmH$_2$O. As can be seen, the membrane 3430 has been deflected against the membrane spacers 3409 and the first vent flow 6003 is traveling through the membrane spacer gaps 3412 and out to atmosphere 6005 via the first orifices 3407. The second vent flow 6002 can also be seen traveling via the second orifices 3404 to atmosphere 6005 without obstruction from the membrane 3430. Accordingly, the total vent flow is approximately 20 L/min, which is equal to the sum of the second vent flow 6002 and the first vent flow 6003, both of which are approximately 10 L/min. Since the membrane 3430 has not been pressed down over the first orifices 3407 by the pressure within the pressurized volume 6004, the flow obstruction due to the membrane 3430 is negligible and, as such, the second vent flow 6002 and the first vent flow 6003 are approximately equal.

FIGS. 16A and 16B and FIGS. 32A and 32B show an example where the RPT device flow 6000 has been increased such that the pressure within the pressurized volume 6004 is at 12 cmH$_2$O. As can be seen, the membrane 3430 has been deflected further against the membrane spacers 3409 relative to FIGS. 15A and 31A, and the first vent flow 6003 is traveling through the membrane spacer gaps 3412 and out to atmosphere 6005 via the first orifices 3407. The second vent flow 6002 can also be seen traveling via the second orifices 3404 to atmosphere 6005 without obstruction from the membrane 3430. Accordingly, the total vent flow is approximately 25 L/min, which is equal to the sum of the second vent flow 6002 and the first vent flow 6003, which are approximately 17 L/min and 8 L/min, respectively. Since the membrane 3430 has been pressed down over the first orifices 3407 more substantially by the pressure within the pressurized volume 6004, the flow obstruction due to the membrane 3430 is greater and, as such, the second vent flow 6002 and the first vent flow 6003 are no longer approximately equal.

FIGS. 17A and 17B and FIGS. 33A and 33B show an example where the RPT device flow 6000 has been increased such that the pressure within the pressurized volume 6004 is at approximately 20 cmH$_2$O. As can be seen, the membrane 3430 has been deflected further against the membrane spacers 3409 relative to FIGS. 16A and 32A, and the first vent flow 6003 is traveling through the membrane spacer gaps 3412 and out to atmosphere 6005 via the first orifices 3407, albeit at a lesser magnitude due to flow restriction by the membrane 3430. The second vent flow 6002 can also be seen traveling via the second orifices 3404 to atmosphere 6005 without obstruction from the membrane 3430. Accordingly, the total vent flow is approximately 25 L/min, which is equal to the sum of the second vent flow 6002 and the first vent flow 6003, which are approximately 24 L/min and 1 L/min, respectively. Since the membrane 3430 has been pressed down over the first orifices 3407 more substantially by the pressure within the pressurized volume 6004, the flow obstruction due to the membrane 3430 is greater and, as such, the second vent flow 6002 and the first vent flow 6003 are no longer approximately equal. Indeed, the flow restriction due to the membrane's 3430 deflection is so substantial that there is relatively little first vent flow 6003 and most of the total vent flow is provided by the second vent flow 6002.

Thus, as the pressure within the pressurized volume 6004 increases and the membrane 3430 is pressed closer against the first orifices 3407, the first vent flow 6003 continues to decrease. Accordingly, the second vent flow 6002 increases, because more of the vent flow must escape from the second orifices 3404 due to increasing occlusion of the first orifices 3407. However, it should also be understood that at least within a range of typical therapeutic pressures, such as those described immediately above, the vent flow may travel out through both the first orifices 3407 and the second orifices 3404 at the same time, while the membrane 3430 regulates the apportionment of vent flow as between both sets of orifices.

FIGS. 17B and 33B also illustrate how the total vent flow can be maintained within a substantially constant or a relatively narrow range, i.e., ±1 L/min, over a relatively large range of pressures for the pressurized volume 6004. The range of pressure may be a typical range of therapeutic pressure, e.g., from approximately 6 cmH$_2$O to approximately 20 cmH$_2$O. As can be seen, the total vent flow curve begins to flatten at a pressure of approximately 6 cmH$_2$O and remains so up to a pressure of approximately 20 cmH$_2$O, which is the range of pressures typically used for the respiratory therapies described in section 2.2.2. Thus, the vent system 3400 is capable of maintaining an approximately constant vent flow rate over the typical range of therapeutic pressures. As such, the RPT device 4000 itself can be relied upon less to regulate and maintain the desired therapeutic pressure and vent flow rate, because the vent system 3400 can provide this functionality. Accordingly, the RPT device 4000 requires less complex hardware, because it is not relied upon as much to regulate flow and pressure. Furthermore, the RPT device 4000 requires less complex control features, because, again, it is not relied upon as much regulate flow and pressure.

FIGS. 18 and 34 show an example of how the exemplary vent system 3400 may be cleaned. It should be understood that the vent system 3400 is subject to moist exhalation airflow from the patient-generated flow 6001, which may provide an environment for bacterial growth. Additionally, the vent system 3400 may accumulate other particulate matter, such as dust and dirt. Therefore, it may be advantageous to be able to clean the vent system 3400. Accordingly, FIGS. 18 and 34 show a water flow 6006 being introduced into the vent system 3400 from a direction opposite the vent flow. The water flow 6006 can be seen displacing the membrane 3430. The relatively open design of the vent system 3400 lends itself to easy cleaning because the various flow paths can readily receive the water flow 6006 for cleaning.

5.3.4.5 Exemplary Vent Adaptor

FIGS. 20A-20E show a vent diffuser cover 9330 according to one example of the present technology. FIGS. 24A-24F show an exemplary vent system 3400 according to an example of the present technology that includes the vent diffuser cover 9330 of FIGS. 20A-20E. In these examples, the vent diffuser cover 9330 has radial diffuser retainers 9149 that retain the diffuser 9146 within the vent system 3400. When assembled, the radial diffuser retainers 9149 space the vent diffuser cover 9330 from the vent housing 3401 to form posterior vent outlets 9340. The posterior vent outlets 9340 allow vent flow passing through first orifices 3407 and the second orifices 3404 in the vent housing 3401, then through the diffuser 9146, and on to atmosphere to travel radially out of the vent system 3400. In an example, vent flow may exit to atmosphere only through the posterior vent outlets 9340. In another example, vent flow may exit to atmosphere through the posterior vent outlets 9340 and at least one other vent opening, e.g., an opening on the patient interface 3000.

FIGS. 21A-21E show a vent diffuser cover 9330 according to one example of the present technology. FIGS. 25A-25F show an exemplary vent system 3400 according to an example of the present technology that includes the vent diffuser cover 9330 of FIGS. 21A-21E. In these examples, the vent diffuser cover 9330 has radial diffuser retainers 9149 that retain the diffuser 9146 within the vent system 3400. When assembled, the radial diffuser retainers 9149 space the vent diffuser cover 9330 from the vent housing 3401 to form posterior vent outlets 9340. The posterior vent outlets 9340 allow vent flow passing through first orifices 3407 and the second orifices 3404 in the vent housing 3401, then through the diffuser 9146, and on to atmosphere to travel radially out of the vent system 3400. The vent diffuser cover 9330 may also include cover spacers 9332 forming anterior vent outlets 9342, in addition to the posterior vent outlets 9340. In an example, vent flow may exit to atmosphere only through the posterior vent outlets 9340 and the anterior vent outlets 9342. In another example, vent flow may exit to atmosphere through the posterior vent outlets 9340, the anterior vent outlets 9342, and at least one other vent opening, e.g., an opening on the patient interface 3000.

FIGS. 35A to 35I depict another example of a vent adaptor 9100 according to an example of the present technology. This vent adaptor 9100 may be connected to a patient interface 3000, as shown in FIG. 35 for example, to provide the functions of its components.

The vent adaptor includes an elbow assembly 9220 to provide a fluid connection with the patient interface 3000, e.g., via a connection port 3600 on the plenum chamber 3200. This example of the elbow assembly 9220 includes an elbow frame 9222 and an elbow overmould 9224. The elbow assembly 9220 may provide a releasable connection with the plenum chamber 3200 at the connection port. The elbow frame 9222 may include tabs that are elastically deformable for the releasable connection and the elbow overmould 9224 may provide a fluid-tight seal around openings in the elbow frame 9222, as well as added resiliency for the elbow frame 9222. The elbow assembly 9220 may also be rotatable relative to the plenum chamber 3200 to reduce the effects of tube drag from the other components of the vent adaptor 9100 and the air circuit 4170. The elbow assembly 9220 may also be removably connected to a patient interface 3000 and may be able to swivel relative to the patient interface 3000.

The vent adaptor 9100 may also include a short tube assembly 9210. The short tube assembly 9210 may decouple the other components of the vent adaptor 9110, e.g., the vent housing 9320 and the vent core structure 9300, from the elbow assembly's 9220 connection with the plenum chamber 3200. By decoupling the other components of the vent adaptor 9110 in this manner, the mass that must be carried directly on the patient's head via the patient interface 3000 can be reduced, which in turn provides a lighter and more comfortable experience for the patient. The short tube assembly 9210 may include a tube 9212, which may be comprised of one or more helical coils. The short tube assembly 9210 may include a tube-elbow connector 9216 to provide a connection with the elbow assembly 9220. The connection between the tube-elbow connector 9216 and the elbow assembly 9220 may comprise a snap-fit. The connection between the tube-elbow connector 9216 and the elbow assembly 9220 may be permanent—in other words, the connection may not be separated without damaging the components. The short tube assembly 9210 may include a tube-housing connector 9214 to provide a connection with the vent housing connector 9160. The connection between the tube-housing connector 9214 and the vent housing connector 9160 may comprise a snap-fit. The connection between the tube-housing connector 9214 and the vent housing connector 9160 may be permanent—in other words, the connection may not be separated without damaging the components.

The vent adaptor 9100 may include a vent housing connector 9160 to join the short tube assembly 9210 with the vent housing 9320. As described above, the vent housing connector 9160 may be joined to the short tube assembly 9210 with the tube-housing connector 9214 that may be a snap-fit and that may be permanent. The vent housing connector 9160 may also include a bayonet connector 9166 to facilitate a releasable bayonet-style connection with the vent housing 9320 or a heat and moisture exchanger (HME) housing 9400. Thus the HME associated with the HME housing 9400 may be optional and, as such, is not shown in FIGS. 35A to 35F. The bayonet connectors 9166 may be male or female. Also, making the vent housing 9320 removably connectable to the vent housing connector 9160 allows the vent components to be removed and disassembled for cleaning.

The HME housing 9400 may also be at least partially enclosed within the vent adaptor 9100. FIGS. 35G to 35I depict examples of the vent adaptor 9100 of FIGS. 35A to 35F with the HME housing 9400 enclosed therein. The examples shown in FIGS. 35G to 35I omit the HME material 9145 so that features of the vent adaptor 9100 and the HME housing 9400 are not obstructed in the drawings. However, it should be understood that the HME material 9145 may be included therein when the vent adaptor 9100 is used for therapy. FIG. 35F shows the vent adaptor 9100 without the HME housing 9400 and FIGS. 35G and 35H show the vent adaptor 9100 with the HME housing 9400—it should be understood that the vent housing connector 9160 and the vent housing 9320 connect the same way, as described above, regardless of whether the HME housing 9400 is present.

The HME housing 9400 is shown in these examples installed within a cavity 9167 that is defined at least in part by the vent housing connector 9160 and/or the vent housing 9320. When the vent housing connector 9160 and the vent housing 9320 are joined together, the cavity 9167 is formed. Alternatively, the vent housing connector 9160 or the vent housing 9320 may comprise substantially all of the cavity 9167. If the HME housing 9400 is not provided, the cavity 9167 may be empty, as shown in FIG. 35F. The vent housing 9320 and the vent housing connector 9160 may be shaped and dimensioned such that exterior surfaces of the HME housing 9400 are in direct contact with or adjacent to interior surfaces of the vent housing 9320 and the vent housing connector 9160. The HME housing 9400 may occupy substantially all of the cavity 9167 when installed therein.

The vent housing 9320 or the vent housing connector 9160 may also include a structure to facilitate a removable connection with a corresponding structure of the HME housing 9400. For example, the interior of the vent housing 9320 may also include an annular lip 9326 around all or part of the inner periphery of the vent housing 9320. The annular lip 9326 may include at least one retaining protrusion 9328 to removably connect the HME housing 9400 to the vent housing 9320. FIG. 37C shows an example of the vent housing 9320 with four retaining protrusions 9328. The retaining protrusions 9328 are also spaced approximately evenly around the annular lip 9326 in FIG. 37C. The HME housing 9400 may also include an annular recess 9405 around the outer periphery of the atmosphere-side HME housing portion 9404 that removably receives the retaining protrusions 9328. The annular recess 9405 may be continuous about the outer periphery of the atmosphere-side HME housing portion 9404, which allows the HME housing 9400 to be attached to the vent housing 9320 without regard to the relative orientation of the components.

The removable connection between the annular recess 9405 and the retaining protrusions 9328 may be a snap-fit or a friction fit. The removable connection between the annular recess 9405 and the retaining protrusions 9328 may be sufficiently secure (e.g., due to friction) to prevent relative rotation between the HME housing 9400 and the vent housing 9320, while allowing the patient or a clinician to manually separate the components for replacement and/or cleaning.

An alternative arrangement is also envisioned in the outer periphery of the HME housing 9400 includes protrusions that may be removably received by a recess around the inner periphery of the vent housing 9320. It is also envisioned that the removable connection interface between the HME housing 9400 and the vent adaptor 9100 may occur between the patient-side HME housing portion 9402 and the vent housing connector 9160, instead of between the atmosphere-side HME housing portion 9404 and the vent housing 9320. Instead of the annular recess 9405 and the retaining protrusions 9328, it is also envisioned that the HME housing 9400 and the vent adaptor 9100 may each have threads to provide a threaded connection that is removable. In another alternative, the HME housing 9400 may be connected to the vent housing connector 9160 or the vent housing 9320 with a bayonet connection.

Alternatively, the HME housing 9400 may be retained by the vent adaptor 9100 by being sandwiched between the vent housing connector 9160 and the vent housing 9320. There may be no positive connection between the HME housing 9400 and the vent adaptor 9100, and the HME housing 9400 may only be retained by being enclosed by the vent housing connector 9160 and the vent housing 9320.

FIGS. 37A to 37G show examples of the vent housing 9320, the flap or membrane 9140, the vent core structure 9300, the diffusing member 9146, the diffuser retaining ring 9148, and the vent diffuser cover 9330. These components may be assembled into a sub-assembly, as shown in FIGS. 37A to 37G, and joined to the vent housing connector 9160 for use. The components of the sub-assembly depicted in FIGS. 37A to 37G may be inseparable via a permanent snap-fit or the components may be separable by the user. In the case of inseparability, the snap-fit may be permanent such that the components cannot be separated without damaging them.

The vent housing 9320 may also include bayonet connectors 9322 to correspondingly connect with the bayonet connectors 9166 of the vent housing connector 9160 to removably connect the vent housing 9320 to the vent housing connector 9160. The vent housing 9320 may also include a membrane retainer 9324 to hold the membrane 9140 against the vent core structure 9300 when assembled. The membrane retainer 9324 may comprise an open, radial, and cage-like structure to allow the vent flow to travel through the membrane retainer 9324 for discharge by the vent core structure 9300. The membrane retainer 9324 may also be open in its center to allow the therapy flow to pass along to the patient from the RPT device 4000.

The flap or membrane 9140 may be positioned between the membrane retainer 9324 and the vent core structure 9300. The membrane 9140 may be held in position between these two structures, but may be otherwise be free to be deformed by pressure within the vent adaptor 9100. The membrane 9140 may function similarly to other examples of the membrane 9140 disclosed above.

The vent core structure 9300 may include an inlet 9301 to allow the flow of gas generated by the RPT device 4000 to pass through the vent adaptor 9100 and along to the patient for therapy. The vent core structure 9306 may include a vent core extension 9306 through which the inlet 9301 may be defined. The vent core extension 9306 may extend axially and may include air circuit connectors 9302 to connect the vent core 9300 to the air circuit 4170. As can be seen, the vent core extension 9306 is shaped and dimensioned to extend through the diffuser retaining ring 9148, the diffuser 9146, and the vent diffuser cover 9330 to align these components when the vent adaptor 9100 is assembled. The vent core structure 9300 may also include clips 9304 on an alignment structure 9312 that connect to the connection surface 9334 of the vent diffuser cover 9330. The clips 9304 may be connected to the connection surface 9334 with a snap-fit to allow the vent diffuser cover 9330 to be removed for disassembly to allow cleaning and/or replacement of vent adaptor components 9100 such as the diffuser 9146. The alignment structure 9312 may also facilitate axial alignment of the vent core structure 9300 with the diffuser 9146 and the vent diffuser cover 9330 by virtue of corresponding shapes.

The vent core structure 9300 may also include a plurality of outer orifices 9308 and a plurality of inner orifices 9310. The plurality of inner orifices 9310 may be configured such that vent flow to atmosphere through the inner orifices 9310 may be obstructed or restricted by the membrane 9140 in use. The plurality of outer orifices 9308 may be configured such that vent flow to atmosphere through the outer orifices 9308 may not be obstructed or restricted at any point by the membrane 9140 in use. However, the membrane 9140 may also be configured such that it does not completely occlude the inner orifices 9310 at any pressure at least within a typical range of therapeutic pressure (e.g., between about 6 cmH2O and about 20 cmH2O). In other words, vent flow may be discharged through both the inner orifices 9310 and the outer orifices 9308 at any pressure within a typical range of therapeutic pressure, while the pressure within the vent adaptor 9110 deforms the membrane 9140 to vary the proportion of vent flow traveling through the outer orifices 9308 and the inner orifices 9310 so as to maintain a constant vent flow rate, as described above.

The diffuser 9146 may include a diffuser opening 9147 through which the vent core extension 9306 may pass. The diffuser 9146 may include similar features to the diffusers described above.

The diffuser 9146 may be held in position downstream of the inner orifices 9310 and the outer orifices 9308 relative to the vent flow by the diffuser retaining ring 9148 and the vent diffuser cover 9330. The diffuser retaining ring 9148 may be secured to the vent diffuser cover 9330, e.g., with a snap-fit, to retain the diffuser 9146. The diffuser retaining ring 9148 may include radial diffuser retainers 9149 to hold the diffuser 9146 against the vent diffuser cover 9330. The diffuser retaining ring 9148 and the radial diffuser retainers 9149 may define posterior vent outlets 9342 around the vent housing 9320. Vent flow exiting the vent core structure 9300 may pass through the diffuser 9148 and out through the posterior vent outlets 9340. The vent diffuser cover 9330 may include a series of cover spacers 9332 spaced radially about the vent diffuser cover 9330 to define the anterior vent outlets 9342. Vent flow exiting the vent core structure 9300 may pass through the diffuser 9148 and out through the anterior vent outlets 9342.

The exemplary vent adaptor 9100 disclosed above and in FIGS. 35A to 37G is shown connected to a patient interface 3000 in FIG. 35. The elbow assembly 9220 is excluded in this example, because the plenum chamber 3200 includes a connection port 3600 that is angled so as to point in an inferior direction relative to the patient's head in use, thereby directing the vent adaptor 9100 away from the patient's head. Also, the short tube assembly 9210 may be permanently connected to the plenum chamber 3200 at the connection port 3600.

FIGS. 37A to 37E depict another example of a vent adaptor 9100 according to the present technology. The vent adaptor 9100 may include a plenum chamber connector 9700 to connect the vent adaptor 9100 directly to the connection port 3600 of the plenum chamber 3200 and/or to a shroud 3305 thereof to provide a fluid connection for the flow of pressurized gas from the vent adaptor 9100 to the plenum chamber 3200.

The vent adaptor 9100 may also include a baffle 9600. The baffle 9600 may separate the incoming flow of pressurized gas from the RPT device 4000 from the outgoing vent flow exiting via the outer orifices 9308 and the inner orifices 9310 of the vent housing 9120. The baffle 9600 may be positioned internally of the plenum chamber connector 9700. The baffle 9600 and the plenum chamber connector 9700 may be aligned when connected to form concentric circles.

The vent adaptor 9100 may also include a lip seal 9500 that fits around the exterior periphery of the plenum chamber connector 9700. The lip seal 9500 may form a seal with the interior periphery of the connection port 3600 of the plenum chamber 3200 and/or the shroud 3305 thereof to provide a pneumatic seal while allow rotation of the vent adaptor 9100 relative to the patient interface 3000.

The vent adaptor 9140 may also include the flap or membrane 9140 to regulate the vent flow through the inner orifices 9310 and the outer orifices 9308 of the vent housing 9120 in accordance with the examples described above, e.g., the examples pictured in FIGS. 35A to 37G.

The vent housing 9120 may include inner orifices 9310 and outer orifices 9308 and these orifices may permit vent flow to exit the vent adaptor 9100 to atmosphere, as described in the examples above such as the examples of FIGS. 35A to 37G.

The vent housing 9120 may also include tabs 9123 and lips 9124 to provide a releasable and rotatable connection with the connection port 3600 of the plenum chamber 3200 and/or the shroud 3305 thereof. The tabs 9123 may be manually depressed to release the lips 9123 from a corresponding annular protrusion (not shown) of the connection port 3600 of the plenum chamber 3200 and/or the shroud 3305 thereof. When connected, the lips 9124 allow the vent adaptor 9100 to maintain a connection with the connection port 3600 of the plenum chamber 3200 and/or the shroud 3305 thereof while being rotatable to reduce the effects of tube drag.

The vent housing 9120 may be connected to a conduit connector 9110 that in turn may connect the vent adaptor 9100 to an air circuit. The conduit connector 9110 may be in the form of an elbow. The conduit connector 9110 may have a conduit end 9111 that connects to the air circuit 4170 and a vent adaptor end 9112 that connects to the vent housing 9120. The connection between the vent adaptor end 9112 of the conduit connector 9110 and the vent housing 9120 may comprise a snap-fit, may be permanent such that the connection cannot be separated without damaging at least one of the components, and/or may be non-rotatable to prevent the conduit connector 9110 from contacting the tabs 9123. The conduit connector 9110 may also include one or more anti-asphyxia valve (AAV) openings 9113 for the AAV 9135.

The vent adaptor 9100 may also include an air circuit connector 9116 that may be attached to the conduit end 9111 of the conduit connector 9110. The air circuit connector 9116 may include bayonet connectors 9117 to correspondingly connect to the connectors 4175 of the exemplary air circuit 4170 of FIGS. 36A to 36C. The connection between the air circuit connector 9116 and the air circuit 4170 may be releasable.

The vent adaptor depicted in FIGS. 37A to 37E may not include heat and moisture exchanger (HME) material 9145. The absence of a heat and moisture exchanger material 9145 positioned within the vent flow path may minimise vent flow impedance, thereby minimising $CO_2$ build up within the plenum chamber 3200. The depicted vent adaptor 9100 may be, for example, suitable for use with a full face patient interface.

The vent adaptor 9100 depicted in FIGS. 37A to 37E may form an elbow assembly that may be removably connected to a patient interface 3000, and may be able to swivel relative to the patient interface.

5.3.5 Decoupling Structure(s)

In one form, the patient interface 3000 includes at least one decoupling structure, for example, a swivel or a ball and socket.

5.3.6 Connection Port

A connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form, this allows a clinician to supply supplemental oxygen. In one form, this allows for the direct measurement of a property of gases within the plenum chamber 3200, such as the pressure.

5.4 Breathing Waveforms

FIG. 4 shows a model typical breath waveform of a person while sleeping. The horizontal axis is time, and the vertical axis is respiratory flow rate. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/min. A typical duty cycle, the ratio of Ti to Ttot, is about 40%.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g., atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g., the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g., from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes, e.g., certain silicones, and thermoplastic elastomers.

Hardness: The ability of a material per se to resist deformation (e.g., described by a Young's Modulus, or an indentation hardness scale measured on a standardised sample size).

'Soft' materials may include silicone or thermo-plastic elastomer (TPE), and may, e.g., readily deform under finger pressure.

'Hard' materials may include polycarbonate, polypropylene, steel or aluminium, and may not e.g., readily deform under finger pressure.

Stiffness (or rigidity) of a structure or component: The ability of the structure or component to resist deformation in response to an applied load. The load may be a force or a moment, e.g., compression, tension, bending or torsion. The structure or component may offer different resistances in different directions.

Floppy structure or component: A structure or component that will change shape, e.g., bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g., at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g., 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Gamma(\Phi)$ is zero-valued at the end of expiration, i.e. $\Gamma(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

Typical recent ventilation: The typical recent ventilation Vtyp is the value around which recent measures of ventilation over some predetermined timescale tend to cluster. For example, a measure of the central tendency of the measures of ventilation over recent history may be a suitable value of a typical recent ventilation.

5.5.4 Anatomy

5.5.4.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

Bony framework (nose): The bony framework of the nose comprises the nasal bones, the frontal process of the maxillae and the nasal part of the frontal bone.

Cartilaginous framework (nose): The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear) dividing the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.5.4.2 Anatomy of the Skull

Frontal bone: The frontal bone includes a large vertical portion, the *squama frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g., about 360 degrees. In certain forms an elbow may be removable from a mating component, e.g., via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example, a structure may comprise one or more of an anterior surface, a posterior surface, an interior surface and an exterior surface. In another example, a seal-forming structure may comprise a face-contacting (e.g., outer) surface, and a separate non-face-contacting (e.g., underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g., positive, negative) and a magnitude (e.g., 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g., relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g., curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g., both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g., a continuous space curve from f(0) to f(1) on a surface. In certain forms of the present technology, a 'path' may be described as a route or course, including e.g., a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g., the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g., FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g., a gently sloping helical path). A space curve which deviates a relatively large amount from the osculating plane will have a relatively large magnitude of torsion (e.g., a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g., a right-hand helix as shown in FIG. 3S). A space curve turning away from the direction of the right-hand binormal may be considered as having a right-hand negative torsion (e.g., a left-hand helix).

Equivalently, and with reference to a left-hand rule (see FIG. 3O), a space curve turning towards the direction of the left-hand binormal may be considered as having a left-hand positive torsion (e.g., a left-hand helix). Hence left-hand positive is equivalent to right-hand negative. See FIG. 3T.

5.5.6.4 Holes

A surface may have a one-dimensional hole, e.g., a hole bounded by a plane curve or by a space curve. Thin structures (e.g., a membrane) with a hole, may be described as having a one-dimensional hole. See, for example, the one dimensional hole in the surface of structure shown in FIG. 3I, bounded by a plane curve.

A structure may have a two-dimensional hole, e.g., a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g., at its entrance or at its exit), and a two-dimension hole bounded by the inside surface of the conduit. See also the two dimensional hole through the structure shown in FIG. 3K, bounded by a surface as shown.

5.6 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

| | |
|---|---|
| patient | 1000 |
| bed partner | 1100 |
| patient interface | 3000 |
| seal - forming structure | 3100 |
| plenum chamber | 3200 |
| structure | 3300 |
| vent system | 3400 |
| vent housing | 3401 |
| outer wall | 3402 |
| outer base | 3403 |
| second orifice | 3404 |
| lateral membrane support | 3405 |
| inner base | 3406 |
| first orifice | 3407 |
| base connector | 3408 |
| membrane spacer | 3409 |
| inner wall | 3410 |
| inlet | 3411 |
| membrane spacer gap | 3412 |
| inner base slot | 3413 |
| recess divider | 3414 |
| recess | 3415 |
| inner base membrane passage | 3416 |
| inner wall membrane passage | 3417 |
| base divider | 3418 |
| shaft | 3419 |
| membrane | 3430 |
| membrane opening | 3431 |
| patient-side surface | 3432 |
| atmosphere-side surface | 3433 |
| inner surface | 3434 |
| outer surface | 3435 |
| active length | 3450 |
| membrane thickness | 3451 |
| spacer height | 3452 |
| membrane-inner base gap | 3453 |
| first orifice radius | 3454 |
| first orifice width | 3455 |
| first orifice length | 3456 |
| overlap length | 3457 |
| overhang length | 3458 |
| connection port | 3600 |
| forehead support | 3700 |

-continued

| | |
|---|---|
| heat and moisture exchanger | 3800 |
| RPT device | 4000 |
| air circuit | 4170 |
| air circuit connector | 4171 |
| vent connector tube | 4180 |
| elbow | 4181 |
| tube connector | 4182 |
| humidifier | 5000 |
| RPT device flow | 6000 |
| patient-generated flow | 6001 |
| second vent flow | 6002 |
| first vent flow | 6003 |
| pressurized volume | 6004 |
| atmosphere | 6005 |
| water flow | 6006 |
| flap | 9140 |
| opening | 9141 |
| diffuser | 9146 |
| opening | 9147 |
| diffuser retainer | 9149 |
| vent diffuser cover | 9330 |
| cover spacers | 9332 |
| opening | 9336 |
| first notch | 9337 |
| second notch | 9338 |
| posterior vent outlet | 9340 |
| anterior vent outlet | 9342 |

The invention claimed is:

1. A patient interface system configured to provide respiratory therapy to a patient with a therapy flow of gas pressurized above ambient pressure throughout the patient's respiratory cycle, the patient interface system comprising:
a seal-forming structure constructed from a soft, flexible, resilient material and configured to seal against the patient's face in use to provide the therapy flow of gas to the patient's airways;
a plenum chamber joined to the seal-forming structure and having a connection port configured to receive the therapy flow of gas during use;
a positioning and stabilising structure comprising at least one strap and configured to secure the seal-forming structure on the patient in use; and
a vent system configured to provide a vent flow of gas to discharge gas exhaled by the patient from a pressurized volume, the vent flow being continuous during the respiratory therapy,
a vent housing comprising a base having at least one first orifice extending through the base to allow gas to be discharged to atmosphere from the pressurized volume;
at least one second orifice to allow gas to be discharged to atmosphere from the pressurized volume; and
a membrane positioned adjacent to the base,
wherein the pressurized volume is in fluid communication with atmosphere through the at least one first orifice and the at least one second orifice throughout a therapeutic pressure range, and
wherein the membrane is elastically deformable due to pressure within the pressurized volume to apportion the vent flow between the at least one first orifice and the at least one second orifice throughout the therapeutic pressure range, and
wherein the membrane is not attached to the vent system such that the membrane is freely movable towards and away from the base.

2. The patient interface system of claim 1, wherein the vent housing comprises an outer wall and an inner wall, the inner wall defining an inlet for the therapy flow of gas, and wherein the base is positioned between the outer wall and the inner wall.

3. The patient interface system of claim 2, wherein the base further comprises an inner base and an outer base.

4. The patient interface system of claim 3, wherein the outer base is adjacent to the outer wall, the inner base is adjacent to the outer base, and the inner base is adjacent to the inner wall.

5. The patient interface system of claim 4, wherein the at least one first orifice further comprises a plurality of first orifices and the at least one second orifice further comprises a plurality of second orifices.

6. The patient interface system of claim 5, wherein the plurality of second orifices pass through the outer base and the plurality of first orifices pass between the outer base and the inner base.

7. The patient interface system of claim 6, further comprising a plurality of base connectors to join the inner base and the outer base and to divide the plurality of first orifices.

8. The patient interface system of claim 7, further comprising a plurality of membrane spacers extending from the inner base.

9. The patient interface system of claim 8, wherein the membrane is supported over the plurality of first orifices on the outer base and the membrane spacers.

10. The patient interface system of claim 8, wherein the vent housing comprises a base divider between the inner base and the outer base, and
wherein the membrane is supported over the plurality of first orifices on the base divider and the membrane spacers.

11. The patient interface system of claim 8, wherein the plurality of membrane spacers define a plurality of membrane spacer gaps between adjacent ones of the plurality of membrane spacers.

12. The patient interface system of claim 8, wherein the membrane includes an atmosphere-side surface adjacent to the inner base and the outer base of the vent housing and an inner surface defining a membrane opening, and
wherein an inner base membrane passage for the vent flow is defined between the atmosphere-side surface of the membrane and the inner base of the vent housing.

13. The patient interface system of claim 12, wherein an inner wall membrane passage for the vent flow is defined between the inner surface of the membrane and the inner wall of the vent housing.

14. The patient interface system of claim 8, wherein the inner base comprises a plurality of inner base slots positioned between individual membrane spacers.

15. The patient interface system of claim 5, wherein the outer base comprises a plurality of lateral membrane supports that are configured to prevent the membrane from covering the plurality of second orifices.

16. The patient interface system of claim 5, wherein the vent housing comprises a plurality of recesses opposite the outer base, and
wherein at least one of the plurality of second orifices opens into a corresponding one of the plurality of recesses.

17. The patient interface system of claim 3 wherein the inner wall extends above the inner base and the outer base.

18. The patient interface system of claim 3, wherein the inner wall extends below the inner base and the outer base.

19. The patient interface system of claim 3, wherein the outer wall, the inner wall, the inner base, the outer base, and the membrane are circular.

20. The patient interface system of claim 19, wherein the outer wall, the inner wall, the inner base, the outer base, and the membrane are concentric.

21. The patient interface system of claim 1, wherein the vent housing comprises a shaft extending from the base to receive the therapy flow of gas, the at least one first orifice passing through the base, and the at least one second orifice passing through the shaft.

22. The patient interface system of claim 21, wherein the at least one first orifice and the at least one second orifice are oriented such that the vent flow passing through the at least one first orifice and the at least one second orifice intersects outside of the vent housing.

23. The patient interface system of claim 22, further comprising a diffuser,
wherein the vent flow passing through the at least one first orifice and the at least one second orifice intersects within the diffuser.

24. The patient interface system of claim 23, wherein the at least one first orifice further comprises a plurality of first orifices and the at least one second orifice further comprises a plurality of second orifices.

25. The patient interface system of claim 1, wherein the membrane comprises an elastically deformable material.

26. The patient interface system of claim 25, wherein the elastically deformable material comprises silicone.

27. The patient interface system of claim 1, wherein the vent housing is formed from a single, homogeneous piece of a relatively rigid material.

28. The patient interface system of claim 27, wherein the relatively rigid material is polycarbonate.

29. The patient interface system of claim 1, further comprising a tube that connects the vent system to the plenum chamber at the connection port to allow gas to flow between the vent system and the plenum chamber during use.

30. The patient interface system of claim 1, further comprising an air circuit removably connected to the vent system to direct the therapy flow of gas to the patient from a respiratory pressure therapy device during use.

* * * * *

UNITED STATES PATENT AND TRADEMARK OFFICE
CERTIFICATE OF CORRECTION

PATENT NO. : 11,420,008 B2
APPLICATION NO. : 16/334442
DATED : August 23, 2022
INVENTOR(S) : Muditha Pradeep Dantanarayana It is certified that error appears in the above-identified patent and that said Letters Patent is hereby corrected as shown below:

In the Claims

In Claim 1, Column 56, Lines 44 and 45, "…the vent flow being continuous during the respiratory therapy," should read -- …the vent flow being continuous during the respiratory therapy, the vent system comprising: --

Signed and Sealed this
Eighth Day of November, 2022

Katherine Kelly Vidal
*Director of the United States Patent and Trademark Office*